United States Patent
Mound et al.

(10) Patent No.: US 9,615,577 B2
(45) Date of Patent: *Apr. 11, 2017

(54) HERBICIDALLY ACTIVE CYCLIC DIONE COMPOUNDS, OR DERIVATIVES THEREFOR, SUBSTITUTED BY A PHENYL WHICH HAS AN ALKYNYL-CONTAINING SUBSTITUENT

(71) Applicant: Syngenta Limited, Guildford, Surrey (CH)

(72) Inventors: William Roderick Mound, Bracknell (GB); James Nicholas Scutt, Bracknell (GB); Mark Slater, Bracknell (GB); Nigel James Willetts, Bracknell (GB)

(73) Assignee: Syngenta Limited, Guildford, Surrey (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/653,674

(22) PCT Filed: Dec. 19, 2013

(86) PCT No.: PCT/EP2013/077541
§ 371 (c)(1),
(2) Date: Jun. 18, 2015

(87) PCT Pub. No.: WO2014/096289
PCT Pub. Date: Jun. 26, 2014

(65) Prior Publication Data
US 2015/0342185 A1 Dec. 3, 2015

(30) Foreign Application Priority Data

Dec. 21, 2012 (GB) .................................. 1223429.0
May 31, 2013 (GB) .................................. 1309728.2
Dec. 4, 2013 (GB) .................................. 1321553.8

(51) Int. Cl.
*C07D 309/06* (2006.01)
*C07C 321/20* (2006.01)
(Continued)

(52) U.S. Cl.
CPC ............ *A01N 43/16* (2013.01); *A01N 35/06* (2013.01); *A01N 37/02* (2013.01); *A01N 43/18* (2013.01);
(Continued)

(58) Field of Classification Search
CPC .. C07D 309/06; C07D 309/32; C07D 311/96; C07D 213/50; C07C 49/747;
(Continued)

(56) References Cited

U.S. PATENT DOCUMENTS 4,659,372 A * 4/1987 Wheeler ................ A01N 35/06
504/182
4,678,501 A * 7/1987 Manning ................ A01N 43/40
504/229
(Continued)

FOREIGN PATENT DOCUMENTS

WO   2008110307 A1   9/2008
WO   2008110308 A2   9/2008
(Continued)

OTHER PUBLICATIONS

International Search Report for International Application PCT/EP2013/077541, mailed Sep. 29, 2014.
(Continued)

*Primary Examiner* — Noble Jarrell
*Assistant Examiner* — Daniel Carcanague
(74) *Attorney, Agent, or Firm* — James Cueva

(57) ABSTRACT

The present invention relates to a compound of formula (I), wherein: X is methyl or chlorine; $R^1$ is methyl or chlorine; $R^2$ is hydrogen, methyl, ethyl, n-propyl, cyclopropyl, vinyl, ethynyl, fluorine, chlorine, bromine, $C_1$-$C_3$alkoxy, $C_1$-$C_2$-fluoroalkoxy, $C_1$-$C_2$alkoxy-$C_1$-$C_3$alkoxy- or $C_1$fluoroalkoxy-$C_1$-$C_3$alkoxy-; and Y is O, S, S(O), S(O)$_2$, N($C_1$-$C_2$alkyl), N($C_1$-$C_2$alkoxy), C(O), $CR^8R^9$ or —$CR^{10}R^{11}CR^{12}R^{13}$—; and G, $R^3$, $R^4$, $R^5$ and $R^6$ are as defined herein; wherein the compound of formula (I) is optionally present as an agrochemically acceptable salt thereof. These compounds are suitable for use as herbicides. The invention therefore also relates to a method of controlling weeds, especially grassy monocotyledonous weeds, in crops of useful plants, comprising applying a compound of formula (I), or a herbicidal composition comprising such a compound, to the plants or to the locus thereof.

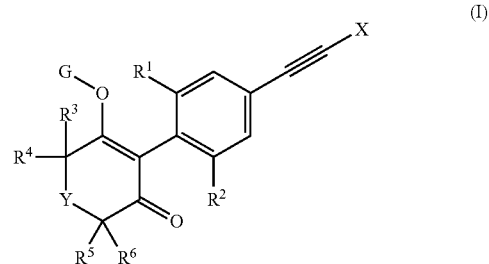

21 Claims, No Drawings

(51) Int. Cl.
| | |
|---|---|
| *A01N 47/06* | (2006.01) |
| *C07D 213/50* | (2006.01) |
| *A01N 43/40* | (2006.01) |
| *C07C 329/06* | (2006.01) |
| *C07C 49/747* | (2006.01) |
| *C07D 309/32* | (2006.01) |
| *A01N 35/06* | (2006.01) |
| *A01N 43/16* | (2006.01) |
| *C07D 311/96* | (2006.01) |
| *C07C 49/697* | (2006.01) |
| *C07C 49/753* | (2006.01) |
| *A01N 43/18* | (2006.01) |
| *A01N 37/02* | (2006.01) |

(52) U.S. Cl.
CPC ............. *A01N 43/40* (2013.01); *A01N 47/06* (2013.01); *C07C 49/697* (2013.01); *C07C 49/747* (2013.01); *C07C 49/753* (2013.01); *C07C 321/20* (2013.01); *C07C 329/06* (2013.01); *C07D 213/50* (2013.01); *C07D 309/06* (2013.01); *C07D 309/32* (2013.01); *C07D 311/96* (2013.01); *C07C 2102/22* (2013.01); *C07C 2102/44* (2013.01)

(58) Field of Classification Search
CPC . C07C 2102/44; C07C 321/20; C07C 329/06; C07C 49/697; C07C 49/753; C07C 2102/22; A01N 47/06; A01N 35/06; A01N 43/16; A01N 43/40; A01N 37/02; A01N 43/18
USPC ........................................................ 546/348
See application file for complete search history.

(56) References Cited

U.S. PATENT DOCUMENTS

| | | | | |
|---|---|---|---|---|
| 8,536,351 B2* | 9/2013 | Mathews | ............. | C07D 305/06 504/103 |
| 8,623,907 B2* | 1/2014 | Scutt | ...................... | A01N 43/16 514/437 |
| 8,680,012 B2* | 3/2014 | Mathews | ............... | A01N 43/16 504/239 |
| 8,680,339 B2* | 3/2014 | Mathews | ............... | A01N 35/06 504/118 |
| 8,735,322 B2* | 5/2014 | Mathews | ............... | A01N 43/08 504/103 |
| 8,828,908 B2* | 9/2014 | Mathews | ............... | A01N 35/06 504/100 |
| 8,865,623 B2* | 10/2014 | Mathews | ............... | A01N 35/06 504/121 |
| 8,895,474 B2* | 11/2014 | Mathews | ............... | A01N 35/06 504/210 |
| 8,895,761 B2* | 11/2014 | Muehlebach | ......... | C07C 49/747 549/28 |
| 9,006,429 B2* | 4/2015 | Mathews | ............... | A01N 43/16 544/238 |
| 9,102,642 B2* | 8/2015 | Mathews | ............... | A01N 43/16 |
| 9,107,415 B2* | 8/2015 | Avery | .................... | C07C 49/683 |
| 2005/0054535 A1* | 3/2005 | Fischer | .................. | A01N 43/08 504/310 |
| 2009/0227563 A1 | 9/2009 | Fischer et al. | | |
| 2010/0113270 A1* | 5/2010 | Mathews | ............. | C07D 305/06 504/108 |
| 2010/0210466 A1* | 8/2010 | Muehlebach | .......... | A01N 43/16 504/239 |
| 2010/0216638 A1* | 8/2010 | Mathews | ............... | A01N 35/06 504/103 |
| 2010/0279872 A1* | 11/2010 | Muehlebach | ......... | C07C 49/747 504/251 |
| 2011/0152095 A1* | 6/2011 | Scutt | ...................... | A01N 43/16 504/103 |
| 2011/0190127 A1* | 8/2011 | Scutt | ..................... | C07C 17/093 504/103 |
| 2012/0021907 A1* | 1/2012 | Mathews | ............... | A01N 35/06 504/121 |
| 2012/0021909 A1* | 1/2012 | Mathews | ............... | A01N 43/16 504/128 |
| 2012/0021912 A1* | 1/2012 | Mathews | ............... | A01N 35/06 504/242 |
| 2012/0028800 A1* | 2/2012 | Mathews | ............... | A01N 35/06 504/103 |
| 2012/0035053 A1* | 2/2012 | Mathews | ............... | A01N 43/08 504/103 |
| 2014/0005389 A1* | 1/2014 | Mathews | ............... | A01N 43/16 544/238 |
| 2014/0323303 A1* | 10/2014 | Avery | .................... | C07C 49/683 504/105 |
| 2016/0143277 A1* | 5/2016 | Black | ..................... | A01N 43/16 504/103 |
| 2016/0207934 A1* | 7/2016 | Black | ..................... | A01N 43/16 |

FOREIGN PATENT DOCUMENTS

| | | | |
|---|---|---|---|
| WO | WO 2008110307 | * | 9/2008 |
| WO | WO 2008110308 | * | 9/2008 |
| WO | 2008145336 A1 | | 12/2008 |
| WO | WO 2008145336 | * | 12/2008 |
| WO | 2010046194 A1 | | 4/2010 |
| WO | WO 2010046194 | * | 4/2010 |
| WO | 2010081687 A1 | | 7/2010 |
| WO | 2010081689 A2 | | 7/2010 |
| WO | WO 2010081687 | * | 7/2010 |
| WO | WO 2010081689 | * | 7/2010 |
| WO | WO 2010081755 | * | 7/2010 |
| WO | WO 2010089210 | * | 8/2010 |
| WO | WO 2010089211 | * | 8/2010 |
| WO | WO 2011006543 | * | 1/2011 |
| WO | 2013079708 A1 | | 6/2013 |
| WO | WO 2013079708 | * | 6/2013 |
| WO | WO 2014191534 | * | 12/2014 |
| WO | WO 2014191535 | * | 12/2014 |
| WO | WO 2015197468 | * | 12/2015 |

OTHER PUBLICATIONS

UK Search Report for GB Application No. GB1309728.2, date of search Nov. 14, 2013.

* cited by examiner

HERBICIDALLY ACTIVE CYCLIC DIONE COMPOUNDS, OR DERIVATIVES THEREFOR, SUBSTITUTED BY A PHENYL WHICH HAS AN ALKYNYL-CONTAINING SUBSTITUENT

RELATED APPLICATION INFORMATION

This application is a 371 of International Application No. PCT/EP2013/077541, filed Dec. 19, 2013, which claims priority to GB Application number 1223429.0 filed Dec. 21, 2012, GB Application number 1309728.2 filed May 31, 2013, and GB Application number 1321553.8 filed Dec. 4, 2013 the contents of which are incorporated herein by reference herein.

The present invention relates to herbicidally active cyclic diones, in particular pyrandione, thiopyrandione, cyclohexanedione, alkanediyl-bridged cyclohexanedione, cyclohexanetrione or cycloheptanedione compounds, or derivatives thereof (e.g. enol ketone tautomer derivatives thereof), to processes for their preparation, to herbicidal compositions comprising those compounds, and to their use in controlling weeds such as grassy monocotyledonous weeds, especially in crops of useful plants, or in inhibiting undesired plant growth. In particular, the present invention relates to herbicidally active cyclic dione compounds, or derivatives thereof (e.g. enol ketone tautomer derivatives thereof), which are substituted by a phenyl which has an alkynyl-containing substituent.

WO 01/17972 A2 (Syngenta Participations AG) discloses phenyl-substituted (such as 4-methyl-2,6-diethyl-phenyl-substituted) heterocycles suitable for use as herbicides.

WO 03/013249 A1 (Bayer AG) and its equivalent US 2005/0054535 A1 disclose selective herbicidal compositions comprising (a) a (substituted-phenyl)-substituted cyclic ketoenol and (b) a compound which improves crop plant compatibility, in particular cloquintocet-mexyl or mefenpyr-diethyl.

WO 2007/068427 A2 (Bayer CropScience AG) and its equivalent US 2009/0227563 A1 disclose a composition comprising (a) a (substituted-phenyl)-substituted cyclic ketoenol as a herbicide, and (b) an ammonium or phosphonium salt to boost activity.

WO 2008/071405 A1 and WO 2009/074314 A1 (both Syngenta Limited and Syngenta Participations AG) each disclose herbicidally active pyran-3,5-diones, thiopyran-3,5-diones and cyclohexane-1,3,5-triones, each substituted at the 4-position of the cyclic dione or trione by an aryl-substituted-phenyl or by a heteroaryl-substituted-phenyl.

WO 2010/081755 A1 and WO 2010/089211 A1 (both Syngenta Limited) each disclose herbicidally active pyran-3,5-diones, thiopyran-3,5-diones, cyclohexanediones, cycloheptanediones and cyclohexanetriones, each substituted by an aryloxy-substituted-phenyl or by a heteroaryloxy-substituted-phenyl.

WO 2008/110308 A1 (Syngenta Participations AG) discloses 2-(substituted-phenyl)-cyclohexane-1,3-dione compounds and derivatives, containing a $R^8$—X—$(CR^6R^7)_n$— substituent (wherein X is O, S, S(O) or $S(O)_2$) or a heteroatom-containing-spirocyle at the 5-position of the cyclohexane-1,3-dione, and having herbicidal properties. WO 2008/110307 A1 (Syngenta Participations AG) discloses 2-(substituted-phenyl)-5-heterocyclyl-cyclohexane-1,3-dione compounds and derivatives, and their use as herbicides.

WO 2010/046194 A1 (Syngenta Limited) discloses 2-(substituted-phenyl)-cyclohexane-1,3-dione compounds and derivatives, containing a Q-$CR^6R^7$— substituent at the 5-position of the cyclohexane-1,3-dione (wherein Q is a saturated or mono-unsaturated heterocycle), and having herbicidal properties.

WO 2008/145336 A1 and A8 (Syngenta Limited) disclose herbicidally active phenyl-substituted bicyclic (carbon-bridged, e.g. alkanediyl-bridged) 1,3-dione compounds, such as 3-(substituted-phenyl)-bicyclo[3.2.1]octane-2,4-diones.

Copending PCT application PCT/EP2012/074118, filed on 30 Nov. 2012 and published on 6 Jun. 2013 as WO 2013/079672 A1 (Syngenta Limited and Syngenta Participations AG) discloses that certain substituted spiroheterocyclic pyrrolidine dione compounds, having an alkynyl-phenyl-headgroup, have herbicidal properties.

Copending PCT application PCT/EP2012/074172, filed on 30 Nov. 2012 and published on 6 Jun. 2013 as WO 2013/079708 A1 (Syngenta Limited and Syngenta Participations AG) discloses cyclopentane-1,3-dione compounds and derivatives (e.g. fused and/or spirocyclic bicyclic derivatives) thereof, which are substituted at the 2-position of the cyclopentane-1,3-dione by a phenyl which itself is substituted at the 4-position by (specifically) either prop-1-ynyl or chloroethynyl, and derivatives of the enol ketone tautomer of such cyclopentanediones, which have herbicidal activity and/or plant-growth-inhibiting properties, especially in the control of grassy monocotyledonous weeds and/or when used post-emergence.

Cyclic dione compounds have now been found, in particular pyran-3,5-dione, thiopyran-3,5-dione, cyclohexane-1,3-dione, alkanediyl-bridged cyclohexane-1,3-dione, cyclohexane-1,3,5-trione or cycloheptane-1,3-dione compounds, which are substituted, at the ring-carbon atom of the cyclic dione which is between the two oxo-substituted ring-carbons of the cyclic dione, by a phenyl which itself is substituted at the 4-position by (specifically) either prop-1-ynyl or chloroethynyl and at the 2-position by (specifically) methyl or chlorine, or derivatives of the enol ketone tautomer of such cyclic diones, which have herbicidal activity and/or plant-growth-inhibiting properties, in particular in the control of grassy monocotyledonous weeds. The herbicidal data available, as shown in the Biological Examples hereinafter, suggests that these 4-(prop-1-ynyl)-2-(methyl or chloro)-phenyl or 4-(chloroethynyl)-2-(methyl or chloro)-phenyl cyclic dione compounds are more potent herbicides against grassy monocotyledonous weeds (e.g. when applied post-emergence) than the corresponding 4-ethynyl-2-(methyl or chloro)-phenyl cyclic dione compounds. The herbicidal activity against "warm-season" (warm climate) grassy monocotyledonous weeds of most of the compounds of the invention which have been exemplified and tested herein (compounds A-1 to A-17, A-18 to A-24, P-1 to P-5, or P-7) appears to be potent, in particular after post-emergence application of the compounds at an application rate of about 250 g/ha. Also, many of the exemplified compounds exhibit a reasonably low phytotoxicity against wheat and/or certain docotyledonous crops, in particular soybean and/or sugar beet (see Biological Examples 1B and 3 hereinafter).

Therefore, in a first aspect of the present invention, there is provided a compound of formula (I):

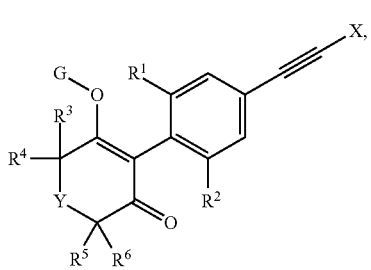

(I)

wherein:
X is methyl or chlorine;
$R^1$ is methyl or chlorine;
$R^2$ is hydrogen, methyl, ethyl, n-propyl, cyclopropyl, vinyl, ethynyl, fluorine, chlorine, bromine, $C_1$-$C_3$alkoxy, $C_1$-$C_2$fluoroalkoxy, $C_1$-$C_2$alkoxy-$C_1$-$C_3$alkoxy-, or $C_1$fluoroalkoxy-$C_1$-$C_3$alkoxy-; and
$R^3$, $R^4$, $R^5$ and $R^6$, independently of each other, are hydrogen, $C_1$-$C_5$alkyl (in particular $C_1$-$C_4$alkyl, e.g. $C_1$-$C_2$alkyl), $C_2$-$C_4$alkenyl (in particular $C_2$-$C_3$alkenyl-$CH_2$—, e.g. ethenyl-$CH_2$—), $C_2$-$C_4$alkynyl (in particular $C_2$-$C_3$alkynyl-$CH_2$—, e.g. ethynyl-$CH_2$—), $C_1$-$C_2$fluoroalkyl, $C_1$-$C_3$alkoxy$C_1$-$C_3$alkyl, $C_1$-$C_3$alkylthio$C_1$-$C_3$alkyl, $C_1$-$C_3$alkylsulfinyl$C_1$-$C_3$alkyl, $C_1$-$C_3$alkylsulfonyl$C_1$-$C_3$alkyl; $C_3$-$C_4$cycloalkyl (in particular cyclopropyl); or an unsubstituted 4, 5 or 6 (e.g. 4 or 5) membered monocyclic heterocyclyl having one ring heteroatom independently selected from oxygen, sulfur and nitrogen, and attached at a ring carbon atom within the heterocyclyl (in particular tetrahydrofuranyl such as tetrahydrofuran-3-yl, or tetrahydropyranyl such as tetrahydropyran-4-yl);
provided that no more than one (in particular none) of $R^3$, $R^4$, $R^5$ and $R^6$ is alkenyl, alkynyl, alkoxyalkyl, alkylthioalkyl, alkylsulfinylalkyl, alkylsulfonylalkyl, cycloalkyl or heterocyclyl;
or $R^3$ and $R^4$ taken together are —$(CH_2)_{n1}$— or —$(CH_2)_{n2}$—$X^1$—$(CH_2)_{n3}$— and $R^5$ and $R^6$ are as defined herein (e.g. hereinabove), or $R^5$ and $R^6$ taken together are —$(CH_2)_{n1}$— or —$(CH_2)_{n2}$—$X^1$—$(CH_2)_{n3}$— and $R^3$ and $R^4$ are as defined herein (e.g. hereinabove);
wherein $X^1$ is O, S, S(O), $S(O)_2$, NH, N($C_1$-$C_2$alkyl), N($C_1$-$C_2$alkoxy), C(H)($C_1$-$C_2$alkyl), C($C_1$-$C_2$alkyl)$_2$ or C(H)($C_1$-$C_2$alkoxy);
n1 is 2, 3, 4 or 5 (in particular 4 or 5); and
n2 and n3 are independently 1, 2 or 3 provided that n2+n3 is 2, 3 or 4 (in particular 3 or 4);
or $R^4$ and $R^5$ taken together are —$(CH_2)_{n4}$— or —$(CH_2)_{n5}$—C($R^{7a}$)($R^{7b}$)—$(CH_2)_{n6}$— or —C($R^{7c}$)=C($R^{7d}$)—;
wherein $R^{7a}$ is $C_1$-$C_2$alkyl or $C_1$-$C_2$alkoxy; and $R^{7b}$ is hydrogen or $C_1$-$C_2$alkyl provided that $R^{7b}$ is hydrogen when $R^{7a}$ is $C_1$-$C_2$alkoxy;
n4 is 1, 2 or 3; and
n5 and n6 are independently 0, 1 or 2 provided that n5+n6 is 0, 1 or 2;
and $R^{7c}$ and $R^{7d}$ independently are hydrogen or $C_1$-$C_2$alkyl; and
Y is O, S, S(O), $S(O)_2$, N($C_1$-$C_2$alkyl), N($C_1$-$C_2$alkoxy), C(O), $CR^8R^9$ or —$CR^{10}R^{11}CR^{12}R^{13}$—; and $R^8$ and $R^9$ are, independently of each other:
hydrogen, $C_1$-$C_6$alkyl (in particular $C_1$-$C_4$alkyl, e.g. $C_1$-$C_2$alkyl), $C_2$-$C_4$alkenyl (in particular $C_2$-$C_3$alkenyl-$CH_2$—, e.g. ethenyl-$CH_2$—), $C_2$-$C_4$alkynyl (in particular $C_2$-$C_3$alkynyl-$CH_2$—, e.g. ethynyl-$CH_2$—), $C_1$-$C_2$fluoroalkyl, $C_1$-$C_3$alkoxy$C_1$-$C_3$alkyl, $C_1$-$C_3$alkylthio$C_1$-$C_3$alkyl, $C_1$-$C_3$alkylsulfinyl$C_1$-$C_3$alkyl, or $C_1$-$C_3$alkylsulfonyl$C_1$-$C_3$alkyl;
$C_3$-$C_6$cycloalkyl or $C_3$-$C_6$cycloalkyl substituted by one or two substituents which independently are $C_1$-$C_3$alkyl (in particular methyl or ethyl) or $C_1$-$C_2$fluoroalkyl; and in which one ring $CH_2$ moiety of a $C_4$-$C_6$cycloalkyl is optionally (e.g. preferably) replaced by an oxygen or sulfur atom or by a S(O), $S(O)_2$, NH, N($C_1$-$C_3$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety;
$C_3$-$C_6$cycloalkyl substituted by one substituent being $C_1$-$C_3$alkoxy (in particular $C_1$-$C_2$alkoxy) and optionally further substituted by one substituent being $C_1$-$C_2$alkyl (in particular methyl);
$C_5$-$C_6$cycloalkenyl or $C_5$-$C_6$cycloalkenyl substituted by one or two $C_1$-$C_3$alkyl (in particular methyl) substituents;
$C_3$-$C_6$cycloalkyl$C_1$-$C_2$alkyl- (in particular $C_3$-$C_6$cycloalkylmethyl-) or $C_3$-$C_6$cycloalkyl$C_1$-$C_2$alkyl- (in particular $C_3$-$C_6$cycloalkylmethyl-) substituted by one or two ring substituents which independently are $C_1$-$C_3$alkyl or $C_1$-$C_2$fluoroalkyl; and in which one ring $CH_2$ moiety of a $C_4$-$C_6$cycloalkyl$C_1$-$C_2$alkyl- (in particular $C_4$-$C_6$cycloalkylmethyl-) is optionally (e.g. preferably) replaced by an oxygen or sulfur atom or by a S(O), $S(O)_2$, NH, N($C_1$-$C_2$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety;
$C_3$-$C_6$cycloalkyl$C_1$-$C_2$alkyl- (in particular $C_3$-$C_6$cycloalkylmethyl-) substituted by one ring substituent being $C_1$-$C_3$alkoxy (in particular $C_1$-$C_2$alkoxy) and optionally further substituted by one ring substituent being $C_1$-$C_2$alkyl (in particular methyl); or
Het or Het-$CH_2$—, wherein Het is a heteroaryl, attached at a ring-carbon, which is optionally substituted by 1, 2 or 3 (in particular 1 or 2, e.g. 1) ring-carbon substituents independently being $C_1$-$C_3$alkyl (e.g. $C_1$-$C_2$alkyl), $C_1$-$C_2$fluoroalkyl, $C_1$-$C_3$alkyl-C(O)—, $C_1$-$C_2$fluoroalkyl-C(O)—, hydroxy (including any oxo tautomer), $C_2$-$C_3$alkenyl (e.g. ethenyl or prop-1-enyl), $C_2$-$C_3$alkynyl (e.g. ethynyl or prop-1-ynyl), $C_1$-$C_3$alkoxy (e.g. $C_1$-$C_2$alkoxy), $C_1$-$C_2$fluoroalkoxy, halogen (e.g. fluorine or chlorine), cyano or nitro, provided that any non-fluorine halogen, alkoxy or fluoroalkoxy is not substituted at any ring-carbon bonded directly to a ring-nitrogen of the heteroaryl; and/or, in the case of a 5-membered heteroaryl ring containing a ring-nitrogen atom not partaking in a C=N ring double bond, the heteroaryl is optionally substituted on the ring-nitrogen atom not partaking in a C=N ring double bond by one $C_1$-$C_3$alkyl, $C_1$-$C_2$fluoroalkyl, $C_1$-$C_3$alkyl-C(O)—, $C_1$-$C_2$fluoroalkyl-C(O)— or $C_1$-$C_2$alkyl-$S(O)_2$— substituent;
provided that no more than one of $R^8$ and $R^9$ is an optionally substituted cycloalkyl; an optionally substituted cycloalkyl in which one ring $CH_2$ moiety has been replaced by an oxygen or sulfur atom or by a S(O), $S(O)_2$, NH, N($C_1$-$C_3$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety; an optionally substituted cycloalkenyl; an optionally substituted cycloalkyl-alkyl-; an optionally substituted cycloalkylalkyl- in which one ring $CH_2$ moiety has been replaced by an oxygen or sulfur atom or by a S(O), $S(O)_2$, NH, N($C_1$-

$C_3$alkyl), $N(C_1-C_2$fluoroalkyl), $N[C(O)C_1-C_3$alkyl], $N[C(O)$ $C_1-C_2$fluoroalkyl] or $N(C_1-C_2$alkoxy) moiety; or Het or Het-$CH_2$—;

or $R^8$ is hydrogen or $C_1-C_2$alkyl (in particular H or Me), and $R^9$ is $C_1-C_2$alkoxy (in particular methoxy);

or $R^8$ and $R^9$ taken together are —$(CH_2)_{n7}$— or —$(CH_2)_{n8}$—$X^2$—$(CH_2)_{n9}$—;

wherein $X^2$ is O, S, S(O), $S(O)_2$, NH, $N(C_1-C_3$alkyl), $N(C_1-C_2$fluoroalkyl), $N[C(O)C_1-C_3$alkyl], $N[C(O)C_1-C_2$fluoroalkyl], $N(C_1-C_2$alkoxy), $C(H)(C_1-C_3$alkyl), $C(C_1-C_2$alkyl)$_2$ or $C(H)(C_1-C_3$alkoxy);

n7 is 2, 3, 4, 5 or 6 (in particular 4 or 5); and n8 and n9 are independently 0, 1, 2 or 3 provided that n8+n9 is 2, 3, 4 or 5 (in particular 3 or 4); and $R^{10}$, $R^{11}$, $R^{12}$ and $R^{13}$ are independently of each other hydrogen or $C_1-C_4$alkyl (in particular $C_1-C_2$alkyl) provided that no more than one of $R^{10}$, $R^{11}$, $R^{12}$ and $R^{13}$ is $C_3-C_4$alkyl; and and wherein:

G is hydrogen; an agriculturally acceptable metal, or an agriculturally acceptable sulfonium or ammonium group; or G is —$C(X^a)$—$R^a$, —$C(X^b)$—$X^c$—$R^b$, —$C(X^d)$—$N(R^c)$—$R^d$, —$SO_2$—$R^e$, —$P(X^e)(R^f)$—$R^g$, —$CH_2$—$X^f$—$R^h$; or phenyl-$CH_2$— or phenyl-$CH(C_1-C_2$alkyl)- (in each of which the phenyl is optionally substituted by 1, 2 or 3 of, independently, $C_1-C_2$alkyl, $C_1$fluoroalkyl, $C_1-C_2$alkoxy, $C_1$fluoroalkoxy, fluorine, chlorine, bromine, cyano or nitro), or heteroaryl-$CH_2$— or heteroaryl-$CH(C_1-C_2$alkyl)- (in each of which the heteroaryl is optionally substituted by 1, 2 or 3 of, independently, $C_1-C_2$alkyl, $C_1$fluoroalkyl, $C_1-C_2$alkoxy, $C_1$fluoroalkoxy, fluorine, chlorine, bromine, cyano or nitro), or phenyl-$C(O)$—$CH_2$— (wherein the phenyl is optionally substituted by 1, 2 or 3 of, independently, $C_1-C_2$alkyl, $C_1$fluoroalkyl, $C_1-C_2$alkoxy, $C_1$fluoroalkoxy, fluorine, chlorine, bromine, cyano or nitro); or $C_1-C_6$alkoxy-$C(O)$—$CH_2$—, $C_1-C_6$alkoxy-$C(O)$—CH=CH—, $C_2-C_7$alken-1-yl-$CH_2$—, $C_2-C_7$alken-1-yl-$CH(C_1-C_2$alkyl)-, $C_2-C_4$fluoroalken-1-yl-$CH_2$—, $C_2-C_7$alkyn-1-yl-$CH_2$—, or $C_2-C_7$alkyn-1-yl-$CH(C_1-C_2$alkyl)-;

wherein $X^a$, $X^b$, $X^c$, $X^d$, $X^e$ and $X^f$ are independently of each other oxygen or sulfur (in particular oxygen); and wherein $R^a$ is H, $C_1-C_{21}$alkyl, $C_2-C_{21}$alkenyl, $C_2-C_{18}$alkynyl, $C_1-C_{10}$fluoroalkyl, $C_1-C_{10}$cyanoalkyl, $C_1-C_{10}$nitroalkyl, $C_1-C_{10}$aminoalkyl, $C_1-C_5$alkylamino($C_1-C_5$)alkyl, $C_2-C_8$dialkylamino($C_1-C_5$)alkyl, $C_3-C_7$cycloalkyl($C_1-C_5$)alkyl, $C_1-C_5$alkoxy($C_1-C_5$)alkyl, $C_3-C_5$alkenyloxy($C_1-C_5$)alkyl, $C_3-C_5$alkynyloxy($C_1-C_5$)alkyl, $C_1-C_5$alkylthio($C_1-C_5$)alkyl, $C_1-C_5$alkylsulfinyl($C_1-C_5$)alkyl, $C_1-C_5$alkylsulfonyl($C_1-C_5$)alkyl, $C_2-C_8$alkylideneaminoxy($C_1-C_5$)alkyl, $C_1-C_5$alkylcarbonyl($C_1-C_5$)alkyl, $C_1-C_5$alkoxycarbonyl($C_1-C_5$)alkyl, aminocarbonyl($C_1-C_5$)alkyl, $C_1-C_5$alkylaminocarbonyl($C_1-C_5$)alkyl, $C_2-C_8$dialkylaminocarbonyl($C_1-C_5$)alkyl, $C_1-C_5$alkylcarbonylamino($C_1-C_5$)alkyl, N—($C_1-C_5$)alkylcarbonyl-N—($C_1-C_5$)alkylamino($C_1-C_5$)alkyl, $C_3-C_6$trialkylsilyl($C_1-C_5$)alkyl, phenyl($C_1-C_5$)alkyl (wherein the phenyl is optionally substituted by 1, 2 or 3 of, independently, $C_1-C_3$alkyl, $C_1-C_3$fluoroalkyl, $C_1-C_3$alkoxy, $C_1-C_3$fluoroalkoxy, $C_1-C_3$alkylthio, $C_1-C_3$alkylsulfinyl, $C_1-C_3$alkylsulfonyl, halogen, cyano, or nitro), heteroaryl($C_1-C_5$)alkyl (wherein the heteroaryl is optionally substituted by 1, 2 or 3 of, independently, $C_1-C_3$alkyl, $C_1-C_3$fluoroalkyl, $C_1-C_3$alkoxy, $C_1-C_3$fluoroalkoxy, $C_1-C_3$alkylthio, $C_1-C_3$alkylsulfinyl, $C_1-C_3$alkylsulfonyl, halogen, cyano, or nitro), $C_2-C_5$fluoroalkenyl, $C_3-C_8$cycloalkyl; phenyl or phenyl substituted by 1, 2 or 3 of, independently, $C_1-C_3$alkyl, $C_1-C_3$fluoroalkyl, $C_1-C_3$alkoxy, $C_1-C_3$fluoroalkoxy, halogen, cyano or nitro; or heteroaryl or heteroaryl substituted by 1, 2 or 3 of, independently, $C_1-C_3$ alkyl, $C_1-C_3$fluoroalkyl, $C_1-C_3$alkoxy, $C_1-C_3$fluoroalkoxy, halogen, cyano or nitro;

$R^b$ is $C_1-C_{18}$alkyl, $C_3-C_{18}$alkenyl, $C_3-C_{18}$alkynyl, $C_2-C_{10}$fluoroalkyl, $C_1-C_{10}$cyanoalkyl, $C_1-C_{10}$nitroalkyl, $C_2-C_{10}$aminoalkyl, $C_1-C_5$alkylamino($C_1-C_5$)alkyl, $C_2-C_8$dialkylamino($C_1-C_5$)alkyl, $C_3-C_7$cycloalkyl($C_1-C_5$) alkyl, $C_1-C_5$alkoxy($C_1-C_5$)alkyl, $C_3-C_5$alkenyloxy($C_1-C_5$) alkyl, $C_3-C_5$alkynyloxy($C_1-C_5$)alkyl, $C_1-C_5$alkylthio($C_1-C_5$)alkyl, $C_1-C_5$alkylsulfinyl($C_1-C_5$)alkyl, $C_1-C_5$alkylsulfonyl($C_1-C_5$)alkyl, $C_2-C_8$alkylideneaminoxy($C_1-C_5$)alkyl, $C_1-C_5$alkylcarbonyl($C_1-C_5$)alkyl, $C_1-C_5$alkoxycarbonyl($C_1-C_5$)alkyl, aminocarbonyl($C_1-C_5$) alkyl, $C_1-C_5$alkylaminocarbonyl($C_1-C_5$)alkyl, $C_2-C_8$dialkylaminocarbonyl($C_1-C_5$)alkyl, $C_1-C_5$alkylcarbonylamino($C_1-C_5$)alkyl, N—($C_1-C_5$)alkylcarbonyl-N—($C_1-C_5$)alkylamino($C_1-C_5$)alkyl, $C_3-C_6$trialkylsilyl($C_1-C_5$)alkyl, phenyl($C_1-C_5$)alkyl (wherein the phenyl is optionally substituted by 1, 2 or 3 of, independently, $C_1-C_3$alkyl, $C_1-C_3$fluoroalkyl, $C_1-C_3$alkoxy, $C_1-C_3$fluoroalkoxy, $C_1-C_3$alkylthio, $C_1-C_3$alkylsulfinyl, $C_1-C_3$alkylsulfonyl, halogen, cyano, or nitro), heteroaryl$C_1-C_5$alkyl (wherein the heteroaryl is optionally substituted by 1, 2 or 3 of, independently, $C_1-C_3$alkyl, $C_1-C_3$fluoroalkyl, $C_1-C_3$alkoxy, $C_1-C_3$fluoroalkoxy, $C_1-C_3$alkyl-thio, $C_1-C_3$alkylsulfinyl, $C_1-C_3$alkylsulfonyl, halogen, cyano, or nitro), $C_3-C_5$fluoroalkenyl, $C_3-C_8$cycloalkyl; phenyl or phenyl substituted by 1, 2 or 3 of, independently, $C_1-C_3$alkyl, $C_1-C_3$fluoroalkyl, $C_1-C_3$alkoxy, $C_1-C_3$fluoroalkoxy, halogen, cyano or nitro; or heteroaryl or heteroaryl substituted by 1, 2 or 3 of, independently, $C_1-C_3$ alkyl, $C_1-C_3$fluoroalkyl, $C_1-C_3$alkoxy, $C_1-C_3$fluoroalkoxy, halogen, cyano or nitro; and $R^c$ and $R^d$ are each independently of each other hydrogen, $C_1-C_{10}$alkyl, $C_3-C_{10}$alkenyl, $C_3-C_{10}$alkynyl, $C_2-C_{10}$fluoroalkyl, $C_1-C_{10}$cyanoalkyl, $C_1-C_{10}$nitroalkyl, $C_1-C_{10}$aminoalkyl, $C_1-C_5$alkylamino($C_1-C_5$)alkyl, $C_2-C_8$dialkylamino($C_1-C_5$)alkyl, $C_3-C_7$cycloalkyl($C_1-C_5$) alkyl, $C_1-C_5$alkoxy($C_1-C_5$)alkyl, $C_3-C_5$alkenyloxy($C_1-C_5$) alkyl, $C_3-C_5$alkynyloxy($C_1-C_5$)alkyl, $C_1-C_5$alkylthio($C_1-C_5$)alkyl, $C_1-C_5$alkylsulfinyl($C_1-C_5$)alkyl, $C_1-C_5$alkylsulfonyl($C_1-C_5$)alkyl, $C_2-C_8$alkylideneaminoxy($C_1-C_5$)alkyl, $C_1-C_5$alkylcarbonyl($C_1-C_5$)alkyl, $C_1-C_5$alkoxycarbonyl($C_1-C_5$)alkyl, aminocarbonyl($C_1-C_5$) alkyl, $C_1-C_5$alkylaminocarbonyl($C_1-C_5$)alkyl, $C_2-C_8$dialkylaminocarbonyl($C_1-C_5$)alkyl, $C_1-C_5$alkylcarbonylamino($C_1-C_5$)alkyl, N—($C_1-C_5$)alkylcarbonyl-N—($C_2-C_5$)alkylaminoalkyl, $C_3-C_6$trialkylsilyl($C_1-C_5$)alkyl, phenyl($C_1-C_5$)alkyl (wherein the phenyl is optionally substituted by 1, 2 or 3 of, independently, $C_1-C_3$alkyl, $C_1-C_3$fluoroalkyl, $C_1-C_3$alkoxy, $C_1-C_3$fluoroalkoxy, $C_1-C_3$alkylthio, $C_1-C_3$alkylsulfinyl, $C_1-C_3$alkylsulfonyl, halogen, cyano, or nitro), heteroaryl($C_1-C_5$)alkyl (wherein the heteroaryl is optionally substituted by 1, 2 or 3 of, independently, $C_1-C_3$alkyl, $C_1-C_3$fluoroalkyl, $C_1-C_3$alkoxy, $C_1-C_3$fluoroalkoxy, $C_1-C_3$alkylthio, $C_1-C_3$alkylsulfinyl, $C_1-C_3$alkylsulfonyl, halogen, cyano, or nitro), $C_2-C_5$fluoroalkenyl, $C_3-C_8$cycloalkyl; phenyl or phenyl substituted by 1, 2 or 3 of, independently, $C_1-C_3$alkyl, $C_1-C_3$fluoroalkyl, $C_1-C_3$alkoxy, $C_1-C_3$fluoroalkoxy, halogen, cyano or nitro; heteroaryl or heteroaryl substituted by 1, 2 or 3 of, independently, $C_1-C_3$alkyl, $C_1-C_3$fluoroalkyl, $C_1-C_3$alkoxy, $C_1-C_3$fluoroalkoxy, halogen, cyano or nitro; heteroarylamino or heteroarylamino substituted by 1, 2 or 3 of, independently, $C_1-C_3$alkyl, $C_1-C_3$fluoroalkyl, $C_1-C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or by nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino or $C_3$-$C_7$cycloalkoxy;

or $R^c$ and $R^d$, together with the nitrogen to which they are bonded, to form an unsubstituted 4, 5, 6 or 7 (e.g. 5 or 6) membered ring, optionally containing one heteroatom selected from O or S; and $R^e$ is $C_1$-$C_{10}$alkyl, $C_2$-$C_{10}$alkenyl, $C_2$-$C_{10}$alkynyl, $C_1$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$) alkyl, $C_1$-$C_5$alkoxy($C_1$-$C_5$)alkyl, $C_3$-$C_5$alkenyloxy($C_1$-$C_5$) alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy ($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$) alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl ($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino, $C_3$-$C_7$cycloalkoxy, $C_1$-$C_{10}$alkoxy, $C_1$-$C_{10}$fluoroalkoxy, $C_1$-$C_5$alkylamino or di($C_1$-$C_4$alkyl)amino;

$R^f$ and $R^g$ are are each independently of each other $C_1$-$C_{10}$alkyl, $C_2$-$C_{10}$alkenyl, $C_2$-$C_{10}$alkynyl, $C_1$-$C_{10}$nitroalkyl, $C_1$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$) alkyl, $C_1$-$C_5$alkoxy($C_1$-$C_5$)alkyl, $C_3$-$C_5$alkenyloxy($C_1$-$C_5$) alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy ($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$) alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$trialkylsilyl ($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl ($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino, $C_3$-$C_7$cycloalkoxy, $C_1$-$C_{10}$fluoroalkoxy, $C_1$-$C_5$alkylamino or di($C_1$-$C_4$alkyl)amino; or benzyloxy or phenoxy, wherein the benzyl and phenyl groups are in turn optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; and $R^h$ is $C_1$-$C_{10}$alkyl, $C_3$-$C_{10}$alkenyl, $C_3$-$C_{10}$alkynyl, $C_1$-$C_{10}$fluoroalkyl, $C_1$-$C_{10}$cyanoalkyl, $C_1$-$C_{10}$nitroalkyl, $C_2$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$) alkyl, $C_1$-$C_5$alkoxy($C_1$-$C_5$)alkyl, $C_3$-$C_5$alkenyloxy($C_1$-$C_5$) alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy ($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$) alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), heteroaryl ($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), phenoxy($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), heteroaryloxy ($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), $C_3$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; $C_1$-$C_6$alkyl-C(O)—; or phenyl-C(O)— wherein the phenyl is optionally substituted by 1 or 2 of, independently, $C_1$-$C_2$alkyl, $C_1$fluoroalkyl, $C_1$-$C_2$alkoxy, $C_1$fluoroalkoxy, fluorine, chlorine, bromine, cyano or nitro;

wherein "heteroaryl" means an aromatic ring system containing at least one ring heteroatom and consisting either of a single ring or of two fused rings;

and wherein the compound of formula (I) is optionally present (e.g. where chemically possible) as an agrochemically acceptable salt thereof.

In the substituent definitions of the compounds of the formula I, each alkyl moiety either alone or as part of a larger group (such as alkoxy, alkylthio, alkoxycarbonyl, alkylcarbonyl, alkylaminocarbonyl, or dialkylaminocarbonyl, et al.) can be straight-chained or branched. Typically, the alkyl is, for example, methyl, ethyl, n-propyl, isopropyl, n-butyl, sec-butyl, isobutyl, tert-butyl, n-pentyl, neopentyl, or n-hexyl. The alkyl groups can e.g. be $C_1$-$C_6$alkyl groups (except where already defined more narrowly), but are preferably $C_1$-$C_4$alkyl or $C_1$-$C_3$alkyl groups (except where already defined more narrowly), and, more preferably, are $C_1$-$C_2$alkyl groups such as methyl.

Alkenyl and alkynyl moieties can be in the form of straight or branched chains, and the alkenyl moieties, where appropriate, can be of either the (E)- or (Z)-configuration. The alkenyl or alkynyl are typically $C_2$-$C_3$alkenyl or $C_2$-$C_3$alkynyl such as vinyl, allyl, ethynyl, propargyl or prop-1-ynyl. Alkenyl and alkynyl moieties can contain one or more double and/or triple bonds in any combination; but preferably contain only one double bond (for alkenyl) or only one triple bond (for alkynyl).

Halogen is fluorine, chlorine, bromine or iodine. Preferred halogens are fluorine, chlorine or bromine.

Fluoroalkyl groups are alkyl groups which are substituted with one or more (e.g. 1, 2, 3, 4 or 5; in particular 1, 2 or 3; e.g. 1 or 2) fluorine atoms. Fluoroalkyl is typically $C_1$-$C_3$fluoroalkyl or $C_1$-$C_2$fluoroalkyl (preferably $C_1$fluoroalkyl), such as $CF_3$, $CHF_2$, $CH_2F$, $CH_3CHF$—, $CF_3CH_2$—, $CHF_2CH_2$—, $CH_2FCH_2$—, $CHF_2CF_2$— or $(CH_3)_2CF$—. Fluoroalkoxy is typically $C_1$-$C_3$fluoroalkoxy or $C_1$-$C_2$fluoroalkoxy (preferably $C_1$fluoroalkoxy), such as $CF_3O$, $CHF_2O$, $CH_2FO$, $CH_3CHFO$—, $CF_3CH_2O$—, $CHF_2CH_2O$— or $CH_2FCH_2O$—.

In the context of the present specification the term "aryl" means phenyl or naphthyl. A preferred aryl group is phenyl.

The term "heteroaryl" as used herein means an aromatic ring system containing at least one ring heteroatom and consisting either of a single ring or of two fused rings. Preferably, single rings will contain 1, 2 or 3 ring heteroatoms and bicyclic systems 1, 2, 3 or 4 ring heteroatoms which will preferably be selected from nitrogen, oxygen and sulfur. Typically, a "heteroaryl" is furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl or indolizinyl; optionally present, where chemically possible, as an agrochemically acceptable salt thereof.

The term "heterocyclyl" as used herein, except where explicitly stated otherwise, means a 4, 5, 6 or 7 (in particular 5, 6 or 7) membered monocyclic organic ring or a 8, 9, 10 or 11 (in particular 8, 9 or 10) membered fused bicyclic organic ring system, which is fully saturated, and which has one or two (preferably one) ring heteroatoms independently selected from oxygen, sulfur and nitrogen. Where the heterocyclyl has two ring heteroatoms, preferably, the two ring heteroatoms are separated by at least two ring carbon atoms. Preferably, the heterocyclyl is attached at a ring carbon atom within the heterocyclyl. In particular, the heterocyclyl can be tetrahydrofuranyl, tetrahydropyranyl, tetrahydrothiophenyl, 1,4-dioxanyl, 1,4-dithianyl, morpholinyl, thiomorpholinyl, pyrrolidinyl, piperidinyl or piperazinyl; more particularly tetrahydrofuranyl (e.g. tetrahydrofuran-2-yl or particularly tetrahydrofuran-3-yl), tetrahydropyranyl (e.g. tetrahydropyran-2-yl, tetrahydropyran-3-yl or particularly tetrahydropyran-4-yl), morpholinyl, pyrrolidinyl (e.g. pyrrolidin-2-yl or particularly pyrrolidin-3-yl), piperidinyl (e.g. piperidin-2-yl, piperidin-3-yl or particularly piperidin-4-yl) or piperazinyl. In a particular embodiment, the heterocyclyl, when optionally substituted, is optionally substituted by 1 or 2 (e.g. 1) ring-carbon substituents independently being $C_1$-$C_3$alkyl (e.g. $C_1$-$C_2$alkyl), $C_1$-$C_2$fluoroalkyl or oxo (=O), and/or is optionally substituted by one $C_1$-$C_3$alkyl (e.g. $C_1$-$C_2$alkyl), $C_1$-$C_2$fluoroalkyl or $C_1$-$C_3$alkoxy (e.g. $C_1$-$C_2$alkyl or $C_1$-$C_2$fluoroalkyl) substituent on a ring nitrogen if present, and/or is optionally substituted by one or two oxo (=O) substituents on a ring sulfur if present.

Preferably, a cycloalkyl is cyclopropyl, cyclobutyl, cyclopentyl or cyclohexyl. (Cycloalkyl)alkyl is preferably (cycloalkyl)methyl such as ($C_3$-$C_6$cycloalkyl)methyl in particular cyclopropylmethyl. Preferably, cycloalkenyl is cyclopentenyl or cyclohexenyl.

The invention relates also to the agriculturally acceptable salts which the compounds of formula I are able to form with transition metal, alkali metal and alkaline earth metal bases, amines, quaternary ammonium bases or tertiary sulfonium bases.

Among the transition metal, alkali metal and alkaline earth metal salt formers, special mention should be made of the hydroxides of copper, iron, lithium, sodium, potassium, magnesium and calcium, and preferably the hydroxides, bicarbonates and carbonates of sodium and potassium. Accordingly, in one particular embodiment of the invention, G is an agriculturally acceptable metal such as copper, iron, lithium, sodium, potassium, magnesium or calcium (more particularly an agriculturally acceptable alkali metal or alkaline earth metal).

Examples of amines suitable for ammonium salt formation include ammonia as well as primary, secondary and tertiary $C_1$-$C_{18}$alkylamines, $C_1$-$C_4$hydroxyalkylamines and $C_2$-$C_4$alkoxyalkyl-amines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, di-isopropylamine, di-n-butylamine, di-n-amylamine, di-isoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-but-2-enylamine, n-pent-2-enylamine, 2,3-dimethylbut-2-enylamine, dibut-2-enylamine, n-hex-2-enylamine, propylenediamine, trimethylamine, triethylamine, tri-n-propylamine, tri-isopropylamine, tri-n-butylamine, tri-isobutylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary arylamines, for example anilines, methoxyanilines, ethoxyanilines, o-, m- and p-toluidines, phenylenediamines, benzidines, naphthylamines and o-, m- and p-chloroanilines; but especially triethylamine, isopropylamine and di-isopropylamine. Accordingly, in one particular embodiment of the invention, G is an agriculturally acceptable ammonium group, wherein the compound of formula (I) is an ammonium salt formed from: ammonia, a primary, secondary or tertiary $C_1$-$C_{18}$alkylamine, a $C_1$-$C_4$hydroxyalkylamine, or a $C_2$-$C_4$alkoxyalkyl-amine.

Preferred quaternary ammonium bases suitable for salt formation correspond, for example, to the formula $[N(R^{aa}R^{bb}R^{cc}R^{dd})]OH$, wherein $R^{aa}$, $R^{bb}$, $R^{cc}$ and $R^{dd}$ are each independently of the others hydrogen or $C_1$-$C_4$alkyl. Further suitable tetraalkylammonium bases with other anions can be obtained, for example, by anion exchange reactions. Accordingly, in one particular embodiment of the invention, G is an agriculturally acceptable ammonium group, wherein the compound of formula (I) is a salt formed from a quaternary ammonium base of formula $[N(R^{aa}R^{bb}R^{cc}R^{dd})]OH$, wherein $R^{aa}$, $R^{bb}$, $R^{cc}$ and $R^{dd}$ are each independently of the others hydrogen or $C_1$-$C_4$alkyl.

Preferred tertiary sulfonium bases suitable for salt formation correspond, for example, to the formula $[SR^{ee}R^{ff}R^{gg}]OH$, wherein $R^{ee}$, $R^{ff}$ and $R^{gg}$ are each independently of the others $C_1$-$C_4$ alkyl. Trimethylsulfonium hydroxide is especially preferred. Suitable sulfonium bases may be obtained from the reaction of thioethers, in particular dialkylsulfides, with alkylhalides, followed by conversion to a suitable base, for example a hydroxide, by anion exchange reactions. Accordingly, in one particular embodiment of the invention, G is an agriculturally acceptable sulfonium group, wherein the compound of formula (I) is a salt formed from a tertiary sulfonium base of formula $[SR^{ee}R^{ff}R^{gg}]OH$, wherein $R^{ee}$, $R^{ff}$ and $R^{gg}$ are each independently of the others $C_1$-$C_4$ alkyl.

It should be understood that in those compounds of formula I, where G is a metal, ammonium group or sulfonium group as mentioned above, and as such represents a cation, the corresponding negative charge is largely delocalised across the O—C=C—C=O unit within formula (I).

The compounds of formula I according to the invention also include hydrates which may be formed during the salt formation.

When G is —C($X^a$)—$R^a$, —C($X^b$)—$X^c$—$R^b$, —C($X^d$)—N($R^c$)—$R^d$, —$SO_2$—$R^e$, —P($X^e$)($R^f$)—$R^g$, —$CH_2$—$X^f$—$R^h$; or phenyl-$CH_2$— or phenyl-CH($C_1$-$C_2$alkyl)- (in each of which the phenyl is optionally substituted), or heteroaryl-$CH_2$— or heteroaryl-CH($C_1$-$C_2$alkyl)- (in each of which the heteroaryl is optionally substituted), or phenyl-C(O)—$CH_2$— (wherein the phenyl is optionally substituted); or $C_1$-$C_6$alkoxy-C(O)—$CH_2$—, $C_1$-$C_6$alkoxy-C(O)—CH=CH—, $C_2$-$C_7$alken-1-yl-$CH_2$—, $C_2$-$C_7$alken-1-yl-CH($C_1$-$C_2$alkyl)-, $C_2$-$C_4$fluoroalken-1-yl-$CH_2$—, $C_2$-$C_7$alkyn-1-yl-$CH_2$—, or $C_2$-$C_7$alkyn-1-yl-CH($C_1$-$C_2$alkyl)-; generally these G groups are latentiating groups (i.e. leaving or removeable groups), which are generally selected to allow their removal, typically by one or a combination of biochemical, chemical or physical processes, to afford the corresponding compound of formula (I) where G is H, before, during or following (preferably during or following, more preferably following) application of the compound of formula (I) to the treated area (e.g. field) or to plants. Examples of these processes include enzymatic cleavage or other in/on-plant cleavage (e.g. cleavage of ester and/or carbonate moieties), chemical hydrolysis, and/or photoloysis. Some compounds bearing such groups G occasionally offer certain advantages or different technical properties, such as improved and/or more consistent and/or different penetration of the cuticula of the plants treated, increased and/or different tolerance of certain crops, improved and/or different compatibility or stability in formulated mixtures containing other herbicides, herbicide safeners, plant growth regulators, fungicides or insecticides, or reduced and/or different leaching properties in soils.

The preferred, suitable and/or particular values of the substituents in or other features of the compound of formula (I), in particular G, X, $R^1$, $R^2$, $R^{2A}$, $R^{2B}$, $R^{2C}$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^a$, $R^b$, $R^c$, $R^d$, $R^e$, $R^f$, $R^g$, $R^h$, $X^a$, $X^b$, $X^c$, $X^d$, $X^e$, $X^f$, Q, Het, $X^1$, n1, n2 and/or n3, are set out below (and/or generally herein), and can be either taken alone or taken together with one or more of any other preferred, suitable and/or particular features in any combination(s) thereof. In this paragraph, "preferred" is intended to encompass more preferred, even or still or yet more preferred, particularly or highly preferred, most preferred and all similar terms.

In a particular embodiment, G is hydrogen; an agriculturally acceptable metal (e.g. an agriculturally acceptable alkali metal or alkaline earth metal, e.g. lithium, sodium, potassium, magnesium or calcium), or an agriculturally acceptable sulfonium or ammonium group; or G is —C($X^a$)—$R^a$, —C($X^b$)—$X^c$—$R^b$ or —$SO_2$—$R^e$, wherein $X^a$, $R^a$, $X^b$, $X^c$, $R^b$ and $R^e$ are as defined herein.

In one preferred embodiment, G is hydrogen; an agriculturally acceptable metal (e.g. an agriculturally acceptable alkali metal or alkaline earth metal, e.g. lithium, sodium, potassium, magnesium or calcium), or an agriculturally acceptable sulfonium or ammonium group; or G is —C($X^a$)—$R^a$ or —C($X^b$)—$X^c$—$R^b$, wherein $X^a$, $R^a$, $X^b$, $X^c$ and $R^b$ are as defined herein.

In a particular embodiment, G is a group —C($X^a$)—$R^a$ or —C($X^b$)—$X^c$—$R^b$, wherein $X^a$, $R^a$, $X^b$, $X^c$ and $R^b$ are as defined herein.

Preferably, $X^a$, $X^b$, $X^c$, $X^d$, $X^e$ and/or $X^f$ are oxygen. Alternatively, preferably, $X^c$ is sulfur.

More preferably, $X^a$, $X^b$, $X^c$, $X^d$, $X^e$ and $X^f$ are oxygen.

Preferably, $R^a$ is $C_1$-$C_{10}$alkyl (e.g. $C_1$-$C_6$alkyl), $C_2$-$C_6$alkenyl (e.g. $C_2$-$C_4$alkenyl), $C_2$-$C_6$alkynyl (e.g. $C_2$-$C_4$alkynyl), $C_3$-$C_6$cycloalkyl or $C_1$-$C_4$alkoxy$C_1$-$C_4$alkyl.

Alternatively, preferably, $R^a$ is $C_3$-$C_7$cycloalkyl($C_1$-$C_5$)alkyl, or phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro.

Preferably, $R^b$ is $C_1$-$C_{10}$alkyl (e.g. $C_1$-$C_6$alkyl), $C_2$-$C_5$alkenyl-$CH_2$— (e.g. $C_2$-$C_3$alkenyl-$CH_2$—), $C_2$-$C_4$alkenyl-CH(Me)- (e.g. $C_2$-$C_3$alkenyl-CH(Me)-), $C_2$-$C_5$alkynyl-$CH_2$—(e.g. $C_2$-$C_3$alkynyl-$CH_2$—), $C_2$-$C_4$alkynyl-CH(Me)- (e.g. $C_2$-$C_3$alkynyl-CH(Me)-), $C_3$-$C_6$cycloalkyl or $C_1$-$C_4$alkoxy$C_1$-$C_4$alkyl. Alternatively, preferably, $R^b$ is $C_3$-$C_7$cycloalkyl($C_1$-$C_5$)alkyl, or phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro.

Preferably, $R^e$ is $C_1$-$C_{10}$alkyl (e.g. $C_1$-$C_6$alkyl or $C_1$-$C_4$alkyl) or $C_1$-$C_{10}$fluoroalkyl (e.g. $C_1$-$C_3$fluoroalkyl). In particular, $R^e$ is $C_1$-$C_{10}$alkyl (e.g. $C_1$-$C_6$alkyl or $C_1$-$C_4$alkyl).

When G is —$C(X^a)$—$R^a$ or —$C(X^b)$—$X^c$—$R^b$, then preferably $X^a$, $X^b$ and $X^c$ are oxygen, $R^a$ is $C_1$-$C_{10}$alkyl (e.g. $C_1$-$C_6$alkyl), $C_2$-$C_6$alkenyl (e.g. $C_2$-$C_4$alkenyl), $C_2$-$C_6$alkynyl (e.g. $C_2$-$C_4$alkynyl), $C_3$-$C_6$cycloalkyl or $C_1$-$C_4$alkoxy$C_1$-$C_4$alkyl; and $R^b$ is $C_1$-$C_{10}$alkyl (e.g. $C_1$-$C_6$alkyl), $C_2$-$C_5$alkenyl-$CH_2$— (e.g. $C_2$-$C_3$alkenyl-$CH_2$—), $C_2$-$C_4$alkenyl-CH(Me)- (e.g. $C_2$-$C_3$alkenyl-CH(Me)-), $C_2$-$C_5$alkynyl-$CH_2$—(e.g. $C_2$-$C_3$alkynyl-$CH_2$—), $C_2$-$C_4$alkynyl-CH(Me)- (e.g. $C_2$-$C_3$alkynyl-CH(Me)-), $C_3$-$C_6$cycloalkyl or $C_1$-$C_4$alkoxy$C_1$-$C_4$alkyl.

In a preferable embodiment, G is hydrogen, or an agriculturally acceptable alkali metal or alkaline earth metal, or an agriculturally acceptable sulfonium or ammonium group. More preferably, G is hydrogen, or an agriculturally acceptable alkali metal or alkaline earth metal.

In a preferable embodiment, G is hydrogen, —$C(X^a)$—$R^a$ or —$C(X^b)$—$X^c$—$R^b$.

Most preferably G is hydrogen.

In one particular embodiment of the invention, X is chlorine.

However, in the present invention, most preferably, X is methyl.

In one preferable embodiment of the invention, $R^1$ is chlorine.

However, in the present invention, most preferably, $R^1$ is methyl.

Therefore, e.g. in all aspects and/or embodiments of the invention, most preferably, X is methyl, and $R^1$ is methyl.

In an alternative, also highly preferable, embodiment of the invention (which e.g. can apply to all aspects and/or embodiments of the invention), X is methyl, and $R^1$ is chlorine.

In another alternative preferable embodiment of the invention (which e.g. can apply to all aspects and/or embodiments of the invention), X is chlorine, and $R^1$ is methyl.

In an alternative particular embodiment of the invention (which e.g. can apply to all aspects and/or embodiments of the invention), X is chlorine, and $R^1$ is chlorine.

In the invention, $R^2$ is hydrogen, methyl, ethyl, n-propyl, cyclopropyl, vinyl, ethynyl, fluorine, chlorine, bromine, $C_1$-$C_3$alkoxy (e.g. methoxy, ethoxy, n-propoxy or iso-propoxy), $C_1$-$C_2$fluoroalkoxy (e.g. $C_1$fluoroalkoxy such as difluoromethoxy or trifluoromethoxy; or e.g. $CF_3CH_2O$—), $C_1$-$C_2$alkoxy-$C_1$-$C_3$alkoxy-, or $C_1$fluoroalkoxy-$C_1$-$C_3$alkoxy-.

Preferably, when $R^2$ is $C_1$-$C_2$alkoxy-$C_1$-$C_3$alkoxy- or $C_1$fluoroalkoxy-$C_1$-$C_3$alkoxy-, then $R^2$ is $R^{2A}O$—CH($R^{2B}$)—CH($R^{2C}$)—O—;
wherein $R^{2A}$ is $C_1$-$C_2$alkyl (in particular methyl) or $C_1$fluoroalkyl; and $R^{2B}$ and $R^{2C}$ are independently hydrogen or methyl, provided that one or both of $R^{2B}$ and $R^{2C}$ are hydrogen.

Preferably, $R^{2A}$ is methyl or $C_1$fluoroalkyl, more preferably methyl.

Preferably, both of $R^{2B}$ and $R^{2C}$ are hydrogen.

More preferably, when $R^2$ is $C_1$-$C_2$alkoxy-$C_1$-$C_3$alkoxy- or $C_1$fluoroalkoxy-$C_1$-$C_3$alkoxy- (in particular when $R^2$ is $R^{2A}O$—CH($R^{2B}$)—CH($R^{2C}$)—O—), then $R^2$ is MeO—$CH_2$—$CH_2$—O—.

Preferably, e.g. in all aspects and/or embodiments of the invention, $R^2$ is hydrogen, methyl, ethyl, n-propyl, cyclopropyl, vinyl, ethynyl, fluorine, chlorine, bromine, methoxy, ethoxy or fluoromethoxy (i.e. $C_1$fluoroalkoxy). Alternatively, preferably, $R^2$ is MeO—$CH_2$—$CH_2$—O—.

Preferably, e.g. in all aspects and/or embodiments of the invention, $R^2$ is methyl, ethyl, n-propyl, cyclopropyl, vinyl, ethynyl, fluorine, chlorine, bromine, methoxy, ethoxy or fluoromethoxy (i.e. $C_1$fluoroalkoxy). Alternatively, preferably, $R^2$ is MeO—$CH_2$—$CH_2$—O—.

Alternatively or additionally, preferably, e.g. in all aspects and/or embodiments of the invention, $R^2$ is hydrogen, methyl, ethyl, ethynyl, chlorine, methoxy or fluoromethoxy (i.e. $C_1$fluoroalkoxy, e.g. monofluoromethoxy, difluoromethoxy or trifluoromethoxy). Alternatively, preferably, $R^2$ is ethoxy or MeO—$CH_2$—$CH_2$—O—.

More preferably, e.g. in all aspects and/or embodiments of the invention, $R^2$ is not hydrogen.

More preferably, e.g. in all aspects and/or embodiments of the invention, $R^2$ is methyl, ethyl, ethynyl, chlorine, methoxy or fluoromethoxy (i.e. $C_1$fluoroalkoxy, e.g. monofluoromethoxy, difluoromethoxy or trifluoromethoxy). Alternatively, more preferably, $R^2$ is ethoxy or MeO—$CH_2$—$CH_2$—O—, preferably ethoxy.

Even more preferably, e.g. in all aspects and/or embodiments of the invention, $R^2$ is methyl, ethynyl, chlorine or methoxy. Alternatively, even more preferably, $R^2$ is ethoxy.

Still more preferably, e.g. in all aspects and/or embodiments of the invention, $R^2$ is methyl, chlorine or methoxy. Alternatively, still more preferably, $R^2$ is ethoxy.

Yet more preferably, e.g. in all aspects and/or embodiments of the invention, $R^2$ is methyl or methoxy.

Most preferably, e.g. in all aspects and/or embodiments of the invention, $R^2$ is methyl.

Therefore, more preferably, e.g. in all aspects and/or embodiments of the invention:
$R^1$ is methyl, and
$R^2$ is methyl, ethyl, ethynyl, chlorine, methoxy or fluoromethoxy; still more preferably methyl, chlorine or methoxy; yet more preferably methyl or methoxy; most preferably methyl.

In an alternative more preferable embodiment, e.g. in all aspects and/or embodiments of the invention:
$R^1$ is chlorine, and
$R^2$ is ethyl, ethynyl, chlorine, methoxy or fluoromethoxy; still more preferably chlorine or methoxy; most preferably methoxy.

In a further alternative more preferable embodiment, e.g. in all aspects and/or embodiments of the invention:
$R^1$ is chlorine, and
$R^2$ is ethoxy or MeO—$CH_2$—$CH_2$—O—, still more preferably ethoxy.

In a most preferable embodiment of the invention (which e.g. can apply to all aspects and/or embodiments of the invention), $R^1$ is methyl, $R^2$ is methyl, and X is methyl or chlorine (most preferably methyl).

In an alternative highly preferable embodiment of the invention (which e.g. can apply to all aspects and/or embodiments of the invention), $R^1$ is methyl, $R^2$ is chlorine, and X is methyl or chlorine (preferably methyl).

In an alternative preferable embodiment of the invention (which e.g. can apply to all aspects and/or embodiments of the invention), $R^1$ is methyl, $R^2$ is ethynyl, and X is methyl or chlorine (preferably methyl).

In an alternative preferable embodiment of the invention (which e.g. can apply to all aspects and/or embodiments of the invention), $R^1$ is methyl, $R^2$ is methoxy, and X is methyl or chlorine (preferably methyl).

In an alternative particular embodiment of the invention (which e.g. can apply to all aspects and/or embodiments of the invention), $R^1$ is methyl, $R^2$ is hydrogen, and X is methyl or chlorine (preferably methyl).

In an alternative very highly preferable embodiment of the invention (which e.g. can apply to all aspects and/or embodiments of the invention), $R^1$ is chlorine, $R^2$ is methoxy, and X is methyl or chlorine (preferably methyl).

In an alternative highly preferable embodiment of the invention (which e.g. can apply to all aspects and/or embodiments of the invention), $R^1$ is chlorine, $R^2$ is chlorine, and X is methyl or chlorine (preferably methyl).

In an alternative particular embodiment of the invention (which e.g. can apply to all aspects and/or embodiments of the invention), $R^1$ is chlorine, $R^2$ is hydrogen, and X is methyl or chlorine (preferably methyl).

In an alternative highly preferable embodiment of the invention (which e.g. can apply to all aspects and/or embodiments of the invention), $R^1$ is chlorine, $R^2$ is ethoxy, and X is methyl or chlorine (preferably methyl).

Preferably, e.g. in all aspects and/or embodiments of the invention, when $R^4$ and $R^5$ are taken together, then $R^4$ and $R^5$ taken together are —$(CH_2)_{n4}$— or —$(CH_2)_{n5}$—$C(R^{7a})(R^{7b})$—$(CH_2)_{n6}$—.

Preferably, $R^{7a}$ is $C_1$-$C_2$alkyl; and $R^{7b}$ is hydrogen or $C_1$-$C_2$alkyl.

Preferably, n4 is 2 or 3.

Preferably, n5 and n6 are independently 0, 1 or 2 provided that n5+n6 is 1 or 2.

Preferably, e.g. in all aspects and/or embodiments of the invention, when $R^4$ and $R^5$ are taken together (which is preferable), then $R^4$ and $R^5$ taken together are —$(CH_2)_{n4}$— or —$(CH_2)_{n5}$—$C(R^{7a})(R^{7b})$—$(CH_2)_{n6}$—;
wherein $R^{7a}$ is $C_1$-$C_2$alkyl; $R^{7b}$ is hydrogen or $C_1$-$C_2$alkyl; n4 is 1, 2 or 3 (preferably 2 or 3); and
n5 and n6 are independently 0, 1 or 2 provided that n5+n6 is 0, 1 or 2 (preferably 1 or 2).

Preferably, e.g. in all aspects and/or embodiments of the invention, $R^3$, $R^4$, $R^5$ and/or $R^6$, independently of each other, are hydrogen, $C_1$-$C_4$alkyl (e.g. $C_1$-$C_2$alkyl), $C_2$-$C_4$alkynyl (in particular $C_2$-$C_3$alkynyl-$CH_2$—, e.g. ethynyl-$CH_2$—), $C_1$-$C_3$alkoxy$C_1$-$C_3$alkyl, $C_1$-$C_3$alkylthio$C_1$-$C_3$alkyl, $C_1$-$C_3$alkylsulfinyl$C_1$-$C_3$alkyl, $C_1$-$C_3$alkylsulfonyl$C_1$-$C_3$alkyl; $C_3$-$C_4$cycloalkyl (in particular cyclopropyl); or an unsubstituted 4, 5 or 6 (e.g. 4 or 5) membered monocyclic heterocyclyl having one ring heteroatom independently selected from oxygen, sulfur and nitrogen, and attached at a ring carbon atom within the heterocyclyl (in particular tetrahydrofuranyl such as tetrahydrofuran-3-yl, or tetrahydropyranyl such as tetrahydropyran-4-yl);
provided that no more than one (in particular none) of $R^3$, $R^4$, $R^5$ and $R^6$ is alkenyl, alkynyl, alkoxyalkyl, alkylthioalkyl, alkylsulfinylalkyl, alkylsulfonylalkyl, cycloalkyl or heterocyclyl;
or $R^3$ and $R^4$ taken together are —$(CH_2)_{n1}$— or —$(CH_2)_{n2}$—X—$(CH_2)_{n3}$— and $R^5$ and $R^6$ are as defined herein (e.g. hereinabove), or $R^5$ and $R^6$ taken together are —$(CH_2)_{n1}$— or —$(CH_2)_{n2}$—X—$(CH_2)_{n3}$— and $R^3$ and $R^4$ are as defined herein (e.g. hereinabove);
wherein $X^1$ is O, S, S(O), S(O)$_2$, NH, N($C_1$-$C_2$alkyl), N($C_1$-$C_2$alkoxy), C(H)($C_1$-$C_2$alkyl), C($C_1$-$C_2$alkyl)$_2$ or C(H)($C_1$-$C_2$alkoxy);
n1 is 4 or 5; and
n2 and n3 are independently 1, 2 or 3 provided that n2+n3 is 3 or 4;
and/or $R^4$ and $R^5$ taken together are —$(CH_2)_{n4}$— or —$(CH_2)_{n5}$—$C(R^{7a})(R^{7b})$—$(CH_2)_{n6}$—;
wherein $R^{7a}$ is $C_1$-$C_2$alkyl; $R^{7b}$ is hydrogen or $C_1$-$C_2$alkyl; n4 is 1, 2 or 3 (in particular 2 or 3); and
n5 and n6 are independently 0, 1 or 2 provided that n5+n6 is 0, 1 or 2 (in particular 1 or 2).

More preferably, e.g. in all aspects and/or embodiments of the invention, $R^3$, $R^4$, $R^5$ and/or $R^6$, independently of each other, are hydrogen, $C_1$-$C_4$alkyl (e.g. $C_1$-$C_2$alkyl), $C_2$-$C_4$alkynyl (in particular $C_2$-$C_3$alkynyl-$CH_2$—, e.g. ethynyl-$CH_2$—), $C_1$-$C_3$alkoxy$C_1$-$C_3$alkyl (in particular $C_1$-$C_2$alkoxy$C_1$-$C_2$alkyl), $C_1$-$C_3$alkylthio$C_1$-$C_3$alkyl (in particular $C_1$-$C_2$alkylthio$C_1$-$C_2$alkyl), $C_1$-$C_3$alkylsulfinyl$C_1$-$C_3$alkyl (in particular $C_1$-$C_2$alkylsulfinyl$C_1$-$C_2$alkyl), $C_1$-$C_3$alkylsulfonyl$C_1$-$C_3$alkyl (in particular $C_1$-$C_2$alkylsulfonyl$C_1$-$C_2$alkyl); $C_3$-$C_4$cycloalkyl (in particular cyclopropyl); or an unsubstituted 4, 5 or 6 (e.g. 4 or 5) membered monocyclic heterocyclyl having one ring heteroatom independently selected from oxygen, sulfur and nitrogen, and attached at a ring carbon atom within the heterocyclyl (in particular tetrahydrofuranyl such as tetrahydrofuran-3-yl, or tetrahydropyranyl such as tetrahydropyran-4-yl);
provided that no more than one (in particular none) of $R^3$, $R^4$, $R^5$ and $R^6$ is alkenyl, alkynyl, alkoxyalkyl, alkylthioalkyl, alkylsulfinylalkyl, alkylsulfonylalkyl, cycloalkyl or heterocyclyl;
and/or $R^4$ and $R^5$ taken together are —$(CH_2)_{n4}$— or —$(CH_2)_{n5}$—$C(R^{7a})(R^{7b})$—$(CH_2)_{n6}$—; wherein $R^{7a}$ is $C_1$-$C_2$alkyl; $R^{7b}$ is hydrogen or $C_1$-$C_2$alkyl;
n4 is 2 or 3; and
n5 and n6 are independently 0, 1 or 2 provided that n5+n6 is 1 or 2.

Still more preferably, $R^3$, $R^4$, $R^5$ and/or $R^6$, independently of each other, are hydrogen, $C_1$-$C_3$alkyl (in particular $C_1$-$C_2$alkyl such as methyl) or $C_1$-$C_3$alkoxy$C_1$-$C_3$alkyl (in particular $C_1$-$C_2$alkoxy$C_1$-$C_2$alkyl); provided that no more than one (in particular none) of $R^3$, $R^4$, $R^5$ and $R^6$ is alkoxyalkyl;
and/or $R^4$ and $R^5$ taken together are —$(CH_2)_{n4}$— or —$(CH_2)_{n5}$—$C(R^{7a})(R^{7b})$—$(CH_2)_{n6}$—;
wherein $R^{7a}$ is $C_1$-$C_2$alkyl; $R^{7b}$ is hydrogen or $C_1$-$C_2$alkyl; n4 is 2 or 3; and
n5 and n6 are independently 0, 1 or 2 provided that n5+n6 is 1 or 2.

Even more preferably, $R^3$, $R^4$, $R^5$ and/or $R^6$, independently of each other, are hydrogen or $C_1$-$C_2$alkyl (preferably hydrogen or methyl); and/or $R^4$ and $R^5$ taken together are —$(CH_2)_{n4}$— wherein n4 is 2 or 3.

Most preferably (especially when Y is $CR^8R^9$ or —$CR^{10}R^{11}CR^{12}R^{13}$—), $R^3$, $R^4$, $R^5$ and $R^6$ are hydrogen; or $R^4$ and $R^5$ taken together are —$(CH_2)_{n4}$— wherein n4 is 2 or 3, and $R^3$ and $R^6$ are hydrogen.

Preferably, e.g. in all aspects and/or embodiments of the invention, at least one (more preferably 2, 3 or 4, still more preferably 3 or 4, most preferably all four) of $R^3$, $R^4$, $R^5$ and $R^6$, independently of each other, are hydrogen or $C_1$-$C_4$alkyl (e.g. H or $C_1$-$C_3$alkyl, or H or $C_1$-$C_2$alkyl);

or $R^4$ and $R^5$ are taken together as described herein.

Preferably, e.g. in all aspects and/or embodiments of the invention, Y is O, S, S(O), S(O)$_2$, C(O), $CR^8R^9$ or —$CR^{10}R^{11}CR^{12}R^{13}$—.

More preferably, Y is O, C(O), $CR^8R^9$ or —$CR^{10}R^{11}CR^{12}R^{13}$—.

Even more preferably, Y is O or $CR^8R^9$, in particular O or $CH_2$.

Most preferably, Y is $CR^8R^9$, in particular $CH_2$.

Preferably, e.g. in all aspects and/or embodiments of the invention, in $R^8$ and $R^9$, one or both of $R^8$ and $R^9$ is or are hydrogen; or $R^8$ and $R^9$ taken together are —$(CH_2)_{n7}$— or preferably —$(CH_2)_{n8}$—$X^2$—$(CH_2)_{n9}$—. In this embodiment, preferably Y is $CR^8R^9$ and/or preferably $X^2$ is O.

In one particular embodiment, $R^8$ and $R^9$ are taken together and are —$(CH_2)_{n7}$— or preferably —$(CH_2)_{n8}$—$X^2$—$(CH_2)_{n9}$—. In this embodiment, preferably Y is $CR^8R^9$ and/or preferably $X^2$ is O.

Preferably, e.g. in all aspects and/or embodiments of the invention, $X^2$ is O, S, S(O), S(O)$_2$, C(H)($C_1$-$C_3$alkyl), C($C_1$-$C_2$alkyl)$_2$ or C(H)($C_1$-$C_3$alkoxy). Most preferably, $X^2$ is O.

Preferably, n7 is 2, 3, 4 or 5, more preferably 4 or 5.

Preferably, n8 and n9 are independently 1, 2 or 3 provided that n8+n9 is 2, 3 or 4.

Preferably, n8+n9 is 3 or 4. Most preferably, n8 is 2 and n9 is 2 (in which case, preferably, $X^2$ is O).

Preferably, e.g. in all aspects and/or embodiments of the invention, $R^8$ and $R^9$ are, independently of each other:
hydrogen, $C_1$-$C_4$alkyl (in particular $C_1$-$C_2$alkyl), $C_2$-$C_3$alkenyl-$CH_2$— (in particular ethenyl-$CH_2$—), $C_2$-$C_3$alkynyl-$CH_2$— (in particular ethynyl-$CH_2$—), $C_1$-$C_2$fluoroalkyl (in particular $C_1$fluoroalkyl), $C_1$-$C_3$alkoxy$C_1$-$C_3$alkyl, $C_1$-$C_3$alkylthio$C_1$-$C_3$alkyl, $C_1$-$C_3$alkylsulfinyl$C_1$-$C_3$alkyl, or $C_1$-$C_3$alkylsulfonyl$C_1$-$C_3$alkyl;

$C_3$-$C_6$cycloalkyl or $C_3$-$C_6$cycloalkyl substituted by one or two substituents which independently are $C_1$-$C_3$alkyl (in particular methyl or ethyl) or $C_1$-$C_2$fluoroalkyl; and in which one ring $CH_2$ moiety of a $C_4$-$C_6$cycloalkyl is optionally (e.g. preferably) replaced by an oxygen or sulfur atom or by a S(O), S(O)$_2$, NH, N($C_1$-$C_3$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety;

$C_3$-$C_6$cycloalkyl substituted by one substituent being $C_1$-$C_3$alkoxy (in particular $C_1$-$C_2$alkoxy) and optionally further substituted by one substituent being $C_1$-$C_2$alkyl (in particular methyl);

$C_3$-$C_6$cycloalkyl$C_1$-$C_2$alkyl- (in particular $C_3$-$C_6$cycloalkylmethyl-) or $C_3$-$C_6$cycloalkyl$C_1$-$C_2$alkyl- (in particular $C_3$-$C_6$cycloalkylmethyl-) substituted by one or two ring substituents which independently are $C_1$-$C_3$alkyl or $C_1$-$C_2$fluoroalkyl; and in which one ring $CH_2$ moiety of a $C_4$-$C_6$cycloalkyl$C_1$-$C_2$alkyl- (in particular $C_4$-$C_6$cycloalkylmethyl-) is optionally (e.g. preferably) replaced by an oxygen or sulfur atom or by a S(O), S(O)$_2$, NH, N($C_1$-$C_2$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety;

$C_3$-$C_6$cycloalkyl$C_1$-$C_2$alkyl- (in particular $C_3$-$C_6$cycloalkylmethyl-) substituted by one ring substituent being $C_1$-$C_3$alkoxy (in particular $C_1$-$C_2$alkoxy) and optionally further substituted by one ring substituent being $C_1$-$C_2$alkyl (in particular methyl); or Het or Het-$CH_2$—, wherein Het is a heteroaryl, attached at a ring-carbon, which is optionally substituted by 1, 2 or 3 (in particular 1 or 2, e.g. 1) ring-carbon substituents independently being $C_1$-$C_3$alkyl (e.g. $C_1$-$C_2$alkyl), $C_1$-$C_2$fluoroalkyl, $C_1$-$C_3$alkyl-C(O)—, $C_1$-$C_2$fluoroalkyl-C(O)—, hydroxy (including any oxo tautomer), $C_2$-$C_3$alkenyl (e.g. ethenyl or prop-1-enyl), $C_2$-$C_3$alkynyl (e.g. ethynyl or prop-1-ynyl), $C_1$-$C_3$alkoxy (e.g. $C_1$-$C_2$alkoxy), $C_1$-$C_2$fluoroalkoxy, halogen (e.g. fluorine or chlorine), cyano or nitro, provided that any non-fluorine halogen, alkoxy or fluoroalkoxy is not substituted at any ring-carbon bonded directly to a ring-nitrogen of the heteroaryl; and/or, in the case of a 5-membered heteroaryl ring containing a ring-nitrogen atom not partaking in a C=N ring double bond, the heteroaryl is optionally substituted on the ring-nitrogen atom not partaking in a C=N ring double bond by one $C_1$-$C_3$alkyl, $C_1$-$C_2$fluoroalkyl, $C_1$-$C_3$alkyl-C(O)—, $C_1$-$C_2$fluoroalkyl-C(O)— or $C_1$-$C_2$alkyl-S(O)$_2$— substituent;

provided that no more than one of $R^8$ and $R^9$ is an optionally substituted cycloalkyl; an optionally substituted cycloalkyl in which one ring $CH_2$ moiety has been replaced by an oxygen or sulfur atom or by a S(O), S(O)$_2$, NH, N($C_1$-$C_3$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety; an optionally substituted cycloalkenyl; an optionally substituted cycloalkyl-alkyl-; an optionally substituted cycloalkyl-alkyl- in which one ring $CH_2$ moiety has been replaced by an oxygen or sulfur atom or by a S(O), S(O)$_2$, NH, N($C_1$-$C_3$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety; or Het or Het-$CH_2$—;

or $R^8$ is hydrogen or $C_1$-$C_2$alkyl (in particular H or Me), and $R^9$ is $C_1$-$C_2$alkoxy (in particular methoxy);

or $R^8$ and $R^9$ taken together are —$(CH_2)_{n7}$— or —$(CH_2)_{n8}$—$X^2$—$(CH_2)_{n9}$—.

In the above preferred embodiment, preferably Y is $CR^8R^9$ and/or preferably $X^2$ is O.

More preferably, e.g. in all aspects and/or embodiments of the invention:

$R^8$ is hydrogen or $C_1$-$C_2$alkyl (preferably H or Me, more preferably hydrogen); and $R^9$ is:
$C_1$-$C_2$alkoxy (in particular methoxy);
$C_2$-$C_3$alkynyl-$CH_2$— (in particular ethynyl-$CH_2$—);
$C_1$-$C_3$alkoxy$C_1$-$C_3$alkyl;
$C_1$-$C_3$alkylthio$C_1$-$C_3$alkyl (preferably $C_1$-$C_2$alkylthio-$CH_2CH_2$— or more preferably $C_1$-$C_2$alkylthio-CH(Me)$CH_2$—);
$C_1$-$C_3$alkylsulfinyl$C_1$-$C_3$alkyl;
$C_1$-$C_3$alkylsulfonyl$C_1$-$C_3$alkyl;
$C_3$-$C_6$cycloalkyl or $C_3$-$C_6$cycloalkyl substituted by one or two substituents which independently are $C_1$-$C_3$alkyl (in particular methyl or ethyl) or $C_1$-$C_2$fluoroalkyl; and in which one ring $CH_2$ moiety of a $C_4$-$C_6$cycloalkyl is optionally (e.g. preferably) replaced by an oxygen or sulfur atom or by a S(O), S(O)$_2$, NH, N($C_1$-$C_3$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety (or more preferably is replaced by an oxygen or sulfur atom or by a S(O), S(O)$_2$, NH, N($C_1$-$C_3$alkyl) or N($C_1$-$C_2$alkoxy) moiety; or still more preferably is replaced by an oxygen or sulfur atom);

$C_3$-$C_6$cycloalkyl substituted by one substituent being $C_1$-$C_3$alkoxy (in particular $C_1$-$C_2$alkoxy) and optionally further substituted by one substituent being $C_1$-$C_2$alkyl (in particular methyl);

$C_3$-$C_6$cycloalkylmethyl- or $C_3$-$C_6$cycloalkylmethyl-substituted by one or two ring substituents which independently are $C_1$-$C_3$alkyl (in particular $C_1$-$C_2$alkyl) or $C_1$-$C_2$fluoroalkyl; and in which one ring $CH_2$ moiety of a $C_4$-$C_6$cycloalkylmethyl- is optionally (e.g. preferably) replaced by an oxygen or sulfur atom or by a $S(O)$, $S(O)_2$, $NH$, $N(C_1$-$C_2$alkyl)$, $N(C_1$-$C_2$fluoroalkyl)$, $N[C(O)C_1$-$C_3$alkyl]$, $N[C(O)C_1$-$C_2$fluoroalkyl]$ or $N(C_1$-$C_2$alkoxy)$ moiety (or more preferably is replaced by an oxygen or sulfur atom or by a $N[C(O)C_1$-$C_3$alkyl]$ or $N[C(O)C_1$-$C_2$fluoroalkyl]$ moiety);

$C_3$-$C_6$cycloalkylmethyl-substituted by one ring substituent being $C_1$-$C_3$alkoxy (in particular $C_1$-$C_2$alkoxy) and optionally further substituted by one ring substituent being $C_1$-$C_2$alkyl (in particular methyl); or Het or Het-$CH_2$—, wherein Het is a heteroaryl, attached at a ring-carbon, which is optionally substituted by 1, 2 or 3 (in particular 1 or 2, e.g. 1) ring-carbon substituents independently being $C_1$-$C_3$alkyl (in particular $C_1$-$C_2$alkyl), $C_1$-$C_2$fluoroalkyl (in particular $C_1$fluoroalkyl), $C_1$-$C_3$alkyl-$C(O)$—, $C_1$-$C_2$fluoroalkyl-$C(O)$—, hydroxy (including any oxo tautomer), $C_2$-$C_3$alkenyl (in particular ethenyl or prop-1-enyl), $C_2$-$C_3$alkynyl (in particular ethynyl or prop-1-ynyl), $C_1$-$C_3$alkoxy (in particular $C_1$-$C_2$alkoxy), $C_1$-$C_2$fluoroalkoxy (in particular $C_1$fluoroalkoxy), halogen (in particular fluorine or chlorine), cyano or nitro, provided that any non-fluorine halogen, alkoxy or fluoroalkoxy is not substituted at any ring-carbon bonded directly to a ring-nitrogen of the heteroaryl; and/or, in the case of a 5-membered heteroaryl ring containing a ring-nitrogen atom not partaking in a $C=N$ ring double bond, the heteroaryl is optionally substituted on the ring-nitrogen atom not partaking in a $C=N$ ring double bond by one $C_1$-$C_3$alkyl, $C_1$-$C_2$fluoroalkyl, $C_1$-$C_3$alkyl-$C(O)$—, $C_1$-$C_2$fluoroalkyl-$C(O)$— or $C_1$-$C_2$alkyl-$S(O)_2$— substituent;

or $R^8$ and $R^9$ taken together are —$(CH_2)_{n7}$— or —$(CH_2)_{n8}$—$X^2$—$(CH_2)_{n9}$—.

In the above more preferred embodiment, preferably Y is $CR^8R^9$ and/or preferably $X^2$ is O.

Even more preferably, e.g. in all aspects and/or embodiments of the invention:

$R^8$ is hydrogen or $C_1$-$C_2$alkyl (preferably H or Me, more preferably hydrogen); and $R^9$ is:

$C_1$-$C_3$alkylthio$C_1$-$C_3$alkyl (preferably $C_1$-$C_2$alkylthio-$CH_2CH_2$— or more preferably $C_1$-$C_2$alkylthio-$CH(Me)CH_2$—);

$C_3$-$C_6$cycloalkyl or $C_3$-$C_6$cycloalkyl substituted by one or two substituents which independently are $C_1$-$C_3$alkyl (in particular methyl or ethyl) or $C_1$-$C_2$fluoroalkyl; and in which one ring $CH_2$ moiety of a $C_4$-$C_6$cycloalkyl is replaced by an oxygen or sulfur atom or by a $S(O)$, $S(O)_2$, $NH$, $N(C_1$-$C_3$alkyl)$, $N(C_1$-$C_2$fluoroalkyl)$, $N[C(O)C_1$-$C_3$alkyl]$, $N[C(O)C_1$-$C_2$fluoroalkyl]$ or $N(C_1$-$C_2$alkoxy)$ moiety (or preferably is replaced by an oxygen or sulfur atom or by a $S(O)$, $S(O)_2$, $NH$, $N(C_1$-$C_3$alkyl)$ or $N(C_1$-$C_2$alkoxy)$ moiety; or more preferably is replaced by an oxygen or sulfur atom);

$C_3$-$C_6$cycloalkylmethyl- or $C_3$-$C_6$cycloalkylmethyl-substituted by one or two ring substituents which independently are $C_1$-$C_3$alkyl (in particular $C_1$-$C_2$alkyl) or $C_1$-$C_2$fluoroalkyl; and in which one ring $CH_2$ moiety of a $C_4$-$C_6$cycloalkylmethyl- is replaced by an oxygen or sulfur atom or by a $S(O)$, $S(O)_2$, $NH$, $N(C_1$-$C_2$alkyl)$, $N(C_1$-$C_2$fluoroalkyl)$, $N[C(O)C_1$-$C_3$alkyl]$, $N[C(O)C_1$-$C_2$fluoroalkyl]$ or $N(C_1$-$C_2$alkoxy)$ moiety (or preferably is replaced by an oxygen or sulfur atom or by a $N[C(O)C_1$-$C_3$alkyl]$ or $N[C(O)C_1$-$C_2$fluoroalkyl]$ moiety); or Het or Het-$CH_2$—, wherein Het is a heteroaryl, attached at a ring-carbon, which is optionally substituted by 1, 2 or 3 (in particular 1 or 2, e.g. 1) ring-carbon substituents independently being $C_1$-$C_3$alkyl (in particular $C_1$-$C_2$alkyl), $C_1$-$C_2$fluoroalkyl (in particular $C_1$fluoroalkyl), $C_1$-$C_3$alkyl-$C(O)$—, $C_1$-$C_2$fluoroalkyl-$C(O)$—, hydroxy (including any oxo tautomer), $C_2$-$C_3$alkenyl (in particular ethenyl or prop-1-enyl), $C_2$-$C_3$alkynyl (in particular ethynyl or prop-1-ynyl), $C_1$-$C_3$alkoxy (in particular $C_1$-$C_2$alkoxy), $C_1$-$C_2$fluoroalkoxy (in particular $C_1$fluoroalkoxy), halogen (in particular fluorine or chlorine), cyano or nitro, provided that any non-fluorine halogen, alkoxy or fluoroalkoxy is not substituted at any ring-carbon bonded directly to a ring-nitrogen of the heteroaryl; and/or, in the case of a 5-membered heteroaryl ring containing a ring-nitrogen atom not partaking in a $C=N$ ring double bond, the heteroaryl is optionally substituted on the ring-nitrogen atom not partaking in a $C=N$ ring double bond by one $C_1$-$C_3$alkyl, $C_1$-$C_2$fluoroalkyl, $C_1$-$C_3$alkyl-$C(O)$—, $C_1$-$C_2$fluoroalkyl-$C(O)$— or $C_1$-$C_2$alkyl-$S(O)_2$— substituent;

or $R^8$ and $R^9$ taken together are —$(CH_2)_{n7}$— or —$(CH_2)_{n8}$—$X^2$—$(CH_2)_{n9}$—.

In the above even more preferred embodiment, preferably Y is $CR^8R^9$ and/or preferably $X^2$ is O.

In one preferable embodiment (which e.g. can apply to all aspects and/or embodiments of the invention), $R^8$ and $R^9$ are, independently of each other, hydrogen or $C_1$-$C_3$alkyl (preferably hydrogen or $C_1$-$C_2$alkyl, such as hydrogen or methyl). In this embodiment, preferably, Y is $CR^8R^9$.

In another preferable embodiment (which e.g. can apply to all aspects and/or embodiments of the invention), $R^8$ is hydrogen, and $R^9$ is $C_1$-$C_3$alkylthio$C_1$-$C_3$alkyl. In this embodiment, $R^9$ preferably is $C_1$-$C_2$alkylthio-$CH_2CH_2$— or more preferably is $C_1$-$C_2$alkylthio-$CH(Me)CH_2$—. In this embodiment, preferably, Y is $CR^8R^9$.

In another preferable embodiment (which e.g. can apply to all aspects and/or embodiments of the invention), $R^8$ is hydrogen and $R^9$ is $C_4$-$C_6$cycloalkylmethyl- or $C_4$-$C_6$cycloalkylmethyl-substituted by one or two ring substituents which independently are $C_1$-$C_3$alkyl (in particular $C_1$-$C_2$alkyl) or $C_1$-$C_2$fluoroalkyl, and in which one ring $CH_2$ moiety is replaced by an oxygen or sulfur atom or by a $S(O)$, $S(O)_2$, $NH$, $N(C_1$-$C_2$alkyl)$, $N(C_1$-$C_2$fluoroalkyl)$, $N[C(O) C_1$-$C_3$alkyl]$, $N[C(O)C_1$-$C_2$fluoroalkyl]$ or $N(C_1$-$C_2$alkoxy)$ moiety (or more preferably is replaced by an oxygen or sulfur atom or by a $N[C(O)C_1$-$C_3$alkyl]$ or $N[C(O)C_1$-$C_2$fluoroalkyl]$ moiety). In this embodiment, preferably, Y is $CR^8R^9$.

In this preferable embodiment, then more preferably $R^8$ is hydrogen and $R^9$ is a heterocyclyl-methyl-, wherein the heterocyclyl is Q, wherein Q is one of the following subformulae $Q_1$, $Q_2$, $Q_3$, $Q_4$, $Q_5$, $Q_6$, $Q_7$, $Q_{33}$, $Q_{34}$, $Q_{37}$, $Q_{38}$, $Q_{41}$, $Q_{42}$, $Q_{43}$, $Q_{44}$, $Q_{47}$, $Q_{87}$, $Q_{89}$, $Q_{90}$ or $Q_{107}$:

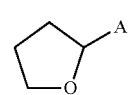

-continued

Q2 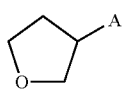

Q3 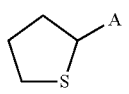

Q4 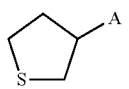

Q5 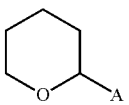

Q6 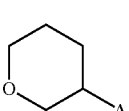

Q7 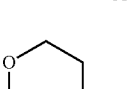

Q33 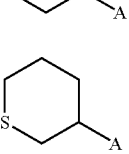

Q34 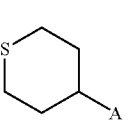

Q37 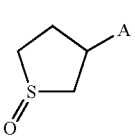

Q38 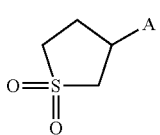

Q41 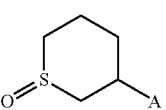

Q42 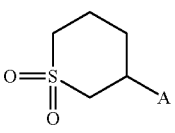

Q43 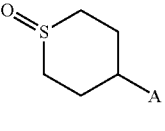

Q44 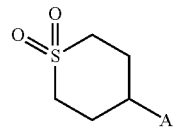

Q47 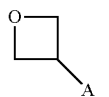

Q87 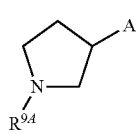

Q89 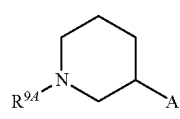

Q90 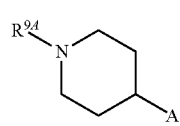

Q107 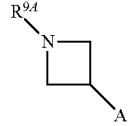

wherein:

A is the position of attachment to the -methyl- moiety; and $R^{9A}$ is hydrogen, $C_1$-$C_2$alkyl (e.g. methyl), $C_1$-$C_2$fluoroalkyl (e.g. $C_1$fluoroalkyl), —C(O)$C_1$-$C_3$alkyl (e.g. —C(O)methyl), —C(O)$C_1$-$C_2$fluoroalkyl (e.g. —C(O)$C_1$fluoroalkyl) or $C_1$-$C_2$alkoxy.

More preferably, Q is one of the sub-formulae $Q_1$, $Q_2$, $Q_4$, $Q_6$, $Q_7$, $Q_{33}$, $Q_{34}$, $Q_{41}$, $Q_{42}$, $Q_{43}$, $Q_{44}$, $Q_{87}$, $Q_{89}$ or $Q_{90}$. Even more preferably, Q is one of the sub-formulae $Q_2$, $Q_6$, $Q_7$, $Q_{33}$, $Q_{34}$, $Q_{41}$, $Q_{42}$, $Q_{43}$, $Q_{44}$, $Q_{87}$, $Q_{89}$ or $Q_{90}$.

Yet more preferably, Q is one of the sub-formulae $Q_2$, $Q_7$, $Q_{87}$ or $Q_{90}$. Further more preferably, Q is one of the sub-formulae $Q_2$, $Q_7$ or $Q_{90}$.

Most preferably, Q is sub-formula $Q_7$.

Preferably, $R^{9A}$ is —C(O)$C_1$-$C_3$alkyl (e.g. —C(O)methyl) or —C(O)$C_1$-$C_2$fluoroalkyl (e.g. —C(O)$C_1$fluoroalkyl).

In one preferable embodiment of the invention (which e.g. can apply to all aspects and/or embodiments of the invention), $R^8$ is hydrogen, and $R^9$ is tetrahydro-2H-pyran-4-yl

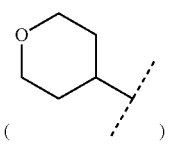

or (tetrahydro-2H-pyran-4-yl)-methyl-. In this embodiment, preferably, Y is $CR^8R^9$. When $R^9$ is (tetrahydro-2H-pyran-4-yl)-methyl-, then $R^9$ is $Q_7$-methyl- wherein $Q_7$ is

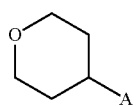

wherein A is the position of attachment to the -methyl-moiety.

In another preferable embodiment (which e.g. can apply to all aspects and/or embodiments of the invention), $R^8$ is hydrogen and $R^9$ is Het or Het-$CH_2$— as defined herein. In this embodiment, more preferably, $R^8$ is hydrogen and $R^9$ is Het as defined herein. In this embodiment, preferably, Y is $CR^8R^9$.

Preferably, e.g. in all aspects and/or embodiments of the invention, Het is a heteroaryl (in particular monocyclic heteroaryl), attached at a ring-carbon, which is optionally substituted by 1, 2 or 3 (in particular 1 or 2, e.g. 1) ring-carbon substituents independently being $C_1$-$C_2$alkyl, $C_1$fluoroalkyl, $C_1$-$C_2$alkyl-C(O)—, $C_1$fluoroalkyl-C(O)—, hydroxy (including any oxo tautomer), ethynyl, prop-1-ynyl, $C_1$-$C_2$alkoxy, $C_1$fluoroalkoxy, fluorine, chlorine, bromine, cyano or nitro, provided that any chlorine, bromine, alkoxy or fluoroalkoxy is not substituted at any ring-carbon bonded directly to a ring-nitrogen of the heteroaryl;
and/or, in the case of a 5-membered heteroaryl ring containing a ring-nitrogen atom not partaking in a C=N ring double bond, the heteroaryl is optionally substituted on the ring-nitrogen atom not partaking in a C=N ring double bond by one $C_1$-$C_3$alkyl, $C_1$-$C_2$fluoroalkyl, $C_1$-$C_3$alkyl-C(O)—, $C_1$-$C_2$fluoroalkyl-C(O)— or $C_1$-$C_2$alkyl-S(O)$_2$— substituent.

More preferably, e.g. in all aspects and/or embodiments of the invention, Het is a heteroaryl (in particular monocyclic heteroaryl), attached at a ring-carbon, which is optionally substituted by 1 or 2 (in particular 1) ring-carbon substituents independently being $C_1$-$C_2$alkyl (in particular methyl), $C_1$fluoroalkyl (in particular $CF_3$), $C_1$-$C_2$alkyl-C(O)— (in particular Me-C(O)—), $C_1$fluoroalkyl-C(O)—, ethynyl, prop-1-ynyl, fluorine or cyano;
and/or, in the case of a 5-membered heteroaryl ring containing a ring-nitrogen atom not partaking in a C=N ring double bond, the heteroaryl is optionally substituted on the ring-nitrogen atom not partaking in a C=N ring double bond by one $C_1$-$C_2$alkyl (e.g. methyl), $C_1$fluoroalkyl, methyl-C(O)— or $C_1$fluoroalkyl-C(O)— substituent.

More preferably, e.g. in all aspects and/or embodiments of the invention, Het is a heteroaryl (in particular monocyclic heteroaryl), attached at a ring-carbon, which is optionally substituted by 1 or 2 (in particular 1) ring-carbon substituents independently being $C_1$-$C_2$alkyl (in particular methyl), $C_1$fluoroalkyl (in particular $CF_3$), fluorine or cyano;
and/or, in the case of a 5-membered heteroaryl ring containing a ring-nitrogen atom not partaking in a C=N ring double bond, the heteroaryl is optionally substituted on the ring-nitrogen atom not partaking in a C=N ring double bond by one methyl substituent.

Preferably, e.g. in all aspects and/or embodiments of the invention, Het is an optionally substituted monocyclic heteroaryl, attached at a ring-carbon. Such as monocyclic heteroaryl can be 5-membered or 6-membered monocyclic heteroaryl.

More preferably, e.g. in all aspects and/or embodiments of the invention, Het is an optionally substituted monocyclic heteroaryl, attached at a ring-carbon, which is:
pyridinyl (preferably pyridin-3-yl or most preferably pyridin-2-yl), pyrazolyl (preferably pyrazol-5-yl or pyrazol-4-yl, or most preferably pyrazol-3-yl), imidazolyl (preferably imidazol-2-yl), pyrazinyl, pyrimidinyl (preferably pyrimidin-4-yl), pyridazinyl (preferably pyridazin-3-yl), triazolyl (e.g. 1,2,3-triazolyl), tetrazol-5-yl, oxazolyl, thiazolyl, isoxazolyl, isothiazolyl or oxadiazolyl; optionally present (e.g. where chemically possible) as an agrochemically acceptable salt thereof (such as an agrochemically acceptable acid addition salt thereof).

Even more preferably, e.g. in all aspects and/or embodiments of the invention, Het is an optionally substituted monocyclic heteroaryl, attached at a ring-carbon, which is:
pyridinyl (preferably pyridin-3-yl or most preferably pyridin-2-yl), pyrazolyl (preferably pyrazol-5-yl or pyrazol-4-yl, or most preferably pyrazol-3-yl), imidazolyl (preferably imidazol-2-yl), pyrazinyl, pyrimidinyl (preferably pyrimidin-4-yl), pyridazinyl (preferably pyridazin-3-yl), triazolyl (e.g. 1,2,3-triazolyl), or tetrazol-5-yl; optionally present (e.g. where chemically possible) as an agrochemically acceptable salt thereof (such as an agrochemically acceptable acid addition salt thereof).

Still more preferably, e.g. in all aspects and/or embodiments of the invention, Het is an optionally substituted monocyclic heteroaryl, attached at a ring-carbon, which is:
pyridinyl (preferably pyridin-3-yl or most preferably pyridin-2-yl), pyrazolyl (preferably pyrazol-5-yl or pyrazol-4-yl, or most preferably pyrazol-3-yl), imidazolyl (preferably imidazol-2-yl), pyrazinyl, pyrimidinyl (preferably pyrimidin-4-yl), or pyridazinyl (preferably pyridazin-3-yl); optionally present (e.g. where chemically possible) as an agrochemically acceptable salt thereof (such as an agrochemically acceptable acid addition salt thereof).

Yet more preferably, e.g. in all aspects and/or embodiments of the invention, Het is an optionally substituted monocyclic heteroaryl, attached at a ring-carbon, which is: pyridin-3-yl, pyridin-2-yl, or pyrazolyl (preferably pyrazol-5-yl or pyrazol-4-yl, or most preferably pyrazol-3-yl); optionally present (e.g. where chemically possible) as an agrochemically acceptable salt thereof (such as an agrochemically acceptable acid addition salt thereof).

Most preferably, e.g. in all aspects and/or embodiments of the invention, Het is an optionally substituted monocyclic heteroaryl, attached at a ring-carbon, which is: pyridin-2-yl or pyrazol-3-yl; optionally present (e.g. where chemically possible) as an agrochemically acceptable salt thereof (such as an agrochemically acceptable acid addition salt thereof).

It is particularly preferred (e.g. in all aspects and/or embodiments of the invention) that, in Het, any ring-carbon atom, which is directly bonded to the ring-carbon atom which is the point of attachment (e.g. or i.e. which is the point of attachment to the central carbon atom within the Y=$CR^8R^9$ moiety (for Het), or which is the point of attachment to the —$CH_2$— moiety (for Het-$CH_2$—), is unsubstituted. Therefore, for example, preferably, when Het is an optionally substituted pyridin-2-yl (optionally present as an agrochemically acceptable salt thereof), then the ring-carbon atom at the 3-position of the ring (calculated with respect to the pyridine ring nitrogen atom) is unsubstituted.

Preferably, e.g. in all aspects and/or embodiments of the invention, $R^{10}$, $R^{11}$, $R^{12}$ and/or $R^{13}$ are, independently of each other, hydrogen or $C_1$-$C_2$alkyl (in particular hydrogen or methyl).

Preferably, two, three or all of $R^{10}$, $R^{11}$, $R^{12}$ and $R^{13}$ are hydrogen.

Most preferably, $R^{10}$, $R^{11}$, $R^{12}$ and $R^{13}$ are hydrogen.

In a particularly preferable embodiment of the invention (which e.g. can apply to all aspects and/or embodiments of the invention):
Y is O or $CR^8R^9$ (preferably $CR^8R^9$); and
$R^4$ and $R^5$ are taken together and are —$(CH_2)_{n4}$— or —$(CH_2)_{n5}$—$C(R^{7a})(R^{7b})$—$(CH_2)_{n6}$—;
wherein $R^{7a}$ is $C_1$-$C_2$alkyl; $R^{7b}$ is hydrogen or $C_1$-$C_2$alkyl;
n4 is 2 or 3; and
n5 and n6 are independently 0, 1 or 2 provided that n5+n6 is 1 or 2.

In this particularly preferable embodiment, more preferably, Y is O or $CR^8R^9$ (preferably $CR^8R^9$) wherein $R^8$ and $R^9$ are, independently of each other, hydrogen or $C_1$-$C_3$alkyl (in particular, this $C_1$-$C_3$alkyl can be $C_1$-$C_2$alkyl such as methyl).

In this particularly preferable embodiment, even more preferably Y is O or $CH_2$; or, most preferably, Y is $CH_2$.

In this particularly preferable embodiment, more preferably, $R^3$ and $R^6$, independently of each other, are hydrogen, $C_1$-$C_3$alkyl (in particular $C_1$-$C_2$alkyl such as methyl) or $C_1$-$C_3$alkoxy$C_1$-$C_3$alkyl (in particular $C_1$-$C_2$alkoxy$C_1$-$C_2$alkyl); provided that no more than one (in particular none) of $R^3$ and $R^6$ is alkoxyalkyl.

In this particularly preferable embodiment, even more preferably, $R^3$ and $R^6$, independently of each other, are hydrogen or $C_1$-$C_2$alkyl (preferably hydrogen or methyl); and $R^4$ and $R^5$ taken together are —$(CH_2)_{n4}$— wherein n4 is 2 or 3.

In a particularly preferable embodiment of the invention (which e.g. can apply to all aspects and/or embodiments of the invention), the compound of formula (I) is a compound described in any of Tables 1 to 25, as described and/or illustrated herein, optionally present (e.g. where chemically possible) as an agrochemically acceptable salt thereof. In an alternative particularly preferable embodiment of the invention (which e.g. can apply to all aspects and/or embodiments of the invention), the compound of formula (I) is a compound described Table 26 or 27, as described and/or illustrated herein, optionally present (e.g. where chemically possible) as an agrochemically acceptable salt thereof. More preferably (e.g. in all aspects and/or embodiments of the invention), the compound of formula (I) is a compound described in any of Tables 1, 3, 5, 8, 9, 10, 11, 12, 14, 15, 16, 17, 18, 19, 20, 21, 22, 23, 24 or 25 (or alternatively in Table 26 or 27), as described and/or illustrated herein, optionally present (e.g. where chemically possible) as an agrochemically acceptable salt thereof. Even more preferably (e.g. in all aspects and/or embodiments of the invention), the compound of formula (I) is a compound described in any of Tables 1, 3, 5, 8, 9, 10, 11, 12, 14, 15, 16 or 25 (or alternatively in Table 26 or 27), as described and/or illustrated herein, optionally present (e.g. where chemically possible) as an agrochemically acceptable salt thereof.

In one more particularly preferable embodiment of the invention (which e.g. can apply to all aspects and/or embodiments of the invention), the compound of formula (I) is compound A-1, A-2, A-3, A-4, A-5, A-6, A-7, A-8, A-9, A-10, A-11, A-12, A-13, A-14 or A-15, as described and/or illustrated herein, optionally present (e.g. where chemically possible) as an agrochemically acceptable salt thereof. In an alternative more particularly preferable embodiment of the invention (which e.g. can apply to all aspects and/or embodiments of the invention), the compound of formula (I) is compound A-16, A-17 or A-18, as described and/or illustrated herein, optionally present (e.g. where chemically possible) as an agrochemically acceptable salt thereof. In a further alternative more particularly preferable embodiment of the invention (which e.g. can apply to all aspects and/or embodiments of the invention), the compound of formula (I) is compound A-20 (=compound 11.10), A-22 (=compound 1.10), A-25 (=compound 14.23), A-27 (=compound 12.02), A-28 (=compound 12.10), A-30 (=compound 12.15), A-31 (=compound 9.02), A-32 (=compound 9.10), A-33 (=compound 1.02), A-34 (=compound 1.15), A-35 (=compound 5.02), A-36 (=compound 5.10), A-37 (compound 5.15), A-38 (=compound 11.02), A-39 (=compound 11.15), A-40 (=compound 25.10) or A-41 (=compound 14.06), as described and/or illustrated herein, optionally present (e.g. where chemically possible) as an agrochemically acceptable salt thereof. In a further alternative more particularly preferable embodiment of the invention (which e.g. can apply to all aspects and/or embodiments of the invention), the compound of formula (I) is compound A-19, A-21, A-23, A-24, A-26, A-29, P-3, P-4, P-5 or P-7, as described and/or illustrated herein, optionally present (e.g. where chemically possible) as an agrochemically acceptable salt thereof.

In a yet more particularly preferable embodiment of the invention (which e.g. can apply to all aspects and/or embodiments of the invention), the compound of formula (I) is compound A-2, A-3, A-4, A-5, A-8, A-9, A-10, A-12, A-13, A-14, A-15, A-16, A-17 or A-18, as described and/or illustrated herein, optionally present (e.g. where chemically possible) as an agrochemically acceptable salt thereof; or alternatively is compound A-6, as described and/or illustrated herein, optionally present as an agrochemically acceptable salt thereof. In an alternative yet more particularly preferable embodiment of the invention (which e.g. can apply to all aspects and/or embodiments of the invention), the compound of formula (I) is compound A-20, A-22, A-27, A-28, A-33, A-34, A-35, A-36, A-38, A-39, A-40 or A-41, as described and/or illustrated herein, optionally present (e.g. where chemically possible) as an agrochemically acceptable salt thereof. In a further alternative yet more particularly preferable embodiment of the invention (which e.g. can apply to all aspects and/or embodiments of the invention), the compound of formula (I) is compound A-19, A-21, A-23, A-24, A-26, P-3, P-5 or P-7, as described and/or illustrated herein, optionally present (e.g. where chemically possible) as an agrochemically acceptable salt thereof.

Depending on the nature of the substituents G, $R^1$, $R^2$, $R^3$, $R^4$, $R^5$, $R^6$, $R^7$ and $R^8$, compounds of formula (I) may exist in different isomeric forms. When G is hydrogen, for example, compounds of formula (I) may exist in different tautomeric forms:

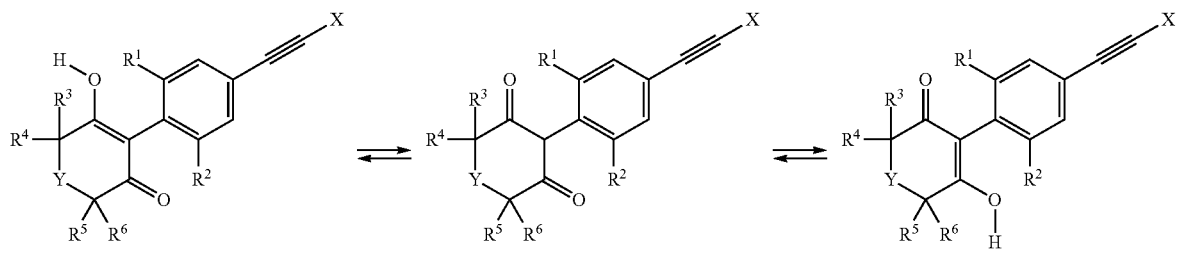

Also, when substituents contain double bonds, cis- and trans-isomers can exist. This invention covers all such isomers and tautomers and mixtures thereof in all proportions. These isomers, too, are within the scope of the claimed compounds of the formula (I). According to a further aspect of the invention, there is provided a compound of formula (ZZ):

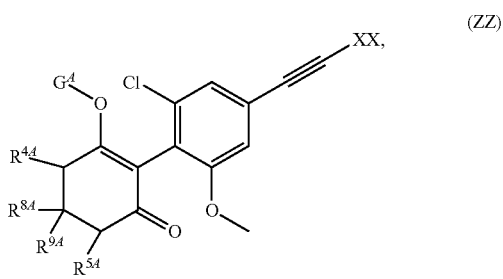

wherein:

XX is hydrogen or ethyl; and $R^{8A}$ is hydrogen, and $R^{9A}$ is hydrogen, methyl, $C_1$-$C_2$alkylthio-$CH_2CH_2$—, $C_1$-$C_2$alkylthio-CH(Me)$CH_2$—, tetrahydro-2H-pyran-4-yl, (tetrahydro-2H-pyran-4-yl)-methyl-, or pyridin-2-yl;

or $R^{8A}$ and $R^{9A}$ are methyl;

or $R^{8A}$ and $R^{9A}$ taken together are —$CH_2CH_2$—O—$CH_2CH_2$—; and $R^{4A}$ and $R^{5A}$ are hydrogen; or $R^{4A}$ and $R^{5A}$ taken together are —$CH_2$—$CH_2$—; provided that when $R^{4A}$ and $R^{5A}$ taken together are —$CH_2$—$CH_2$— then $R^{8A}$ and $R^{9A}$ are hydrogen; and $G^A$ is hydrogen, an agriculturally acceptable metal, or an agriculturally acceptable sulfonium or ammonium group; or G is —C(O)—$R^{a1}$ or —C(O)—O—$R^{b1}$;

wherein $R^{a1}$ is $C_1$-$C_6$alkyl, $C_2$-$C_4$alkenyl, $C_2$-$C_4$alkynyl, $C_3$-$C_6$cycloalkyl, $C_3$-$C_6$cycloalkyl-methyl-, $C_1$-$C_4$alkoxy$C_1$-$C_4$alkyl, or phenyl or phenyl substituted by 1, 2 or 3 of, independently, methyl, $C_1$fluoroalkyl, methoxy, $C_1$fluoroalkoxy, halogen, cyano or nitro;

and $R^{b1}$ is $C_1$-$C_6$alkyl, $C_2$-$C_3$alkenyl-$CH_2$—, $C_2$-$C_3$alkenyl-CH(Me)-, $C_2$-$C_3$alkynyl-$CH_2$—, $C_2$-$C_3$alkynyl-CH(Me)-, $C_3$-$C_6$cycloalkyl, $C_3$-$C_6$cycloalkyl-methyl-, $C_1$-$C_4$alkoxy$C_1$-$C_4$alkyl, or phenyl or phenyl substituted by 1, 2 or 3 of, independently, methyl, $C_1$fluoroalkyl, methoxy, $C_1$fluoroalkoxy, halogen, cyano or nitro;

and wherein the compound of formula (ZZ) is optionally present (e.g. where chemically possible) as an agrochemically acceptable salt thereof.

Preferably, $R^{8A}$ is hydrogen, and $R^{9A}$ is hydrogen, $C_1$-$C_2$alkylthio-CH(Me)$CH_2$—, (tetrahydro-2H-pyran-4-yl)-methyl-, or pyridin-2-yl;

or $R^{8A}$ and $R^{9A}$ are methyl;

or $R^{8A}$ and $R^{9A}$ taken together are —$CH_2CH_2$—O—$CH_2CH_2$—.

More preferably, $R^{8A}$ is hydrogen, and $R^{9A}$ is hydrogen, $C_1$-$C_2$alkylthio-CH(Me)$CH_2$—, or pyridin-2-yl;

or $R^{8A}$ and $R^{9A}$ are methyl;

or $R^{8A}$ and $R^{9A}$ taken together are —$CH_2CH_2$—O—$CH_2CH_2$—.

Most preferably, $R^{8A}$ and $R^{9A}$ are hydrogen; or $R^{8A}$ and $R^{9A}$ taken together are —$CH_2CH_2$—O—$CH_2CH_2$—.

Preferably, $R^{a}1$ is $C_1$-$C_6$alkyl. Preferably, $R^{b1}$ is $C_1$-$C_6$alkyl.

Preferably, $G^A$ is hydrogen, an agriculturally acceptable metal, or an agriculturally acceptable sulfonium or ammonium group. Most preferably, $G^A$ is hydrogen.

In one particular embodiment, XX is hydrogen. In an alternative particular embodiment, XX is ethyl.

Preferably, the compound of formula (ZZ) is (B-1),

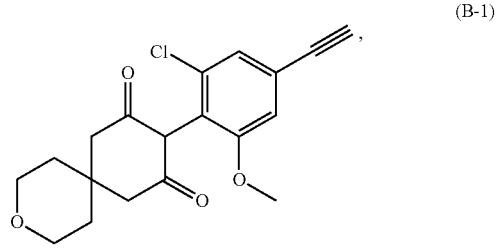

(B-1)

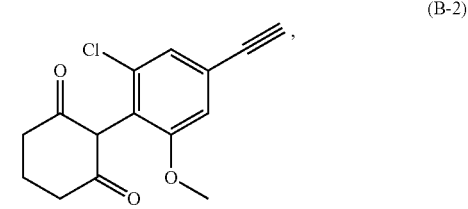

(B-2)

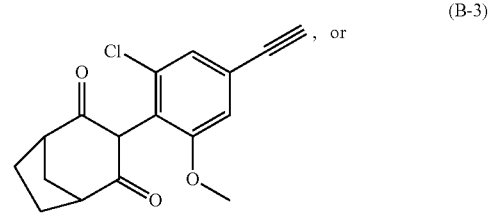

(B-3) or

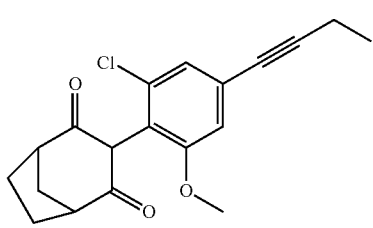

(B-4)

optionally present as an agrochemically acceptable salt thereof.

According to a further aspect of the invention, there is provided a method of controlling weeds in crops of useful plants, comprising applying a compound of formula (ZZ), as defined herein, or a herbicidal composition comprising such a compound, to the plants or to the locus thereof. Preferably, the weeds comprise grassy monocotyledonous weeds. More preferably, the grassy monocotyledonous weeds comprise "warm season" (warm climate) grassy monocotyledonous weeds, even more preferably weeds from the genus *Brachiaria, Cenchrus, Digitaria, Echinochloa, Eleusine, Eriochloa, Leptochloa, Ottochloa, Panicum, Pennisetum, Phalaris, Rottboellia, Setaria* and/or *Sorghum*. Preferably, the crops of useful plants comprise wheat, barley, rye, triticale, sugarcane, soybean, peanut, pulse crops, cotton, rape, sunflower, linseed, sugarbeet, fodder beet, potato, and/or dicotyledonous vegetables. Typically, the rate of application (typically to the weeds and/or to the crops of useful plants and/or to the locus thereof) of the compound of formula (ZZ) (which optionally may be an agrochemically acceptable salt thereof) will be from 1 to 2000 g, in particular from 5 to 1000 g/ha or from 10 to 1000 g/ha or from 10 to 500 g/ha, of the compound of formula (ZZ) (measured as the salt-free compound, i.e. excluding the weight of any associated salt counterion(s)). The compound of formula (ZZ) can be applied (typically to the weeds and/or to the crops of useful plants and/or to the locus thereof) pre- and/or post-emergence, but preferably is applied post-emergence.

Processes for Preparation of Compounds, e.g. Compounds of Formula (I)

Processes for preparation of compounds, e.g. a compound of formula (I) (which optionally can be an agrochemically acceptable salt thereof), are now described, and form further aspects of the present invention.

A compound of formula I, wherein G is:
—C($X^a$)—$R^a$, —C($X^b$)—$X^c$—$R^b$, —C($X^d$)—N($R^c$)—$R^d$, —SO$_2$—$R^e$, —P($X^e$)($R^f$)—$R^g$, —CH$_2$—$X^f$—$R^h$; or phenyl-CH$_2$— or phenyl-CH(C$_1$-C$_2$alkyl)- (in each of which the phenyl is optionally substituted by 1, 2 or 3 of, independently, C$_1$-C$_2$alkyl, C$_1$fluoroalkyl, C$_1$-C$_2$alkoxy, C$_1$fluoroalkoxy, fluorine, chlorine, bromine, cyano or nitro), or heteroaryl-CH$_2$— or heteroaryl-CH(C$_1$-C$_2$alkyl)- (in each of which the heteroaryl is optionally substituted by 1, 2 or 3 of, independently, C$_1$-C$_2$alkyl, C$_1$fluoroalkyl, C$_1$-C$_2$alkoxy, C$_1$fluoroalkoxy, fluorine, chlorine, bromine, cyano or nitro), or phenyl-C(O)—CH$_2$—(wherein the phenyl is optionally substituted by 1, 2 or 3 of, independently, C$_1$-C$_2$alkyl, C$_1$fluoroalkyl, C$_1$-C$_2$alkoxy, C$_1$fluoroalkoxy, fluorine, chlorine, bromine, cyano or nitro); or C$_1$-C$_6$alkoxy-C(O)—CH$_2$—, C$_1$-C$_6$alkoxy-C(O)—CH=CH—, C$_2$-C$_7$alken-1-yl-CH$_2$—, C$_2$-C$_7$alken-1-yl-CH(C$_1$-C$_2$alkyl)-, C$_2$-C$_4$fluoroalken-1-yl-CH$_2$—, C$_2$-C$_7$alkyn-1-yl-CH$_2$—, or C$_2$-C$_7$alkyn-1-yl-CH(C$_1$-C$_2$alkyl)-;

may be prepared by treating a compound of formula (A), which is a compound of formula I wherein G is H, (a) with a reagent G1-Z, wherein G1-Z is an alkylating agent (wherein G1 is an organic group according to G within the compound of formula (I) and which is linked by a non-carbonyl, non-thiocarbonyl carbon atom) such as an organic halide (in which Z=halogen such as chlorine, bromine or iodine); wherein the organic halide (e.g. chloride) can typically be a substituted alkyl halide (e.g. chloride) such as a chloromethyl alkyl ether Cl—CH$_2$—$X^f$—$R^h$ wherein $X^f$ is oxygen, a chloromethyl alkyl sulfide Cl—CH$_2$—$X^f$—$R^h$ wherein $X^f$ is sulphur, a suitable optionally substituted benzyl halide (e.g. chloride) such as Cl—CH$_2$—[optionally substituted phenyl], [optionally substituted phenyl]-C(O)—CH$_2$—[halogen e.g. Cl], C$_1$-C$_6$alkoxy-C(O)—CH$_2$—[halogen e.g. Cl], C$_1$-C$_6$alkoxy-C(O)—CH=CH-[halogen e.g. Cl], a suitable alkenyl or alkynyl halide (e.g. chloride) such as C$_2$-C$_7$alken-1-yl-CH$_2$—[halogen e.g. Cl] or C$_2$-C$_7$alkyn-1-yl-CH$_2$—[halogen e.g. Cl], or another organic halide suitable for preparing a (non-carbonyl, non-thiocarbonyl carbon)-linked G (or G1) group; or (b) [e.g. to prepare carbonyl-carbon-linked or thiocarbonyl-carbon-linked G groups] with an acylating agent such as a carboxylic acid, HO—C($X^a$)$R^a$, wherein $X^a$ is oxygen, an acid chloride, Cl—C($X^a$)$R^a$, wherein $X^a$ is oxygen, or an acid anhydride, [$R^a$C($X^a$)]$_2$O, wherein $X^a$ is oxygen, or an isocyanate, $R^c$N=C=O, or a carbamoyl chloride, Cl—C($X^d$)—N($R^c$)—$R^d$ (wherein $X^d$ is oxygen and with the proviso that neither $R^c$ or $R^d$ is hydrogen), or a thiocarbamoyl chloride Cl—($X^d$)—N($R^c$)—$R^d$ (wherein $X^d$ is sulfur and with the proviso that neither $R^c$ or $R^d$ is hydrogen), or a chloroformate, Cl—C($X^b$)—$X^c$—$R^b$ (wherein $X^b$ and $X^c$ are oxygen), or a chlorothioformate Cl—C($X^b$)—$X^c$—$R^b$ (wherein $X^b$ is oxygen and $X^c$ is sulfur), or a chlorodithioformate Cl—C($X^b$)—$X^c$—$R^b$ (wherein $X^b$ and $X^c$ are sulfur), or an isothiocyanate, $R^c$N=C=S; or (c) by sequential treatment with carbon disulfide and an alkylating agent; or (d) with a phosphorylating agent such as a phosphoryl chloride, Cl—P($X^e$)($R^f$)—$R^g$; or (e) with a sulfonylating agent such as a sulfonyl chloride Cl—SO$_2$—$R^e$, preferably in the presence of at least one equivalent of base.

Where substituents $R^4$ and $R^5$ are not equal to substituents $R^6$ and $R^7$, these reactions may produce, in addition to a compound of formula I, a second compound of formula (IA).

This invention covers both a compound of formula (I) and a compound of formula (IA), together with mixtures of these compounds in any ratio.

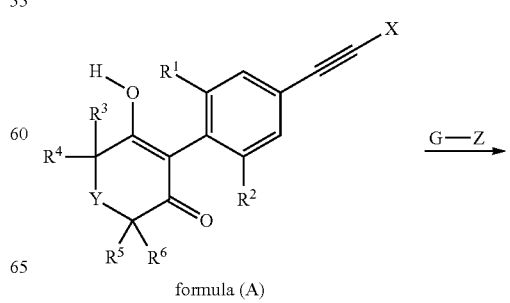

formula (A)

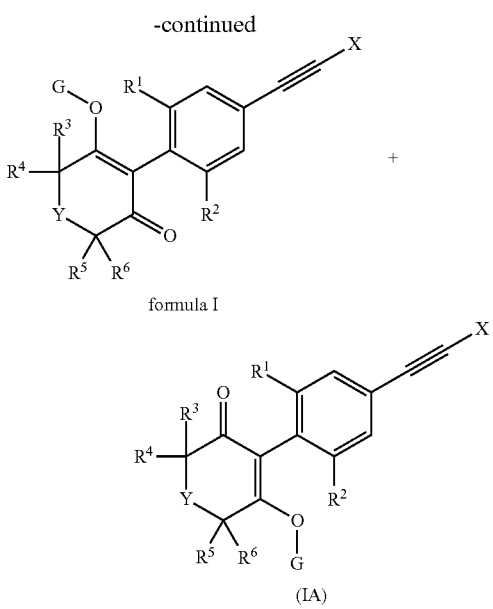

formula I formula (IA)

The O-alkylation of cyclic 1,3-diones is known; suitable methods are described, for example, by T. Wheeler, U.S. Pat. No. 4,436,666. Alternative procedures have been reported by M. Pizzorno and S. Albonico, Chem. Ind. (London), (1972), 425-426; H. Born et al., J. Chem. Soc., (1953), 1779-1782; M. G. Constantino et al., Synth. Commun., (1992), 22 (19), 2859-2864; Y. Tian et al., Synth. Commun., (1997), 27 (9), 1577-1582; S. Chandra Roy et al., Chem. Letters, (2006), 35 (1), 16-17; P. K. Zubaidha et al., Tetrahedron Lett., (2004), 45, 7187-7188.

The O-acylation of cyclic 1,3-diones may be effected e.g. by procedures similar to those described, for example, by R. Haines, U.S. Pat. No. 4,175,135, and by T. Wheeler, U.S. Pat. No. 4,422,870, U.S. Pat. No. 4,659,372 and U.S. Pat. No. 4,436,666. Typically diones of formula (A) may be treated with an acylating agent preferably in the presence of at least one equivalent of a suitable base, and optionally in the presence of a suitable solvent. The base may be inorganic, such as an alkali metal carbonate or hydroxide, or a metal hydride, or an organic base such as a tertiary amine or metal alkoxide. Examples of suitable inorganic bases include sodium carbonate, sodium or potassium hydroxide, sodium hydride, and suitable organic bases include trialkylamines, such as trimethylamine and triethylamine, pyridines or other amine bases such as 1,4-diazobicyclo[2.2.2]-octane and 1,8-diazabicyclo[5.4.0]undec-7-ene. Preferred bases include triethylamine and pyridine. Suitable solvents for this reaction are selected to be compatible with the reagents and include ethers such as tetrahydrofuran and 1,2-dimethoxyethane and halogenated solvents such as dichloromethane and chloroform. Certain bases, such as pyridine and triethylamine, may be employed successfully as both base and solvent. For cases where the acylating agent is a carboxylic acid, acylation is preferably effected in the presence of a known coupling agent such as 2-chloro-1-methylpyridinium iodide, N,N'-dicyclohexylcarbodiimide, 1-(3-dimethylaminopropyl)-3-ethylcarbodiimide and N,N'-carbodiimidazole, and optionally in the presence of a base such as triethylamine or pyridine in a suitable solvent such as tetrahydrofuran, dichloromethane or acetonitrile. Suitable procedures are described, for example, by W. Zhang and G. Pugh, Tetrahedron Lett., (1999), 40 (43), 7595-7598; T. Isobe and T. Ishikawa, J. Org. Chem., (1999), 64 (19), 6984-6988 and K. Nicolaou, T. Montagnon, G. Vassilikogiannakis, C. Mathison, J. Am. Chem. Soc., (2005), 127(24), 8872-8888.

Phosphorylation of cyclic 1,3-diones may be effected e.g. using a phosphoryl halide or thiophosphoryl halide and a base e.g. by procedures analogous to those described by L. Hodakowski, U.S. Pat. No. 4,409,153.

Sulfonylation of a compound of formula (A) may be achieved e.g. using an alkyl or aryl sulfonyl halide, preferably in the presence of at least one equivalent of base, for example by the procedure of C. Kowalski and K. Fields, J. Org. Chem., (1981), 46, 197-201.

Compounds of formula (A), wherein Y is S(O) or S(O)$_2$ may be prepared from compounds of formula (A) wherein Y is S by oxidation, e.g. according to a procedure analogous to that of E. Fehnel and A. Paul, J. Am. Chem. Soc., (1955), 77, 4241-4244.

A compound of formula (A), wherein Y is O, S, C(O) or CR$^8$R$^9$ may be prepared via the cyclisation of a compound of formula (B), preferably in the presence of an acid or base, and optionally in the presence of a suitable solvent, e.g. by analogous methods to those described by T. Wheeler, U.S. Pat. No. 4,209,532. The compounds of the formula (B) have been particularly designed as intermediates in the synthesis of the compounds of the formula I. Compounds of formula (B) wherein R is hydrogen or C$_1$-C$_4$alkyl, (especially methyl, ethyl and tert-butyl) may be cyclised under acidic conditions, preferably in the presence of a strong acid such as sulfuric acid, polyphosphoric acid or Eaton's reagent, optionally in the presence of a suitable solvent such as acetic acid, toluene or dichloromethane. A compound of formula (B) wherein R is alkyl (preferably methyl or ethyl) may also be cyclised under basic conditions in the presence of at least one equivalent of a strong base in a solvent such as tetrahydrofuran, toluene, dimethylsulfoxide or N,N-dimethylformamide. Suitable bases include potassium tert-butoxide, lithium diisopropylamide, sodium bis(trimethylsilyl)amide or sodium hydride. A compound of formula (B), wherein R is alkyl, may be produced from a compound of formula (B), wherein R is H, by esterification under known conditions (for example by treatment with an alcohol, R—OH, in the presence of an acid catalyst).

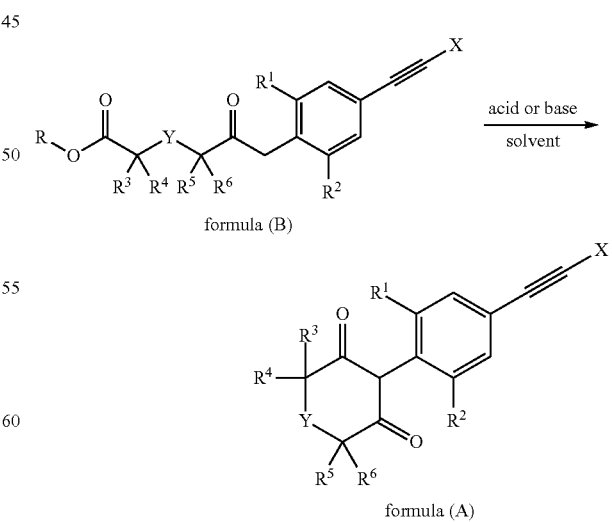

formula (B)

formula (A)

A compound of formula (B), wherein R is H may be prepared by hydrolysis of a compound of formula (C)

wherein R is H or alkyl and R' is alkyl (preferably methyl or ethyl), followed by acidification of the reaction mixture to effect decarboxylation, e.g. by similar processes to those described by, for example, T. Wheeler, U.S. Pat. No. 4,209,532. Alternatively, a compound of formula (B), wherein R is alkyl or H may be prepared from a compound of formula (C), wherein R' is alkyl (preferably methyl), through a Krapcho decarboxylation procedure, e.g. under known conditions using known reagents (see for example G. Quallich, P. Morrissey, Synthesis, (1993), (1), 51-53).

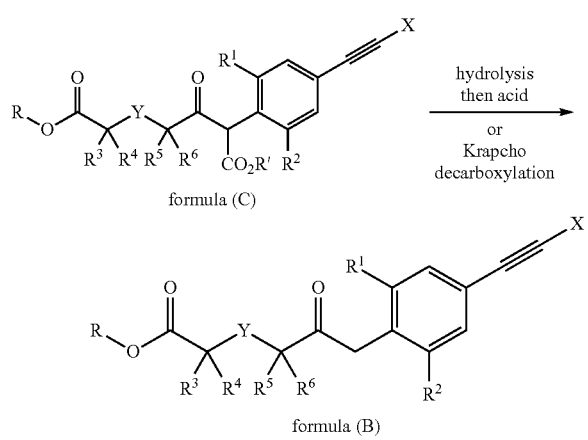

formula (C)

hydrolysis then acid
or
Krapcho decarboxylation formula (B)

A compound of formula (C) wherein R is alkyl may be prepared by treating a compound of formula (D) with a suitable carboxylic acid chloride of formula (E) wherein R is alkyl under basic conditions. Suitable bases include potassium tert-butoxide, sodium bis(trimethyl-silyl)amide and lithium diisopropylamide and the reaction is preferably conducted in a suitable solvent (such as tetrahydrofuran or toluene) at a temperature between −78° C. and 30° C. Under similar conditions a compound of formula (C), wherein R is H, may be prepared from a suitable anhydride of formula (F).

(1977), 42 (7), 1163-1169; G. Bennett, W. Houlihan, R. Mason; R. Engstrom, J. Med. Chem., (1976), 19 (5), 709-14; L. J. J. Hronowski, Lucjan W. A. Szarek, Canadian Journal of Chemistry (1988), 66(1), 61-70; S. F. Birch, V. E. Gripp, D. T. McAllan, W. S. Nathan, Journal of the Chemical Society (1952), 1363-8; S. Kitamura, T. D. Aicher, Gonzales, Steve; Y. Le Huerou, S. A. Pratt, Y. Nakada, WO 2008011130; O. Jentzer, M. Guglieri, WO 2009092795), or may be made by similar methods from commercially available starting materials.

Compounds of formula (D), wherein X is methyl and R' is $C_1$-$C_4$alkyl, can be prepared by reacting compounds of formula (G) with propyne in the presence of a suitable catalyst, optionally a suitable additive, optionally in a suitable solvent at a suitable temperature. Suitable catalysts include transition metal salts or complexes of transition metal salts (for example palladium acetate, bis(triphenylphosphine) palladium(II) dichloride, tetrakis(triphenylphosphine)palladium(0), bis(triphenylphosphine) nickel(II) dichloride and tris(acetylacetonato) iron(III)), in an amount typically 0.001-25% with respect to a compound of formula (G). Suitable additives include copper salts (for example copper(I) iodide in an amount typically 0.001-50% with respect to a compound of formula (G)), and tetraalkyl ammonium salts. Suitable bases include diethylamine, triethylamine, piperidine and pyrrolidine, and suitable solvents include 1,4-dioxane, N,N-dimethylacetamide or N,N-dimethylformamide. Preferably the reaction is carried out using 0.05-10% bis(triphenylphosphine) palladium(II) dichloride (with respect to a compound of formula (G)), 0.05-10% triphenylphosphine (with respect to a compound of formula (G)), 0.05-25% copper(I) iodide (with respect to a compound of formula (G)), 5-200% tetrabutyl ammonium iodide (with respect to a compound of formula (G)), triethylamine and N,N-dimethylformamide at a temperature between 25° C. to 150° C. Such a reaction is an example of a Sonogashira coupling and similar reactions are known in the literature (see for example F. Labrie, S. Gauthier, J. Cloutier, J. Mailhot, S. Potvin, S. Dion, J-Y. Sanceau, WO 2008124922; M. S. Viciu, S. P. Nolan, Modern Arylation Methods (2009),

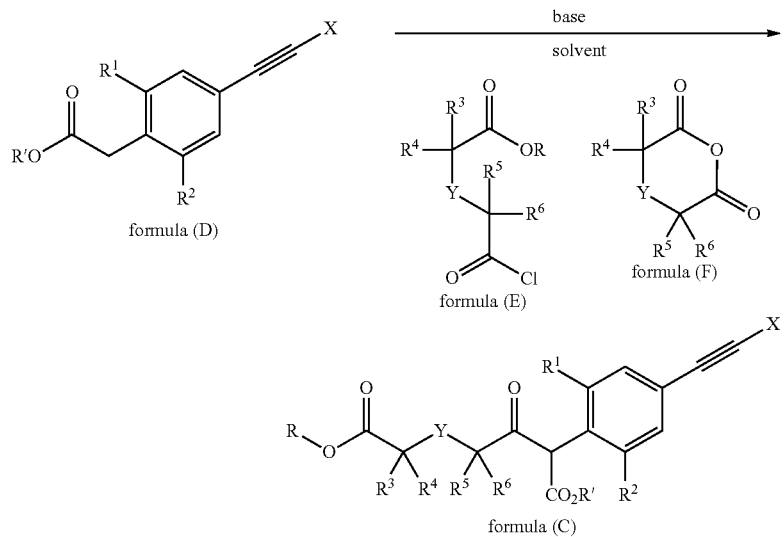

formula (D)

base
solvent formula (E)

formula (F)

formula (C)

Compounds of formula (E) and formula (F) are known (see, for example T. Terasawa and T. Okada, J. Org. Chem., 183-220; R. Chinchilla, C. Najera, Chemical Reviews (2007), 107(3), 874-922; I. P. Beletskaya, G. V. Latyshev, A.

V. Tsvetkov, N. V. Lukashev, Tetrahedron Letters (2003), 44(27), 5011-5013 and J. Mao, G. Xie, M. Wu, J. Guo, S. Ji, Advanced Synthesis & Catalysis (2008), 350(16), 2477-2482). In an alternative approach a compound of formula (D) may be prepared from a compound of formula (G) by reaction with a propynyl transfer reagent such as 1-propynyllithium, 1-propynylmagnesium bromide, 1-propynylmagnesium chloride, 1-propynylmagnesium iodide, 1-propynylzinc chloride, 1-propynylzinc bromide, 1-propynylzinc iodide, tributylpropynylstannane, 1-propyne-1-boronic acid (or ester thereof), 2-butynoic acid or 1-(trimethylsilyl)propyne, with a transition metal catalyst system under suitable conditions (see for example P. Wessig, G. Mueller, C. Pick, A. Matthes, Synthesis (2007), (3), 464-477; J. H. Chaplin, G. S. Gill, D. W. Grobelny, B. L. Flynn, G. Kremmidiotis, WO07087684; A. Akao, T. Tsuritani, S. Kii, K. Sato, N. Nonoyama, T. Mase, N. Yasuda, Synlett (2007), (1), 31-36. A. Coelho Coton, E. Sotelo Perez, F. Guitian Rivera, A. Gil Gonzalez, WO 2011048247; C. H. Oh, S. H. Jung, Tetrahedron Letters (2000), 41(44), 8513-8516; D. Zhao, C. Gao, X. Su, Y. He, J. You, Y. Xue, Chemical Communications (2010), 46(47), 9049-9051; C. Yang, S. P. Nolan, Organometallics (2002), 21(6), 1020-1022). In another set of preferred conditions a compound of formula (G) is reacted with 1-propynylmagnesium bromide in the presence of 0.05-10% bis(triphenylphosphine) palladium(II) dichloride (with respect to a compound of formula (G)), in tetrahydrofuran at a temperature between 25° C. and 100° C., as described by J. H. Chaplin, G. S. Gill, D. W. Grobelny, B. L. Flynn, G. Kremmidiotis, WO 07087684. Compounds of formula (G) are known, or can be prepared by known methods using known reagents.

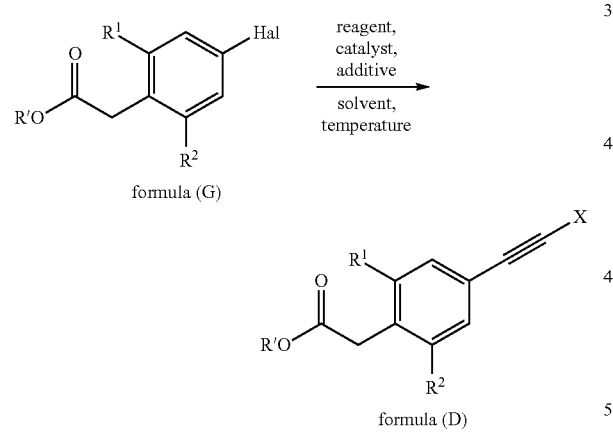

formula (G)

formula (D)

Compounds of formula (D), wherein X is chlorine and R' is $C_1$-$C_4$alkyl, can be prepared from compounds of formula (H) or compounds of formula (I). In one approach a compound of formula (H) is first deprotonated with a base such as butyllithium, sodium hydride, lithium diisopropylamide or ethylmagnesium bromide, then reacted with a chlorine source such as N-chloro succinimide, chlorine or carbon tetrachloride. The specific chlorine source is selected to provide the required chloro-acetylene. Similar reactions and conditions are reported in the literature (see for example M. Tajbakhsh, S. Habibzadeh, Letters in Organic Chemistry (2007), 4(7), 512-514; D. Sud, T. J. Wigglesworth, N. R. Branda, Angewandte Chemie, International Edition (2007), 46(42), 8017-8019; M. A. P. Martins, D. J. Emmerich, C. M. P. Pereira, W. Cunico, M. Rossato, N. Zanatta, H. G. Bonacorso, Tetrahedron Letters (2004), 45(25), 4935-4938; A. Poloukhtine, V. Rassadin, A. Kuzmin, V. V. Popik, Journal of Organic Chemistry (2010), 75(17), 5953-5962; C. R. Hickenboth, J. D. Rule, J. S. Moore, Tetrahedron (2008), 64(36), 8435-8448; F. H. M. Graichen, A. C. Warden, S. Kyi, M. S. O'Shea, Australian Journal of Chemistry (2010), 63(4), 719-722; and M. L. Narayana, M. L. N. Rao, M. Periasamy, Synthetic Communications (1995), 25(15), 2295-9).

In another approach a compound of formula (D), wherein X is chlorine and R' is $C_1$-$C_4$alkyl, can be prepared from a compound of formula (H) by treatment with a mixture of reagents that are known to promote chlorination, such as potassium carbonate, tetrabutylammonium bromide and carbon tetrachloride (see for example T. Matsuda, S. Kadowaki, Y. Yamaguchi, M. Murakami, Chemical Communications (2008), (24), 2744-2746), pyridine and chlorine (see for example R. B. Gutsulyak, V. N. Britsuk, L. A. Kostrikina, Y. Serguchev, Ukrainskii Khimicheskii Zhurnal (1993), 59(10), 1062-7), silver nitrate and N-chloro succinimide, N-chloro succinimide and hexamethylphosphoramide (see for example G. Pangon, J. L. Philippe, P. Cadiot, Comptes Rendus des Seances de l'Academie des Sciences, Serie C: Sciences Chimiques (1973), 277(18), 879-81), and/or perchloric acid and acetic acid (see for example J. P. Montheard, M. Camps, M. Chatzopoulos, M. O. A. Yahia, R. Guilluy, D. Deruaz, Journal of Chemical Research, Synopses (1983), (9), 224-5). Conditions are selected to provide the required chloro-acetylene. When X is chlorine, preferred conditions include reacting a compound of formula (H) with 1-5 equivalents of N-chloro succinimide and 0.05-50% silver acetate (with respect to a compound of formula (H)) in acetone at a temperature between 25° C. and 100° C.

Compounds of formula (I), wherein R' is $C_1$-$C_4$alkyl and R" is $C_1$-$C_4$alkyl, can also be directly converted to compounds of formula (D), e.g. by treatment with isocyanuric chloride or N-chloro succinimide and silver nitrate (see for example M. H. Vilhelmsen, A. S. Andersson, M B. Nielsen, Synthesis (2009), (9), 1469-1472).

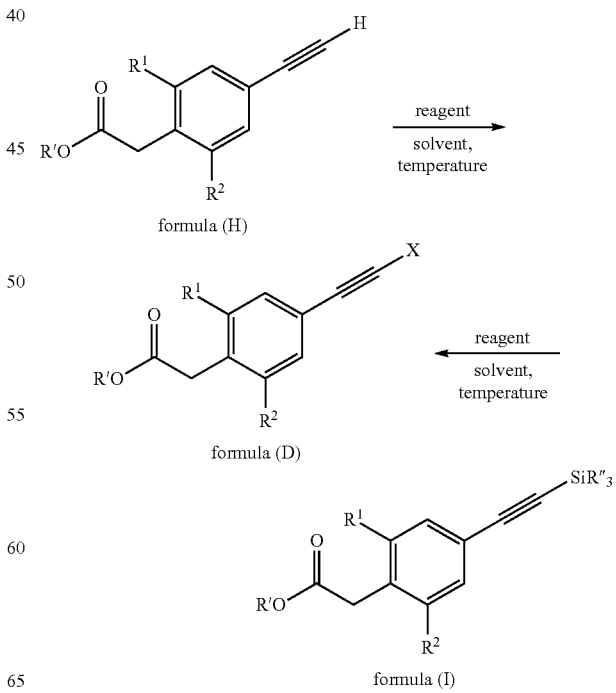

formula (H)

formula (D)

formula (I)

A compound of formula (I), wherein R' is $C_1$-$C_4$alkyl and R'' is $C_1$-$C_4$alkyl, can be prepared by reacting a compound of formula G with a trialkylsilylacetylene, under similar conditions described previously to convert a compound of formula (G) to a compound of formula (D) (wherein X is methyl).

A compound of formula (H) can either be prepared by deprotection of a compound of formula (I), e.g. under known conditions, or by reacting a compound of formula (G) with an ethynyl transfer reagent such as tributylstannylacetylene, lithium acetylide ethylenediamine complex, ethynylzinc bromide or ethynylmagnesium chloride in the presence of a suitable catalyst system, e.g. under conditions similar to those described previously (see for example C. Fischer, J. Methot, H. Zhou, A. J. Schell, B. Munoz, A. A. Rivkin, S. P. Ahearn, S. Chichetti, R. N. Maccoss, S. D. Kattar, M. Christopher, C. Li, A. Rosenau, W. C. Brown, WO 2010071741; M. Behler, A. Eluntlaut, C. Ferman, A. Chapuf, CN 101195641; G. Wang, G. Zhu, E. Negishi, Journal of Organometallic Chemistry (2007), 692(21), 4731-4736 and E. Negishi, M. Kotora, C. Xu, Journal of Organic Chemistry (1997), 62(25), 8957-8960).

temperature between 25° C. and 150° C., or lithium 2,2,6,6-tetramethylpiperidine in tetrahydrofuran at a temperature between −25° C. and 50° C. (see for example E. Bartmann, R. Hittich, H. Plach, U. Finkenzeller, U.S. Pat. No. 5,188,759 and Indian Journal of Chemistry, Section B: Organic Chemistry Including Medicinal Chemistry, 1978, vol. 16, 1051-1054). A compound of formula (K) can also be converted to a compound of formula (D) under conditions similar to those described in the literature, for example by treatment with cesium carbonate in N,N-dimethylformamide at a temperature between 25° C. and 150° C., sodium tert-butoxide in toluene at a temperature between 25° C. and 150° C., 1,8-diazabicyclo[5.4.0]undec-7-ene in dimethylsulfoxide at a temperature between 0° C. and 50° C., or potassium tert-butoxide in tetrahydrofuran at a temperature between −78° C. and 25° C. (see for example B. C. G. Soederberg, S. P. Gorugantula, C. R. Howerton, J. L. Petersen, S. W. Dantale, Tetrahedron (2009), 65(36), 7357-7363; S-C. Lo, R. E. Harding, E. Brightman, P. L. Burn, I. D. W. Samuel, Journal of Materials Chemistry (2009). 19(20), 3213-3227; S. Wang, T. Kohn, Z. Fu, X. Y. Jiao, S.

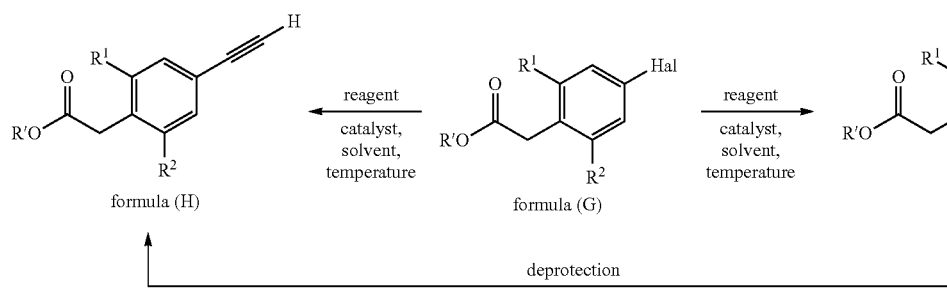

In a further approach, a compound of formula (D) (wherein X is chlorine) can either be prepared from a compound of formula (J) or a compound of formula (K), by treatment with a suitable base, in a suitable solvent, at a suitable temperature. A compound of formula (J) can be converted to a compound of formula (D) under conditions similar to those described in the literature, for example treatment using potassium tert-butoxide in tert-butanol at a Lai, M. Schmitt, Tetrahedron Letters (2008), 49(51), 7284-7286 and M. L. G. Borst, R. E. Bulo, D. J. Gibney, Y. Alem, F. J. J. de Kanter, A. W. Ehlers, M. Schakel, M. Lutz, A. L. Spek, K. Lammertsma, Journal of the American Chemical Society (2005), 127(48), 16985-16999). Compounds of formula (J) and (K) (wherein X is chlorine) can be prepared from known compounds using known methods and reagents.

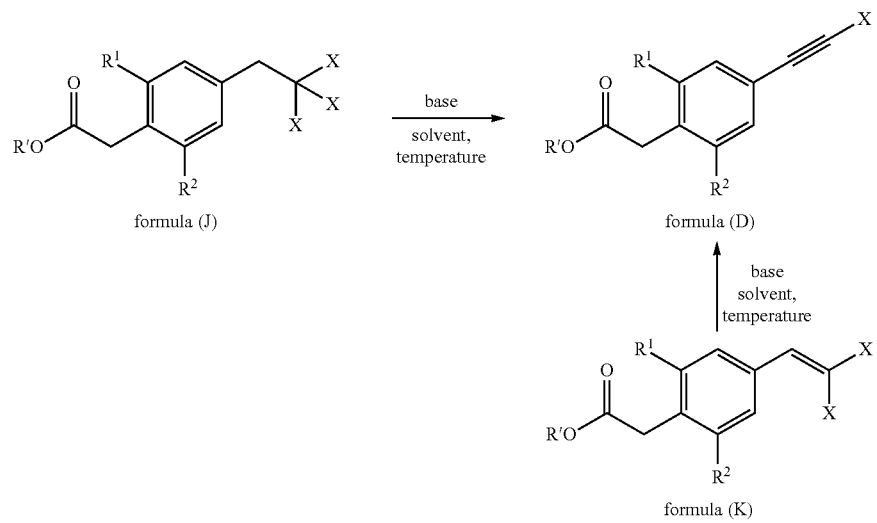

In a further approach a compound of formula (A), wherein X is methyl, can be prepared directly from a compound of formula (L), under similar conditions described previously to convert a compound of formula (G) to a compound of formula (D).

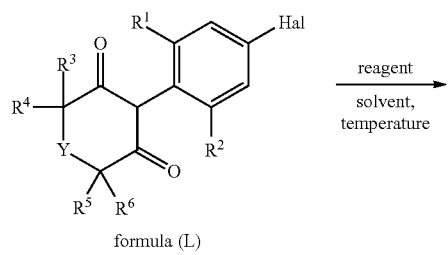

formula (L)

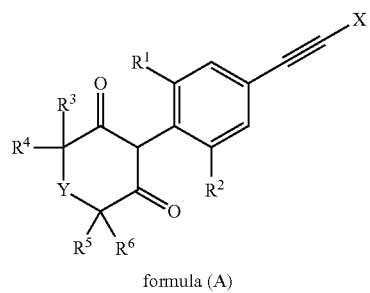

formula (A)

A compound of formula (L) can be prepared from a compound of formula (G) using similar procedures to those outlined previously.

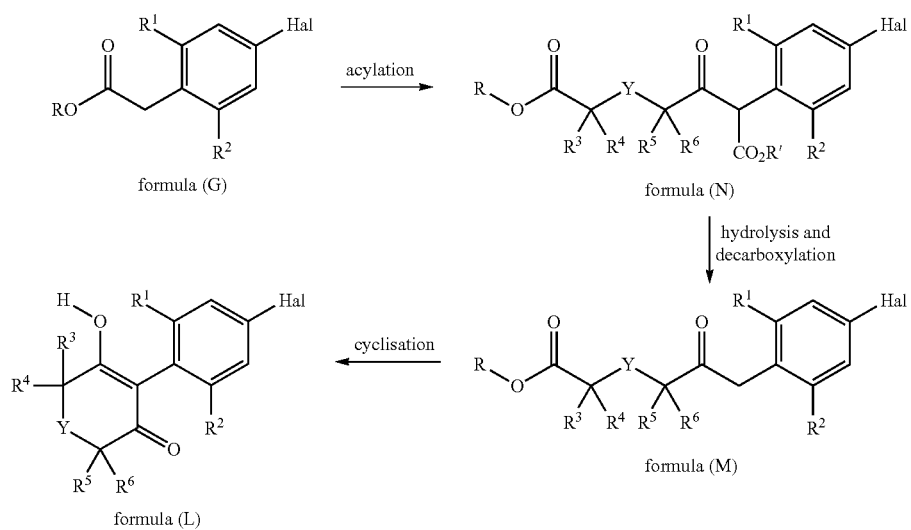

A compound of formula (A), wherein X is chlorine, can be prepared from a compound of formula (L), via either a compound of formula (O) or a compound of formula (P) (wherein R" is $C_1$-$C_4$alkyl), e.g. under similar conditions to those described previously.

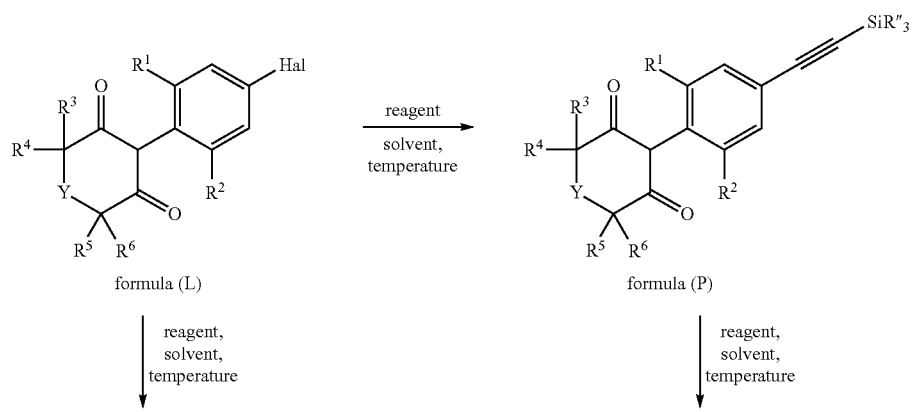

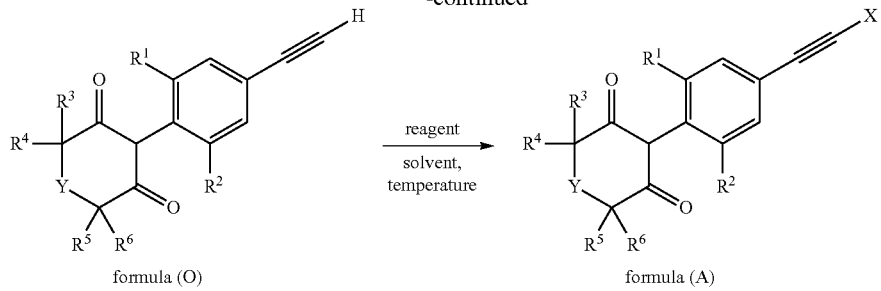

A compound of formula (A), wherein X is chlorine, can also be prepared from a compound of formula (Q), e.g. under conditions similar to those described for converting a compound of formula (K) to a compound of formula (D).

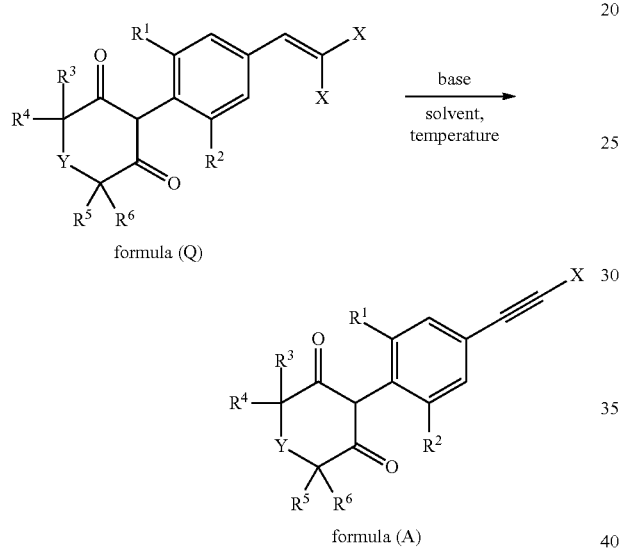

A compound of formula (Q), wherein X is chlorine may be prepared from an aldehyde of formula (R) by treatment with triphenylphosphine in the presence of carbon tetrachloride in a suitable solvent at a suitable temperature. Carbon tetrachloride is selected to provide the required dichloroalkene, and similar reactions are known in the literature (see for example A. Poloukhtine, V. V. Popik, Journal of the American Chemical Society (2007), 129(40), 12062-12063; L. N. Michaelides, B. Darses, D. J. Dixon, Organic Letters (2011), 13(4), 664-667 and F. Gavina, S. V. Luis, P. Ferrer, A. M. Costero, J. A. Marco, Journal of Chemical Research, Synopses (1986), (9), 330-1).

A compound of formula (R) may be prepared by the formylation of a compound of formula (L) (wherein Hal is chlorine, bromine or iodine, preferably bromine or iodine). Suitable conditions for effecting the formylation of aryl halides are known, and include, for example, the treatment of an aryl halide with a suitable organometallic reagent (such as isopropyl magnesium chloride, n-butyllithium, sec-butyllithium or tert-butyllithium), or by treatment with a suitable alkali metal or alkali earth metal (such as lithium or magnesium) in a suitable solvent (such as diethyl ether, dimethoxyethane or tetrahydrofuran). The resulting arylmetal reagent is then reacted with a suitable formylating agent such as N,N-dimethylformamide or N-formylmorpholine. Alternatively a compound of formula (R) may be prepared from a compound of formula (L) (wherein Hal can also be a pseudohalogen such as triflate) by treatment with a carbonylating agent (such as carbon monoxide) in the presence of a suitable catalyst system, base, and reducing agent (see for example L. Ashfield and C. Barnard, Org. Process Res. Dev., 11 (1), 39-43, 2007).

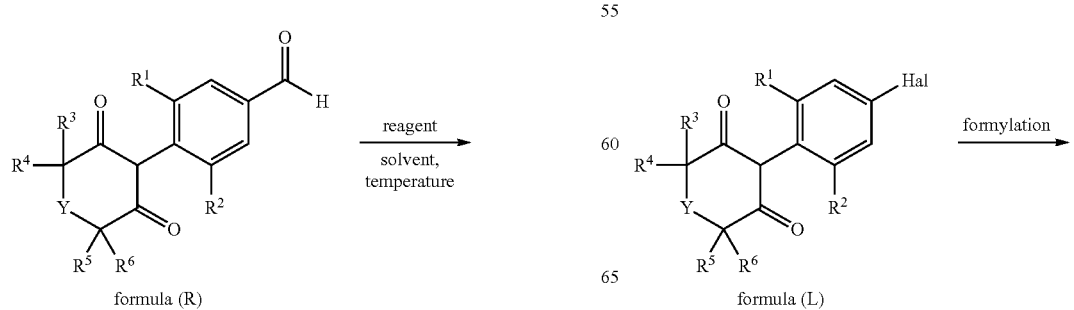

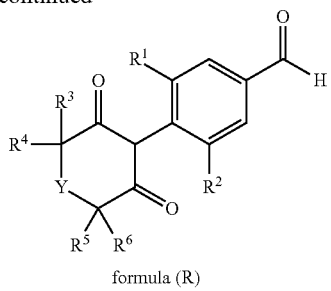

formula (R)

In an alternative approach a compound of formula I, wherein X is methyl and G is preferably methyl of ethyl, may be prepared from a boronic acid or boronic ester of formula (S) (as shown below) by treatment with either 1-bromo-1-propyne or 1-iodo-1-propyne, preferably in the presence of a suitable catalyst system, a suitable base and/or a suitable solvent and/or at a suitable temperature. Similar reactions are known in the literature, and preferred conditions involve reacting a compound of formula (S) with 1-iodo-propyne in the presence of 0.005-25% palladium(II) chloride (with respect to a compound of formula (S)) and 1-10 equivalents potassium carbonate, preferably in a mixture of toluene, water and methanol at a temperature between 50° C.-150° C., as described by Y. Shi, X. Li, J. Liu, W. Jiang, L. Sun, Tetrahedron Letters (2010), 51(28), 3626-3628. A compound of formula (T), wherein G is preferably methyl of ethyl and R" is $C_1$-$C_4$alkyl, may be prepared under similar conditions using either 1-bromo-2-(trimethylsilyl) acetylene or 1-iodo-2-(trimethylsilyl)acetylene as the coupling partner. Compounds of formula (A) and (P) may be prepared from compounds of formula I and (T) respectively, by hydrolysis of the enol ether.

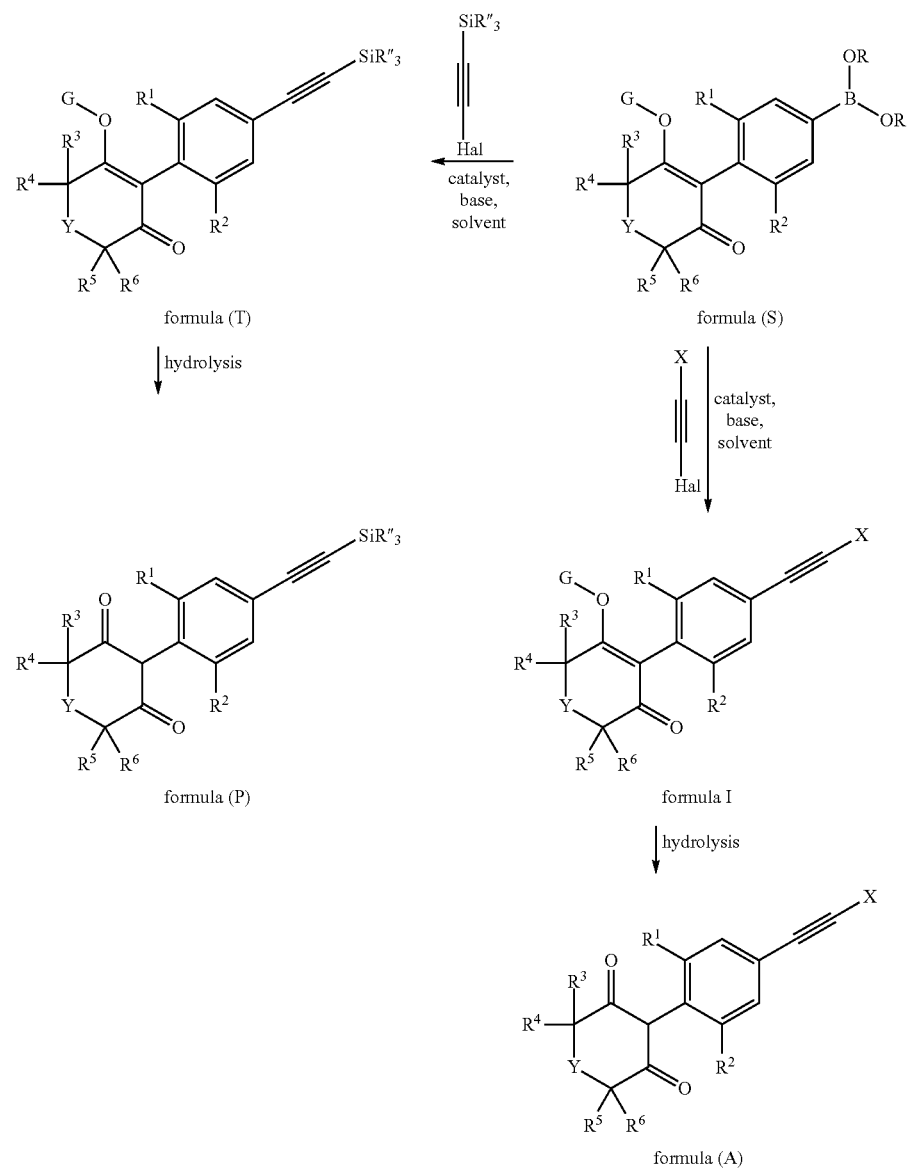

In one approach a compound of formula (S) may be prepared from a compound of formula (L) (wherein Hal is preferably iodine or bromine), preferably by treatment with a suitable base (such as sodium hydride, potassium hydride or isopropylmagnesium chloride), in a suitable solvent (such as tetrahydrofuran or diethyl ether), followed by a metal-halogen exchange reaction (preferably by treatment with an alkyllithium reagent such as n-butyllithium, sec-butyllithium or tert-butyllithium, or an organomagnesium reagent such as isopropyl magnesium chloride) and subsequent treatment with a trialkylborate, B(OR")$_3$, (preferably trimethylborate) to give the corresponding boronate ester of formula (S).

include 1,5-cyclooctadiene)(methoxy)iridium(I) dimer in combination with 4,4'-di-tert-butyl-2,2'-dipyridyl, suitable borylating agents include bis(pinacolato)diboron or pinacol borane, and suitable solvents include hexane, octane, tetrahydrofuran and methyl tert-butyl ether. Similar examples are known in the literature (see for example J. F. Hartwig, Chemical Society Reviews (2011), 40(4), 1992-2002 and T. Ishiyama, N. Miyaura, Pure and Applied Chemistry (2006), 78(7), 1369-1375). Preferred conditions include treating a compound of formula (V) with 0.05-10% 1,5-cyclooctadiene)(methoxy)iridium(I) dimer (with respect to a compound of formula (V)), 0.05-10% 4,4'-di-tert-butyl-2,2'-dipyridyl (with respect to a compound of formula (V)), and 1-2 equivalents bis(pinacolato)diboron (with respect to a compound of formula (V)) in methyl tert-butyl ether at a temperature between 50° C.-150° C., optionally under microwave irradiation, as described by P. Harrisson, J. Morris, T. B. Marder, P. G. Steel, Organic Letters (2009), 11(16), 3586-3589.

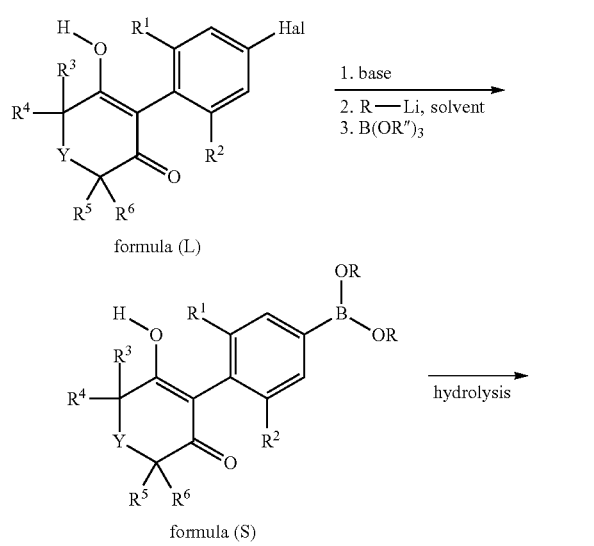

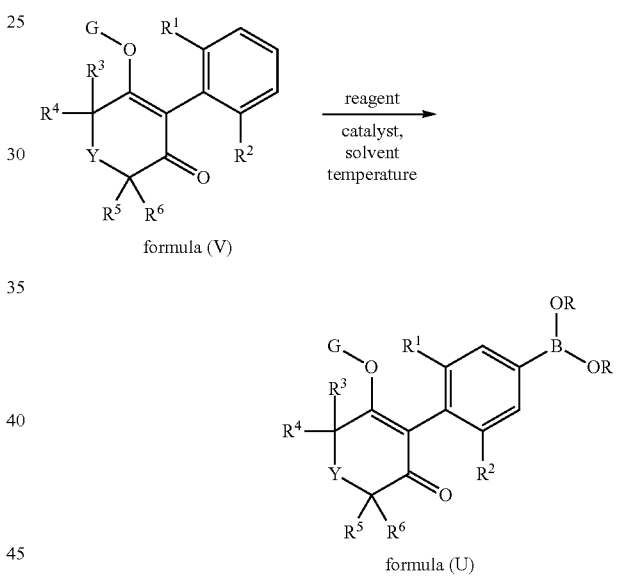

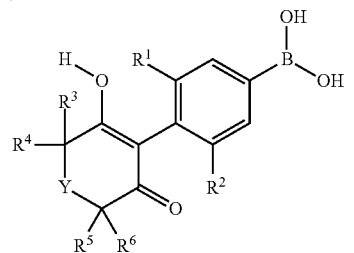

In an alternative approach a compound of formula (U) may be prepared from a compound of formula (V), wherein G is preferably methyl or ethyl, by C—H borylation with a suitable borylating agent, a suitable catalyst system, in a suitable solvent at a suitable temperature. Suitable catalysts Compounds of formula (W) can be prepared from compounds of formula (X) using similar procedures described above, starting from compounds of formula (Z) which are known compounds.

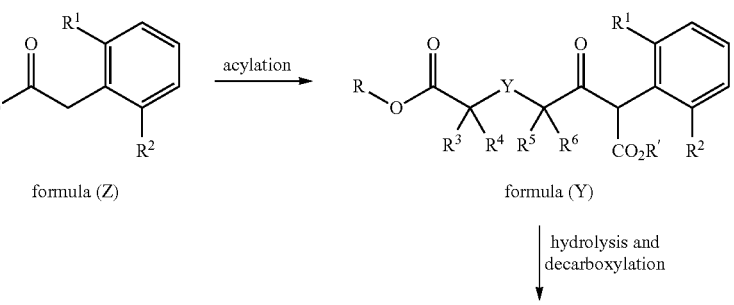

-continued

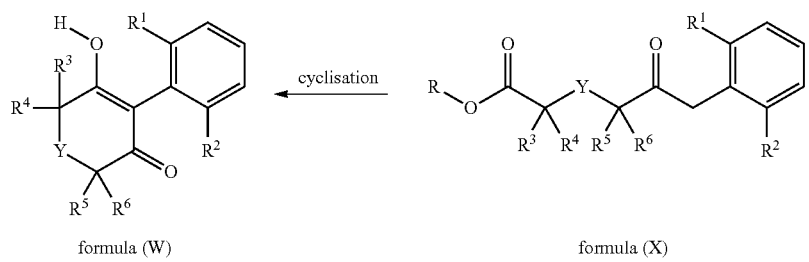

formula (W)    formula (X)

In a further approach a compound of formula (A), wherein X is methyl, may be prepared via the rearrangement of a compound of formula (AA), in the presence of a reagent which promotes rearrangement, such as a metal alkoxide (preferably in an amount equal to or greater than 100% with respect to compound of formula (AA)) or cyanide anion (for example 0.001-25% potassium cyanide or 0.001-25% sodium cyanide with respect to a compound of formula (AA)), or a cyanohydrin (preferably 0.001-25% acetone cyanohydrin with respect to a compound of formula (AA)). This reaction is preferably performed in a suitable solvent at a suitable temperature (typically 25-150° C.). Preferably a compound of formula (AA) is treated with 1-3 equivalents of sodium methoxide in N, N-dimethylformamide at a temperature between 50° C. and 100° C.

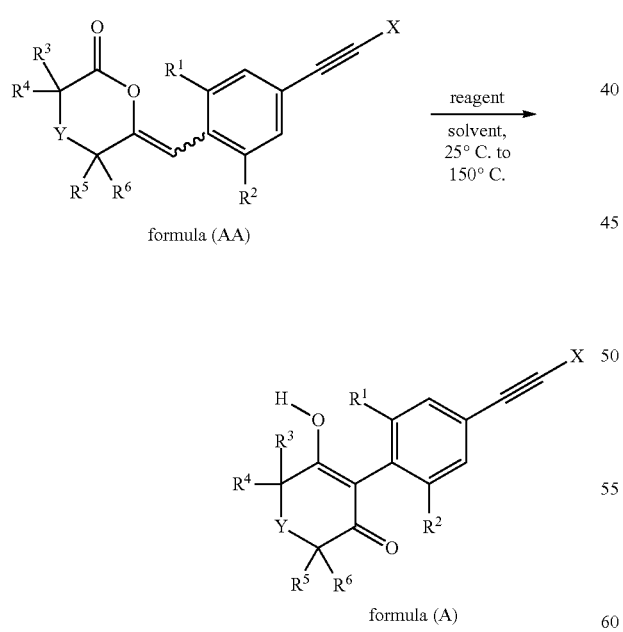

formula (AA)

formula (A)

In one approach a compound of formula (AA), wherein X is methyl, may be prepared from a compound of formula (AB) by treatment with a catalyst system which promotes lactonization (such as palladium(II) dichloride, gold(I) chloride or silver carbonate), preferably 0.001-50% silver carbonate with respect to compound of formula (AB), in the presence of a suitable solvent (for example acetonitrile) at a suitable temperature (typically 25° C. to 150° C.), and optionally under microwave irradiation. Similar lactonizations are known in the literature (see for example WO 2008/071405, P. Huang and W. Zhou, Tetrahedron Asymmetry (1991), 2 (9), 875-878; and H. Harkat, J-M. Weibel, P. Pale, Tetrahedron Letters (2006), 47(35), 6273-6276).

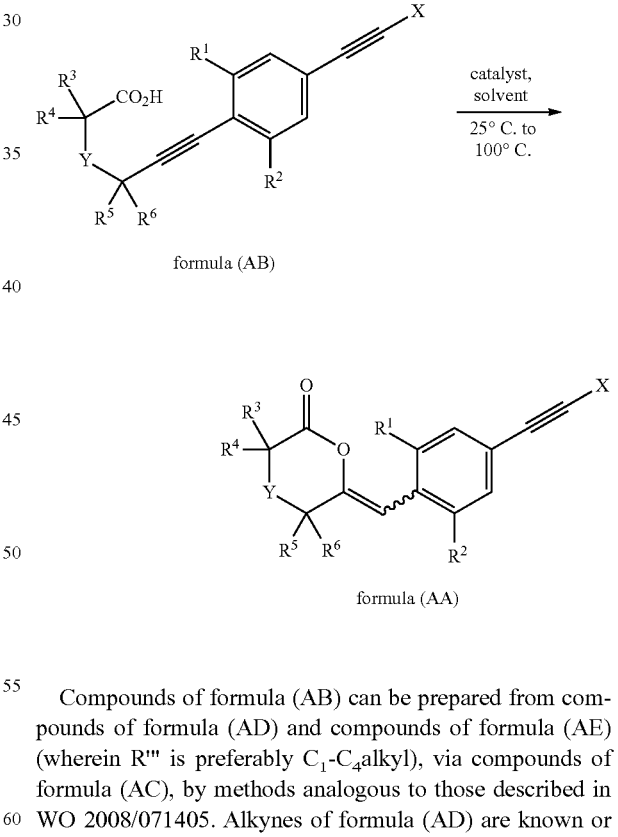

formula (AB)

formula (AA)

Compounds of formula (AB) can be prepared from compounds of formula (AD) and compounds of formula (AE) (wherein R''' is preferably $C_1$-$C_4$alkyl), via compounds of formula (AC), by methods analogous to those described in WO 2008/071405. Alkynes of formula (AD) are known or can be prepared by known methods (see for example WO 2008/071405 and references therein, and J. P. Burke, M. Sabat, D. A. Iovan, W. H. Myers, J. J. Chruma, Organic Letters (2010), 12(14), 3192-3195). Compounds of formula (AE) are either known compounds or can be prepared from known reagents using known methods.

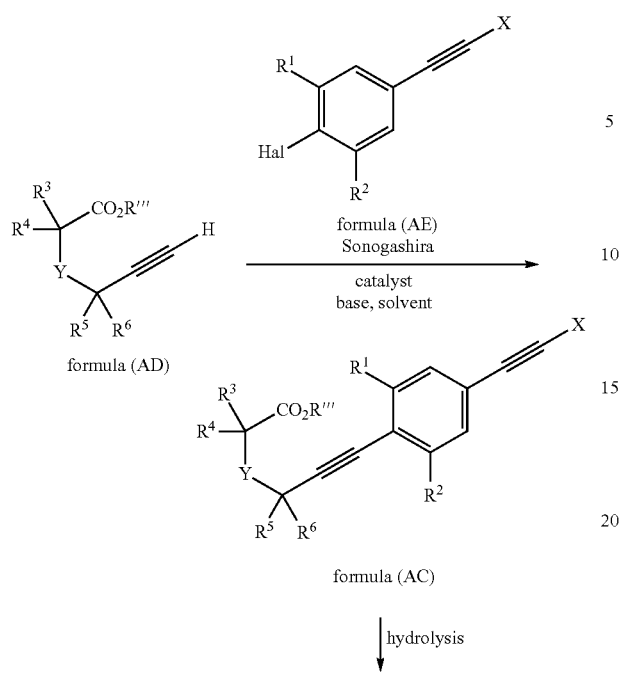

formula (AD)

formula (AE)
Sonogashira
catalyst
base, solvent formula (AC)

↓ hydrolysis

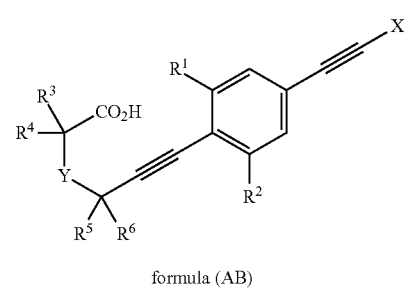

formula (AB)

A compound of formula (P), wherein R''' is $C_1$-$C_4$alkyl, can also be prepared using similar chemistry to that described previously, starting with a compound of formula (AD) and a compound of formula (AI) which are both known in the literature or can be prepared using known methods and known reagents.

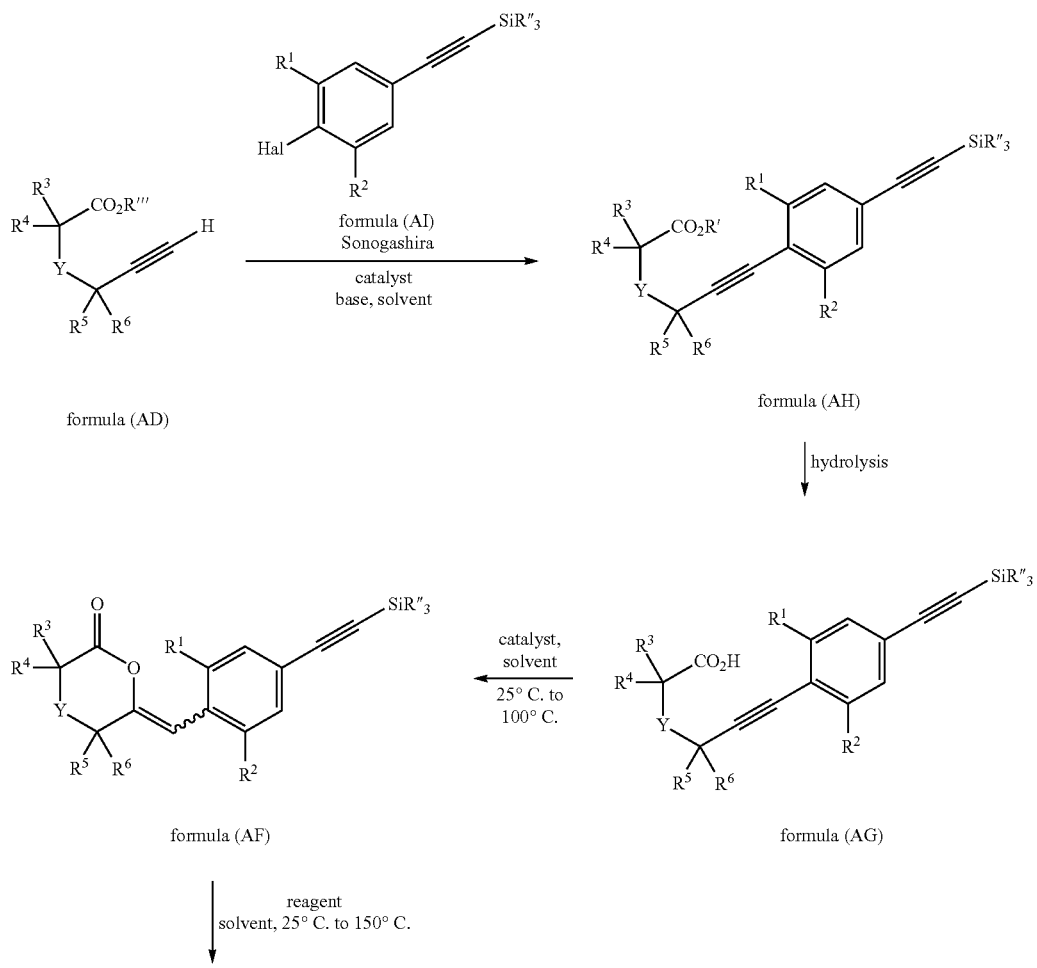

formula (AD)

formula (AI)
Sonogashira
catalyst
base, solvent formula (AH)

↓ hydrolysis formula (AF)

← catalyst, solvent
25° C. to 100° C.

formula (AG)

↓ reagent
solvent, 25° C. to 150° C.

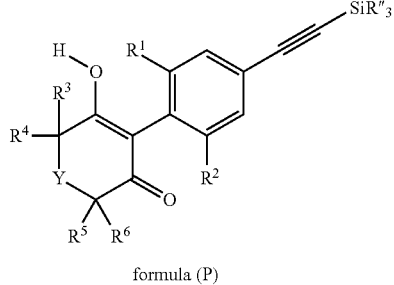
formula (P)
Similarly, a compound of formula (L) can be prepared from a compound of formula (AJ) using similar chemistry to that described previously.
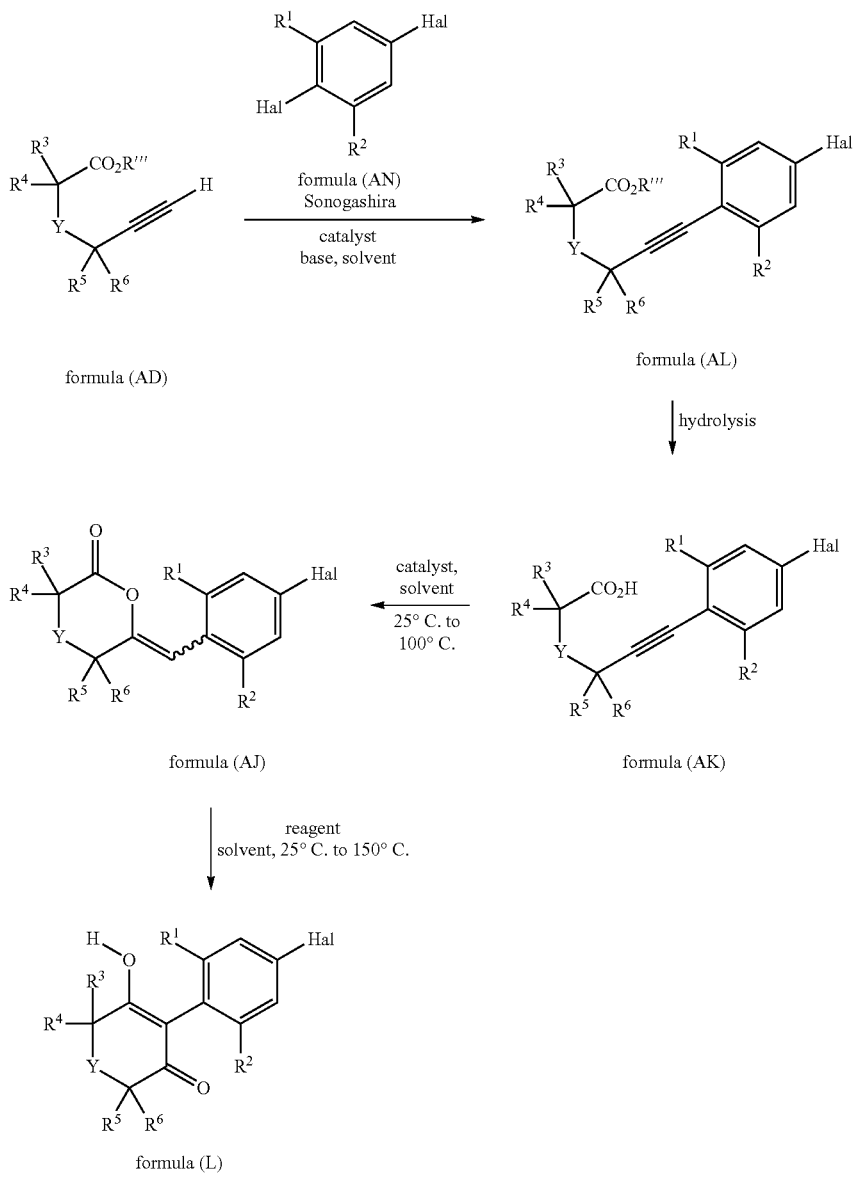

Similarly, a compound of formula (W) can be prepared from a compound of formula (AO) using similar chemistry to that described previously.

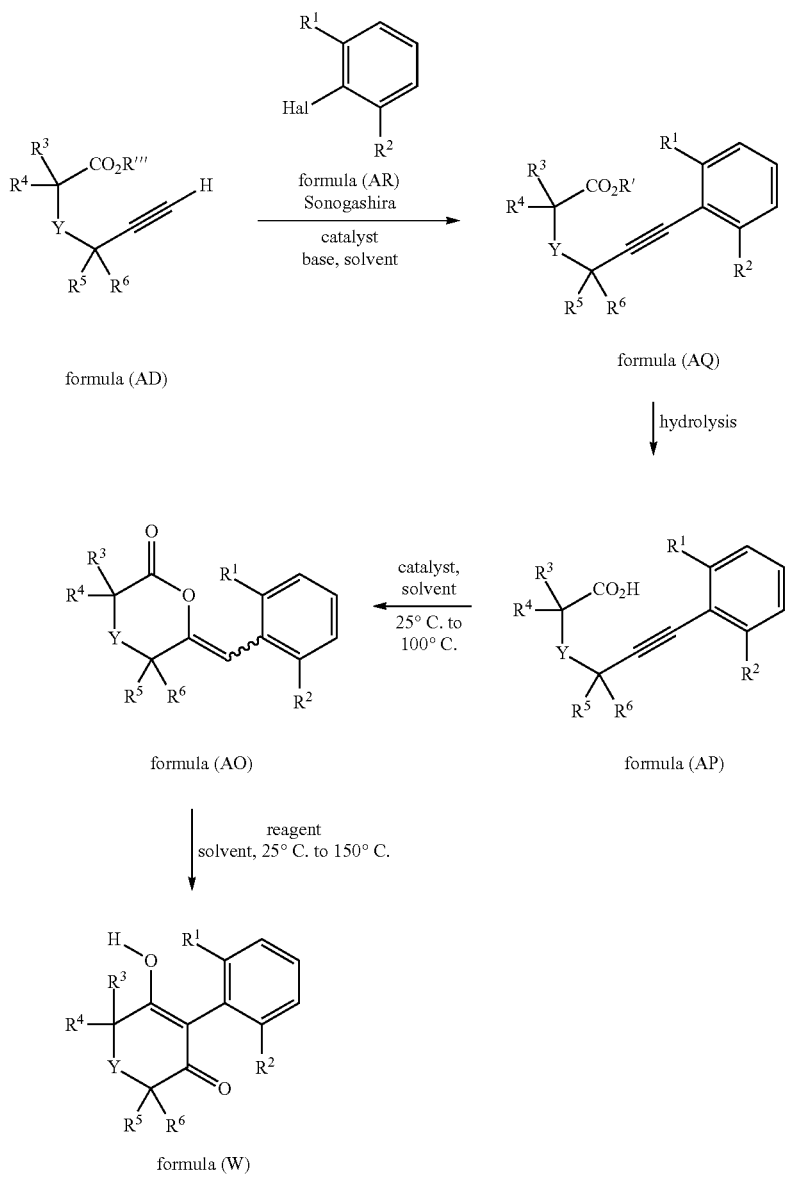

In a second approach a compound of formula (AA), wherein X is methyl, may be prepared via the Baeyer-Villiger oxidation of a compound of formula (AS), preferably in a suitable solvent and/or at a suitable temperature (e.g. from 0° C. to 100° C.), and optionally in the presence of a suitable catalyst system. Suitable oxidants include peracetic acid and hydrogen peroxide. Preferred conditions are hydrogen peroxide and catalytic selenium dioxide (0.001-25 mol %) in tert-butanol at a temperature of from 0° C. to 100° C., as described by J. A. Guzman, V. Mendoza, E. Garcia, C. F. Garibay, L. Z. Olivares, L. A. Maldonado, Synthetic Communications (1995), 25(14), 2121-33.

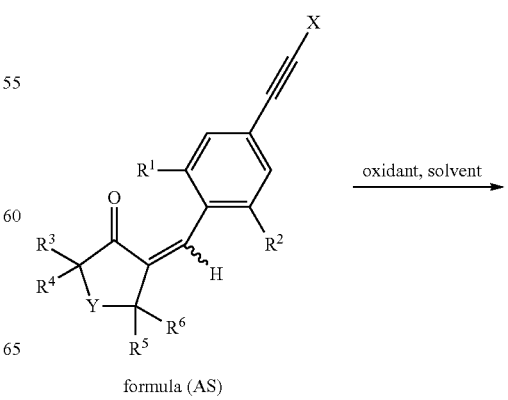

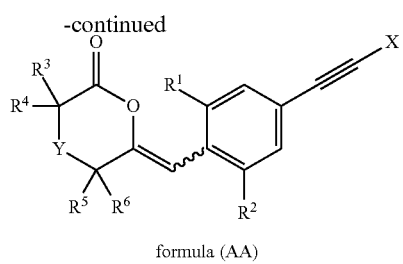

formula (AA)

A compound of formula (AS), wherein X is methyl, may be prepared from a compound of formula (AU) by condensation with a benzaldehyde of formula (AT), in the presence of a suitable base and optionally in the presence of a suitable solvent (for similar examples see WO 2010136431; A. Lagrange, S. Forestier, G. Lang and B. Luppi, EP368717 A1; D. C. Rowlands, U.S. Pat. No. 2,776,239; E. Tamate, Journal of the Chemical Society of Japan, (1957), 78, 1293-7; R. Hernandez, D. Melian, T. Prange, E. Suarez, Heterocycles (1995), 41(3), 439-54; and J. Sotiropoulos, N. El Batouti, A. M. Lamazouere, Journal of Heterocyclic Chemistry (1987), 24(4), 907-12).

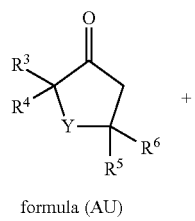

formula (AU)

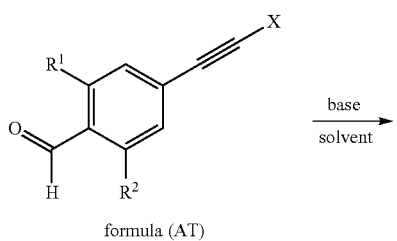

formula (AT)

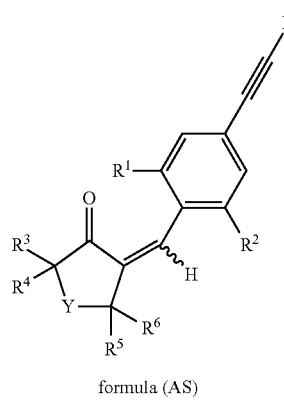

formula (AS)

Preferably the base is a metal hydroxide, such as sodium hydroxide or potassium hydroxide, metal alkoxide such as sodium methoxide, sodium ethoxide or potassium tert-butoxide, or metal amide such as sodium amide. Preferably the solvent is dimethoxyethane, dioxane, tetrahydrofuran, diethyl ether or an alkyl alcohol, such as methanol, ethanol or isopropanol.

Compounds of formula (AU), wherein Y is O and or $CR^8R^9$, are known compounds (see for example X. Ye, M. D. Johnson, T. Diao, M. H. Yates, S. S. Stahl, Green Chemistry (2010), 12(7), 1180-1186; M. Newman and W. Reichle, Org. Synth. Coll. Vol. V., (1973), 1024; Y. Zal'kind, E. Venus-Danilova and V. Ryabtseva, Russian Journal of General Chemistry, (1950), 20, 2222-9; M. Bertrand, J. Dulcere, G. Gil, J. Grimaldi and P. Sylvestre-Panthet, Tetrahedron Letters (1976), (18), 1507-8), or may be prepared from known compounds by known methods.

Compounds of formula (AU), wherein Y is C(O), are known compounds (see for example N. J. Turro, D. R. Morton, E. Hedaya, M. E. Kent, P. D'Angelo, P. Schissel, Tetrahedron Letters (1971), (27), 2535-8; P. A. Krapcho, D. R. Rao, M. P. Silvon, B. Abegaz, Journal of Organic Chemistry (1971), 36(25), 3885-90; S. N. Crane, T. J. Jenkins, D. J. Burnell, Journal of Organic Chemistry (1997), 62(25), 8722-8729; S. N. Crane, D. J. Burnell, Journal of Organic Chemistry (1998), 63(4), 1352-1355; S. N. Crane, D. J. Burnell, Journal of Organic Chemistry (1998), 63(16), 5708-5710; C. E. Elliott, D. O. Miller, D. J. Burnell, Journal of the Chemical Society, Perkin Transactions 1 (2002), (2), 217-226), or may be prepared from known compounds by known methods.

Compounds of formula (AU), wherein Y is S, S(O) or $S(O)_2$ are known compounds (see for example E. R. Buchman, H. Cohen, Journal of the American Chemical Society (1944), 66, 847-8; A. W. D. Avison, F. Bergel, J. W. Haworth, U.S. Pat. No. 2,408,519: K. G. Mason, M. A. Smith, E. S. Stern, EJ. A. Elvidge, Journal of the Chemical Society [Section]C: Organic (1967), (21), 2171-6; T. A. Magee, Thomas A. DE 2033454; I. Tabushi, Y. Tamaru, Z. Yoshida, T. Sugimoto, Journal of the American Chemical Society (1975), 97(10), 2886-91; P. E. Aldrich, G. H. Berezin, B. I. Dittmar, I. Bruce, DE 2516554; I. Tabushi, Y. Tamaru, Z. Yoshida, Bulletin of the Chemical Society of Japan (1978), 51(4), 1178-82; D. N. Reinhoudt, J. Geevers, W. P. Trompenaars, S. Harkema, G. J. Van Hummel, Journal of Organic Chemistry (1981), 46(2), 424-34; F. Duus, Synthesis (1985), (6-7), 672-4; J. Schatz, Science of Synthesis (2002), 9, 287-422), or may be prepared from known compounds by known methods.

A compound of formula (AT), wherein X is methyl, can be prepared from known compounds by known methods.

A compound of formula (P), wherein R" is $C_1$-$C_4$alkyl, can also be prepared from a compound of formula (AF), by rearrangement under conditions similar to those described for the conversion of a compound of formula (AA) to a compound of formula (A). A compound of formula (AW) is known, or can be prepared by known methods using known reagents.

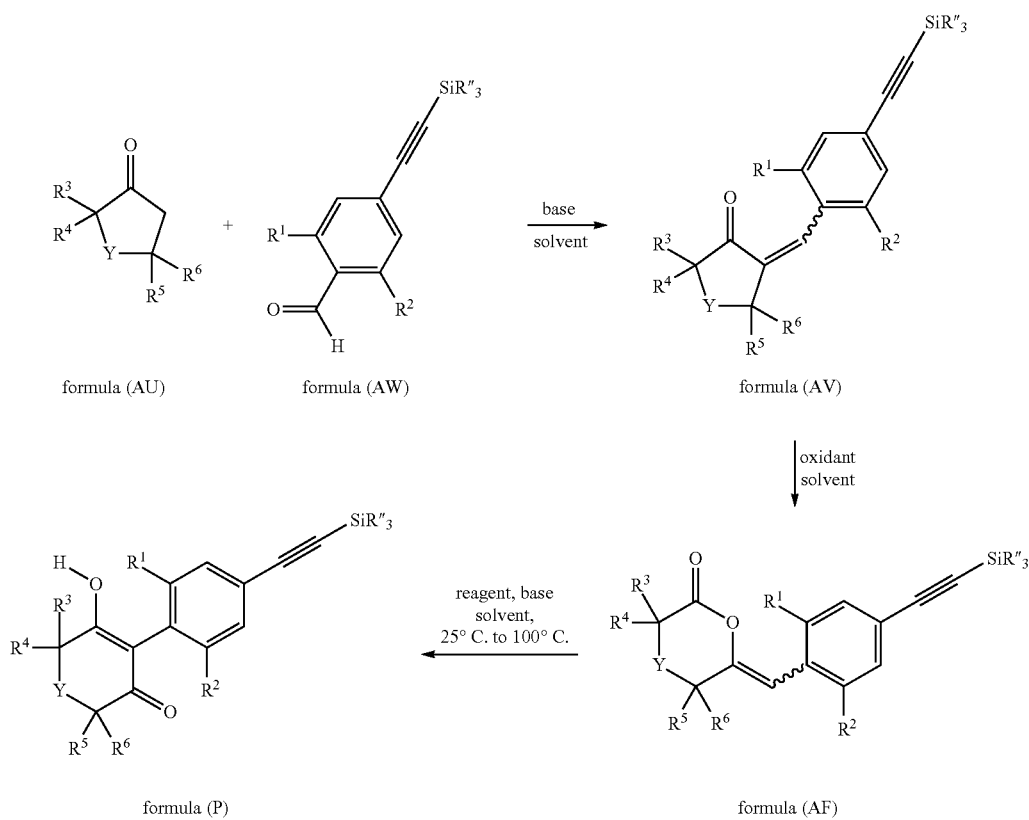
Similarly, a compound of formula (L) can also be prepared from a compound of formula (AJ) by rearrangement under similar conditions. Compounds of formula (AY) are known compounds, or can be prepared from known reagents using known methods.
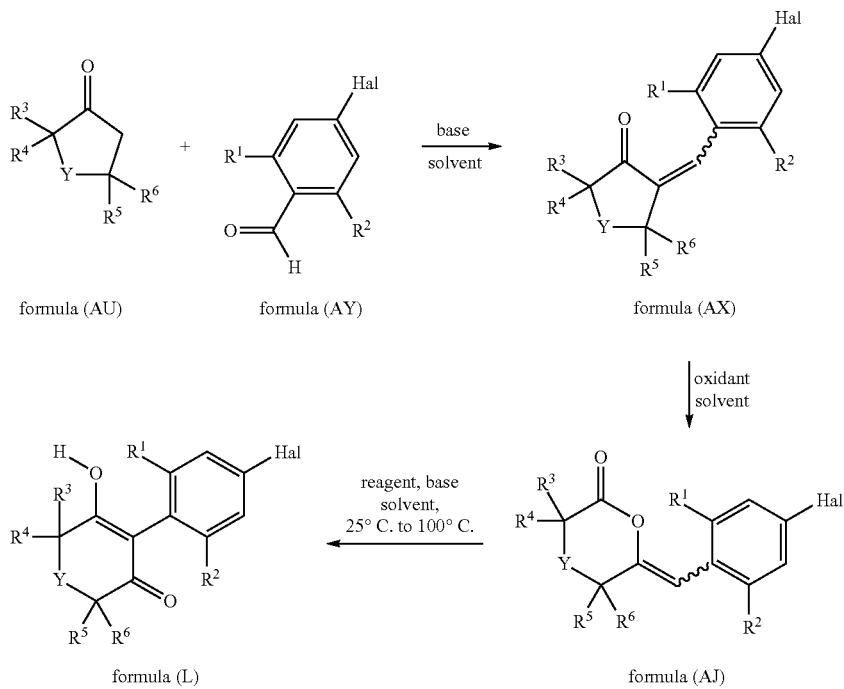

Similarly, a compound of formula (W) can also be prepared from a compound of formula (AO) by rearrangement under similar conditions. Compounds of formula (AAA) are known compounds, or can be prepared from known reagents using known methods.

For the rearrangement of (AAB) to (A), suitable acids include a Brönsted acid such as a mineral acid or an organic acid, for example sulfuric acid, hydrochloric acid, hydrogen chloride, p-toluenesulfonic acid, methanesulfonic acid, acetic acid or formic acid, or a Lewis acid such as a metal

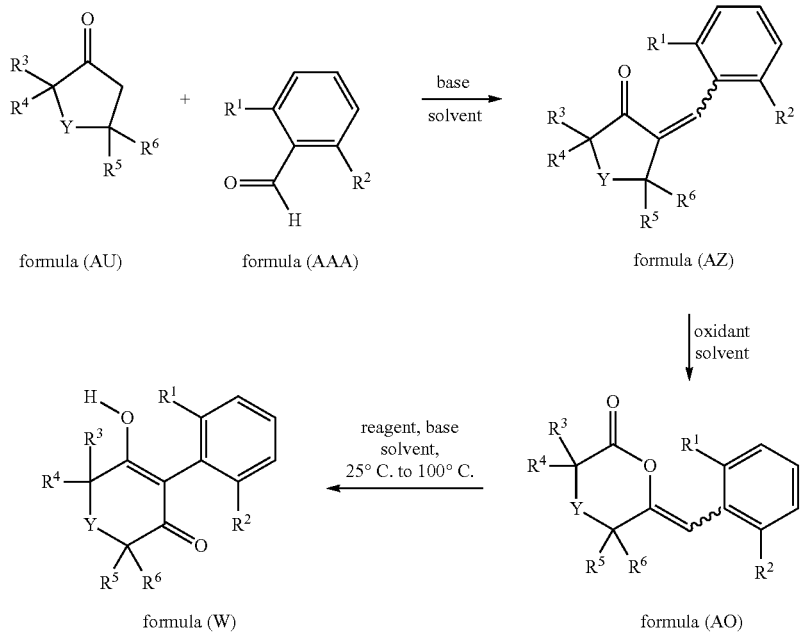

In a further approach, a compound of formula (A), wherein X is methyl, can be prepared by a rearrangement of an epoxide of formula (AAB) catalysed by the presence of an acid, e.g. in the presence of a suitable solvent.

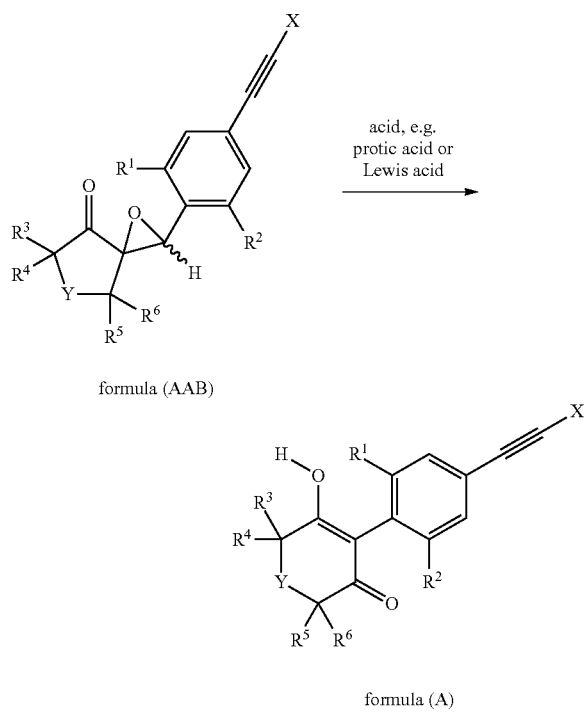

halide, for example boron trifluoride, aluminium chloride, iron chloride, tin(IV) chloride, zinc chloride, zinc bromide, or lithium perchlorate, or a metal triflate such as scandium triflate or ytterbium triflate. Mixtures of such acids can also be used. The conversion of a compound of formula (AAB) into a compound of formula (A) may be considered to be an example of a semi-Pinacol rearrangement (see for example WO 2010136431; M. Paulson, M. Daliya and C. Asokan, Synth. Commun. (2007), 37(5), 661-665; S. Sankararaman and J. Nesakumar, J. Chem. Soc, Perkin Trans. 1, (1999), (21), 3173-3175; K. Rehse and R. Bienfait, Archiv der Pharmazie, (1984), 317(5), 385-93; H. Kamath, A. Sahasrabudhe, B. Bapat and S. Kulkarni, Indian J. Chem., Section B: (1981), 20B(12), 1094-6; G. Buchanan and D. Jhaveri, J. Org. Chem. (1961), 26 4295-9; and H. House, Richard L. Wasson, J. Am. Chem. Soc., (1956), 78, 4394-400). For the rearrangement of (AAB) to (A), a suitable solvent is generally a solvent chosen to be compatible with the acid used, and include a chlorinated hydrocarbon, an alcohol, an ether, an aromatic solvent or an organic acid, for example dichloromethane, dichloroethane, diethyl ether, acetic acid, formic acid, toluene, benzene, methanol, ethanol, isopropanol or tetrahydrofuran. Preferably the reaction is performed using methanesulfonic acid in toluene at a temperature between 25° C. and 150° C.

A compound of formula (AAB) can be prepared by the epoxidation of a compound of formula (AS). Epoxidation may be effected by treatment of a compound of formula (AS) with a suitable oxidising agent such as an organic peroxide or metal hyperchlorite, for example dimethyldioxirane, sodium hypochlorite, hydrogen peroxide, tert-butyl peroxide or trifluoroperacetic acid, optionally in combination with a suitable base (such as an alkali metal hydroxide or carbonate, alkaline earth metal hydroxide or carbonate, or an amine base such as 1,8-diazabicyclo[5.4.0]-undec-7-ene), optionally in a suitable solvent (such as an alcohol or halogenated hydrocarbon, for example methanol, ethanol or dichloromethane) and at a suitable temperature. The reaction can also be performed under biphasic conditions, in which a phase-transfer reagent is also typically used in 0.001-50 mol %. The phase transfer reagent is preferably a quaternary ammonium salt, a crown ether, a polyethylene glycol, or phosphonium salt. Similar reactions are known in the literature (see for example WO 2010136431; I. K. Korobitsyna, O. P. Studzinskii, The Russian Journal of Organic Chemistry (1969), 5(8), 1493-5; A. Halasz, Z. Jambor, A. Levai, C. Nemes, T. Patonay and G. Toth, J. Chem. Soc, Perkin Trans. 1, (1996), (4), 395-400; N. Yousif, F. Gad, A. Fahmy, M. Amine and H. Sayed, Phosphorus, Sulfur and Silicon and the Related Elements (1996), 117, 11-19; T. Ooi, D. Ohara, M. Tamura and K. Maruoka, J. Am. Chem. Soc., (2004), 126(22), 6844-6845; A. Amr, H. Hayam and M. Abdulla, Archiv der Pharmazie, (2005), 338(9), 433-440; K. Drauz, S. M. Roberts, T. Geller and A. Dhanda, U.S. Pat. No. 6,538,105 B1; and L. S. Chagonda and B. A. Marples, J. Chem. Soc. Perkin 1, 1988, 875-879). Preferably, epoxidation is carried out using hydrogen peroxide and a metal hydroxide (especially lithium hydroxide or sodium hydroxide), in methanol at a temperature of between −10° C. and 60° C.

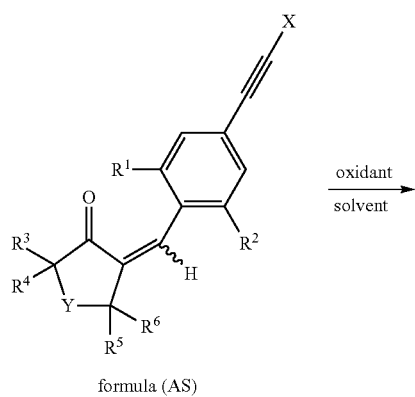

formula (AS)

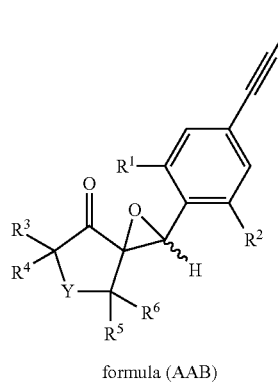

formula (AAB)

Alternatively a compound of formula (AAB), wherein X is methyl, may be prepared by reacting a compound of formula (AAC) (wherein halogen is chlorine, bromine or iodine, preferably chlorine or bromine) with a compound of formula (AT), in the presence of a suitable base, optionally in a suitable solvent, at a suitable temperature.

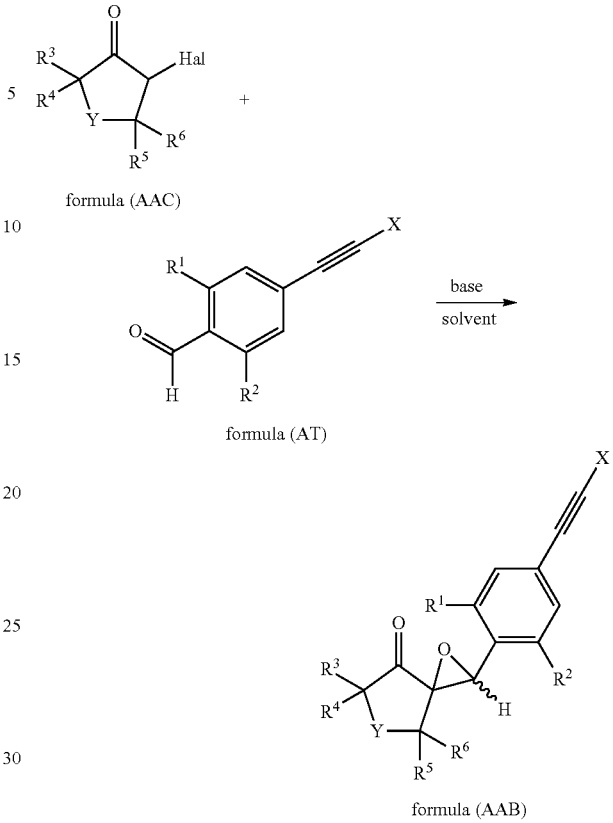

formula (AAC)

formula (AT)

formula (AAB)

Suitable bases include alkali or alkali earth metal hydroxides (such as sodium hydroxide, lithium hydroxide or potassium hydroxide), alkali or alkali earth metal alkoxides (such as sodium methoxide, sodium ethoxide, potassium tert-butoxide or sodium tert-butoxide), alkali or alkali earth metal carbonates (such as potassium carbonate or sodium carbonate, or sodium bicarbonate), metal amides (such as lithium diisopropylamide, lithium hexamethyldisilazide or lithium 2,2,6,6-tetramethylpiperidide), organometallics (such as butyl lithium or ethylmagnesium bromide) or metal hydrides (such as sodium hydride or potassium hydride). Suitable solvents include chlorinated hydrocarbons, ethers, alcohols, aromatics and various polar aprotic solvents, for example 1,2-dimethoxyethane, tetrahydrofuran, 1,4-dioxane, diethyl ether, dibutyl ether, dichloromethane, dichloroethane, acetonitrile, dimethyl sulfoxide, N, N-dimethylformamide, benzene, toluene, methanol, ethanol, isopropanol or tert-butanol, and is chosen to be compatible with the base under the reaction conditions. The reaction can also be performed under biphasic conditions, in which a phase-transfer reagent is also typically used in 0.001-50 mol %. The phase transfer reagent is preferably a quaternary ammonium salt, a crown ether, a polyethylene glycol, or phosphonium salt. Most preferably the reaction is performed using lithium diisopropylamide in tetrahydrofuran at a temperature range of −100° C. to 60° C. The conversion of a compound of formula (AAC) into a compound of formula (AAB) may be considered to be an example of a Darzens condensation (see for example WO 2010136431; W. N. Wassef, M. M. El-Barky, Journal of Chemical Research, Synopses (1990), (12), 402-3; J. Li, X. Liu, X. Li, Youji Huaxue (2007), 27(11), 1428-1431; Y. Tong, Y. Cheng, X. Guo, S. Wu, Hecheng Huaxue (2007), 15(1), 102-104; C.

Parmenon, J. Guillard, D. Caignard, N. Hennuyer, B. Staels, V. Audinot-Bouchez, J. Boutin, C. Dacquet, A. Ktorza, M. Viaud-Massuard, Bioorganic & Medicinal Chemistry Letters (2008), 18(5), 1617-1622; H. Xiao, X. Han, J. Xiong, Faming Zhuanli Shenqing Gongkai Shuomingshu (2007), p 11; J. M. Concellon, E. Bardales, R. Llavona, Journal of Organic Chemistry (2003), 68(4), 1585-1588).

Compounds of formula (AAC), wherein Y is O or $CR^8R^9$ are either known compounds (see for example WO 2010136431; B. Sreedhar, P. S. Reddy, M. Madhavi, Synthetic Communications (2007), 37(23), 4149-4156; R. R. Agarwal, S. S. Deshapande, Journal of the Indian Chemical Society (1949), 26, 483-6; H. Richet, R. Dulou, R., G. Dupont, Bulletin de la Societe Chimique de France (1947), 693-9; H. Richet, Ann. Chim. [12](1948), 3 317-54; I. K. Korobitsyna, Yu. K. Yur'ev, Yu. A. Cheburkov, E. M. Lukina, Russian Journal of General Chemistry (1955), 25, 734-8; I. K. Korobitsyna, Yu. K. Yur'ev, Yu. A. Cheburkov, E. M. Lukina, Russian Journal of General Chemistry (1955), 25, 690-702; F. Leonard, A. Wajngurt, H. Horn, Journal of Organic Chemistry (1956), 21, 1400-4; I. K. Korobitsyna, I. G. Zhukova, V. A. Kuvshinova, N. N. Gaidamovich, Yu. K. Yur'ev, Doklady Akademii Nauk SSSR (1957), 114, 327-30; I. K. Korobitsyna, I. G. Zhukova, I. G, Yu. K. Yur'ev, Russian Journal of General Chemistry (1959), 29, 2190-6; I. K. Korobitsyna, L. L. Rodina, L. M. Stashkova, Chemistry of Heterocyclic Compounds (1966), (6), 843-7; G. Hoehne, F. Marschner, K. Praefcke, P. Weyerstahl, Chem. Ber. (1975), 108(2), 673-82; H. Saimoto, T. Hiyama, H. Nozaki, Bull. Chem. Soc. Jpn., (1983), 56(10), 3078-87; A. M. Zvonok, N. M. Kuz'menok, I. G. Tishchenko, L. S. Stanishevskii, Russian Journal of General Chemistry (1985), 21(6), 1330-4) or can be prepared from compounds of formula (AU) under known conditions.

Compounds of formula (AAC), wherein Y is S, S(O) and $S(O)_2$, are either known compounds (see for example M. Polievka, L. Uhlar, V. Patek, Petrochemia (1973), 13(5-6), 156-60; N. N. Novitskaya, B. V. Flekhter, G. M. Prokhorov, A. S. Lukmanova, G. A. Tolstikov, G. V. Leplyanin, S. A. Lange, M. V. Strashnov, SU 468920 A1; P. H. McCabe, W. Routledge, Tetrahedron Letters (1976), (1), 85-6; T. S. Chou, C. Y. Tsai, Tetrahedron Letters (1992), 33(29), 4201-4), or can be prepared from compounds of formula (AU) under known conditions. Compounds of formula (AAC), wherein Y is C(O), can be prepared from compounds of formula (AU) under similar halogenation conditions.

Compounds of formula (P), wherein R" is $C_1$-$C_4$alkyl, can also be prepared from compounds of formula (AAD), using similar procedures and conditions described previously. Compounds of formula (AAD) can either be prepared from compounds of formula (AU) and (AW), via compounds of formula (AV), or from compounds of formula (AAC) and (AW).

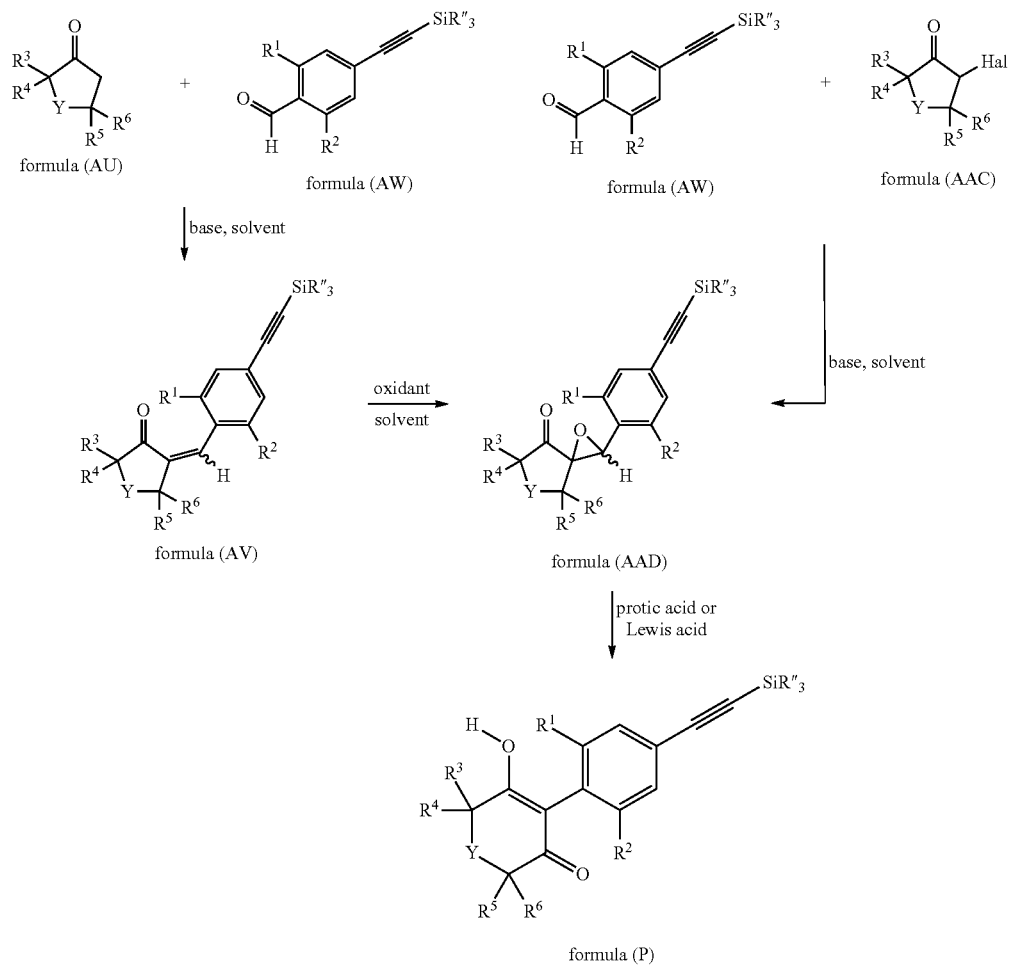

Similarly, a compound of formula (L) can also be prepared from a compound of formula (AAE). A compound of formula (AY) is known in the literature or can be prepared from known reagents using known methods.
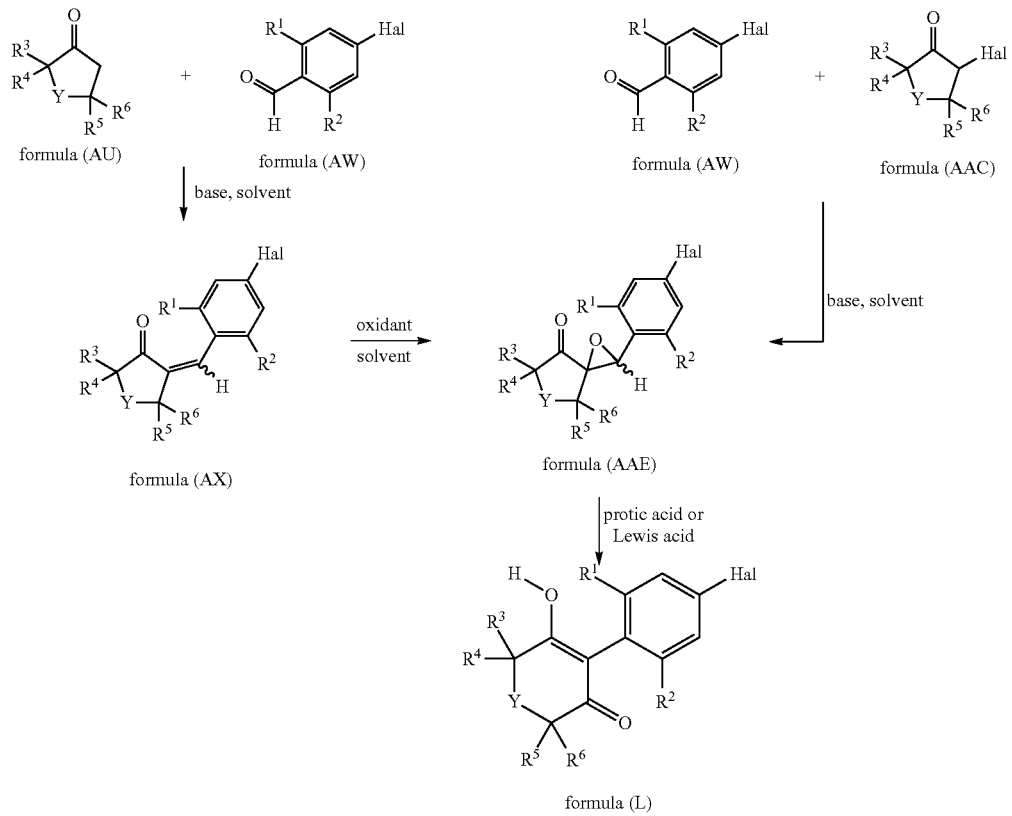
Similarly, a compound of formula (W) can also be prepared from a compound of formula (AAF), which can be prepared using similar chemistry to that described previously.
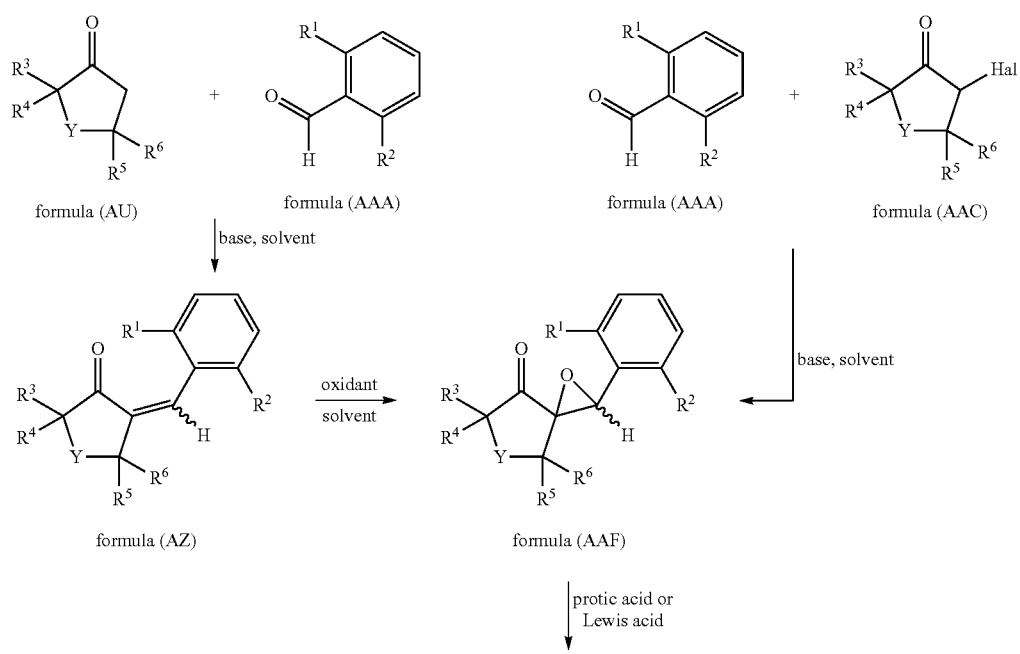

-continued

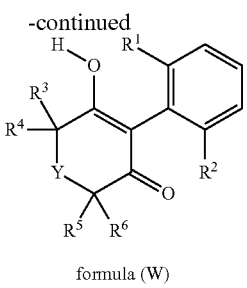

formula (W)

In a further approach, a compound of formula (A), wherein X is methyl, may be prepared by reacting a compound of formula (AAH) with a with an aryllead tricarboxylate, in the presence of a suitable ligand and in a suitable solvent. Similar reactions are described in the literature (see for example M. Muehlebach et al., WO08/071405; J. Pinhey, B. Rowe, Aust. J. Chem., (1979), 32, 1561-6; J. Morgan, J. Pinhey, J. Chem. Soc. Perkin Trans. 1, (1990), 3, 715-20). Preferably the aryllead tricarboxylate is an aryllead triacetate of formula (AAG). Preferably the ligand is a nitrogen containing heterocycle such as N,N-dimethylaminopyridine, 1,10-phenanthroline pyridine, bipyridine, or imidazole, and one to ten equivalents of ligand with respect to a compound of formula (AAG) is preferably used. Most preferably the ligand is N,N-dimethylaminopyridine. The solvent is preferably chloroform, dichloromethane or toluene, most preferably chloroform, or a mixture of chloroform and toluene. Preferably the reaction is conducted at a temperature of $-10°$ C. to $100°$ C., most preferably at $40\text{-}90°$ C.).

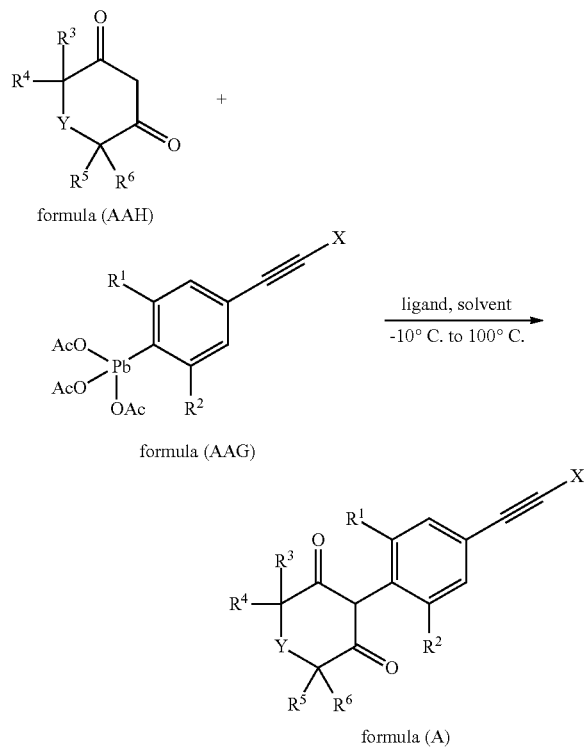

Compounds of formula (AAH), wherein Y is O, are known compounds or may be prepared by routes analogous to those described in the literature (see, for example, M. Muehlebach et al., WO08/071405; M. Morgan and E. Heyningen, J. Am. Chem Soc., (1957), 79, 422-424; I. Korobitsyna and K. Pivnitskii, Russian Journal of General Chemistry, (1960), 30, 4016-4023; T. Terasawa, and T. Okada, J. Org. Chem., (1977), 42 (7), 1163-1169; R. Anderson et al. U.S. Pat. No. 5,089,046; R. Altenbach, K. Agrios, I. Drizin and W. Carroll, Synth. Commun., (2004), 34 (4) 557-565; R. Beaudegnies et al., WO2005/123667; W. Li, G. Wayne, J. Lallaman, S. Chang, and S. Wittenberger, J. Org. Chem. (2006), 71, 1725-1727; R. Altenbach, M. Brune, S. Buckner, M. Coghlan, A. Daza, A. Fabiyi, M. Gopalakrishnan, R. Henry, A. Khilevich, M. Kort, I. Milicic, V. Scott, J. Smith, K. Whiteaker, and W. Carroll, J. Med. Chem, (2006), 49(23), 6869-6887; Carroll et al., WO 2001/083484 A1; J. K. Crandall, W. W. Conover, J. Org. Chem. (1978), 43(18), 3533-5; I. K. Korobitsyna, O. P. Studzinskii, Chemistry of Heterocyclic Compounds (1966), (6), 848-854).

Compounds of formula (AAH), wherein Y is S, are known compounds or may be prepared by routes analogous to those described in the literature (see, for example, E. Fehnel and A. Paul, J. Am. Chem Soc., (1955), 77, 4241-4244; E. Er and P. Margaretha, Helvetica Chimica Acta (1992), 75(7), 2265-69; H. Gayer et al., DE 3318648 A1).

Compounds of formula (AAH), wherein Y is C(O), are known compounds or may be prepared by routes analogous to those described in the literature (see, for example, R. Götz and N. Götz, WO2001/060776 R. Götz et al. WO 2000/075095; M. Benbakkar et al., Synth. Commun. (1989) 19(18) 3241-3247; A. Jain and T. Seshadri, Proc. Indian Acad. Sci. Sect. A, (1955), 42, 279); N. Ahmad et al., J. Org. Chem., (2007), 72(13), 4803-4815); F. Effenberger et al., Chem. Ber., (1986), 119, 3394-3404 and references therein).

Compounds of formula (AAH), wherein Y is $CR^8R^9$ are known compounds of may be prepared by routes analogous to those described in the literature (see for example, M. Muehlebach et al., WO08/110307; M. Muehlebach et al., WO08/110308; S. Spessard and B. Stoltz, Organic Letters, (2002), Vol. 4, No. 11, 1943-1946; F. Effenberger et al., Chem. Ber., (1984), 117, 3280-3296; W. Childers et al., Tetrahedron Lett., (2006), 2217-2218; W. Childers et al., US2006/0004108; H. Schneider and C. Luethy, EP1352890; D. Jackson, A. Edmunds, M. Bowden and B. Brockbank, WO2005/105745 and WO2005/105717; R. Beaudegnies, C. Luethy, A. Edmunds, J. Schaetzer and S. Wendeborn, WO2005/123667; J-C. Beloeil, J-Y. Lallemand, T. Prange, Tetrahedron, (1986), Vol. 42. No. 13, 3491-3502; G. Stork and R. Danheiser, J. Org. Chem., (1973), 38 (9), 1775-1776; H. Favre et al., Can. J. Chem. (1956), 34 1329-39; R. Shriner and H. Todd, Org. Synth. Coll. Vol. II, (1943), 200-202).

A compound of formula (AAI), wherein X is methyl, may be prepared from a compound of formula (AAJ) by treatment with lead tetraacetate in a suitable solvent (for example chloroform) at 25° C. to 100° C. (preferably 25-50° C.), and optionally in the presence of a catalyst such as mercury diacetate, according to procedures described in the literature (for example see, K. Shimi, G. Boyer, J-P. Finet and J-P. Galy, Letters in Organic Chemistry, (2005), 2, 407-409; J. Morgan and J. Pinhey, J. Chem. Soc. Perkin Trans. 1; (1990), 3, 715-720).

under acidic conditions. Alternatively the same overall transformation of compound (AE) to compound (AAJ), wherein X is methyl, may be achieved through a palladium-catalysed borylation reaction under known conditions using known reagents (see for example T. Ishiyama, M. Murata, N. Miyaura, J. Org. Chem. (1995), 60, 7508-7501; and K. L. Billingsley, T. E. Barder, S. L. Buchwald, Angew. Chem. Int. Ed. (2007), 46, 5359-5363), followed by hydrolysis of the intermediate boronate ester.

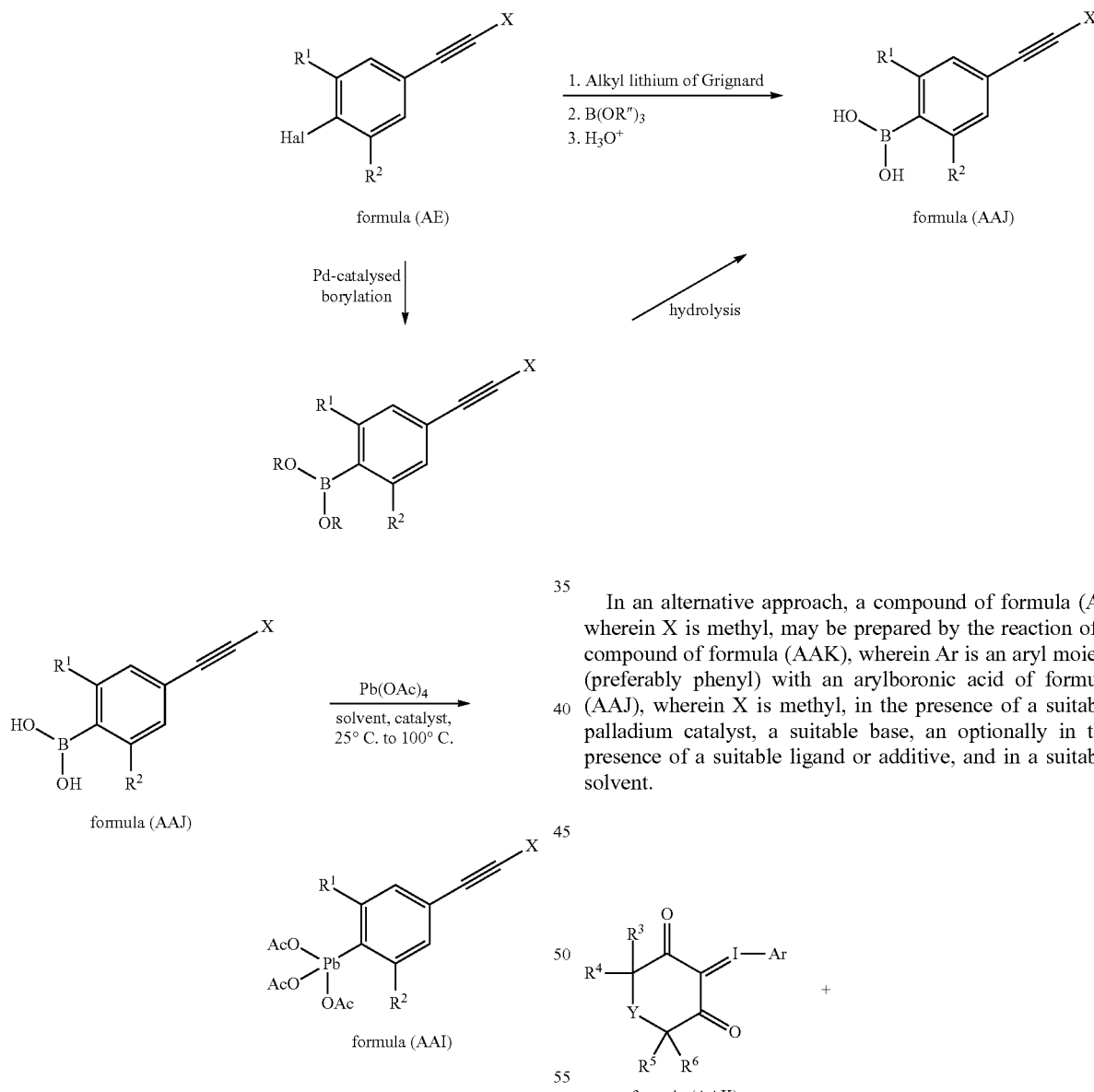

In an alternative approach, a compound of formula (A), wherein X is methyl, may be prepared by the reaction of a compound of formula (AAK), wherein Ar is an aryl moiety (preferably phenyl) with an arylboronic acid of formula (AAJ), wherein X is methyl, in the presence of a suitable palladium catalyst, a suitable base, an optionally in the presence of a suitable ligand or additive, and in a suitable solvent.

An aryl boronic acid of formula (AAJ), wherein X is methyl, may be prepared from an aryl halide of formula (AE), wherein Hal is bromine or iodine by known methods (see, for example, W. Thompson and J. Gaudino, J. Org. Chem, (1984), 49, 5237-5243 and R. Hawkins et al., J. Am. Chem. Soc., (1960), 82, 3053-3059). Thus an aryl halide of formula (AE) may be treated with an alkyl lithium or alkyl magnesium halide at low temperature, and the aryl magnesium or aryl lithium reagent obtained is allowed to react with a trialkyl borate, B(OR″)₃, preferably trimethylborate, to give an aryl dialkylboronate which may be hydrolysed to the desired boronic acid of formula (AAJ), where X is methyl,

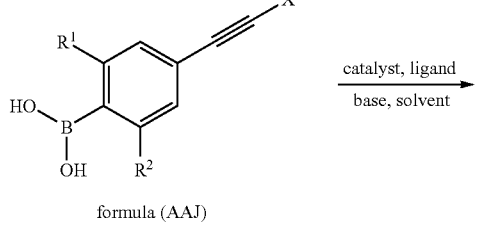

-continued

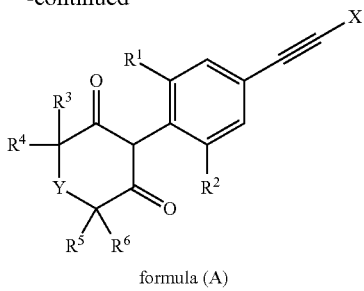

formula (A)

Suitable palladium catalysts include, for example palladium(II) dihalides, palladium(II) acetate and palladium(II) sulfate, and is preferably palladium(II) acetate. Suitable ligands include triphenylphosphine, tricyclopentylphosphine, tricyclohexylphosphine, 2-dicyclo-hexylphosphino-2',6'-dimethoxybiphenyl, 2-dicyclohexylphosphino-2',4',6'-triisopropyl-biphenyl, 1,1'-bis(diphenylphosphino)ferrocene and 1,2-bis(diphenylphosphino)ethane. The reaction may also be carried out in the presence of other additives, such as tetralkylammonium salts, for example, tetrabutylammonium bromide. Suitable bases include alkali metal hydroxides, especially lithium hydroxide. A suitable solvent is aqueous 1,2-dimethoxyethane.

A compound of formula (AAK), wherein Ar is phenyl, may be prepared from a compound of formula (AAH) by treatment with a hypervalent iodine reagent such as a (diacetoxy)iodobenzene or iodosylbenzene and a base such as aqueous sodium carbonate, lithium hydroxide or sodium hydroxide in a solvent such as water or an aqueous alcohol such as aqueous ethanol according to the procedures of K. Schank and C. Lick, Synthesis (1983), 392; R. Moriarty et al, J. Am. Chem. Soc, (1985), 107, 1375, or of Z. Yang et al., Org. Lett., (2002), 4 (19), 3333:

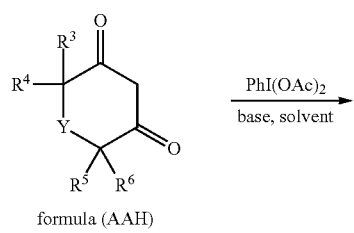

formula (AAH)

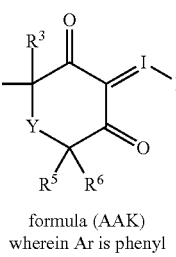

formula (AAK)
wherein Ar is phenyl

In a further approach, a compound of formula I, wherein X is methyl, may be prepared by reacting a compound of formula (AAL) (wherein G is preferably $C_{1-4}$ alkyl, and Hal is a halogen, preferably bromine or iodine), with an arylboronic acid of formula (AAJ) in the presence of a suitable palladium catalyst (for example 0.001-50% palladium(II) acetate with respect to compound (AAL)) and a base (for example 1 to 10 equivalents potassium phosphate with respect to compound (AAL)) and preferably in the presence of a suitable ligand (for example 0.001-50% (2-dicyclohexylphosphino)-2',6'-dimethoxybiphenyl with respect to compound (AAL)), and in a suitable solvent (for example toluene), preferably between 25° C. and 200° C. Similar couplings are known in the literature (see for example, Y. Song, B. Kim and J.-N. Heo, Tetrahedron Letters (2005), 46 (36), 5987-5990). A compound of formula I, wherein X is preferably methyl, can be converted to a compound of formula (A) by hydrolysis of the enol ether under known conditions.

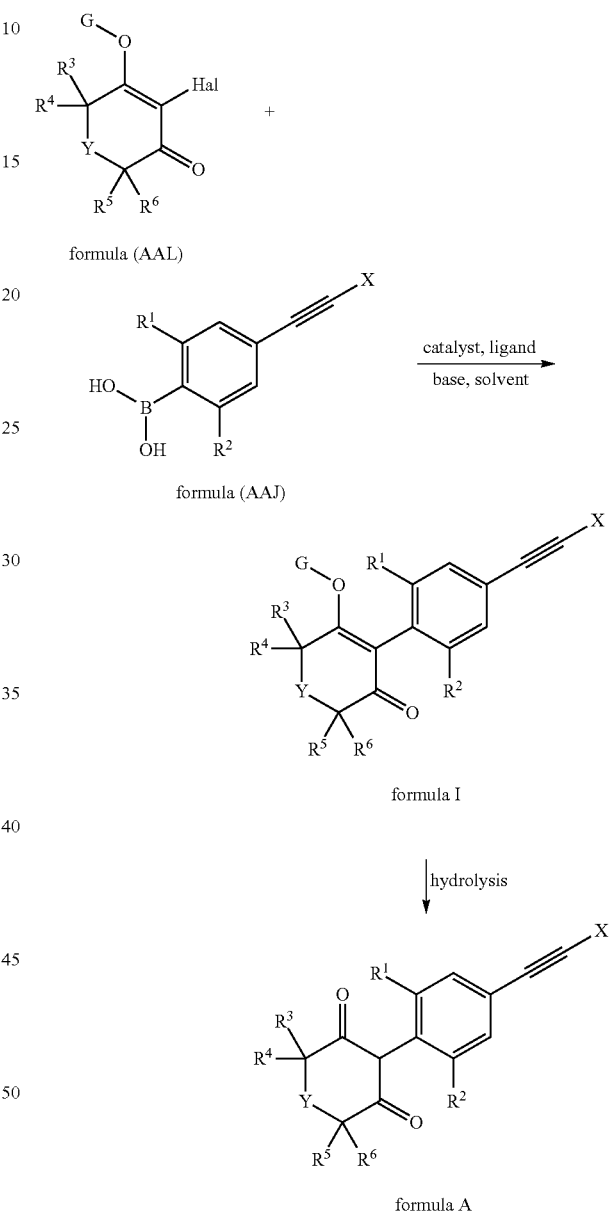

A compound of formula (AAL) may be prepared by halogenating a compound of formula (AAH), followed by reaction of the resulting halide of formula (AAN) with a $C_1$-$C_4$ alkyl halide or tri-$C_1$-$C_4$-alkylorthoformate under known conditions, for example by the procedures of R. Shepherd and A. White (J. Chem. Soc. Perkin Trans. 1 (1987), 2153-2155) and Y.-L. Lin et al. (Bioorg. Med. Chem. (2002), 10, 685-690). Alternatively, a compound of formula (AAL) may be prepared by reacting a compound of formula (AAH) with a $C_1$-$C_4$ alkyl halide or a tri-$C_1$-$C_4$-alkylorthoformate, and halogenating the resulting enol ether of formula (AAM) under known conditions (see for example Y. Song, B. Kim and J.-N. Heo, Tetrahedron Letters (2005), 46(36), 5987-5990).

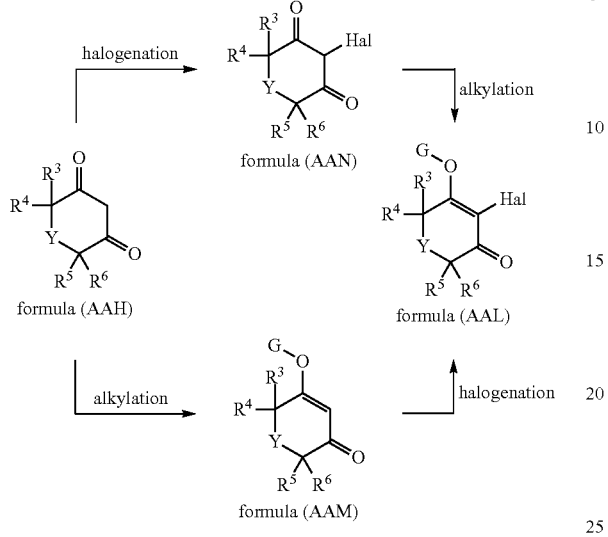

In a further approach, a compound of formula (A), wherein X is methyl, may be prepared by reacting a compound of formula (AAH) with a compound of formula (AE) in the presence of a suitable palladium catalyst (for example 0.001-50% palladium(II) acetate with respect to compound (AAH)) and a base (for example 1 to 10 equivalents potassium phosphate with respect to compound (AAH)) and preferably in the presence of a suitable ligand (for example 0.001-50% (2-dicyclohexylphosphino)-2',4',6'-triisopropylbiphenyl with respect to compound (AAH)), and in a suitable solvent (for example dioxane), preferably between 25° C. and 200° C. and optionally under microwave heating.

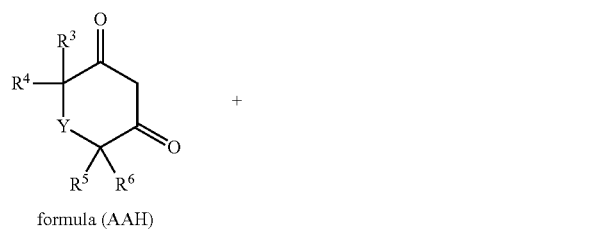

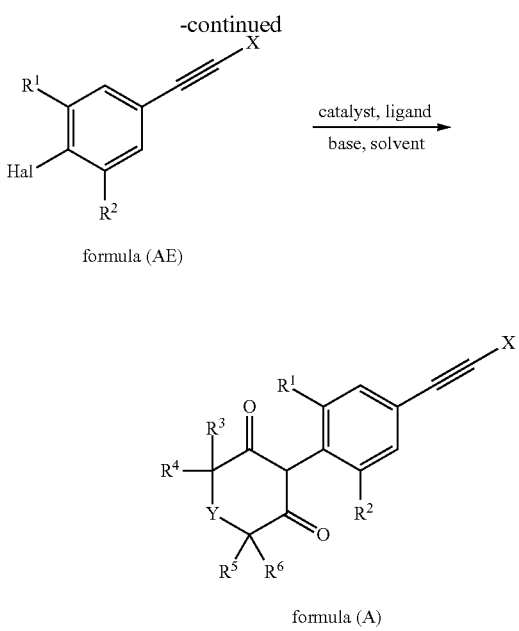

Similar couplings are known in the literature (see for example, S. Buchwald et al., J. Am. Chem. Soc. (2000), 122, 1360-1370; B. Hong et al. WO 2005/000233). Alternatively, a compound of formula (A) may be prepared by reacting a compound of formula (AAH) with a compound of formula (AE) in the presence of a suitable copper catalyst (for example 0.001-50% copper(I) iodide with respect to compound (AAH)) and a base (for example 1 to 10 equivalents cesium carbonate with respect to compound (AAH)) and preferably in the presence of a suitable ligand (for example 0.001-50% L-proline with respect to compound (AAH)), and in a suitable solvent (for example dimethylsulfoxide), preferably between 25° C. and 200° C. Similar couplings are known in the literature (see for example, Y. Jiang et al., Synlett, (2005), 18, 2731-2734, and X. Xie et al., Organic Letters (2005), 7(21), 4693-4695).

A compound of formula (P), wherein R" is $C_1$-$C_4$alkyl, can also be prepared using using similar methods described previously, starting from silylated precursors (AAO), (AAP) and (AAI). Compounds (AAO), (AAP) and (AAI) are known compounds, or can be prepared using similar methods to those described previously.

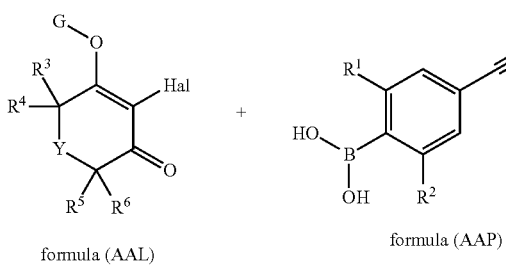

catalyst, ligand
base, solvent

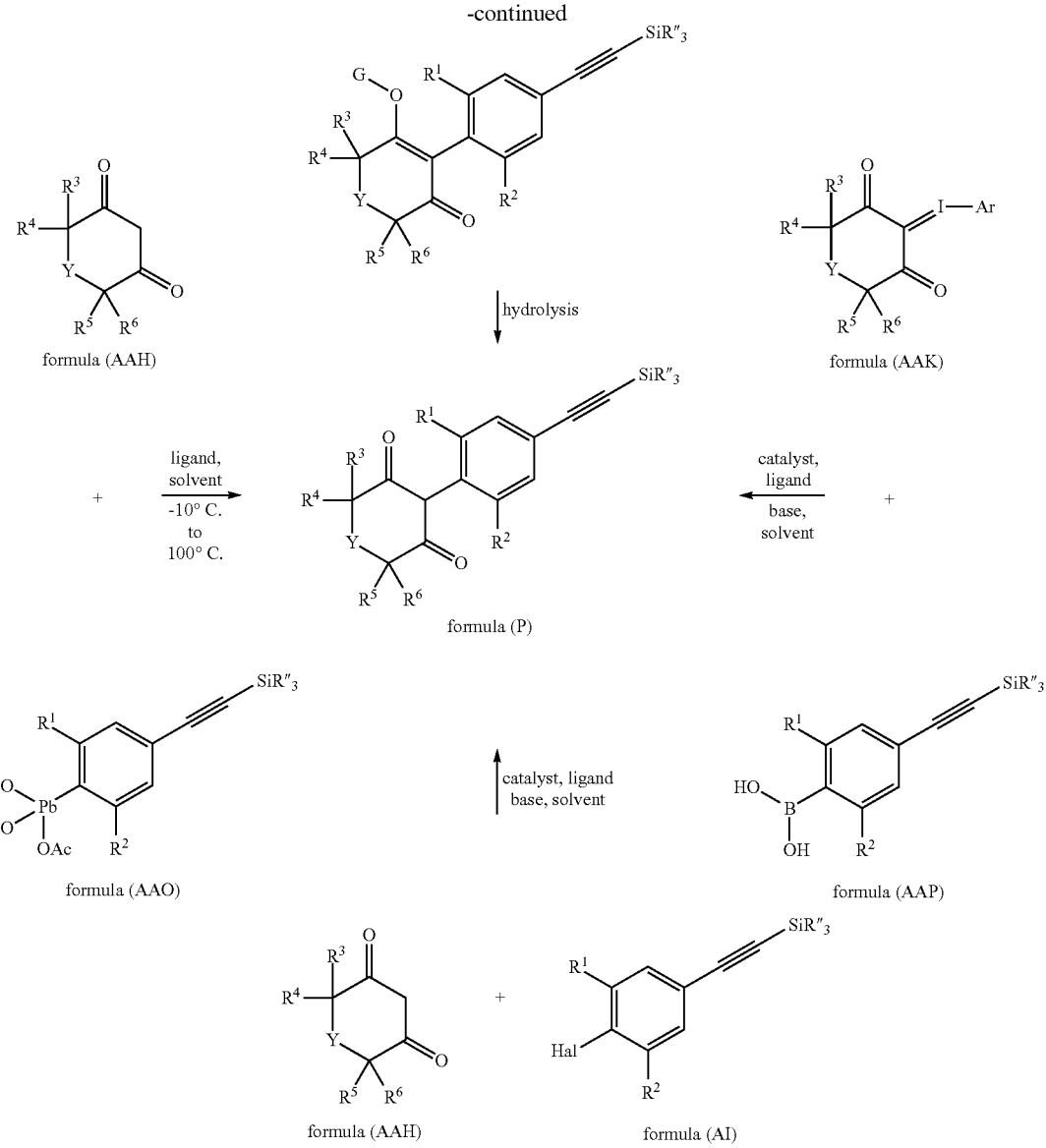
Similarly, a compound of formula (L) can also be prepared from suitable halogenated precursors, using similar methods to those described previously.
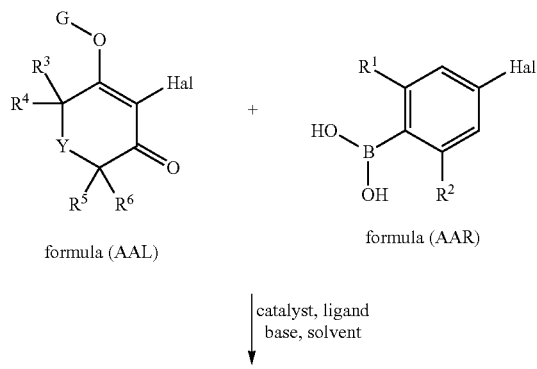

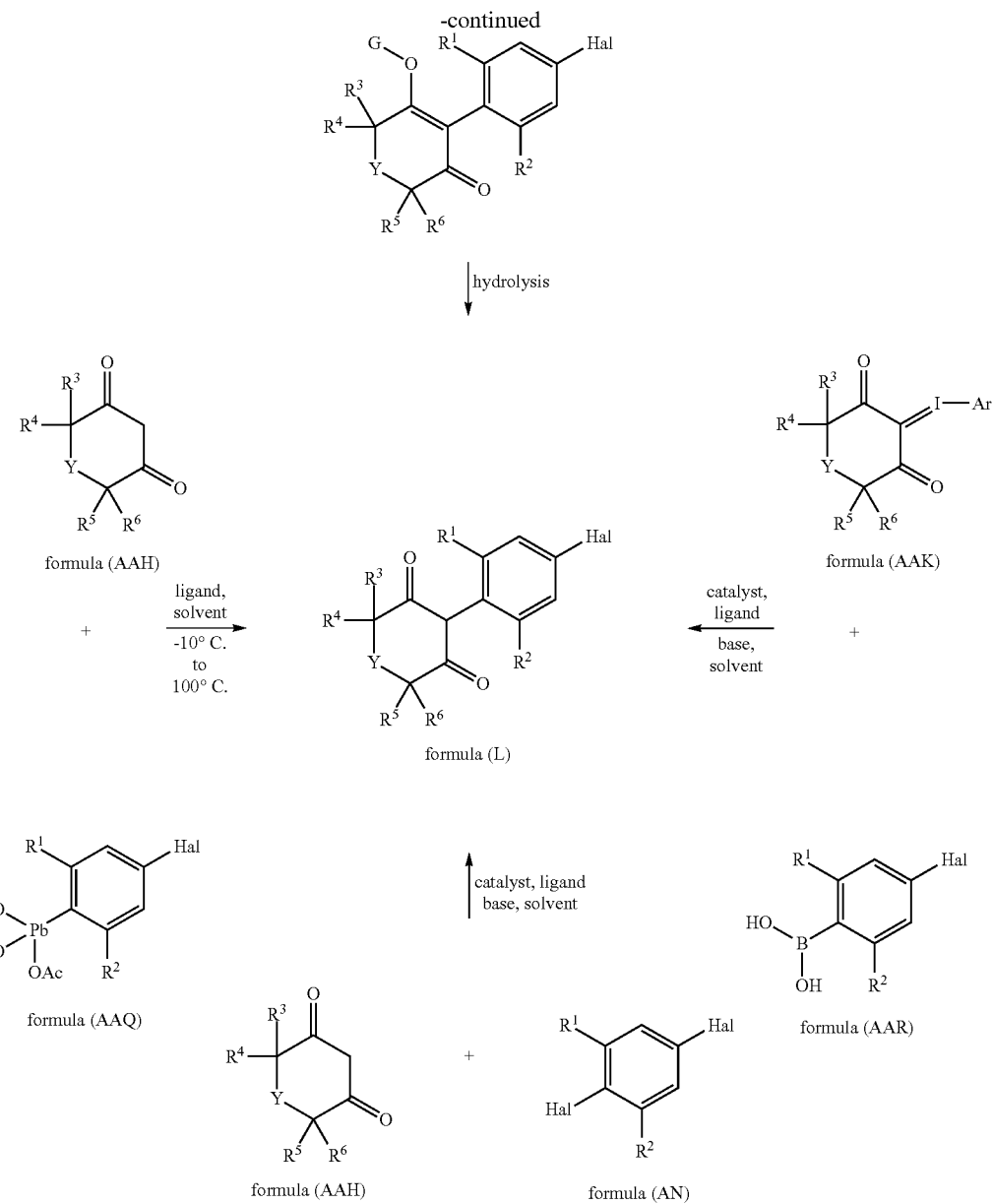
Similarly, a compound of formula (W) can also be prepared from suitable precursors, using similar methods to those described previously.
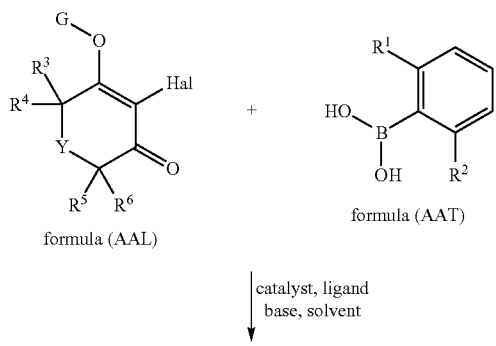

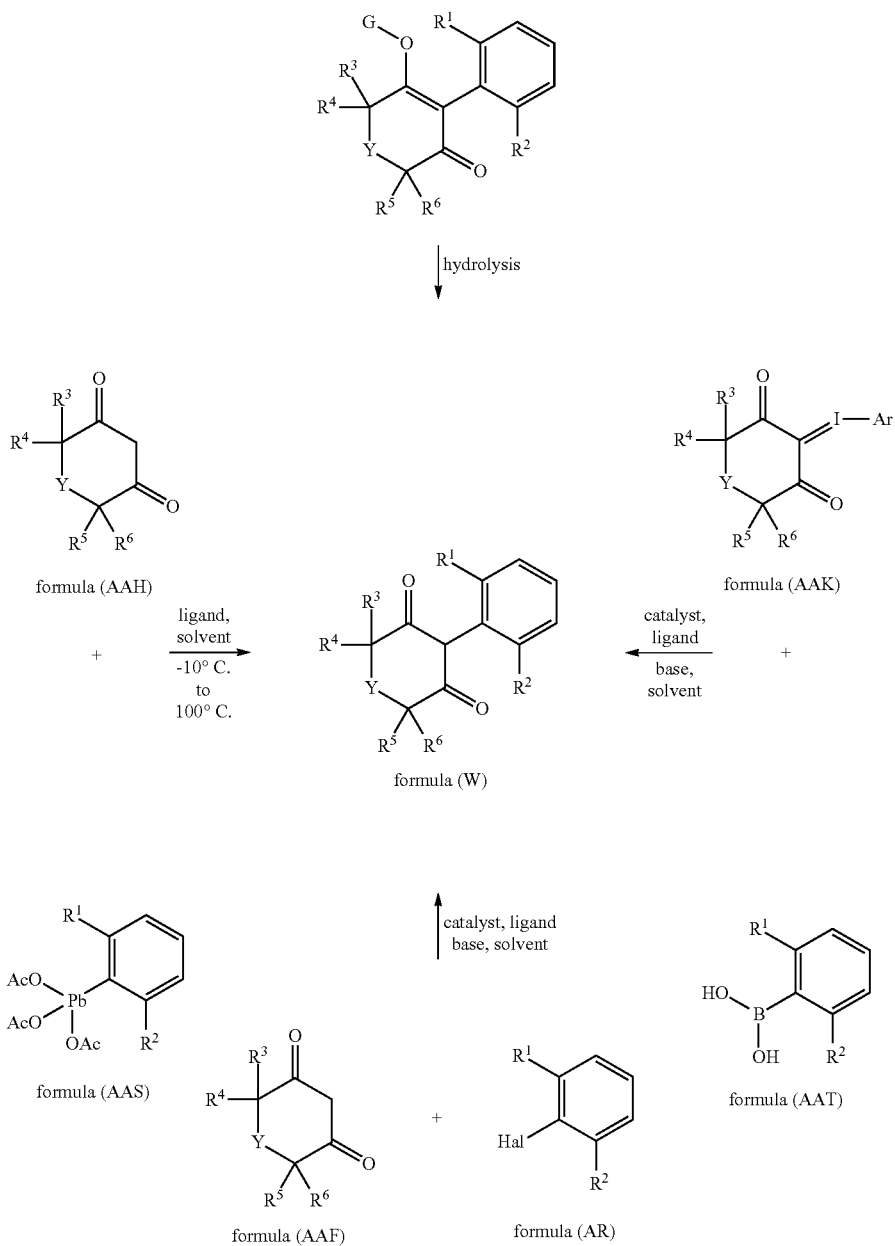

Furthermore, a compound of formula (L) can be prepared by reacting a compound of formula (AAH) with a halonitrobenzene of formula (AAX) (under conditions similar to those described for coupling a compound of formula (AAH) and a compound of formula (AE) to produce a compound of formula (A)), to produce a compound of formula (AAW) which is then reduced under standard conditions (for a similar example see T. N. Wheeler, CA1113959). The aniline (AAV) is then converted to the aryl halide (L) under Sandmeyer conditions (for a similar example see T. N. Wheeler, CA1113959). Alternatively, a compound of formula AAU, wherein X is chlorine, can be prepared by reacting the aniline of formula AAV with 1,1-dichloroethylene, a suitable metal salt such as copper(II) chloride, a suitable metal or alkyl nitrite in a suitable solvent at a suitable temperature. Such a reaction is an example of a Meerwein arylation, and examples are known in the literature (see for example T. Himmler, US 20100234651 and J-P. A. M. Bongartz, J. T. M. Linders, L. Meerpoel, G. S. E. Van Lommen, E. Coesemans, M. Braeken, C. F. R. N. Buyck, M. J. M. Berwaer, K. A. G. J. M. De Waepenaert, P. W. M. Roevens, G. M. Boeckx, P. V. Davidenko, WO 2008148868).

A compound of formula (A) can be prepared from a compound of formula (AAU) under similar conditions to those described to convert a compound of formula (J) to a compound of formula (D).

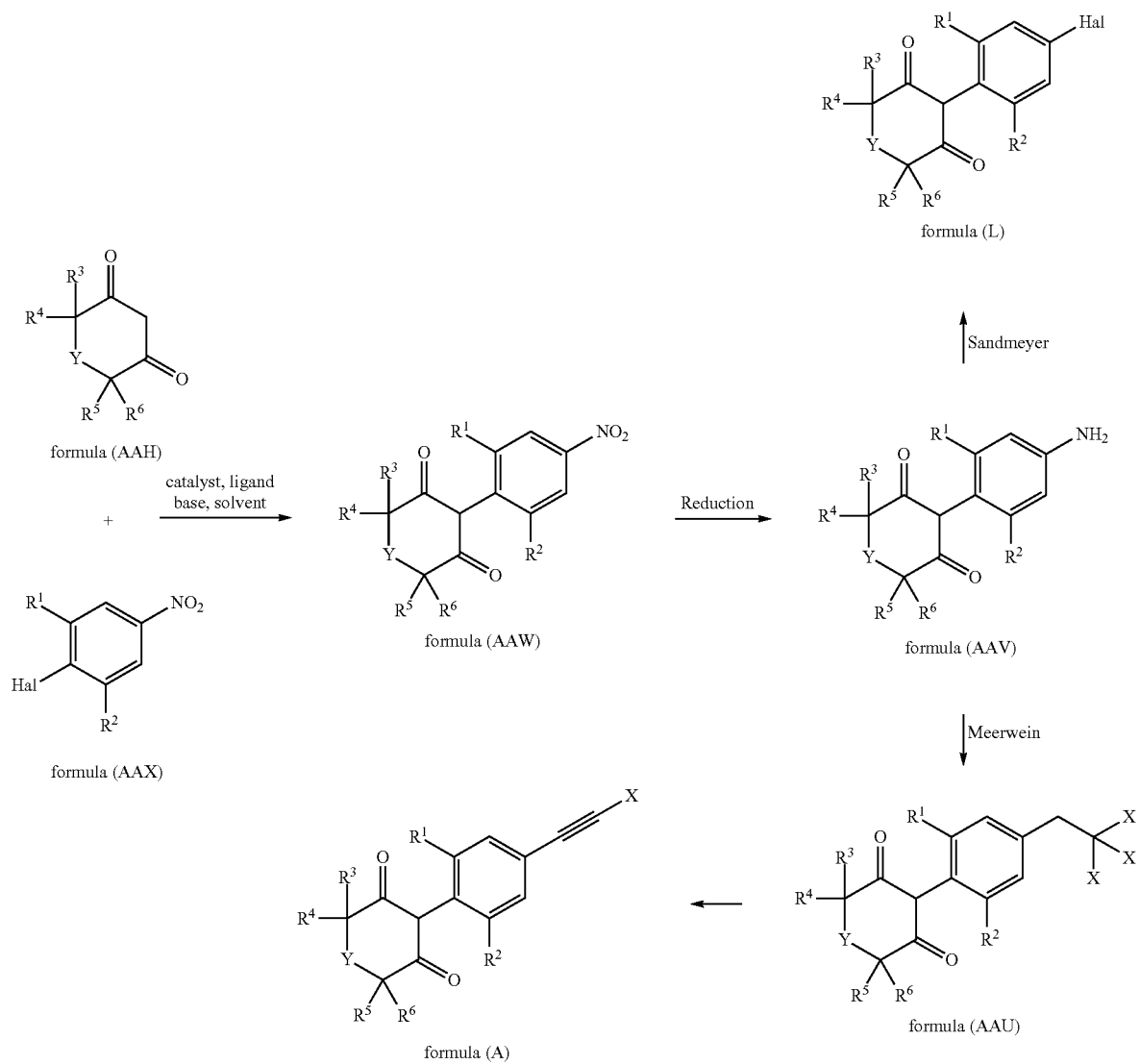

Processes for Preparation of 4-Ethynyl-Phenyl or 4-(but-1-Ynyl)-Phenyl Cyclic Dione Compounds within Formula (ZZ)

4-Ethynyl-phenyl cyclic dione compounds (and keto-enol derivatives thereof), within formula (ZZ) as disclosed herein in which XX is hydrogen, can be prepared following the procedures described herein, e.g. hereinabove, by substituting, in the relevant cases, the appropriate acetylene-based reagents in the relevant reaction(s), particularly with reference to literature precedence, or by deprotection of silyl (SiR"$_3$) substituted acetylene compounds (such as a compound of formula (P), (AI), (AW), (AAP), (AAO), provided that in this case these have a narrowly defined cyclic dione (or cyclic keto-enol derivative thereof) according to/corresponding to the cyclic dione or cyclic keto-enol as defined in in formula (ZZ)), e.g. using known conditions. See for example Examples 17, 18 and 19 hereinafter.

In one embodiment, 4-(but-1-ynyl)-phenyl cyclic dione compounds (and keto-enol derivatives thereof), within formula (ZZ) as disclosed herein in which XX is ethyl, are prepared using an appropriate modification of the processes to prepare the 4-(prop-1-ynyl)-phenyl cyclic dione compounds within formula (I).

Herbicidal Compositions

In another aspect, the present invention provides a herbicidal composition, e.g. for use in a method of controlling weeds (e.g. monocotyledonous such as grassy weeds) in crops of useful plants, which composition comprises a compound of formula (I) as defined herein (e.g. a herbicidally effective amount thereof), and a substantially-inert agrochemically acceptable substance (e.g. an agrochemically acceptable carrier, diluent and/or solvent, an agrochemically acceptable adjuvant, an an agrochemically acceptable emulsifier/surfactant/surface-active substance, and/or another agrochemically acceptable additive). In a further aspect, the present invention provides a herbicidal composition, e.g. for use in a method of controlling weeds (e.g. monocotyledonous such as grassy weeds) in crops of useful plants, comprising a compound of formula (I) as defined herein (e.g. a herbicidally effective amount thereof), and an agrochemically acceptable carrier, diluent and/or solvent.

In all aspects of the invention, the compound of the formula (I) is optionally present (e.g. where chemically possible) as an agrochemically acceptable salt thereof.

The compounds of formula (I) according to the invention can be used as crop protection agents in unmodified form, as obtained by synthesis, but, for use as herbicides, they are generally formulated into herbicidal compositions (formulations), e.g. in a variety of ways, containing one or more substantially-inert agrochemically acceptable substances (e.g. an agrochemically acceptable carrier, diluent and/or solvent, an agrochemically acceptable adjuvant, an an agrochemically acceptable emulsifier/surfactant/surface-active substance, and/or another agrochemically acceptable additive).

The formulations (herbicidal compositions) can be in various physical forms, for example in the form of dusting powders, gels, wettable powders, coated or impregnated granules for manual or mechanical distribution on target sites, water-dispersible granules, water-soluble granules, emulsifiable granules, water-dispersible tablets, effervescent compressed tablets, water-soluble tapes, emulsifiable concentrates, microemulsifiable concentrates, oil-in-water (EW) or water-in-oil (WO) emulsions, other multiphase systems such as oil/water/oil and water/oil/water products, oil flowables, aqueous dispersions, oily dispersions, suspoemulsions, capsule suspensions, soluble liquids, water-soluble concentrates (with water or a water-miscible organic solvent as carrier), impregnated polymer films or in other forms known, for example, from the Manual on Development and Use of FAO Specifications for Plant Protection Products, 5th Edition, 1999. The active ingredient may be incorporated into microfibers or micro-rods formed of polymers or polymerizable monomers and having diameter of about 0.1 to about 50 microns and aspect ratio of between about 10 and about 1000.

Such formulations can either be used directly or are diluted prior to use. They can then be applied through suitable ground or aerial application spray equipment or other ground application equipment such as central pivot irrigation systems or drip/trickle irrigation means. Diluted formulations can be prepared, for example, with water, liquid fertilizers, micronutrients, biological organisms, oil or solvents.

The formulations can be prepared, for example, by mixing the active ingredient with formulation adjuvants in order to obtain compositions in the form of finely divided solids, granules, solutions, dispersions or emulsions. The active ingredients can also be contained in fine microcapsules consisting of a core and a polymeric shell. Microcapsules usually have a diameter of from 0.1 to 500 microns. They contain active ingredients in an amount of about from 25 to 95% by weight of the capsule weight. The active ingredients can be present in the form of liquid technical material, in the form of a suitable solution, in the form of fine particles in solid or liquid dispersion or as a monolithic solid. The encapsulating membranes comprise, for example, natural and synthetic gums, cellulose, styrene-butadiene copolymers or other similar suitable membrane forming material, polyacrylonitrile, polyacrylate, polyester, polyamides, polyureas, polyurethane, aminoplast resins or chemically modified starch or other polymers that are known to the person skilled in the art in this connection.

Alternatively it is possible for fine so called "microcapsules" to be formed wherein the active ingredient is present in the form of finely divided particles in a solid matrix of a base substance, but in that case the microcapsule is not encapsulated with a diffusion limiting membrane as outlined in the preceding paragraph.

The active ingredients may be adsorbed on a porous carrier. This may enable the active ingredients to be released into their surroundings in controlled amounts (e.g. slow release). Other forms of controlled release formulations are granules or powders in which the active ingredient is dispersed or dissolved in a solid matrix consisting of a polymer, a wax or a suitable solid substance of lower molecular weight. Suitable polymers are polyvinyl acetates, polystyrenes, polyolefins, polyvinyl alcohols, polyvinyl pyrrolidones, alkylated polyvinyl pyrrolidones, copolymers of polyvinyl pyrrolidones and maleic anhydride and esters and half-esters thereof, chemically modified cellulose esters like carboxymethyl cellulose, methyl cellulose, hydroxyethyl cellulose, examples of suitable waxes are polyethylene wax, oxidized polyethylene wax, ester waxes like montan waxes, waxes of natural origin like carnauba wax, candelilla wax, bees wax etc. Other suitable matrix materials for slow release formulations are starch, stearin, lignin.

The formulation ingredients (e.g. inert ingredients) suitable for the preparation of the compositions according to the invention are generally known per se.

As a liquid carrier and/or solvent (e.g. organic solvent), e.g. for use in the herbicidal composition(s) according to the invention, there may be used: water, an aromatic solvent such as toluene, m-xylene, o-xylene, p-xylene or a mixture thereof, cumene, an aromatic hydrocarbon blend with a boiling range between 140 and 320° C. (e.g. known under various trademarks such as Solvesso®, Shellsol A®, Caromax®, Hydrosol®), a paraffinic or isoparaffinic carrier such as paraffin oil, mineral oil, a de-aromatized hydrocarbon solvent with a boiling range between 50 and 320° C. (e.g. known for instance under the trademark Exxsol®), a non-dearomatized hydrocarbon solvent with a boiling range between 100 and 320° C. (e.g. known under the tradename Varsol®), an isoparaffinic solvent with a boiling range between 100 and 320° C. (e.g. known known under tradenames like Isopar® or Shellsol T®), a hydrocarbon such as cyclohexane, tetrahydronaphthalene (tetralin), decahydronaphthalene, alpha-pinene, d-limonene, hexadecane, isooctane; an ester solvent such as ethyl acetate, n- or iso-butyl acetate, amyl acetate, i-bornyl acetate, 2-ethyl-hexyl acetate, a $C_6$-$C_{18}$ alkyl ester of acetic acid (e.g. known under the tradename Exxate®), lactic acid ethylester, lactic acid propylester, lactic acid butylester, benzyl benzoate, benzyl lactate, dipropyleneglycol dibenzoate, or a dialkyl ester of succinic, maleic or fumaric acid; a polar solvent such as N-methyl pyrrolidone, N-ethyl pyrrolidone, $C_3$-$C_{18}$-alkyl pyrrolidones, gamma-butyrolactone, dimethylsulfoxide, N,N-dimethylformamide, N,N-dimethylacetamide, N,N-dimethyllactamide, a $C_4$-$C_{18}$ fatty acid dimethylamide, benzoic acid dimethylamide, acetonitrile, acetone, methyl ethyl ketone, methyl-isobutyl ketone, isoamyl ketone, 2-heptanone, cyclohexanone, isophorone, methyl isobutenyl ketone (mesityl oxide), acetophenone, ethylene carbonate, propylene carbonate, or butylene carbonate; an alcoholic solvent or diluent such as methanol, ethanol, propanol, n- or iso-butanol, n- or iso-pentanol, 2-ethyl hexanol, n-octanol, tetrahydrofurfuryl alcohol, 2-methyl-2,4-pentanediol, 4-hydroxy-4-methyl-2-pentanone, cyclohexanol, benzyl alcohol, ethylene glycol, ethylene glycol butyl ether, ethylene glycol methyl ether, diethylene glycol, diethylene glycol butyl ether, diethylene glycol monoethyl ether, diethylene glycol monomethyl ether, propylene glycol, dipropylene glycol, dipropylene glycol monomethyl ether, or another similar glycol monoether solvent based on a ethylene glycol, propylene glycol or butylene glycol feedstock, triethylene glycol, polyethylene glycol (e.g. PEG 400), a polypropylenglycol with a molecular mass of 400-4000, or glycerol; glycerol acetate, glycerol diacetate, glycerol triacetate, 1,4-dioxane, diethylene glycol abietate, chlorobenzene, chlorotoluene; a fatty acid ester such as methyl octanoate, isopropyl myristate, methyl laurate, methyl oleate, a mixture of $C_8$-$C_{10}$ fatty acid methyl esters, rapeseed oil methyl ester, rapeseed oil ethyl ester, soybean oil methyl ester, soybean oil ethyl ester; a vegetable oil (e.g. rapeseed oil or soybean oil); a fatty acid such as oleic acid, linoleic acid, or linolenic acid; or an ester of phosphoric or phosphonic acid such as triethyl phosphate, a $C_3$-$C_{18}$-tris-alkyl phosphate, an alkylaryl phosphate, or bis-octyl-octyl phosphonate.

Water is generally the liquid carrier of choice for the dilution of the concentrates.

Suitable solid carriers are, for example, talc, titanium dioxide, pyrophyllite clay, silica (fumed or precipitated silica and optionally functionalised or treated, for instance silanised), attapulgite clay, kieselguhr, limestone, calcium carbonate, bentonite, calcium montomorillonite, cottonseed husks, wheatmeal, soybean flour, pumice, wood flour, ground walnut shells, lignin and similar materials, as described, for example, in the EPA CFR 180.1001. (c) & (d). Powdered or granulated fertilizers can also be used as solid carriers.

A large number of surface-active substances can advantageously be used both in solid and in liquid formulations (herbicidal compositions), especially in those formulations (herbicidal compositions) which can be diluted with a carrier prior to use. Surface-active substances may be anionic, cationic, amphoteric, non-ionic or polymeric and they may be used as emulsifying, wetting, dispersing or suspending agents or for other purposes. Typical surface-active substances include, for example, salts of alkyl sulfates, such as diethanolammonium lauryl sulfate; Sodium lauryl sulfate, salts of alkylarylsulfonates, such as calcium or sodium dodecylbenzenesulfonate; alkylphenol-alkylene oxide addition products, such as nonylphenol ethoxylates; alcohol-alkylene oxide addition products, such as tridecyl alcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride, polyethylene glycol esters of fatty acids, such as polyethylene glycol stearate; block copolymers of ethylene oxide and propylene oxide; and salts of mono- and di-alkyl phosphate esters; and also further substances described e.g. in "McCutcheon's Detergents and Emulsifiers Annual", MC Publishing Corp., Ridgewood, N.J., 1981.

Further formulation ingredients (e.g. inert ingredients) which can typically be used in formulations (herbicidal compositions) include crystallisation inhibitors, viscosity-modifying substances, suspending agents, dyes, anti-oxidants, foaming agents, light absorbers, mixing aids, anti-foams, complexing agents, neutralizing or pH-modifying substances and/or buffers, corrosion-inhibitors, fragrances, wetting agents, absorption improvers, micronutrients, plasticizers, glidants, lubricants, dispersants, thickeners, antifreezes, microbiocides, compatibility agents and/or solubilisers; and/or also liquid and solid fertilizers.

The compositions (formulations) may also comprise additional active substances, for example further herbicides, herbicide safeners, plant growth regulators, fungicides or insecticides.

The compositions according to the invention can additionally include an additive (commonly referred to as an adjuvant), comprising a mineral oil, an oil of vegetable or animal origin, alkyl (e.g. $C_1$-$C_6$alkyl) esters of such oils, or mixtures of such oils and oil derivatives/oil esters. The amount of oil additive (oil adjuvant) used in the composition according to the invention is generally from 0.01 to 10%, based on the spray mixture. For example, the oil additive (oil adjuvant) can be added to the spray tank in the desired concentration after the spray mixture has been prepared. Preferred oil additives (oil adjuvants) comprise mineral oils or an oil of vegetable origin, for example rapeseed oil, olive oil or sunflower oil, emulsifiable vegetable oil, such as AMIGO® (Loveland Products Inc.), $C_1$-$C_6$alkyl esters of oils of vegetable origin, for example the methyl esters, or an oil of animal origin, such as fish oil or beef tallow. A preferred oil additive (oil adjuvant) contains methylated rapeseed oil (rapeseed oil methyl ester). Another preferred oil additive (oil adjuvant) contains, for example, as active components essentially 80% by weight alkyl esters of fish oils and 15% by weight methylated rapeseed oil (rapeseed oil methyl ester), and also 5% by weight of customary emulsifiers and pH modifiers. Especially preferred oil additives (oil adjuvants) comprise $C_1$-$C_6$alkyl ester(s) of $C_8$-$C_{22}$ fatty acid(s), especially the methyl ester(s) of $C_8$-$C_{22}$ (especially $C_{12}$-$C_{18}$) fatty acid(s); preferably the methyl ester of lauric acid, of palmitic acid, or of oleic acid. Those esters are known as methyl laurate (CAS-111-82-0), methyl palmitate (CAS-112-39-0) and methyl oleate (CAS-112-62-9) respectively. A preferred fatty acid methyl ester derivative is AGNIQUE ME 18 RD-F® (e.g. available from Cognis). Those and other oil derivatives are also known from the Compendium of Herbicide Adjuvants, 5th Edition, Southern Illinois University, 2000.

The application and action of the above-mentioned oil additives (oil adjuvants) can be further improved by combining them with surface-active substances, such as non-ionic, anionic, cationic or amphoteric surfactants. Examples of suitable anionic, non-ionic, cationic or amphoteric surfactants, e.g. for this purpose, are listed on pages 7 and 8 of WO97/34485. Preferred surface-active substances are anionic surfactants of the dodecylbenzylsulfonate type, especially the calcium salts thereof, and also non-ionic surfactants of the fatty alcohol ethoxylate type. As non-ionic surfactants, special preference is given to ethoxylated $C_{12}$-$C_{22}$ fatty alcohols preferably having a degree of ethoxylation of from 5 to 40. Examples of commercially available surfactants are the Genapol types (Clariant). Also preferred are silicone surfactants, especially polyalkyl-oxide-modified heptamethyltrisiloxanes, which are commercially available e.g. as SILWET L-77®, and also perfluorinated surfactants. The concentration of surface-active substances in relation to the total oil additive (oil adjuvant) is generally from 1 to 50% by weight of the oil additive (oil adjuvant). Examples of oil additives (oil adjuvants) that consist of mixtures of oils and/or mineral oils and/or derivatives thereof with surfactants are TURBOCHARGE®, ADIGOR® (both Syngenta Crop Protection AG), ACTIPRON® (BP Oil UK Limited), AGRI-DEX® (Helena Chemical Company).

The above-mentioned surface-active substances may also be used in the formulations alone, that is to say without oil additives (oil adjuvants).

Furthermore, the addition of an organic solvent to the oil additive (oil adjuvant)/surfactant mixture can contribute to a further enhancement of action. Suitable solvents are, for example, heavy aromatic hydrocarbon solvents such as SOLVESSO® or AROMATIC® solvents (Exxon Corporation). The concentration of such solvents can e.g. be from 10 to 80% by weight of the oil additive (oil adjuvant). Such oil additives (oil adjuvants), which may be in admixture with solvents, are described, for example, in U.S. Pat. No. 4,834,908. A commercially available oil additive disclosed therein is known by the name MERGE® (BASF). Further such oil additives (oil adjuvants) that are preferred according to the invention are SCORE® and ADIGOR® (both Syngenta Crop Protection AG).

In addition to the oil additives (oil adjuvants) listed above, in order to enhance the activity of the compositions according to the invention it is also possible for formulations of alkylpyrrolidones, (e.g. AGRIMAX® from ISP) to be added to the spray mixture. Formulations of synthetic latices, such as, for example, polyacrylamide, polyvinyl compounds or poly-1-p-menthene (e.g. BOND®, COURIER® or EMERALD®) can also be used.

A particularly preferred oil adjuvant (oil additive), e.g. for use in the herbicidal composition as of the invention, is an emulsifiable concentrate which consists of:
(i) ethoxylated alcohols, which preferably includes ethoxylated $C_{12}$-$C_{22}$ fatty alcohols (preferably having a degree of ethoxylation of from 5 to 40); and
(ii) a mixture of heavy aromatic hydrocarbons, which preferably includes (or more preferably includes 50% or more by weight of the heavy aromatic hydrocarbons of) a mixture of naphthalenes each of which is substituted by one or more alkyls wherein the alkyl(s) in total have 1-4 carbon atoms per naphthalene molecule (e.g. Solvesso 200 ND™); and
(iii) methylated rapeseed oil (rapeseed oil methyl ester) (e.g. Agnique ME 18 RD-F™), as an adjuvant; preferably present at about 47% w/w and/or about 45% w/v of the oil adjuvant/oil additive/emulsifiable concentrate. One example of such a emulsifiable concentrate oil adjuvant (oil additive) is ADIGOR™, currently available in many countries from Syngenta.

When the above emulsifiable concentrate oil adjuvant is used, it is preferably added to the herbicidal composition after dilution (e.g. with water and/or in a spray tank), typically before application to weeds and/or to crops of useful plants and/or to the locus thereof. In one particular embodiment, the herbicidal composition, e.g. after dilution (e.g. with water and/or in a spray tank), contains the above emulsifiable concentrate oil adjuvant, and additionally ammonium sulphate and/or isopropyl alcohol.

Such adjuvant oils as described in the preceding paragraphs may be employed as a or the carrier liquid in which an active compound is dissolved, emulsified or dispersed as appropriate to the physical form of the active compound.

In an alternative particular embodiment, the herbicidal composition of the invention comprises an agrochemically acceptable adjuvant comprising 1,2-cyclohexane dicarboxylic acid di-isononyl ester (e.g. CAS Registry no. 166412-78-8), e.g. as available from BASF as Hexamoll™ DINCH™. "Isononyl" in this context is thought to mean one or more, preferably a mixture of two or more, branched isomers of $C_9H_{19}$. In one particular embodiment, the herbicidal composition, e.g. after dilution (e.g. with water and/or in a spray tank), contains 1,2-cyclohexane dicarboxylic acid di-isononyl ester, and additionally ammonium sulphate and/or isopropyl alcohol.

In an alternative particular embodiment, the herbicidal composition of the invention comprises an agrochemically acceptable adjuvant comprising an organic phosphate and/or organic phosphonate adjuvant. Preferably, the phosphate adjuvant is a tris-[$C_4$-$C_{12}$alkyl or 2-($C_2$-$C_6$alkoxy)ethyl-] ester of phosphoric acid, or more preferably is tris-(2-ethylhexyl)phosphate, tris-n-octyl phosphate and/or tris-[2-(n-butoxy)ethyl]phosphate, or most preferably is tris-(2-ethylhexyl)phosphate. Preferably, the phosphonate adjuvant is a bis-($C_3$-$C_{12}$alkyl) ester of a $C_3$-$C_{12}$alkyl-phosphonic acid, or more preferably is bis-(2-ethylhexyl) (2-ethylhexyl) phosphonate, bis-(2-ethylhexyl) (n-octyl)phosphonate and/or di-n-butyl(n-butyl)phosphonate.

The formulations (herbicidal compositions) generally contain from 0.1 to 99% by weight, especially from 0.1 to 95% by weight, of a compound of formula I and from 1 to 99.9% by weight of a substantially-inert agrochemically acceptable substance, which preferably includes a formulation adjuvant and/or from 0 to 30% or from 0 to 25% (e.g. from 0.5 to 30% or from 0.5 to 25%) by weight of a surface-active substance. Whereas herbicidal compositions (especially commercial products) will preferably be formulated as concentrates, the end user will normally employ dilute formulations (compositions), e.g. formulations (compositions) diluted with water, in particular when applying the herbicidal composition to weeds and/or to crops of useful plants and/or to the locus thereof.

The rate of application of the compounds of formula I may vary within wide limits and depends upon the nature of the soil, the method of application (pre- or post-emergence; seed dressing; application to the seed furrow; no tillage application etc.), the crop plant, the weed or grass to be controlled, the prevailing climatic conditions, and other factors governed by the method of application, the time of application and the target crop. The compounds of formula I according to the invention are generally applied (preferably post-emergence) at a rate of from 1 to 2000 g/ha, preferably from 1 to 1000 g/ha and most preferably at from 1 to 500 g/ha or from 5 to 500 g/ha.

Preferred formulations/compositions have especially the following representative compositions:
(%=percent by weight of the composition):
Emulsifiable Concentrates:
active ingredient: 0.3 to 95%, preferably 0.5 to 60% such as 1 to 40%
surface-active agents: 1 to 30%, preferably 3 to 20% such as 5 to 15%
solvents as liquid carrier: 1 to 80%, preferably 1 to 60% such as 1 to 40%
Dusts:
active ingredient: 0.1 to 10%, preferably 0.1 to 5%
solid carriers: 99.9 to 90%, preferably 99.9 to 99%
Suspension Concentrates:
active ingredient: 1 to 75%, preferably 3 to 50% or 10 to 50%
water: 98 to 24%, preferably 95 to 30% or 88 to 30%
surface-active agents: 1 to 40%, preferably 2 to 30%
Wettable Powders:
active ingredient: 0.5 to 90%, preferably 1 to 80%
surface-active agents: 0.5 to 20%, preferably 1 to 15%
solid carriers: 5 to 95%, preferably 15 to 90%
Granules:
active ingredient: 0.1 to 30%, preferably 0.1 to 15%
solid carriers: 99.5 to 70%, preferably 97 to 85%

Water Dispersible Granules:
active ingredient: 1 to 90%, preferably 10 to 80%
surface-active agents: 0.5 to 80%, preferably 5 to 30%
solid carriers: 90 to 10%, preferably 70 to 30%

The following Examples further illustrate, but do not limit, the invention.

| F1. Emulsifiable concentrates | a) | b) | c) | d) |
|---|---|---|---|---|
| active ingredient | 5% | 10% | 25% | 50% |
| calcium dodecylbenzene-sulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| NMP (N-methyl-2-pyrrolidone) | — | 10% | — | 20% |
| aromatic hydrocarbon mixture $C_9$-$C_{12}$ | 85% | 68% | 65% | 16% |

Emulsions of any desired concentration can be prepared from such concentrates by dilution with water.

| F2. Solutions | a) | b) | c) | d) |
|---|---|---|---|---|
| active ingredient | 5% | 10% | 50% | 90% |
| 1-methoxy-3-(3-methoxy-propoxy)-propane | 40% | 50% | — | — |
| polyethylene glycol MW 400 | 20% | 10% | — | — |
| NMP (N-methyl-2-pyrrolidone) | — | — | 50% | 10% |
| aromatic hydrocarbon mixture $C_9$-$C_{12}$ | 35% | 30% | — | — |

The solutions are suitable for application undiluted or after dilution with water.

| F3. Wettable powders | a) | b) | c) | d) |
|---|---|---|---|---|
| active ingredient | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly disperse silicic acid | 1% | 3% | 5% | 10% |
| kaolin | 88% | 62% | 35% | — |

The active ingredient is thoroughly mixed with the adjuvants and the mixture is thoroughly ground in a suitable mill, yielding wettable powders which can be diluted with water to give suspensions of any desired concentration.

| F4. Coated granules | a) | b) | c) |
|---|---|---|---|
| active ingredient | 0.1% | 5% | 15% |
| highly dispersed silica | 0.9% | 2% | 2% |
| inorganic carrier (diameter 0.1-1 mm) e.g. $CaCO_3$ or $SiO_2$ | 99.0% | 93% | 83% |

The active ingredient is dissolved in methylene chloride, the solution is sprayed onto the carrier and the solvent is subsequently evaporated off in vacuo.

| F5. Coated granules | a) | b) | c) |
|---|---|---|---|
| active ingredient | 0.1% | 5% | 15% |
| polyethylene glycol MW 200 | 1.0% | 2% | 3% |
| highly dispersed silica | 0.9% | 1% | 2% |
| inorganic carrier (diameter 0.1-1 mm) e.g. $CaCO_3$ or $SiO_2$ | 98.0% | 92% | 80% |

The finely ground active ingredient is applied uniformly, in a mixer, to the carrier moistened with polyethylene glycol. Non-dusty coated granules are obtained in this manner.

| F6. Extruded granules | a) | b) | c) | d) |
|---|---|---|---|---|
| active ingredient | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants and the mixture is moistened with water. The resulting mixture is extruded and then dried in a stream of air.

| F7. Water-dispersible granules | a) | b) | c) | d) |
|---|---|---|---|---|
| active ingredient | 5% | 10% | 40% | 90% |
| sodium lignosulfonate | 20% | 20% | 15% | 7% |
| dibutyl naphthalene sulfonate | 5% | 5% | 4% | 2% |
| Gum arabic | 2% | 1% | 1% | 1% |
| Diatomaceous earth | 20% | 30% | 5% | — |
| Sodium sulfate | — | 4% | 5% | — |
| kaolin | 48% | 30% | 30% | — |

The active ingredient is mixed and ground with the adjuvants and the mixture is moistened with water. The resulting mixture is extruded and then dried in a stream of air.

| F8. Dusts | a) | b) | c) |
|---|---|---|---|
| active ingredient | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

| F9. Suspension concentrates | a) | b) | c) | d) |
|---|---|---|---|---|
| active ingredient | 3% | 10% | 25% | 50% |
| propylene glycol | 5% | 5% | 5% | 5% |
| nonylphenol polyglycol ether (15 mol of ethylene oxide) | — | 1% | 2% | — |
| sodium lignosulfonate | 3% | 3% | 7% | 6% |
| heteropolysaccharide (Xanthan) | 0.2% | 0.2% | 0.2% | 0.2% |
| 1,2-benzisothiazolin-3-one | 0.1% | 0.1% | 0.1% | 0.1% |
| silicone oil emulsion | 0.7% | 0.7% | 0.7% | 0.7% |
| water | 88% | 80% | 60% | 38% |

The finely ground active ingredient is intimately mixed with the adjuvants, yielding a suspension concentrate from which suspensions of any desired concentration can be prepared by dilution with water.

Herbicidal Uses—Crops of Useful Plants, Weeds, Application Rates, et al.

In a further aspect, the present invention provides a method of controlling weeds (e.g. monocotyledonous such as grassy weeds) in crops of useful plants, which comprises applying a compound of the formula (I), or a herbicidal composition comprising such a compound, to the weeds and/or to the plants and/or to the locus thereof.

In a further aspect, the present invention provides a herbicidal composition, in particular for use in a method of controlling weeds (e.g. monocotyledonous such as grassy weeds) in crops of useful plants, comprising a compound of formula (I) as defined herein (e.g. a herbicidally effective amount thereof), and an agrochemically acceptable carrier, diluent and/or solvent.

In all aspects of the invention, the compound of the formula (I) is optionally present (e.g. where chemically possible) as an agrochemically acceptable salt thereof.

In one embodiment, the herbicidal composition also comprises one or more further herbicides, e.g. as mixture partner(s) for the compound of formula (I), and/or a safener. See the combinations and mixtures section herein for more details of examples of these.

In all aspects of the invention (e.g. the methods of use of the invention), crops of useful plants, e.g. on or in which or at the locus of which the compounds or compositions according to the invention can be used, comprise (e.g. are), in particular: cereals (e.g. non-oat cereals, in particular non-oat non-*sorghum* non-millet cereals, more particularly wheat, barley, rye and/or triticale), rice, corn (maize), sugarcane, leguminous crops [preferably soybean, peanut, and/or pulse crops; more preferably soybean; wherein typically the pulse crops comprise dry beans (e.g. kidney or haricot or pinto bean which is *Phaseolus vulgaris*, or mung bean which is *Vigna radiata*), chickpea, blackeye bean (i.e. black-eyed pea, *Vigna unguiculata*), lentil, dry broad beans, and/or dry peas such as garden peas], cotton, rape (in particular oilseed rape or canola), sunflower, linseed, sugarbeet, fodder beet, potato, vegetables (preferably dicotyledonous vegetables), flax, tobacco, plantation crops (such as conifer trees, olives and/or olive trees, oil palms, coffee, or vines), and/or fruit crops (in particular dicotyledonous and/or broadleaved fruit, and/or in particular pome fruit, stone fruit, bush fruit, citrus fruit, pineapple, banana, and/or strawberry).

Preferably, in all aspects of the invention, the crops of useful plants, e.g. on or in which or at the locus of which the compounds or compositions according to the invention can be used, comprise (e.g. are): cereals (in particular non-oat cereals, more particularly non-oat non-*sorghum* non-millet cereals, even more particularly wheat, barley, rye and/or triticale), rice, corn (maize), sugarcane, leguminous crops [preferably soybean, peanut, and/or pulse crops (more preferably soybean)], cotton, rape (in particular oilseed rape or canola), sunflower, linseed, sugarbeet, fodder beet, potato, and/or vegetables (preferably dicotyledonous vegetables).

More preferably, in all aspects of the invention, the crops of useful plants, e.g. on or in which or at the locus of which the compounds or compositions according to the invention can be used, comprise (e.g. are): wheat (e.g. winter wheat, spring wheat, or durum wheat), barley (e.g. winter or spring barley), rye, triticale, sugarcane, leguminous crops [preferably soybean, peanut, and/or pulse crops (more preferably soybean)], cotton, rape (in particular oilseed rape or canola), sunflower, linseed, sugarbeet, fodder beet, potato, and/or vegetables (preferably dicotyledonous vegetables).

Even more preferably, in all aspects of the invention, the crops of useful plants, e.g. on or in which or at the locus of which the compounds or compositions according to the invention can be used, comprise (e.g. are): leguminous crops [preferably soybean, peanut, and/or pulse crops; more preferably soybean; wherein typically the pulse crops comprise dry beans (e.g. kidney or haricot or pinto bean which is *Phaseolus vulgaris*, or mung bean which is *Vigna radiata*), chickpea, blackeye bean (i.e. black-eyed pea, *Vigna unguiculata*), lentil, dry broad beans, and/or dry peas such as garden peas], cotton, rape (in particular oilseed rape or canola), sunflower, sugarbeet, fodder beet, potato, and/or vegetables (preferably dicotyledonous vegetables).

The term "crops" is to be understood as also including crops that have been rendered tolerant to herbicides or classes of herbicides (for example ALS, GS, EPSPS, PPO and HPPD inhibitors, and/or 2,4-D or dicamba) as a result of conventional methods of breeding or genetic engineering. Examples of crops that have been rendered tolerant e.g. to imidazolinones (which are ALS inhibitors), such as imazamox, by conventional methods of breeding include Clearfield® summer rape (canola) and/or Clearfield® wheat and/or Clearfield® rice (all from BASF). Examples of crops that have been rendered tolerant to herbicides by genetic engineering methods include e.g. glyphosate-resistant or glufosinate-resistant maize or soybean varieties, in particular those commercially available under the trade name RoundupReady® or RoundupReady® 2 (both from Monsanto, both glyphosate-resistant) or LibertyLink® (from Bayer, glufosinate-resistant). Glufosinate-resistant rice (LibertyLink®) also has been published.

Other crops of useful plants include 2,4-D-tolerant soybean, e.g. soybean genetically-modified to be tolerant to the herbicide 2,4-D, or dicamba-tolerant soybean, e.g. soybean genetically-modified to be tolerant to the herbicide dicamba. Such 2,4-D-tolerant or dicamba-tolerant soybean crops can also, in particular, be tolerant to glyphosate or glufosinate. For example, crops of useful plants include soybeans containing a dicamba-tolerance trait combined (stacked) with a glyphosate-tolerance trait, such that these soybeans have tolerance to the herbicides glyphosate and dicamba (for example Genuity® Roundup Ready® 2 Xtend soybeans, currently under development by Monsanto).

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt-176 maize hybrids of NK® (Syngenta Seeds). The Bt toxin is a protein that is formed naturally by *Bacillus thuringiensis* soil bacteria. Examples of toxins and transgenic plants able to synthesise such toxins are described in EP-A-451 878, EP-A-374 753, WO 93/07278, WO 95/34656, WO 03/052073 and EP-A-427 529. Examples of transgenic plants that contain one or more genes which code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops and their seed material can be resistant to herbicides and at the same time also to insect feeding ("stacked" transgenic events). Seed can, for example, have the ability to express an insecticidally active Cry3 protein and at the same time be glyphosate-tolerant. The term "crops" is to be understood as also including crops obtained as a result of conventional methods of breeding or genetic engineering which contain so-called output traits (e.g. improved flavour, storage stability, nutritional content).

In all aspects of the invention, the weeds, e.g. to be controlled and/or growth-inhibited, may be either monocotyledonous (e.g. grassy) and/or dicotyledonous weeds.

Preferably the weeds, e.g. to be controlled and/or growth-inhibited, comprise or are monocotyledonous weeds, more preferably grassy monocotyledonous weeds.

In all aspects of the invention, typically, the monocotyledonous (preferably grassy) weeds, e.g. to be controlled and/or growth-inhibited, comprise (e.g. are) weeds from the genus *Agrostis, Alopecurus, Apera, Avena, Brachiaria, Bromus, Cenchrus, Cyperus* (a genus of sedges), *Digitaria, Echinochloa, Eleusine, Eriochloa, Fimbristylis* (a genus of sedges), *Juncus* (a genus of rushes), *Leptochloa, Lolium, Monochoria, Ottochloa, Panicum, Pennisetum, Phalaris, Poa, Rottboellia, Sagittaria, Scirpus* (a genus of sedges), *Setaria* and/or *Sorghum*; in particular: *Alopecurus myosuroides* (ALOMY, English name "blackgrass"), *Apera spica-venti, Avena fatua* (AVEFA, English name "wild oats"), *Avena ludoviciana, Avena sterilis, Avena sativa* (English name "oats" (volunteer)), *Brachiaria decumbens, Brachiaria plantaginea, Bromus tectorum, Digitaria horizontalis, Digitaria insularis, Digitaria sanguinalis* (DIGSA), *Echinochloa crus-galli* (English name "common barnyard grass", ECHCG), *Echinochloa oryzoides, Echinochloa colona* or *colonum, Eleusine indica, Eriochloa villosa* (English name "woolly cupgrass"), *Leptochloa chinensis, Leptochloa panicoides, Lolium perenne* (LOLPE, English name "perennial ryegrass"), *Lolium multiflorum* (LOLMU, English name "Italian ryegrass"), *Lolium persicum* (English name "Persian darnel"), *Lolium rigidum, Panicum miliaceum* (English name "wild proso millet"), *Phalaris minor, Phalaris paradoxa, Poa annua* (POAAN, English name "annual bluegrass"), *Scirpus maritimus, Scirpusjuncoides, Setaria viridis* (SETVI, English name "green foxtail"), *Setaria faberi* (SETFA, English name "giant foxtail"), *Setaria glauca, Setaria lutescens* (English name "yellow foxtail"), *Sorghum bicolor*, and/or *Sorghum halepense* (English name "Johnson grass"); and/or in particular: *Brachiaria platyphylla* (BRAPP), *Panicum dichotomiflorum* (PANDI), and/or *Sorghum vulgare*. Alternatively or additionally, the monocotyledonous (preferably grassy) weeds, e.g. to be controlled and/or growth-inhibited, comprise volunteer corn (volunteer maize) weeds.

In one preferred embodiment of all aspects of the invention, the monocotyledonous weeds, e.g. to be controlled and/or growth-inhibited, are grassy monocotyledonous weeds; in which case they typically comprise (e.g. are) weeds from the genus *Agrostis, Alopecurus, Apera, Avena, Brachiaria, Bromus, Cenchrus, Digitaria, Echinochloa, Eleusine, Eriochloa, Leptochloa, Lolium, Ottochloa, Panicum, Pennisetum, Phalaris, Poa, Rottboellia, Setaria* and/or *Sorghum*. Alternatively or additionally, the monocotyledonous (preferably grassy) weeds, e.g. to be controlled and/or growth-inhibited, comprise volunteer corn (volunteer maize) weeds.

In one preferred embodiment of all aspects of the invention, the grassy monocotyledonous weeds, e.g. to be controlled and/or growth-inhibited, are "warm-season" (warm climate) grassy weeds; in which case they preferably comprise (e.g. are) weeds from the genus *Brachiaria, Cenchrus, Digitaria, Echinochloa, Eleusine, Eriochloa, Leptochloa, Ottochloa, Panicum, Pennisetum, Phalaris, Rottboellia, Setaria* and/or *Sorghum*. Alternatively or additionally, the grassy monocotyledonous weeds, e.g. to be controlled and/or growth-inhibited, comprise volunteer corn (volunteer maize) weeds. More preferably, the grassy monocotyledonous weeds, e.g. to be controlled and/or growth-inhibited, are "warm-season" (warm climate) grassy weeds comprising (e.g. being) weeds from the genus *Brachiaria, Cenchrus, Digitaria, Echinochloa, Eleusine, Eriochloa, Panicum, Setaria* and/or *Sorghum*; and/or the grassy monocotyledonous weeds, e.g. to be controlled and/or growth-inhibited, comprise volunteer corn (volunteer maize) weeds.

In another particular embodiment of all aspects of the invention, the grassy monocotyledonous weeds, e.g. to be controlled and/or growth-inhibited, are "cool-season" (cool climate) grassy weeds; in which case they typically comprise (e.g. are) weeds from the genus *Agrostis, Alopecurus, Apera, Avena, Bromus, Lolium* and/or *Poa*.

In non-oat cereal crops such as wheat and/or barley, control and/or growth inhibition of weeds from the genus *Alopecurus, Apera, Avena*, especially *Avena fatua, Bromus, Lolium, Phalaris*, and/or *Setaria* is preferred; in particular *Alopecurus, Avena* (especially *Avena fatua*), *Lolium* and/or *Setaria* (especially *Setaria viridis, Setaria lutescens, Setaria faberi* and/or *Setaria glauca*).

In all aspects of the invention, in a particular embodiment, the weeds, e.g. to be controlled and/or growth-inhibited e.g. by applying a compound of formula (I), may be grassy monocotyledonous weeds (e.g. *Agrostis, Alopecurus, Apera, Avena, Brachiaria, Bromus, Cenchrus, Digitaria, Echinochloa, Eleusine, Eriochloa, Leptochloa, Lolium, Ottochloa, Panicum, Pennisetum, Phalaris, Poa, Rottboellia, Setaria* and/or *Sorghum* weeds), which are resistant to one or more ACCase inhibitor herbicides (ACCase=acetyl-coenzyme A carboxylase) selected from the group consisting of pinoxaden, clodinafop-propargyl, fenoxaprop-P-ethyl, diclofop-methyl, fluazifop-P-butyl, haloxyfop-P-methyl, quizalofop-P-ethyl, propaquizafop, cyhalofop-butyl, clethodim, sethoxydim, cycloxydim, tralkoxydim and butroxydim;

and/or which are resistant to glyphosate;

and/or which are resistant to one or more ALS inhibitor herbicides (ALS=acetolactate synthase), such as one or more sulfonyl urea herbicides (e.g. iodosulfuron-methyl, mesosulfuron-methyl, tribenuron-methyl, triasulfuron, prosulfuron, sulfosulfuron, pyrazosulfuron-ethyl, bensulfuron-methyl, nicosulfuron, flazasulfuron, iofensulfuron, metsulfuron-methyl, or any other sulfonyl urea herbicide disclosed in The Pesticide Manual, 15th edition, 2009, ed. C. D. S. Tomlin, British Crop Protection Council) and/or one or more triazolopyrimidine herbicides (e.g. florasulam, pyroxsulam or penoxsulam) and/or one or more pyrimidinyl-(thio or oxy)-benzoate herbicides (e.g. bispyribac-sodium or pyriftalid) and/or one or more sulfonylamino-carbonyl-triazolinone herbicides (e.g. thiencarbazone-methyl, propoxycarbazone-sodium or flucarbazone-sodium) and/or one or more imidazolinone herbicides (e.g. imazamox).

Such resistant (in particular ACCase-inhibitor-resistant, glyphosate-resistant, and/or ALS-inhibitor-resistant) grassy weeds can more particularly comprise *Alopecurus myosuroides, Apera spica-venti, Avena fatua, Avena sterilis, Brachiaria decumbens, Brachiaria plantaginea, Digitaria horizontalis, Digitaria insularis, Digitaria sanguinalis, Echinochloa colona, Echinochloa crus-galli, Eleusine indica, Lolium multiflorum, Lolium rigidum, Lolium perenne, Phalaris minor, Phalaris paradoxa, Setaria viridis, Setaria faberi, Setaria glauca*, and/or *Sorghum halepense*.

In an even more particular embodiment of the invention, the compound of formula (I) can be applied to grassy monocotyledonous weeds (e.g. selected from one of the above-mentioned list(s) of grassy weeds):

(a1) which are resistant to one or more ACCase inhibitor herbicides (e.g. selected from the above-mentioned list of ACCase inhibitor herbicides) at least partly by means of mutation (e.g. substitution) of one or more amino acids on the ACCase target site in the weed (e.g. see S. B. Powles and Qin Yu, "Evolution in Action: Plants Resistant to Herbicides", *Annu. Rev. Plant Biol.*, 2010, 61, pp. 317-347, e.g. see pages 325-327 therein in particular Table 3, incorporated herein by reference, for examples of such resistant weeds and/or amino acid substitutions); and/or (a2) which are resistant to glyphosate at least partly by means of mutation (e.g. substitution) of one or more amino acids on the EPSPS target site in the weed targeted by glyphosate (e.g. see above-mentioned S. B. Powles and Qin Yu article, pp. 327-329); and/or (a3) which are resistant to one or more ALS inhibitor herbicides (e.g. selected from the above-mentioned list of ALS inhibitor herbicides) at least partly by mutation (e.g. substitution) of one or more amino acids on the ALS target site in the weed (e.g. see S. B. Powles and Qin Yu, "Evolution in Action: Plants Resistant to Herbicides", *Annu. Rev. Plant Biol.*, 2010, 61, pp. 317-347, e.g. see pages 322-324 therein in particular Table 2, incorporated herein by reference, for examples of such resistant weeds and/or amino acid substitutions); and/or (b) which are resistant to: one or more ACCase inhibitor herbicides (e.g. selected from the above-mentioned list), and/or glyphosate, and/or one or more ALS inhibitor herbicides (e.g. selected from the above-mentioned list); at least partly by metabolic-type herbicidal resistance e.g. at least partly by cytochrome P450-mediated herbicide metabolism (e.g. see S. B. Powles and Qin Yu, "Evolution in Action: Plants Resistant to Herbicides", *Annu. Rev. Plant Biol.*, 2010, 61, pp. 317-347, e.g. see Table 4 on page 328 therein, incorporated herein by reference, for examples of such resistant weeds).

Typically, dicotyledonous weeds, e.g. to be controlled, comprise (e.g. are) *Abutilon, Amaranthus, Chenopodium, Chrysanthemum, Galium, Ipomoea, Kochia, Nasturtium, Polygonum, Sida, Sinapsis, Solanum, Stellaria,* Viola, Veronica and/or *Xanthium.*

Areas under cultivation, and/or the locus (e.g. of weeds and/or of crops of useful plants), are to be understood as including land where the crop plants are already growing as well as land intended for the cultivation of those crop plants.

In all aspects of the invention, the rate of application (typically to the weeds and/or to the crops of useful plants and/or to the locus thereof) of the compound of formula (I) (which optionally may be an agrochemically acceptable salt thereof) is generally from 1 to 2000 g of the compound of formula (I) per hectare (ha) (measured as the salt-free compound, i.e. excluding the weight of any associated salt counterion(s)), in particular from 5 to 1000 g/ha or from 5 to 500 g/ha or from 10 to 500 g/ha, preferably from 10 to 400 g/ha or from 20 to 300 g/ha, of the compound of formula (I) (measured as the salt-free compound, i.e. excluding the weight of any associated salt counterion(s)). In a preferred embodiment, the above rates of application are for post-emergence application of the compound of formula (I) (which optionally may be an agrochemically acceptable salt thereof).

In all aspects of the invention, the compound of formula (I) can be applied (typically to the weeds and/or to the crops of useful plants and/or to the locus thereof) pre- and/or post-emergence, but preferably is applied post-emergence.

Other Possible Uses— e.g. Possible Insecticidal and/or Acaricidal Uses

The main use and purpose of the compounds of formula (I) according to the invention is their herbicidal use. However, at least some of the compounds of formula (I) may have activity against one or more types of pest (in particular pests associated with agriculture and/or food storage). For example, at least some of the compounds of formula (I) may have at least some insecticidal, acaricidal, molluscicidal and/or nematicidal activity.

At least some of the compounds of formula (I) may have activity against (and/or may help to control and/or combat) insect pests, such as one or more of: Coleoptera, Dictyoptera, Diptera, Hemiptera (including Homoptera), Hymenoptera, Isoptera, Lepidoptera, Orthoptera, Siphonaptera and/or Thysanoptera.

At least some of the compounds of formula (I) may have activity against (and/or may help to control and/or combat) acarine pests and/or pests from the order Acarina, such as one or more of: *Acalitus* spp, *Aculus* spp, *Acaricalus* spp, *Aceria* spp, *Acarus siro, Amblyomma* spp., *Argas* spp., *Boophilus* spp., *Brevipalpus* spp., *Bryobia* spp, *Calipitrimerus* spp., *Chorioptes* spp., *Dermanyssus gallinae, Dermatophagoides* spp, *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus, Panonychus* spp., *Phyllocoptruta oleivora, Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and/or *Tetranychus* spp.

At least some of the compounds of formula (I) may have activity against (and/or may help to control and/or combat) other (i.e. non-insect, non-acarine) invertebrate pests, for example, nematode and/or mollusc pests.

Insects, acarines, nematodes and/or molluscs are hereinafter collectively referred to as pests.

Examples of pest species, on and/or to which the compounds of formula (I) can be tried and/or applied, include one or more of: *Myzus* spp. such as *Myzus persicae* (aphid), *Aphis* spp. such as *Aphis gossypii* (aphid) or *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (*thrips*), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus* spp. such as *Tetranychus urticae* (two-spotted spider mite) or *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the Mastotermitidae (for example *Mastotermes* spp.), of the Kalotermitidae (for example *Neotermes* spp.), of the Rhinotermitidae (for example *Coptotermes formosanus, Reticulitermes flavipes, R. sperata, R. virginicus, R. hesperus*, or *R. santonensis*) or of the Termitidae (for example *Globitermes sulphureus*), *Solenopsis geminata* (fire ant), *Monomorium pharaonis* (pharaoh's ant), *Damalinia* spp. or *Linognathus* spp. (biting lice or sucking lice), *Meloidogyne* spp. (root knot nematodes), *Globodera* spp. or *Heterodera* spp. (cyst nematodes), *Pratylenchus* spp. (lesion nematodes), Rhodopholus spp. (banana burrowing nematodes), *Tylenchulus* spp. (citrus nematodes), *Haemonchus contortus* (barber pole worm), *Caenorhabditis elegans* (vinegar eelworm), *Trichostrongylus* spp. (gastro intestinal nematodes) and/or *Deroceras reticulatum* (slug).

Combinations and Mixtures

In a further aspect, the present invention provides a herbicidal composition, e.g. for use in a method of controlling weeds (e.g. monocotyledonous such as grassy weeds) in crops of useful plants, comprising a compound of formula (I) as defined herein (e.g. a herbicidally effective amount thereof), and an agrochemically acceptable carrier, diluent and/or solvent, and also comprising one or more further herbicides, and/or a safener.

In all aspects of the invention, the compound of the formula (I) is optionally present (e.g. where chemically possible) as an agrochemically acceptable salt thereof.

Examples of these mixtures/compositions, comprising one or more further herbicides and/or a safener, follow.

The compounds of formula (I) according to the invention can be used in combination with one or more further herbicides, e.g. as mixture partner(s) for the compound of formula (I).

Preferably, in these mixtures (in particular in the specific mixtures disclosed hereinbelow), the compound of the formula (I) is one of those compounds listed in Tables 1 to 25 or 26 or 27 and/or one of the exemplified compounds (e.g. A-1 to A-18, or A-19 to A-41, or P-3 to P-7) as disclosed herein e.g. hereinbelow.

In particular, the following mixtures of the compound of formula (I) with one or more further herbicides are particularly disclosed:
compound of formula I+acetochlor, compound of formula I+acifluorfen, compound of formula I+acifluorfen-sodium, compound of formula I+aclonifen, compound of formula I+acrolein, compound of formula I+alachlor, compound of formula I+alloxydim, compound of formula I+allyl alcohol, compound of formula I+ametryn, compound of formula I+amicarbazone, compound of formula I+amidosulfuron, compound of formula I+aminopyralid, compound of formula I+amitrole, compound of formula I+ammonium sulfamate, compound of formula I+anilofos, compound of formula I+asulam, compound of formula I+atraton, compound of formula I+atrazine, compound of formula I+azimsulfuron, compound of formula I+BCPC, compound of formula I+beflubutamid, compound of formula I+benazolin, compound of formula I+benfluralin, compound of formula I+benfuresate, compound of formula I+bensulfuron, compound of formula I+bensulfuron-methyl, compound of formula I+bensulide, compound of formula I+bentazone, compound of formula I+benzfendizone, compound of formula I+benzobicyclon, compound of formula I+benzofenap, compound of formula I+bifenox, compound of formula I+bilanafos, compound of formula I+bispyribac, compound of formula I+bispyribac-sodium, compound of formula I+borax, compound of formula I+bromacil, compound of formula I+bromobutide, compound of formula I+bromoxynil, compound of formula I+bromoxynil heptanoate, compound of formula I+bromoxynil octanoate, compound of formula I+bromoxynil heptanoate+bromoxynil octanoate, compound of formula I+butachlor, compound of formula I+butafenacil, compound of formula I+butamifos, compound of formula I+butralin, compound of formula I+butroxydim, compound of formula I+butylate, compound of formula I+cacodylic acid, compound of formula I+calcium chlorate, compound of formula I+cafenstrole, compound of formula I+carbetamide, compound of formula I+carfentrazone, compound of formula I+carfentrazone-ethyl, compound of formula I+CDEA, compound of formula I+CEPC, compound of formula I+chloransulam, compound of formula I+chloransulam-methyl, compound of formula I+chlorflurenol, compound of formula I+chlorflurenol-methyl, compound of formula I+chloridazon, compound of formula I+chlorimuron, compound of formula I+chlorimuron-ethyl, compound of formula I+chloroacetic acid, compound of formula I+chlorotoluron, compound of formula I+chlorpropham, compound of formula I+chlorsulfuron, compound of formula I+chlorthal, compound of formula I+chlorthal-dimethyl, compound of formula I+cinidon-ethyl, compound of formula I+cinmethylin, compound of formula I+cinosulfuron, compound of formula I+cisanilide, compound of formula I+clethodim, compound of formula I+clodinafop, compound of formula I+clodinafop-propargyl, compound of formula I+clomazone, compound of formula I+clomeprop, compound of formula I+clopyralid, compound of formula I+cloransulam, compound of formula I+cloransulam-methyl, compound of formula I+CMA, compound of formula I+4-CPB, compound of formula I+CPMF, compound of formula I+4-CPP, compound of formula I+CPPC, compound of formula I+cresol, compound of formula I+cumyluron, compound of formula I+cyanamide, compound of formula I+cyanazine, compound of formula I+cycloate, compound of formula I+cyclosulfamuron, compound of formula I+cycloxydim, compound of formula I+cyhalofop, compound of formula I+cyhalofop-butyl, compound of formula I+2,4-D, compound of formula I+2,4-D-dimethylammonium, compound of formula I+2,4-D-2-ethylhexyl, compound of formula I+a choline salt of 2,4-D (see e.g. Examples 2 and 3 of WO2010/123871A1), compound of formula I+2,4-D+glyphosate, compound of formula I+2,4-D-dimethylammonium+glyphosate, compound of formula I+2,4-D-2-ethylhexyl+glyphosate, compound of formula I+a choline salt of 2,4-D+glyphosate (see e.g. Examples 2 and 3 of WO2010/123871A1), compound of formula I+3,4-DA, compound of formula I+daimuron, compound of formula I+dalapon, compound of formula I+dazomet, compound of formula I+2,4-DB, compound of formula I+3,4-DB, compound of formula I+2,4-DEB, compound of formula I+desmedipham, compound of formula I+dicamba, compound of formula I+dicamba-dimethylammonium, compound of formula I+dicamba-potassium, compound of formula I+dicamba-sodium, compound of formula I+dicamba-diglycolamine, compound of formula I+a N,N-bis-[aminopropyl]methylamine salt of dicamba (see e.g. US2012/0184434A1), compound of formula I+dicamba+glyphosate, compound of formula I+dicamba-dimethylammonium+glyphosate, compound of formula I+dicamba-potassium+glyphosate, compound of formula I+dicamba-sodium+glyphosate, compound of formula I+dicamba-diglycolamine+glyphosate, compound of formula I+a N,N-bis-[aminopropyl]methylamine salt of dicamba+glyphosate, compound of formula I+dichlobenil, compound of formula I+ortho-dichlorobenzene, compound of formula I+para-dichlorobenzene, compound of formula I+dichlorprop, compound of formula I+dichlorprop-P, compound of formula I+diclofop, compound of formula I+diclofop-methyl, compound of formula I+diclosulam, compound of formula I+difenzoquat, compound of formula I+difenzoquat metilsulfate, compound of formula I+diflufenican, compound of formula I+diflufenzopyr, compound of formula I+dimefuron, compound of formula I+dimepiperate, compound of formula I+dimethachlor, compound of formula I+dimethametryn, compound of formula I+dimethenamid, compound of formula I+dimethenamid-P, compound of formula I+dimethipin, compound of formula I+dimethylarsinic acid, compound of formula I+dinitramine, compound of formula I+dinoterb, compound of formula I+diphenamid, compound of formula I+diquat, compound of formula I+diquat dibromide, compound of formula I+dithiopyr, compound of formula I+diuron, compound of formula I+DNOC, compound of formula I+3,4-DP, compound of formula I+DSMA, compound of formula I+EBEP, compound of formula I+endothal, compound of formula I+EPTC, compound of formula I+esprocarb, compound of formula I+ethalfluralin, compound of formula I+ethametsulfuron, compound of formula I+ethametsulfuron-methyl, compound of formula I+ethofumesate, compound of formula I+ethoxyfen, compound of formula I+ethoxysulfuron, compound of formula I+etobenzanid, compound of formula (I)+fenoxaprop, compound of formula (I)+fenoxaprop-ethyl, compound of formula I+fenoxaprop-P, compound of formula I+fenoxaprop-P-ethyl, compound of formula I+fenoxasulfone (CAS Reg. No. 639826-16-7), compound of formula I+fentrazamide, compound of formula I+ferrous sulfate, compound of formula I+flamprop-M, compound of formula I+flazasulfuron, compound of formula I+florasulam, compound of formula I+fluazifop, compound of formula I+fluazifop-butyl, compound of formula I+fluazifop-P, compound of formula I+fluazifop-P-butyl, compound of formula I+flucarbazone, compound of formula I+flucarbazone-sodium, compound of formula I+flucetosulfuron, compound of formula I+fluchloralin, compound of formula I+flufenacet, compound of formula I+flufenpyr, compound of formula I+flufenpyr-ethyl, compound of formula I+flumetsulam, compound of formula I+flumiclorac, compound of formula I+flumiclorac-pentyl, compound of formula I+flumioxazin, compound of formula I+fluometuron, compound of formula I+fluoroglycofen, compound of formula I+fluoroglycofen-ethyl, compound of formula I+flupropanate, compound of formula I+flupyrsulfuron, compound of formula I+flupyrsulfuron-methyl-sodium, compound of formula I+flurenol, compound of formula I+fluridone, compound of formula I+flurochloridone, compound of formula I+fluroxypyr, compound of formula I+fluroxypyr-meptyl, compound of formula I+fluroxypyr-butometyl, compound of formula I+flurtamone, compound of formula I+fluthiacet, compound of formula I+fluthiacet-methyl, compound of formula I+fomesafen, compound of formula I+foramsulfuron, compound of formula I+fosamine, compound of formula I+glufosinate, compound of formula I+glufosinate-ammonium, compound of formula I+glufosinate-P, compound of formula I+glyphosate, compound of formula I+glyphosate-diammonium, compound of formula I+glyphosate-isopropylammonium, compound of formula I+glyphosate-potassium, compound of formula I+halosulfuron, compound of formula I+halosulfuron-methyl, compound of formula I+haloxyfop, compound of formula I+haloxyfop-P, compound of formula (I)+haloxyfop-methyl, compound of formula (I)+haloxyfop-P-methyl, compound of formula I+HC-252, compound of formula I+hexazinone, compound of formula I+imazamethabenz, compound of formula I+imazamethabenz-methyl, compound of formula I+imazamox, compound of formula I+imazapic, compound of formula I+imazapyr, compound of formula I+imazaquin, compound of formula I+imazethapyr, compound of formula I+imazosulfuron, compound of formula I+indanofan, compound of formula I+iodomethane, compound of formula I+iodosulfuron, compound of formula I+iodosulfuron-methyl-sodium, compound of formula I+ioxynil, compound of formula I+ipfencarbazone (CAS Reg. No. 212201-70-2), compound of formula I+isoproturon, compound of formula I+isouron, compound of formula I+isoxaben, compound of formula I+isoxachlortole, compound of formula I+isoxaflutole, compound of formula I+karbutilate, compound of formula I+lactofen, compound of formula I+lenacil, compound of formula I+linuron, compound of formula I+MAA, compound of formula I+MAMA, compound of formula I+MCPA, compound of formula I+MCPA-thioethyl, compound of formula I+MCPB, compound of formula I+mecoprop, compound of formula I+mecoprop-P, compound of formula I+mefenacet, compound of formula I+mefluidide, compound of formula I+mesosulfuron, compound of formula I+mesosulfuron-methyl, compound of formula I+mesotrione, compound of formula I+metam, compound of formula I+metamifop, compound of formula I+metamitron, compound of formula I+metazachlor, compound of formula I+metazosulfuron (NC-620, CAS Reg. No. 868680-84-6), compound of formula I+methabenzthiazuron, compound of formula I+methylarsonic acid, compound of formula I+methyldymron, compound of formula I+methyl isothiocyanate, compound of formula I+metobenzuron, compound of formula I+metolachlor, compound of formula I+S-metolachlor, compound of formula I+metosulam, compound of formula I+metoxuron, compound of formula I+metribuzin, compound of formula I+metsulfuron, compound of formula I+metsulfuron-methyl, compound of formula I+MK-616, compound of formula I+molinate, compound of formula I+monolinuron, compound of formula I+MSMA, compound of formula I+naproanilide, compound of formula I+napropamide, compound of formula I+naptalam, compound of formula I+neburon, compound of formula I+nicosulfuron, compound of formula I+nonanoic acid, compound of formula I+norflurazon, compound of formula I+oleic acid (fatty acids), compound of formula I+orbencarb, compound of formula I+orthosulfamuron, compound of formula I+oryzalin, compound of formula I+oxadiargyl, compound of formula I+oxadiazon, compound of formula I+oxasulfuron, compound of formula I+oxaziclomefone, compound of formula I+oxyfluorfen, compound of formula I+paraquat, compound of formula I+paraquat dichloride, compound of formula I+pebulate, compound of formula I+pendimethalin, compound of formula I+penoxsulam, compound of formula I+pentachlorophenol, compound of formula I+pentanochlor, compound of formula I+pentoxazone, compound of formula I+pethoxamid, compound of formula I+petrolium oils, compound of formula I+phenmedipham, compound of formula I+phenmedipham-ethyl, compound of formula I+picloram, compound of formula I+picolinafen, compound of formula I+pinoxaden, compound of formula I+piperophos, compound of formula I+potassium arsenite, compound of formula I+potassium azide, compound of formula I+pretilachlor, compound of formula I+primisulfuron, compound of formula I+primisulfuron-methyl, compound of formula I+prodiamine, compound of formula I+profluazol, compound of formula I+profoxydim, compound of formula I+prometon, compound of formula I+prometryn, compound of formula I+propachlor, compound of formula I+propanil, compound of formula I+propaquizafop, compound of formula I+propazine, compound of formula I+propham, compound of formula I+propisochlor, compound of formula I+propoxycarbazone, compound of formula I+propoxycarbazone-sodium, compound of formula I+propyrisulfuron (TH-547, CAS Reg. No. 570415-88-2), compound of formula I+propyzamide, compound of formula I+prosulfocarb, compound of formula I+prosulfuron, compound of formula I+pyraclonil, compound of formula I+pyraflufen, compound of formula I+pyraflufen-ethyl, compound of formula I+pyrazolynate, compound of formula I+pyrazosulfuron, compound of formula I+pyrazosulfuron-ethyl, compound of formula I+pyrazoxyfen, compound of formula I+pyribenzoxim, compound of formula I+pyributicarb, compound of formula I+pyridafol, compound of formula I+pyridate, compound of formula I+pyriftalid, compound of formula I+pyriminobac, compound of formula I+pyriminobac-methyl, compound of formula I+pyrimisulfan, compound of formula I+pyrithiobac, compound of formula I+pyrithiobac-sodium, compound of formula I+quinclorac, compound of formula I+quinmerac, compound of formula I+quinoclamine, compound of formula I+quizalofop, compound of formula I+quizalofop-ethyl, compound of formula I+quizalofop-P, compound of formula I+quizalofop-P-ethyl, compound of formula I+quizalofop-P-tefuryl, compound of formula I+rimsulfuron, compound of formula I+sethoxydim, compound of formula I+siduron, compound of formula I+simazine, compound of formula I+simetryn, compound of formula I+SMA, compound of formula I+sodium arsenite, compound of formula I+sodium azide, compound of formula I+sodium chlorate, compound of formula I+sulcotrione, compound of formula I+sulfentrazone, compound of formula I+sulfometuron, compound of formula I+sulfometuron-methyl, compound of formula I+sulfosate, compound of formula I+sulfosulfuron, compound of formula I+sulfuric acid, compound of formula I+tar oils, compound of formula I+2,3,6-TBA, compound of formula I+TCA, compound of formula I+TCA-sodium, compound of formula I+tebuthiuron, compound of formula I+tepraloxydim, compound of formula I+terbacil, compound of formula I+terbumeton, compound of formula I+terbuthylazine, compound of formula I+terbutryn, compound of formula I+thenylchlor, compound of formula I+thiazopyr, compound of formula I+thifensulfuron, compound of formula I+thifensulfuron-methyl, compound of formula I+thiobencarb, compound of formula I+tiocarbazil, compound of formula I+topramezone, compound of formula I+tralkoxydim, compound of formula I+tri-allate, compound of formula I+triasulfuron, compound of formula I+triaziflam, compound of formula I+tribenuron, compound of formula I+tribenuron-methyl, compound of formula I+tricamba, compound of formula I+triclopyr, compound of formula I+trietazine, compound of formula I+trifloxysulfuron, compound of formula I+trifloxysulfuron-sodium, compound of formula I+trifluralin, compound of formula I+triflusulfuron, compound of formula I+triflusulfuron-methyl, compound of formula I+trihydroxytriazine, compound of formula I+tritosulfuron, compound of formula I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS Reg. No. 353292-31-6), compound of formula I+4-[(4,5-dihydro-3-methoxy-4-methyl-5-oxo)-1H-1,2,4-triazol-1-ylcarbonylsulfamoyl]-5-methylthiophene-3-carboxylic acid (BAY636), compound of formula I+BAY747 (CAS Reg. No. 335104-84-2), compound of formula I+topramezone (CAS Reg. No. 210631-68-8), compound of formula I+4-hydroxy-3-[[2-[(2-methoxyethoxy)-methyl]-6-(trifluoromethyl)-3-pyridinyl]carbonyl]-bicyclo[3.2.1]oct-3-en-2-one (which is bicyclopyrone, CAS Reg. No. 352010-68-5), compound of formula I+4-hydroxy-3-[[2-(3-methoxypropyl)-6-(difluoromethyl)-3-pyridinyl]carbonyl]-bicyclo[3.2.1]oct-3-en-2-one, compound of formula (I)+4-(4'-chloro-4-cyclopropyl-2'-fluorobiphenyl-3-yl)-2,2,6,6-tetramethyl-2H-pyran-3,5(4H,6H)-dione (which is the compound of Example P8 disclosed on pages 31-32 and 35-36 of WO 2010/136431 A9 (Syngenta Limited), and which is also compound A-13 disclosed in pages 4, 5, 7 and 11 of WO 2011/073616 A2 (Syngenta Limited), these parts of these publications being incorporated herein by reference), compound of formula (I)+4-(2',4'-dichloro-4-cyclopropylbiphenyl-3-yl)-2,2,6,6-tetramethyl-2H-pyran-3,5(4H,6H)-dione (which is the compound of Example P9 disclosed on pages 36-37 and 40-41 of WO 2010/136431 A9 (Syngenta Limited), and which is also compound A-12 disclosed in page 10 of WO 2011/073616 A2 (Syngenta Limited), these parts of these publications being incorporated herein by reference), compound of formula (I)+4-(4'-chloro-4-ethyl-2'-fluorobiphenyl-3-yl)-2,2,6,6-tetramethyl-2H-pyran-3,5(4H,6H)-dione (which is compound A-66 disclosed on page 95 of WO 2008/071405 A1 (Syngenta Participations AG and Syngenta Limited), and which is also compound A-4 disclosed on page 7 of WO 2011/073615 A2 (Syngenta Limited), these parts of these publications being incorporated herein by reference), compound of formula (I)+4-(2',4'-dichloro-4-ethylbiphenyl-3-yl)-2,2,6,6-tetramethyl-2H-pyran-3,5(4H,6H)-dione (which is compound A-45 disclosed on page 93 of WO 2008/071405 A1 (Syngenta Participations AG and Syngenta Limited), and which is also the compound of Example P10 disclosed on pages 41 and 45 of WO 2010/136431 A9 (Syngenta Limited), and which is also compound A-7 disclosed on page 7 of WO 2011/073615 A2 (Syngenta Limited), these parts of these publications being incorporated herein by reference), compound of formula (I)+4-(2',4'-dichloro-4-ethylbiphenyl-3-yl)-5-(methoxycarbonyloxy)-2,2,6,6-tetramethyl-2H-pyran-3(6H)-one (which is compound D-26 disclosed on page 231 of WO 2008/071405 A1 (Syngenta Participations AG and Syngenta Limited), and which is also compound A-9 disclosed on page 8 of WO 2011/073615 A2 (Syngenta Limited), these parts of these publications being incorporated herein by reference), compound of formula (I)+one of the specific herbicidal compounds disclosed in WO 2010/059676 (Dow, e.g. as defined in one of the examples therein and/or e.g. can be plus cloquintocet-mexyl as safener) these parts of which are incorporated herein by reference, compound of formula (I)+one of the specific herbicidal compounds disclosed in WO 2010/059680 (Dow, e.g. as defined in one of the examples therein and/or e.g. can be plus cloquintocet-mexyl or another safener) these parts of which are incorporated herein by reference, and compound of formula (I)+one of the specific herbicidal compounds disclosed in WO 2010/059671 (Dow, e.g. as defined in one of the examples therein and/or e.g. can be plus a safener) these parts of which are incorporated herein by reference, compound of formula I+halauxifen (which is 4-amino-3-chloro-6-(4-chloro-2-fluoro-3-methoxyphenyl)pyridine-2-carboxylic acid, CAS Reg. No. 943832-60-8), compound of formula I+halauxifen-methyl (which is methyl 4-amino-3-chloro-6-(4-chloro-2-fluoro-3-methoxyphenyl)pyridine-2-carboxylate, CAS Reg. No. 943831-98-9), compound of formula I+aminocyclopyrachlor (which is 6-amino-5-chloro-2-cyclopropylpyrimidine-4-carboxylic acid, CAS Reg. No. 858956-08-8), compound of formula I+aminocyclopyrachlor-methyl (which is methyl 6-amino-5-chloro-2-cyclopropylpyrachlor-methyl 6-amino-5-chloro-2-cyclopropylpyrimidine-4-carboxylate, CAS Reg. No. 858954-83-3), compound of formula I+aminocyclopyrachlor-potassium (which is potassium 6-amino-5-chloro-2-cyclopropylpyrimidine-4-carboxylate, CAS Reg. No. 858956-35-1), compound of formula I+saflufenacil (which is N-{2-chloro-4-fluoro-5-[1,2,3,6-tetrahydro-3-methyl-2,6-dioxo-4-(trifluoromethyl)pyrimidin-1-yl]benzoyl}-N-isopropyl-N-methylsulfamide, CAS Reg. No. 372137-35-4), compound of formula I+iofensulfuron (which is 1-(2-iodophenylsulfonyl)-3-(4-methoxy-6-methyl-1,3,5-triazin-2-yl) urea, CAS Reg. No. 1144097-22-2), compound of formula I+iofensulfuron-sodium (which is sodium N-(2-iodophenylsulfonyl)-N-(4-methoxy-6-methyl-1,3,5-triazin-2-yl)carbamimidate, CAS Reg. No. 1144097-30-2), compound of formula I+clacyfos (which is dimethyl [(1RS)-1-(2,4-dichlorophenoxyacetoxyl)ethyl]phosphonate, also named Ivxiancaolin or Iüxiancaolin, CAS Reg. No. 215655-76-8), compound of formula I+cyclopyrimorate (which is 6-chloro-3-(2-cyclopropyl-6-methylphenoxy)pyridazin-4-yl morpholine-4-carboxylate, CAS Reg. No. 499231-24-2), or compound of formula I+triafamone (which is N-[2-[(4,6-dimethoxy-1,3,5-triazin-2-yl)carbonyl]-6-fluorophenyl]-N-methyl-1,1-difluoromethanesulfonamide, CAS Reg. No. 874195-61-6).

The mixture partners for the compound of formula (I) are optionally in the form of an ester (in particular an agrochemically acceptable ester) or a salt (in particular an agrochemically acceptable salt) thereof (e.g. where chemically possible). The above-mentioned mixture partners for the compound of formula (I), are generally mentioned e.g. in The Pesticide Manual, 15th Edition, 2009, ed. C. D. S. Tomlin, British Crop Production Council.

In the present patent specification, "CAS Reg. No." or "CAS RN" means the Chemical Abstracts Service Registry Number of the stated compound.

For applications in cereals, the following mixtures are preferred: compound of formula I+aclonifen, compound of formula I+amidosulfuron, compound of formula I+aminopyralid, compound of formula I+beflubutamid, compound of formula I+benfluralin, compound of formula I+bifenox, compound of formula I+bromoxynil, compound of formula I+bromoxynil heptanoate, compound of formula I+bromoxynil octanoate, compound of formula I+bromoxynil heptanoate+bromoxynil octanoate, compound of formula I+butafenacil, compound of formula I+carbetamide, compound of formula I+carfentrazone, compound of formula I+carfentrazone-ethyl, compound of formula I+chlorotoluron, compound of formula I+chlorpropham, compound of formula I+chlorsulfuron, compound of formula I+cinidon-ethyl, compound of formula I+clodinafop, compound of formula I+clodinafop-propargyl, compound of formula I+clopyralid, compound of formula I+2,4-D, compound of formula I+2,4-D-dimethylammonium, compound of formula I+2,4-D-2-ethylhexyl, compound of formula I+a choline salt of 2,4-D (see e.g. Examples 2 and 3 of WO2010/123871A1), compound of formula I+dicamba, compound of formula I+dicamba-dimethylammonium, compound of formula I+dicamba-potassium, compound of formula I+dicamba-sodium, compound of formula I+dicamba-diglycolamine, compound of formula I+a N,N-bis-[aminopropyl] methylamine salt of dicamba (see e.g. US2012/0184434A1), compound of formula I+dichlobenil, compound of formula I+dichlorprop, compound of formula I+diclofop, compound of formula I+diclofop-methyl, compound of formula I+difenzoquat, compound of formula I+difenzoquat metilsulfate, compound of formula I+diflufenican, compound of formula I+diquat, compound of formula I+diquat dibromide, compound of formula (I)+fenoxaprop, compound of formula (I)+fenoxaprop-ethyl, compound of formula I+fenoxaprop-P, compound of formula I+fenoxaprop-P-ethyl, compound of formula I+flamprop-M, compound of formula I+florasulam, compound of formula I+fluazifop-P-butyl, compound of formula I+flucarbazone, compound of formula I+flucarbazone-sodium, compound of formula I+flufenacet, compound of formula I+flupyrsulfuron, compound of formula I+flupyrsulfuron-methyl-sodium, compound of formula I+flurochloridone, compound of formula I+fluroxypyr, compound of formula I+fluroxypyr-meptyl, compound of formula I+fluroxypyr-butometyl, compound of formula I+flurtamone, compound of formula I+imazamethabenz-methyl, compound of formula I+imazamox, compound of formula I+iodosulfuron, compound of formula I+iodosulfuron-methyl-sodium, compound of formula I+ioxynil, compound of formula I+isoproturon, compound of formula I+linuron, compound of formula I+MCPA, compound of formula I+mecoprop, compound of formula I+mecoprop-P, compound of formula I+mesosulfuron, compound of formula I+mesosulfuron-methyl, compound of formula I+mesotrione, compound of formula I+metribuzin, compound of formula I+metsulfuron, compound of formula I+metsulfuron-methyl, compound of formula I+pendimethalin, compound of formula I+picolinafen, compound of formula I+pinoxaden, compound of formula I+prodiamine, compound of formula I+propanil, compound of formula I+propoxycarbazone, compound of formula I+propoxycarbazone-sodium, compound of formula I+prosulfocarb, compound of formula I+pyrasulfotole, compound of formula I+pyridate, compound of formula I+pyroxasulfone (KIH-485), compound of formula I+pyroxsulam compound of formula I+sulfosulfuron, compound of formula 1+tembotrione, compound of formula I+terbutryn, compound of formula I+thifensulfuron, compound of formula I+thiencarbazone, compound of formula I+thifensulfuron-methyl, compound of formula I+topramezone, compound of formula I+tralkoxydim, compound of formula I+tri-allate, compound of formula I+triasulfuron, compound of formula I+tribenuron, compound of formula I+tribenuron-methyl, compound of formula I+trifluralin, compound of formula I+trinexapac-ethyl and compound of formula I+tritosulfuron, compound of formula I+4-hydroxy-3-[[2-[(2-methoxyethoxy)methyl]-6-(trifluoromethyl)-3-pyridinyl]carbonyl]-bicyclo[3.2.1]oct-3-en-2-one (which is bicyclopyrone, CAS Reg. No. 352010-68-5), compound of formula (I)+one of the specific herbicidal compounds disclosed in WO 2010/059676 (Dow, e.g. as defined in one of the examples therein and/or e.g. can be plus cloquintocet-mexyl as safener) these parts of which are incorporated herein by reference, compound of formula (I)+one of the specific herbicidal compounds disclosed in WO 2010/059680 (Dow, e.g. as defined in one of the examples therein and/or e.g. can be plus cloquintocet-mexyl or another safener) these parts of which are incorporated herein by reference, compound of formula I+halauxifen (which is 4-amino-3-chloro-6-(4-chloro-2-fluoro-3-methoxyphenyl)pyridine-2-carboxylic acid, CAS Reg. No. 943832-60-8), compound of formula I+halauxifen-methyl (which is methyl 4-amino-3-chloro-6-(4-chloro-2-fluoro-3-methoxyphenyl)pyridine-2-carboxylate, CAS Reg. No. 943831-98-9), compound of formula I+iofensulfuron (which is 1-(2-iodophenylsulfonyl)-3-(4-methoxy-6-methyl-1,3,5-triazin-2-yl)urea, CAS Reg. No. 1144097-22-2), or compound of formula I+iofensulfuron-sodium (which is sodium N-(2-iodophenylsulfonyl)-N-(4-methoxy-6-methyl-1,3,5-triazin-2-yl)carbamimidate, CAS Reg. No. 1144097-30-2);

wherein the mixture partners for the compound of formula (I) may optionally be in the form of an ester (in particular an agrochemically acceptable ester) or a salt (in particular an agrochemically acceptable salt) thereof (e.g. where chemically possible).

For applications in cereals, more preferred is a mixture comprising: a compound of formula (I)+amidosulfuron, compound of formula (I)+aminopyralid, compound of formula (I)+beflubutamid, compound of formula (I)+bromoxynil, compound of formula (I)+bromoxynil heptanoate, compound of formula (I)+bromoxynil octanoate, compound of formula (I)+bromoxynil heptanoate+bromoxynil octanoate, compound of formula (I)+carfentrazone, compound of formula (I)+carfentrazone-ethyl, compound of formula (I)+chlorotoluron, compound of formula (I)+chlorsulfuron, compound of formula (I)+clodinafop, compound of formula (I)+clodinafop-propargyl, compound of formula (I)+clopyralid, compound of formula (I)+2,4-D, compound of formula (I)+2,4-D-dimethylammonium, compound of formula (I)+2,4-D-2-ethylhexyl, compound of formula (I)+a choline salt of 2,4-D (see e.g. Examples 2 and 3 of WO2010/123871A1), compound of formula (I)+dicamba, compound of formula (I)+dicamba, compound of formula (I)+dicamba-dimethylammonium, compound of formula (I)+dicamba-potassium, compound of formula (I)+dicamba-sodium, compound of formula (I)+dicamba-diglycolamine, compound of formula (I)+a N,N-bis-[aminopropyl]methylamine salt of dicamba (see e.g. US2012/0184434A1), compound of formula (I)+difenzoquat, compound of formula (I)+difenzoquat metilsulfate, compound of formula (I)+diflufenican, compound of formula (I)+fenoxaprop-P, compound of formula (I)+fenoxaprop-P-ethyl, compound of formula (I)+florasulam, compound of formula (I)+flucarbazone, compound of formula (I)+flucarbazone-sodium, compound of formula (I)+flufenacet, compound of formula (I)+flupyrsulfuron, compound of formula (I)+flupyrsulfuron-methyl-sodium, compound of formula (I)+fluroxypyr, compound of formula I+fluroxypyr-meptyl, compound of formula I+fluroxypyr-butometyl, compound of formula (I)+flurtamone, compound of formula (I)+iodosulfuron, compound of formula (I)+iodosulfuron-methyl-sodium, compound of formula (I)+MCPA, compound of formula (I)+mesosulfuron, compound of formula (I)+mesosulfuron-methyl, compound of formula (I)+metsulfuron, compound of formula (I)+metsulfuron-methyl, compound of formula (I)+pendimethalin, compound of formula (I)+picolinafen, compound of formula (I)+pinoxaden, compound of formula (I)+prosulfocarb, compound of formula (I)+pyrasulfotole, compound of formula (I)+pyroxasulfone (KIH-485), compound of formula (I)+pyroxsulam, compound of formula (I)+sulfosulfuron, compound of formula (I)+thifensulfuron, compound of formula (I)+thifensulfuron-methyl, compound of formula I+topramezone, compound of formula (I)+tralkoxydim, compound of formula (I)+triasulfuron, compound of formula (I)+tribenuron, compound of formula (I)+tribenuron-methyl, compound of formula (I)+trifluralin, compound of formula (I)+trinexapac-ethyl, compound of formula (I)+tritosulfuron, compound of formula I+4-hydroxy-3-[[2-[(2-methoxyethoxy)methyl]-6-(trifluoromethyl)-3-pyridinyl]carbonyl]-bicyclo[3.2.1]oct-3-en-2-one (which is bicyclopyrone, CAS Reg. No. 352010-68-5), compound of formula (I)+one of the specific herbicidal compounds disclosed in WO 2010/059676 (Dow, e.g. as defined in one of the examples therein and/or e.g. can be plus cloquintocet-mexyl as safener) these parts of which are incorporated herein by reference, compound of formula (I)+one of the specific herbicidal compounds disclosed in WO 2010/059680 (Dow, e.g. as defined in one of the examples therein and/or e.g. can be plus cloquintocet-mexyl or another safener) these parts of which are incorporated herein by reference, compound of formula I+halauxifen (which is 4-amino-3-chloro-6-(4-chloro-2-fluoro-3-methoxyphenyl)pyridine-2-carboxylic acid, CAS Reg. No. 943832-60-8), compound of formula I+halauxifen-methyl (which is methyl 4-amino-3-chloro-6-(4-chloro-2-fluoro-3-methoxyphenyl)pyridine-2-carboxylate, CAS Reg. No. 943831-98-9), compound of formula I+iofensulfuron (which is 1-(2-iodophenylsulfonyl)-3-(4-methoxy-6-methyl-1,3,5-triazin-2-yl)urea, CAS Reg. No. 1144097-22-2), or compound of formula I+iofensulfuron-sodium (which is sodium N-(2-iodophenylsulfonyl)-N-(4-methoxy-6-methyl-1,3,5-triazin-2-yl)carbamimidate, CAS Reg. No. 1144097-30-2);

wherein the mixture partners for the compound of formula (I) may optionally be in the form of an ester (in particular an agrochemically acceptable ester) or a salt (in particular an agrochemically acceptable salt) thereof (e.g. where chemically possible).

For applications in rice, the following mixtures are preferred: compound of formula (I)+azimsulfuron, compound of formula (I)+bensulfuron, compound of formula (I)+bensulfuron-methyl, compound of formula (I)+benzobicyclon, compound of formula (I)+benzofenap, compound of formula (I)+bispyribac, compound of formula (I)+bispyribac-sodium, compound of formula (I)+butachlor, compound of formula (I)+cafenstrole, compound of formula (I)+cinosulfuron, compound of formula (I)+clomazone, compound of formula (I)+clomeprop, compound of formula (I)+cyclosulfamuron, compound of formula (I)+cyhalofop, compound of formula (I)+cyhalofop-butyl, compound of formula (I)+2,4-D, compound of formula (I)+2,4-D-dimethylammonium, compound of formula (I)+2,4-D-2-ethylhexyl, compound of formula (I)+a choline salt of 2,4-D (see e.g. Examples 2 and 3 of WO2010/123871A1), compound of formula (I)+daimuron, compound of formula (I)+dicamba, compound of formula (I)+dicamba-dimethylammonium, compound of formula (I)+dicamba-potassium, compound of formula (I)+dicamba-sodium, compound of formula (I)+dicamba-diglycolamine, compound of formula (I)+a N,N-bis-[aminopropyl]methylamine salt of dicamba (see e.g. US2012/0184434A1), compound of formula (I)+diquat, compound of formula (I)+diquat dibromide, compound of formula (I)+esprocarb, compound of formula (I)+ethoxysulfuron, compound of formula (I)+fenoxaprop, compound of formula (I)+fenoxaprop-ethyl, compound of formula (I)+fenoxaprop-P, compound of formula (I)+fenoxaprop-P-ethyl, compound of formula I+fenoxasulfone (CAS Reg. No. 639826-16-7), compound of formula (I)+fentrazamide, compound of formula (I)+florasulam, compound of formula (I)+glufosinate-ammonium, compound of formula (I)+glyphosate, compound of formula (I)+glyphosate-diammonium, compound of formula (I)+glyphosate-isopropylammonium, compound of formula (I)+glyphosate-potassium, compound of formula (I)+halosulfuron, compound of formula (I)+halosulfuron-methyl, compound of formula (I)+imazosulfuron, compound of formula I+ipfencarbazone (CAS Reg. No. 212201-70-2), compound of formula (I)+MCPA, compound of formula (I)+mefenacet, compound of formula (I)+mesotrione, compound of formula (I)+metamifop, compound of formula I+metazosulfuron (NC-620, CAS Reg. No. 868680-84-6), compound of formula (I)+metsulfuron, compound of formula (I)+metsulfuron-methyl, compound of formula (I)+n-methyl glyphosate, compound of formula (I)+orthosulfamuron, compound of formula (I)+oryzalin, compound of formula (I)+oxadiargyl, compound of formula (I)+oxadiazon, compound of formula (I)+paraquat dichloride, compound of formula (I)+pendimethalin, compound of formula (I)+penoxsulam, compound of formula (I)+pretilachlor, compound of formula (I)+profoxydim, compound of formula (I)+propanil, compound of formula I+propyrisulfuron (TH-547, CAS Reg. No. 570415-88-2), compound of formula (I)+pyrazolynate, compound of formula (I)+pyrazosulfuron, compound of formula (I)+pyrazosulfuron-ethyl, compound of formula (I)+pyrazoxyfen, compound of formula (I)+pyribenzoxim, compound of formula (I)+pyriftalid, compound of formula (I)+pyriminobac, compound of formula (I)+pyriminobac-methyl, compound of formula (I)+pyrimisulfan, compound of formula (I)+quinclorac, compound of formula (I)+tefuryltrione, compound of formula (I)+triasulfuron and compound of formula (I)+trinexapac-ethyl, compound of formula (I)+4-(4'-chloro-4-cyclopropyl-2'-fluorobiphenyl-3-yl)-2,2,6,6-tetramethyl-2H-pyran-3,5(4H,6H)-dione (which is the compound of Example P8 disclosed on pages 31-32 and 35-36 of WO 2010/136431 A9 (Syngenta Limited), and which is also compound A-13 disclosed in pages 4, 5, 7 and 11 of WO 2011/073616 A2 (Syngenta Limited), these parts of these publications being incorporated herein by reference), compound of formula (I)+4-(2',4'-dichloro-4-cyclopropylbiphenyl-3-yl)-2,2,6,6-tetramethyl-2H-pyran-3,5(4H,6H)-dione (which is the compound of Example P9 disclosed on pages 36-37 and 40-41 of WO 2010/136431 A9 (Syngenta Limited), and which is also compound A-12 disclosed in page 10 of WO 2011/073616 A2 (Syngenta Limited), these parts of these publications being incorporated herein by reference), compound of formula (I)+4-(4'-chloro-4-ethyl-2'-fluorobiphenyl-3-yl)-2,2,6,6-tetramethyl-2H-pyran-3,5(4H,6H)-dione (which is compound A-66 disclosed on page 95 of WO 2008/071405 A1 (Syngenta Participations AG and Syngenta Limited), and which is also compound A-4 disclosed on page 7 of WO 2011/073615 A2 (Syngenta Limited), these parts of these publications being incorporated herein by reference), compound of formula (I)+4-(2',4'-dichloro-4-ethylbiphenyl-3-yl)-2,2,6,6-tetramethyl-2H-pyran-3,5(4H,6H)-dione (which is compound A-45 disclosed on page 93 of WO 2008/071405 A1 (Syngenta Participations AG and Syngenta Limited), and which is also the compound of Example P10 disclosed on pages 41 and 45 of WO 2010/136431 A9 (Syngenta Limited), and which is also compound A-7 disclosed on page 7 of WO 2011/073615 A2 (Syngenta Limited), these parts of these publications being incorporated herein by reference), compound of formula (I)+4-(2',4'-dichloro-4-ethylbiphenyl-3-yl)-5-(methoxycarbonyloxy)-2,2,6,6-tetramethyl-2H-pyran-3(6H)-one (which is compound D-26 disclosed on page 231 of WO 2008/071405 A1 (Syngenta Participations AG and Syngenta Limited), and which is also compound A-9 disclosed on page 8 of WO 2011/073615 A2 (Syngenta Limited), these parts of these publications being incorporated herein by reference), compound of formula (I)+one of the specific herbicidal compounds disclosed in WO 2010/059671 (Dow, e.g. as defined in one of the examples therein and/or e.g. can be plus a safener) these parts of which are incorporated herein by reference, compound of formula I+halauxifen (which is 4-amino-3-chloro-6-(4-chloro-2-fluoro-3-methoxyphenyl)pyridine-2-carboxylic acid, CAS Reg. No. 943832-60-8), compound of formula I+halauxifen-methyl (which is methyl 4-amino-3-chloro-6-(4-chloro-2-fluoro-3-methoxyphenyl)pyridine-2-carboxylate, CAS Reg. No. 943831-98-9), compound of formula I+iofensulfuron (which is 1-(2-iodophenylsulfonyl)-3-(4-methoxy-6-methyl-1,3,5-triazin-2-yl)urea, CAS Reg. No. 1144097-22-2), compound of formula I+iofensulfuron-sodium (which is sodium N-(2-iodophenylsulfonyl)-N-(4-methoxy-6-methyl-1,3,5-triazin-2-yl)carbamimidate, CAS Reg. No. 1144097-30-2), or compound of formula I+triafamone (which is N-[2-[(4,6-dimethoxy-1,3,5-triazin-2-yl)carbonyl]-6-fluorophenyl]-N-methyl-1,1-difluoromethanesulfonamide, CAS Reg. No. 874195-61-6);

wherein the mixture partners for the compound of formula (I) may optionally be in the form of an ester (in particular an agrochemically acceptable ester) or a salt (in particular an agrochemically acceptable salt) thereof (e.g. where chemically possible).

For applications in rice, more preferred is a mixture comprising: a compound of formula (I)+azimsulfuron, compound of formula (I)+bensulfuron, compound of formula (I)+bensulfuron-methyl, compound of formula (I)+benzobicyclon, compound of formula (I)+benzofenap, compound of formula (I)+bispyribac, compound of formula (I)+bispyribac-sodium, compound of formula (I)+clomazone, compound of formula (I)+clomeprop, compound of formula (I)+cyhalofop, compound of formula (I)+cyhalofop-butyl, compound of formula (I)+2,4-D, compound of formula (I)+2,4-D-dimethylammonium, compound of formula (I)+2,4-D-2-ethylhexyl, compound of formula (I)+a choline salt of 2,4-D (see e.g. Examples 2 and 3 of WO2010/123871A1), compound of formula (I)+daimuron, compound of formula (I)+dicamba, compound of formula (I)+dicamba-dimethylammonium, compound of formula (I)+dicamba-potassium, compound of formula (I)+dicamba-sodium, compound of formula (I)+dicamba-diglycolamine, compound of formula (I)+a N,N-bis-[aminopropyl]methylamine salt of dicamba (see e.g. US2012/0184434A1), compound of formula (I)+esprocarb, compound of formula (I)+ethoxysulfuron, compound of formula (I)+fenoxaprop-P, compound of formula (I)+fenoxaprop-P-ethyl, compound of formula I+fenoxasulfone (CAS Reg. No. 639826-16-7), compound of formula (I)+fentrazamide, compound of formula (I)+florasulam, compound of formula (I)+halosulfuron, compound of formula (I)+halosulfuron-methyl, compound of formula (I)+imazosulfuron, compound of formula I+ipfencarbazone (CAS Reg. No. 212201-70-2), compound of formula (I)+MCPA, compound of formula (I)+mefenacet, compound of formula (I)+mesotrione, compound of formula I+metazosulfuron (NC-620, CAS Reg. No. 868680-84-6), compound of formula (I)+metsulfuron, compound of formula (I)+metsulfuron-methyl, compound of formula (I)+orthosulfamuron, compound of formula (I)+oxadiargyl, compound of formula (I)+oxadiazon, compound of formula (I)+pendimethalin, compound of formula (I)+penoxsulam, compound of formula (I)+pretilachlor, compound of formula I+propyrisulfuron (TH-547, CAS Reg. No. 570415-88-2), compound of formula (I)+pyrazolynate, compound of formula (I)+pyrazosulfuron, compound of formula (I)+pyrazosulfuron-ethyl, compound of formula (I)+pyrazoxyfen, compound of formula (I)+pyribenzoxim, compound of formula (I)+pyriftalid, compound of formula (I)+pyriminobac, compound of formula (I)+pyriminobac-methyl, compound of formula (I)+pyrimisulfan, compound of formula (I)+quinclorac, compound of formula (I)+tefuryltrione, compound of formula (I)+triasulfuron and compound of formula (I)+trinexapac-ethyl, compound of formula (I)+4-(4'-chloro-4-cyclopropyl-2'-fluorobiphenyl-3-yl)-2,2,6,6-tetramethyl-2H-pyran-3,5(4H,6H)-dione (which is the compound of Example P8 disclosed on pages 31-32 and 35-36 of WO 2010/136431 A9 (Syngenta Limited), and which is also compound A-13 disclosed in pages 4, 5, 7 and 11 of WO 2011/073616 A2 (Syngenta Limited), these parts of these publications being incorporated herein by reference), compound of formula (I)+4-(2',4'-dichloro-4-cyclopropylbiphenyl-3-yl)-2,2,6,6-tetramethyl-2H-pyran-3,5(4H,6H)-dione (which is the compound of Example P9 disclosed on pages 36-37 and 40-41 of WO 2010/136431 A9 (Syngenta Limited), and which is also compound A-12 disclosed in page 10 of WO 2011/073616 A2 (Syngenta Limited), these parts of these publications being incorporated herein by reference), compound of formula (I)+4-(4'-chloro-4-ethyl-2'-fluorobiphenyl-3-yl)-2,2,6,6-tetramethyl-2H-pyran-3,5(4H,6H)-dione (which is compound A-66 disclosed on page 95 of WO 2008/071405 A1 (Syngenta Participations AG and Syngenta Limited), and which is also compound A-4 disclosed on page 7 of WO 2011/073615 A2 (Syngenta Limited), these parts of these publications being incorporated herein by reference), compound of formula (I)+4-(2',4'-dichloro-4-ethylbiphenyl-3-yl)-2,2,6,6-tetramethyl-2H-pyran-3,5(4H,6H)-dione (which is compound A-45 disclosed on page 93 of WO 2008/071405 A1 (Syngenta Participations AG and Syngenta Limited), and which is also the compound of Example P10 disclosed on pages 41 and 45 of WO 2010/136431 A9 (Syngenta Limited), and which is also compound A-7 disclosed on page 7 of WO 2011/073615 A2 (Syngenta Limited), these parts of these publications being incorporated herein by reference), compound of formula (I)+4-(2',4'-dichloro-4-ethylbiphenyl-3-yl)-5-(methoxycarbonyloxy)-2,2,6,6-tetramethyl-2H-pyran-3(6H)-one (which is compound D-26 disclosed on page 231 of WO 2008/071405 A1 (Syngenta Participations AG and Syngenta Limited), and which is also compound A-9 disclosed on page 8 of WO 2011/073615 A2 (Syngenta Limited), these parts of these publications being incorporated herein by reference), compound of formula (I)+one of the specific herbicidal compounds disclosed in WO 2010/059671 (Dow, e.g. as defined in one of the examples therein and/or e.g. can be plus a safener) these parts of which are incorporated herein by reference, compound of formula I+halauxifen (which is 4-amino-3-chloro-6-(4-chloro-2-fluoro-3-methoxyphenyl)pyridine-2-carboxylic acid, CAS Reg. No. 943832-60-8), compound of formula I+halauxifen-methyl (which is methyl 4-amino-3-chloro-6-(4-chloro-2-fluoro-3-methoxyphenyl)pyridine-2-carboxylate, CAS Reg. No. 943831-98-9), compound of formula I+iofensulfuron (which is 1-(2-iodophenylsulfonyl)-3-(4-methoxy-6-methyl-1,3,5-triazin-2-yl)urea, CAS Reg. No. 1144097-22-2), compound of formula I+iofensulfuron-sodium (which is sodium N-(2-iodophenylsulfonyl)-N-(4-methoxy-6-methyl-1,3,5-triazin-2-yl)carbamimidate, CAS Reg. No. 1144097-30-2), or compound of formula I+triafamone (which is N-[2-[(4,6-dimethoxy-1,3,5-triazin-2-yl)carbonyl]-6-fluorophenyl]-N-methyl-1,1-difluoromethanesulfonamide, CAS Reg. No. 874195-61-6);
wherein the mixture partners for the compound of formula (I) may optionally be in the form of an ester (in particular an agrochemically acceptable ester) or a salt (in particular an agrochemically acceptable salt) thereof (e.g. where chemically possible).

For applications in soybean, the following mixtures are preferred:
compound of formula (I)+acifluorfen, compound of formula (I)+acifluorfen-sodium, compound of formula (I)+ametryn, compound of formula (I)+atrazine, compound of formula (I)+bentazone, compound of formula (I)+bicyclopyrone, compound of formula (I)+bromoxynil, compound of formula (I)+bromoxynil heptanoate, compound of formula (I)+bromoxynil octanoate, compound of formula (I)+bromoxynil heptanoate+bromoxynil octanoate, compound of formula (I)+carfentrazone, compound of formula (I)+carfentrazone-ethyl, compound of formula (I)+chloransulam, compound of formula (I)+chloransulam-methyl, compound of formula (I)+chlorimuron, compound of formula (I)+chlorimuron-ethyl, compound of formula (I)+clethodim, compound of formula (I)+clomazone, compound of formula (I)+cyanazine, compound of formula (I)+2,4-D (especially for applications to 2,4-D-tolerant soybean, e.g. genetically-modified), compound of formula (I)+2,4-D-dimethylammonium (especially for applications to 2,4-D-tolerant soybean, e.g. genetically-modified), compound of formula (I)+2,4-D-2-ethylhexyl (especially for applications to 2,4-D-tolerant soybean, e.g. genetically-modified), compound of formula (I)+a choline salt of 2,4-D (see e.g. Examples 2 and 3 of WO2010/123871A1) (especially for applications to 2,4-D-tolerant soybean, e.g. genetically-modified), compound of formula (I)+2,4-D+glyphosate (especially for applications to 2,4-D-tolerant and/or glyphosate-tolerant soybean, e.g. genetically-modified), compound of formula (I)+2,4-D-dimethylammonium+glyphosate (especially for applications to 2,4-D-tolerant and/or glyphosate-tolerant soybean, e.g. genetically-modified), compound of formula (I)+2,4-D-2-ethylhexyl+glyphosate (especially for applications to 2,4-D-tolerant and/or glyphosate-tolerant soybean, e.g. genetically-modified), compound of formula I+a choline salt of 2,4-D+glyphosate (see e.g. Examples 2 and 3 of WO2010/123871A1) (especially for applications to dicamba-tolerant and/or glyphosate-tolerant soybean, e.g. genetically-modified), compound of formula (I)+dicamba (especially for applications to dicamba-tolerant soybean, e.g. genetically-modified), compound of formula (I)+dicamba-dimethylammonium (especially for applications to dicamba-tolerant soybean, e.g. genetically-modified), compound of formula (I)+dicamba-potassium (especially for applications to dicamba-tolerant soybean, e.g. genetically-modified), compound of formula (I)+dicamba-sodium (especially for applications to dicamba-tolerant soybean, e.g. genetically-modified), compound of formula (I)+dicamba-diglycolamine (especially for applications to dicamba-tolerant soybean, e.g. genetically-modified), compound of formula (I)+a N,N-bis-[aminopropyl]methylamine salt of dicamba (see e.g. US2012/0184434A1) (especially for applications to dicamba-tolerant soybean, e.g. genetically-modified), compound of formula (I)+dicamba+glyphosate (especially for applications to dicamba-tolerant and/or glyphosate-tolerant soybean, e.g. genetically-modified), compound of formula (I)+dicamba-dimethylammonium+glyphosate (especially for applications to dicamba-tolerant and/or glyphosate-tolerant soybean, e.g. genetically-modified), compound of formula (I)+dicamba-potassium+glyphosate (especially for applications to dicamba-tolerant and/or glyphosate-tolerant soybean, e.g. genetically-modified), compound of formula (I)+dicamba-sodium+glyphosate (especially for applications to dicamba-tolerant and/or glyphosate-tolerant soybean, e.g. genetically-modified), compound of formula (I)+dicamba-diglycolamine+glyphosate (especially for applications to dicamba-tolerant and/or glyphosate-tolerant soybean, e.g. genetically-modified), compound of formula (I)+a N,N-bis-[aminopropyl]methylamine salt of dicamba+glyphosate (especially for applications to dicamba-tolerant and/or glyphosate-tolerant soybean, e.g. genetically-modified), compound of formula (I)+diclosulam, compound of formula (I)+dimethenamid, compound of formula (I)+dimethenamid-P, compound of formula (I)+diquat, compound of formula (I)+diquat dibromide, compound of formula (I)+diuron, compound of formula (I)+fenoxaprop, compound of formula (I)+fenoxaprop-ethyl, compound of formula (I)+fenoxaprop-P, compound of formula (I)+fenoxaprop-P-ethyl, compound of formula (I)+fluazifop, compound of formula (I)+fluazifop-butyl, compound of formula (I)+fluazifop-P, compound of formula (I)+fluazifop-P-butyl, compound of formula (I)+flufenacet, compound of formula (I)+flumetsulam, compound of formula (I)+flumioxazin, compound of formula (I)+fluthiacet, compound of formula (I)+fluthiacet-methyl, compound of formula (I)+fomesafen, compound of formula (I)+glufosinate, compound of formula (I)+glufosinate-ammonium, compound of formula (I)+glyphosate, compound of formula (I)+glyphosate-diammonium, compound of formula (I)+glyphosate-isopropylammonium, compound of formula (I)+glyphosate-potassium, compound of formula (I)+imazethapyr, compound of formula (I)+lactofen, compound of formula (I)+mesotrione, compound of formula (I)+metolachlor, compound of formula (I)+S-metolachlor, compound of formula (I)+metribuzin, compound of formula (I)+oxyfluorfen, compound of formula (I)+paraquat, compound of formula (I)+paraquat dichloride, compound of formula (I)+pendimethalin, compound of formula (I)+pyroxasulfone, compound of formula I+quizalofop, compound of formula I+quizalofop-ethyl, compound of formula I+quizalofop-P, compound of formula I+quizalofop-P-ethyl, compound of formula I+quizalofop-P-tefuryl, compound of formula (I)+saflufenacil, compound of formula (I)+sethoxydim, compound of formula (I)+sulfentrazone, compound of formula (I)+thifensulfuron, compound of formula (I)+thifensulfuron-methyl, compound of formula (I)+tribenuron, compound of formula (I)+tribenuron-methyl, compound of formula (I)+trifluralin, compound of formula (I)+4-(4'-chloro-4-cyclopropyl-2'-fluorobiphenyl-3-yl)-2,2,6,6-tetramethyl-2H-pyran-3,5(4H,6H)-dione (which is the compound of Example P8 disclosed on pages 31-32 and 35-36 of WO 2010/136431 A9 (Syngenta Limited), and which is also compound A-13 disclosed in pages 4, 5, 7 and 11 of WO 2011/073616 A2 (Syngenta Limited), these parts of these publications being incorporated herein by reference), compound of formula (I)+4-(2',4'-dichloro-4-cyclopropylbiphenyl-3-yl)-2,2,6,6-tetramethyl-2H-pyran-3,5(4H,6H)-dione (which is the compound of Example P9 disclosed on pages 36-37 and 40-41 of WO 2010/136431 A9 (Syngenta Limited), and which is also compound A-12 disclosed in page 10 of WO 2011/073616 A2 (Syngenta Limited), these parts of these publications being incorporated herein by reference), compound of formula (I)+4-(4'-chloro-4-ethyl-2'-fluorobiphenyl-3-yl)-2,2,6,6-tetramethyl-2H-pyran-3,5(4H,6H)-dione (which is compound A-66 disclosed on page 95 of WO 2008/071405 A1 (Syngenta Participations AG and Syngenta Limited), and which is also compound A-4 disclosed on page 7 of WO 2011/073615 A2 (Syngenta Limited), these parts of these publications being incorporated herein by reference), compound of formula (I)+4-(2',4'-dichloro-4-ethylbiphenyl-3-yl)-2,2,6,6-tetramethyl-2H-pyran-3,5(4H, 6H)-dione (which is compound A-45 disclosed on page 93 of WO 2008/071405 A1 (Syngenta Participations AG and Syngenta Limited), and which is also the compound of Example P10 disclosed on pages 41 and 45 of WO 2010/136431 A9 (Syngenta Limited), and which is also compound A-7 disclosed on page 7 of WO 2011/073615 A2 (Syngenta Limited), these parts of these publications being incorporated herein by reference), or compound of formula (I)+4-(2',4'-dichloro-4-ethylbiphenyl-3-yl)-5-(methoxycarbonyloxy)-2,2,6,6-tetramethyl-2H-pyran-3(6H)-one (which is compound D-26 disclosed on page 231 of WO 2008/071405 A1 (Syngenta Participations AG and Syngenta Limited), and which is also compound A-9 disclosed on page 8 of WO 2011/073615 A2 (Syngenta Limited), these parts of these publications being incorporated herein by reference); wherein the mixture partners for the compound of formula (I) may optionally be in the form of an ester (in particular an agrochemically acceptable ester) or a salt (in particular an agrochemically acceptable salt) thereof (e.g. where chemically possible).

In the above-mentioned compositions or mixtures comprising a compound of formula (I) (in particular, one of the specific compounds disclosed herein, e.g. any of compounds A-1 to A-18 or A-19 to A-41 or P-3 to P-7 and/or any of the compounds disclosed in Tables 1 to 25 or 26 or 27 herein, present either as a free compound and/or as an agrochemically acceptable salt thereof) and one or more further herbicides, the weight ratio of the compound of formula (I) to each further herbicide can vary over a large range and is, typically, from 300:1 to 1:500, especially from 150:1 to 1:200, more especially from 100:1 to 1:100, even more especially from 30:1 to 1:30. Typically, these weight ratios are measured as the free compound(s), i.e. excluding the weight of any associated salt counterion(s).

The compounds of formula I according to the invention can also be used in combination with a safener. Preferably, in these mixtures, the compound of the formula I is one of those compounds listed (disclosed) in Tables 1 to 25 or 26 or 27 and/or one of the exemplified compounds (e.g. A-1 to A-18, or A-19 to A-41, or P-3 to P-7) below. The following mixtures with safeners, especially, come into consideration: compound of formula I+cloquintocet-mexyl, compound of formula I+cloquintocet acid or an agrochemically acceptable salt thereof, compound of formula I+fenchlorazole-ethyl, compound of formula I+fenchlorazole acid or an agrochemically acceptable salt thereof, compound of formula I+mefenpyr-diethyl, compound of formula I+mefenpyr diacid, compound of formula I+isoxadifen-ethyl, compound of formula I+isoxadifen acid, compound of formula I+furilazole, compound of formula I+furilazole R isomer, compound of formula (I)+N-(2-methoxybenzoyl)-4-[(methylaminocarbonyl)amino]benzenesulfonamide, compound of formula I+benoxacor, compound of formula I+dichlormid, compound of formula I+AD-67, compound of formula I+oxabetrinil, compound of formula I+cyometrinil, compound of formula I+cyometrinil Z-isomer, compound of formula I+fenclorim, compound of formula I+cyprosulfamide, compound of formula I+naphthalic anhydride, compound of formula I+flurazole, compound of formula I+CL 304,415, compound of formula I+dicyclonon, compound of formula I+fluxofenim, compound of formula I+DKA-24, compound of formula I+R-29148 and compound of formula I+PPG-1292.

The above-mentioned safeners and herbicides are described, for example, in the Pesticide Manual, 14$^{th}$ Edition, British Crop Protection Council, 2006; or The Pesticide Manual, 15$^{th}$ edition, 2009, ed. C. D. S. Tomlin, British Crop Production Council. R-29148 is described, for example by P. B. Goldsbrough et al., Plant Physiology, (2002), Vol. 130 pp. 1497-1505 and references therein. PPG-1292 is known from WO 2009/211761. N-(2-methoxybenzoyl)-4-[(methylaminocarbonyl)amino]benzenesulfonamide is known from EP365484.

Especially preferably, in a composition or mixture comprising a compound of formula (I) (in particular, one of the specific compounds disclosed herein, e.g. any of compounds A-1 to A-18 or A-19 to A-41 or P-3 to P-7 and/or any of the compounds disclosed in Tables 1 to 25 or 26 or 27 herein, present either as a free compound and/or as an agrochemically acceptable salt thereof) and a safener, the safener comprises (e.g. is) benoxacor, cloquintocet-mexyl, cloquintocet acid or an agrochemically acceptable salt thereof, cyprosulfamide, mefenpyr-diethyl, isoxadifen-ethyl and/or N-(2-methoxybenzoyl)-4-[(methylaminocarbonyl)amino]- benzenesulfonamide. In one particular embodiment, the safener comprises (e.g. is) cloquintocet-mexyl, cloquintocet acid or an agrochemically acceptable salt thereof, mefenpyr-diethyl and/or isoxadifen-ethyl; in particular for use on non-oat cereals such as wheat, barley, rye and/or triticale. Cloquintocet-mexyl is particularly valuable and is the most preferred safener, especially for use on non-oat cereals such as wheat, barley, rye and/or triticale.

In the above-mentioned compositions or mixtures comprising a compound of formula (I) (in particular, one of the specific compounds disclosed herein, e.g. any of compounds A-1 to A-18 or A-19 to A-41 or P-3 to P-7 and/or any of the compounds disclosed in Tables 1 to 25 or 26 or 27 herein, present either as a free compound and/or as an agrochemically acceptable salt thereof) with a safener, the weight ratio of the compound of formula (I) to the safener can vary over a large range and is, typically, from 200:1 to 1:200, especially from 50:1 to 1:50 such as from 50:1 to 1:20, more especially from 20:1 to 1:20, even more especially from 20:1 to 1:10. Preferably, the safener comprises (e.g. is) benoxacor, cloquintocet-mexyl, cloquintocet acid or an agrochemically acceptable salt thereof, cyprosulfamide, mefenpyr-diethyl, isoxadifen-ethyl and/or N-(2-methoxybenzoyl)-4-[(methylaminocarbonyl)amino]-benzenesulfonamide, and the weight ratio of the compound of formula (I) to the safener is from 50:1 to 1:20 or from 20:1 to 1:10, more preferably from 15:1 to 1:2. Typically, these weight ratios are measured as the free compound(s), i.e. excluding the weight of any associated salt counterion(s).

Application rates of herbicide (e.g. compound of formula (I)) and/or safener: The rate of application of safener relative to the compound of formula (I) is largely dependent upon the mode of application. In the case of field and/or soil and/or plant treatment (e.g. in a field or glasshouse): for example from 0.5 to 1000 g of safener per ha, or preferably from 1 to 250 g or from 2 to 200 g of safener per ha, are applied; and/or generally from 1 to 2000 g of compound of formula (I) per ha, or preferably from 5 to 500 g or from 10 to 400 g of compound of formula (I) per ha, are applied. ha=hectare. Typically, these application rates are measured as the free compound, i.e. excluding the weight of any associated salt counterion(s). In field treatment, the application of the compound of formula (I) is preferably post-emergence.

The compounds and/or herbicidal compositions according to the invention are suitable for all methods of application customary in agriculture, such as, for example, pre-emergence application, post-emergence application and seed dressing. Post-emergence application is preferred. Depending upon the intended use, the safeners can be used for pretreating the seed material of the crop plant (dressing the seed or seedlings) or introduced into the soil before or after sowing, followed by the application of the (unsafened) compound of the formula (I), optionally in combination with a co-herbicide. It can, however, also be applied alone or together with the herbicide before or after emergence of the plants. The treatment of the plants or the seed material with the safener can therefore take place in principle independently of the time of application of the herbicide. The treatment of the plant by simultaneous application of herbicide and safener (e.g. in the form of a tank mixture) is generally preferred. The rate of application of safener relative to herbicide is largely dependent upon the mode of application. In the case of field and/or soil and/or plant treatment (e.g. in a field or glasshouse), generally from 0.001 to 5.0 kg of safener/ha, preferably from 0.001 to 0.5 kg of safener/ha, are applied. In the case of seed dressing, generally from 0.001 to 10 g of safener/kg of seed, preferably from 0.05 to 2 g of safener/kg of seed, are applied. When the safener is applied in liquid form, with seed soaking, shortly before sowing, it is advantageous to use safener solutions which contain the active ingredient in a concentration of from 1 to 10 000 ppm, preferably from 100 to 1000 ppm.

In the invention, in the case of field and/or soil and/or plant treatment (e.g. post-emergence application), generally from 1 to 2000 g of herbicide (in particular compound of formula (I))/ha, but preferably from 5 to 1000 g of herbicide (in particular compound of formula (I))/ha, more preferably from 10 to 400 g of herbicide (in particular compound of formula (I))/ha, is applied. If a safener is used, in the case of field and/or soil and/or plant treatment (e.g. post-emergence application), generally from 0.5 to 1000 g of safener/ha, preferably from 2 to 500 g of safener/ha, more preferably from 5 to 200 g of safener/ha, is applied.

In one particular embodiment, the composition or mixture comprising the compound of formula (I) and one or more further herbicides (e.g. as mentioned hereinabove) can be applied together with one of the safeners mentioned herein, e.g. hereinabove.

The following Examples illustrate the invention further but do not limit the invention.

PREPARATION EXAMPLES

Those skilled in the art will appreciate that certain compounds described below are β-ketoenols, and as such may exist as a single tautomer or as a mixture of keto-enol and diketone tautomers, as described, for example by J. March, Advanced Organic Chemistry, third edition, John Wiley and Sons. The compounds shown below, and in Table T1 are drawn as an arbitrary single enol tautomer, but it should be inferred that this description covers both the diketone form and any possible enols which could arise through tautomerism. Where more than one tautomer is observed in proton NMR, the data shown are for the mixture of tautomers. Furthermore, some of the compounds shown below are drawn as single enantiomers for the purposes of simplicity, but unless specified as single enantiomers, these structures should be construed as representing a mixture of enantiomers. Additionally, some of the compounds can exist as diastereoisomers, and it should be inferred that these can be present as a mixture of diastereoisomers or as any possible single diastereoisomer. Within the detailed experimental section the diketone tautomer is chosen for naming purposes, even if the predominant tautomer is the enol form.

As used herein, room (ambient) temperature is typically about 15-30° C. (e.g. 15-25° C.). Herein, d4 MeOD means tetradeutero-methanol (CD$_3$OD).

EXAMPLE 1

Preparation of 2,2,6,6-Tetramethyl-4-(2-methyl-4-prop-1-ynylphenyl)pyran-3,5-dione

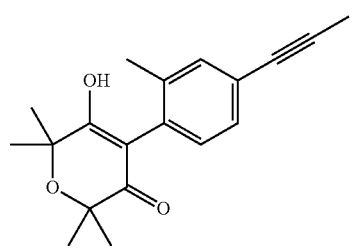 [SMILES: CC#Cc1ccc(C2=C(O)C(C)(C)OC(C)(C)C2=O)c(C)c1]

Step 1: Preparation of 4-(4-Bromo-2-methylbenzylidene)-2,2,5,5-tetramethyldihydrofuran-3-one

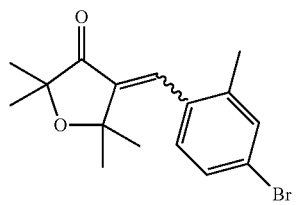 [SMILES: Cc1cc(Br)ccc1C=C1C(=O)C(C)(C)OC1(C)C]

To an ice-cold solution of 2,2,5,5-tetramethyltetrahydrofuran-3-one (34.2 g, 0.24 mol) in anhydrous 1,2-dimethoxyethane (500 ml) is added sodium methoxide (14.0 g, 0.26 mol) in one portion. After stirring at 0° C. for 5 minutes a second solution of 4-bromo-2-methylbenzaldehyde (43.6 g, 0.22 mol) in 1,2-dimethoxyethane (200 ml) is added to the slurry dropwise over 40 minutes. The reaction mixture is next stirred at 0° C. for 2 hours, then diluted with diethyl ether and washed with 2M hydrochloric acid (×2). Organic fractions are combined, dried over magnesium sulfate, filtered and the filtrate evaporated in vacuo. The crude product is then purified by flash column chromatography (5% ethyl acetate in hexanes as eluant) to afford 4-(4-bromo-2-methylbenzylidene)-2,2,5,5-tetramethyldihydrofuran-3-one as a yellow solid.

Step 2: Preparation of 2-(4-Bromo-2-methylphenyl)-4,4,6,6-tetramethyl-1,5-dioxaspiro[2.4]heptan-7-one

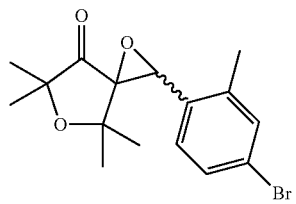 [SMILES: Cc1cc(Br)ccc1C1OC12C(=O)C(C)(C)OC2(C)C]

To a solution of 4-(4-bromo-2-methylbenzylidene)-2,2,5,5-tetramethyldihydrofuran-3-one (52.3 g, 0.16 mol) in methanol (900 ml) at 35° C. is added 50% aqueous hydrogen peroxide (16.7 g, 0.24 mol), followed immediately by a solution of 2M aqueous lithium hydroxide (16 ml, 0.032 mol). After stirring at this temperature for 3 hours additional 50% aqueous hydrogen peroxide (8.0 g, 0.11 mol) is added, and the temperature is increased to 60° C. After heating at 60° C. for a further 1 hour the reaction mixture is cooled to room temperature and 10% sodium metabisulphite solution (900 ml) is added to quench remaining peroxides. The reaction mixture is then extracted with both diethyl ether (100 ml) and ethyl acetate (2×500 ml), then the combined organic phase is washed with saturated sodium bicarbonate then brine. After drying over magnesium sulfate the suspension is filtered and the filtrate evaporated in vacuo to afford 2-(4-bromo-2-methylphenyl)-4,4,6,6-tetramethyl-1,5-dioxaspiro[2.4]heptan-7-one as a yellow solid.

Step 3: Preparation of 4-(4-Bromo-2-methylphenyl)-2,2,6,6-tetramethylpyran-3,5-dione

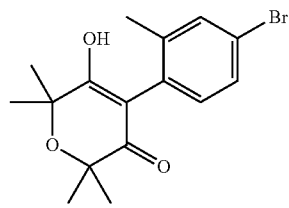 [SMILES: Cc1cc(Br)ccc1C1=C(O)C(C)(C)OC(C)(C)C1=O]

To an ice-cold solution of concentrated sulphuric acid (500 ml) is added a second solution of 2-(4-bromo-2-methylphenyl)-4,4,6,6-tetramethyl-1,5-dioxaspiro[2.4]heptan-7-one (40.9 g 0.12 mol) in dichloromethane (500 ml) at 0° C., dropwise over 1 hour. This biphasic mixture is stirred vigorously for 2.5 hours at 00° C., then poured into ice-cold water (500 ml) and extracted with dichloromethane (3×500 ml). Organic fractions are combined, dried over magnesium sulfate, filtered and the filtrate evaporated in vacuo. The crude product is then purified by flash column chromatography (5% ethyl acetate in isohexane as eluant) to afford 4-(4-bromo-2-methylphenyl)-2,2,6,6-tetramethylpyran-3,5-dione.

Step 4: Preparation of 2,2,6,6-Tetramethyl-4-(2-methyl-4-prop-1-ynylphenyl)pyran-3,5-dione

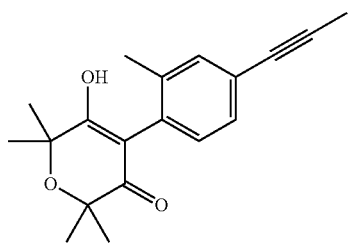 [SMILES: CC#Cc1ccc(C2=C(O)C(C)(C)OC(C)(C)C2=O)c(C)c1]

To a mixture of 4-(4-bromo-2-methylphenyl)-2,2,6,6-tetramethylpyran-3,5-dione (0.200 g, 0.59 mmol), tetrakis(triphenylphosphine)palladium(0) (0.036 g, 0.12 mmol) and tributyl(1-propynyl) tin (0.54 ml, 1.77 mmol) is added degassed toluene (4 ml), and the mixture is heated at 130° C. under microwave irradiation for 45 mins. The reaction mixture is quenched with saturated ammonium chloride, and the crude product is then extracted with ethyl acetate (×3). The solution is passed through a bed of diatomaceous earth, and the combined organics are washed with brine then dried over magnesium sulfate, filtered, and the filtrate concentrated in vacuo. The crude product is then purified by flash column chromatography (20% to 100% ethyl acetate in isohexane as eluant) to afford 2,2,6,6-tetramethyl-4-(2-methyl-4-prop-1-ynylphenyl)pyran-3,5-dione.

EXAMPLE 2

Preparation of 3-(2-Methyl-4-prop-1-ynylphenyl)bicyclo[3.2.1]octane-2,4-dione

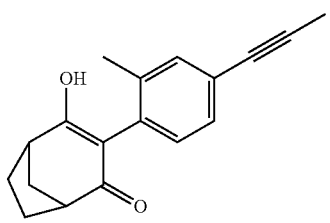 [SMILES: CC#Cc1ccc(C2=C(O)C3CCC(C3)C2=O)c(C)c1]

Step 1: Preparation of 3-(2-Methyl-4-nitrophenyl)bicyclo[3.2.1]octane-2,4-dione

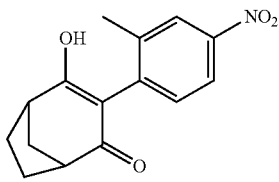

To a mixture of bicyclo[3.2.1]octane-2,4-dione (1.31 g, 9.48 mmol), tris(dibenzylideneacetone)dipalladium(0) (0.550 g, 0.60 mmol), 2-dicyclohexylphosphino-2',4',6'-triisopropylbiphenyl (0.430 g, 0.90 mmol), powdered potassium phosphate (3.68 g, 17.38 mmol) and 2-chloro-5-nitrotoluene (1.36 g, 7.92 mmol) is added dimethoxyethane (24 ml), and the reaction mixture is heated at 160° C. under microwave irradiation for 60 minutes. The mixture is then diluted with ethyl acetate and acidified with 2N aqueous hydrochloric acid. This experimental procedure is repeated ten times, and the combined product is filtered through a bed of diatomaceous earth (and the residue washed with ethyl acetate and 2N aqueous hydrochloric acid). The organic phase is separated and the aqueous phase is washed again with ethyl acetate (×3). Organic fractions are combined, washed with brine, dried over magnesium sulfate, filtered and the filtrate concentrated in vacuo. The crude product is then purified by flash column chromatography (20 to 100% ethyl acetate in isohexane as eluant) to afford 3-(2-methyl-4-nitrophenyl)bicyclo[3.2.1]octane-2,4-dione.

Step 2: Preparation of 3-(4-Amino-2-methylphenyl)bicyclo[3.2.1]octane-2,4-dione

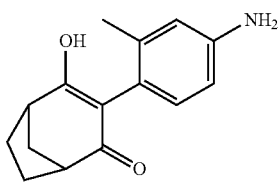 [SMILES: Cc1cc(N)ccc1C1=C(O)C2CCC(C2)C1=O]

To a mixture of 5% palladium on carbon (2.06 g, 0.38 mmol, 60% water paste) and 3-(2-methyl-4-nitrophenyl)bicyclo[3.2.1]octane-2,4-dione (8.64 g, 31.63 mmol) is added ethanol (79 ml) and ethyl acetate (34 ml). The reaction mixture is flushed with nitrogen (×3), then flushed again with hydrogen (×3) and pressurised to 4 bar. After stirring under a hydrogen atmosphere for 8 hours (4 bar pressure, room temperature), the reaction mixture is then flushed again with nitrogen (×3), then filtered through a bed of diatomaceous earth and washed with ethanol (2 L). The crude product is then concentrated in vacuo to afford 3-(4-amino-2-methylphenyl)bicyclo[3.2.1]octane-2,4-dione.

Step 3: Preparation of 3-(4-Bromo-2-methylphenyl)bicyclo[3.2.1]octane-2,4-dione

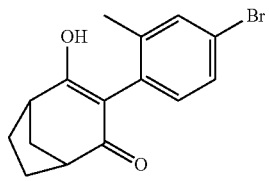 [SMILES: Cc1cc(Br)ccc1C1=C(O)C2CCC(C2)C1=O]

A solution of 3-(4-amino-2-methylphenyl)bicyclo[3.2.1]octane-2,4-dione (1.00 g, 4.11 mmol) in ethanol (20 ml) is cooled to 0° C. then evacuated, flushed with nitrogen, and maintained under a nitrogen atmosphere. Hydrobromic acid (4.9 ml, 14.80 mmol, 48% wt. in water) is added, followed by the dropwise addition of a solution of sodium nitrite (0.528 g, 6.17 mmol) in distilled water (1.2 ml). After stirring at 0° C. for 1 hour a second solution of copper(I) bromide (0.71 g, 4.93 mmol) in hydrobromic acid (4.9 ml, 14.80 mmol, 48% wt. in water) is added dropwise, and the reaction mixture is allowed to warm to room temperature and stir for an additional 20 hours. The reaction mixture is poured into ice water then extracted with ethyl acetate (×3). The combined organic extracts are washed with brine, dried over magnesium sulfate, filtered and the filtrate concentrated in vacuo. The crude product is then purified by flash column chromatography (10-100% ethyl acetate in isohexane as eluant) to afford 3-(4-bromo-2-methylphenyl)bicyclo[3.2.1]octane-2,4-dione.

Step 4: Preparation of 3-(4-Bromo-2-methylphenyl)-4-methoxybicyclo[3.2.1]oct-3-en-2-one

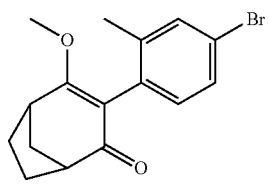 [SMILES: COC1=C(c2ccc(Br)cc2C)C(=O)C2CCC1C2]

To a solution of 3-(4-bromo-2-methylphenyl)bicyclo[3.2.1]octane-2,4-dione (0.25 g, 0.82 mmol) in acetone (10 ml) is added potassium carbonate (0.17 g, 1.23 mmol) followed by iodomethane (0.26 ml, 4.07 mmol), and the suspension is stirred at room temperature for 21 hours. Volatile solvents are removed in vacuo, and the crude product is then washed with distilled water and extracted with ethyl acetate (×3). The combined organic extracts are washed with brine, dried over magnesium sulfate, filtered and the filtrate concentrated in vacuo. Purification by flash column chromatography (20-80% ethyl acetate in isohexane as eluant) affords 3-(4-bromo-2-methylphenyl)-4-methoxybicyclo[3.2.1]oct-3-en-2-one.

Step 5: Preparation of 2-Methoxy-3-(2-methyl-4-prop-1-ynylphenyl)bicyclo[3.2.1]oct-2-en-4-one

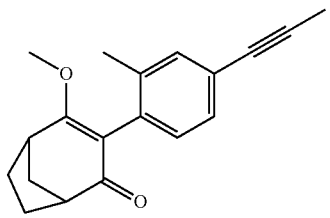 [SMILES: CC#Cc1ccc(C2=C(OC)C3CCC(C3)C2=O)c(C)c1]

A mixture of 3-(4-bromo-2-methylphenyl)-4-methoxybicyclo[3.2.1]oct-3-en-2-one (0.20 g, 0.62 mmol), copper(I) iodide (0.012 g, 0.06 mmol), cesium fluoride (0.188 g, 1.24 mmol), [1,1'-bis(diphenylphosphino)ferrocene]palladium (II)chloride (0.049 g, 0.06 mmol), tributyl(1-propenyl) tin (0.57 ml, 1.87 mmol) and N,N-dimethylformamide (2 ml) is flushed with nitrogen, then heated at 110° C. under microwave irradiation for 30 minutes. Distilled water is added to the reaction mixture and the crude product is extracted with ethyl acetate (×3). Organic fractions are combined, washed with brine, dried over magnesium sulfate, filtered and the filtrate concentrated in vacuo. Purification by flash column chromatography (20-80% ethyl acetate in isohexane as eluant) affords 2-methoxy-3-(2-methyl-4-prop-1-ynylphenyl)bicyclo[3.2.1]oct-2-en-4-one.

Step 6: Preparation of 3-(2-Methyl-4-prop-1-ynylphenyl)bicyclo[3.2.1]octane-2,4-dione

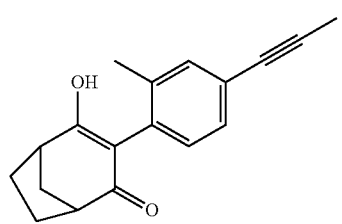 [SMILES: CC#Cc1ccc(C2=C(O)C3CCC(C3)C2=O)c(C)c1]

A solution of 2-methoxy-3-(2-methyl-4-prop-1-ynylphenyl)bicyclo[3.2.1]oct-2-en-4-one (0.150 g, 0.54 mmol) in a mixture of acetone (2 ml) and 2 M hydrochloric acid (0.5 ml, 1.00 mmol) is heated at 120° C. under microwave irradiation for 10 minutes. The reaction mixture is then concentrated in vacuo and partitioned between distilled water and ethyl acetate. The aqueous phase is then washed with additional ethyl acetate (×2). Organic fractions are combined, washed with brine, dried over magnesium sulfate, filtered and the filtrate concentrated in vacuo. Purification by flash column chromatography (20-80% ethyl acetate in isohexane as eluant) affords 3-(2-methyl-4-prop-1-ynylphenyl)bicyclo[3.2.1]octane-2,4-dione.

EXAMPLE 3

Preparation of 3-(2-Chloro-6-ethyl-4-prop-1-ynylphenyl)bicyclo[3.2.1]octane-2,4-dione

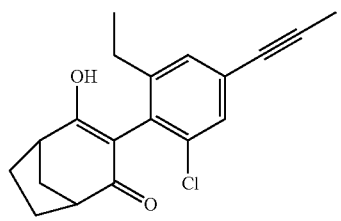 [SMILES: CC#Cc1cc(Cl)c(C2=C(O)C3CCC(C3)C2=O)c(CC)c1]

Step 1: Preparation of 3-[1-(2-Chloro-6-ethylphenyl)methylidene]bicyclo[2.2.1]heptan-2-one

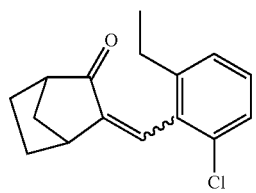 [SMILES: CCc1cccc(Cl)c1C=C1C(=O)C2CCC1C2]

To a solution of norcamphor (3.87 g, 35.18 mmol) and 2-chloro-6-ethylbenzaldehyde (e.g. described in WO2011/023795) (8.31 g, 49.26 mmol) in ethanol (100 ml) is added solid potassium hydroxide (0.60 g, 10.78 mmol). The reaction mixture is then heated at reflux for hours, then cooled to 0° C. followed by the addition of distilled water (30 ml) and 2N aqueous hydrochloric acid (30 ml). The aqueous phase is extracted with ethyl acetate (×3), and the combined organic fractions are washed with brine, dried over anhydrous magnesium sulfate, filtered and the filtrate concentrated in vacuo. Purification by flash column chromatography (5% ethyl acetate in isohexane as eluant) affords 3-[1-(2-chloro-6-ethylphenyl)methylidene]bicyclo[2.2.1]heptan-2-one.

Step 2: Preparation of 4-[1-(2-Chloro-6-ethylphenyl)methylidene]-3-oxabicyclo[3.2.1]octan-2-one

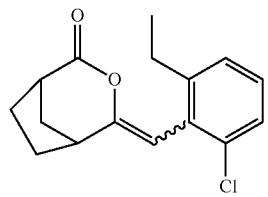 [SMILES: CCc1cccc(Cl)c1C=C1OC(=O)C2CCC1C2]

To a solution of 3-[1-(2-chloro-6-ethylphenyl)methylidene]bicyclo[2.2.1]heptan-2-one (6.80 g, 26.08 mmol) in tert-butanol (32 ml) is added hydrogen peroxide (3.01 ml, 44.33 mmol, 50% aqueous) and selenium dioxide (0.136 g, 1.22 mmol), and the solution is stirred at room temperature for 4 days. To the reaction mixture is then added distilled water and diethyl ether, the phases are separated, and the aqueous phase extracted again with diethyl ether (×3). The combined organic fractions are washed with distilled water (×8), then concentrated in vacuo. The crude product is purified by flash column chromatography (5-25% ethyl acetate in isohexanes as eluant) to afford 4-[1-(2-chloro-6-ethylphenyl)methylidene]-3-oxabicyclo[3.2.1]octan-2-one.

Step 3: Preparation of 3-(2-Chloro-6-ethylphenyl) bicyclo[3.2.1]octane-2,4-dione

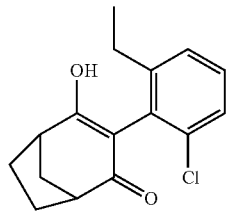 [SMILES: CCc1cccc(Cl)c1C1=C(O)C2CCC(C2)C1=O]

To a solution of 4-[1-(2-chloro-6-ethylphenyl)methylidene]-3-oxabicyclo[3.2.1]octan-2-one (4.03 g, 14.56 mmol) in N,N-dimethylformamide (95 ml) at 80° C. is added a second solution of sodium methoxide (6.29 ml, 29.12 mmol, 25 wt. % in methanol) dropwise. The reaction mixture is stirred at 80° C. for 1 hour 55 minutes, then cooled to to 0° C. 2N aqueous hydrochloric acid (45 ml) and water (45 ml) are added and the crude product is extracted with ethyl acetate (×3). The combined organic extracts are washed successively with distilled water (×3) then brine, and finally dried over magnesium sulfate, filtered and the filtrate concentrated in vacuo. Purification by flash column chromatography (30-100% ethyl acetate in isohexanes as eluant) affords 3-(2-chloro-6-ethylphenyl)bicyclo[3.2.1]octane-2,4-dione.

Step 4: Preparation of 3-(2-Chloro-6-ethylphenyl)-4-methoxybicyclo[3.2.1]oct-3-en-2-one

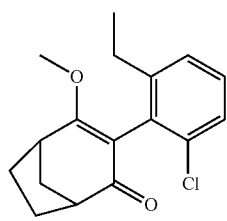 [SMILES: CCc1cccc(Cl)c1C1=C(OC)C2CCC(C2)C1=O]

To a solution of 3-(2-chloro-6-ethylphenyl)bicyclo[3.2.1]octane-2,4-dione (2.25 g, 8.13 mmol) in acetone (100 ml) is added potassium carbonate (1.69 g, 12.20 mmol) then iodomethane (2.53 ml, 40.65 mmol), and the suspension is stirred at room temperature for 18 hours. Volatile solvents are removed in vacuo, and the crude product is partitioned between distilled water and ethyl acetate. The phases are separated and the aqueous phase is extracted again with additional ethyl acetate (×3). Organic fractions are combined, washed with brine, dried over anhydrous magnesium sulfate, filtered and the filtrate concentrated in vacuo. Purification by flash column chromatography (5-50% ethyl acetate in isohexanes as eluant) affords 3-(2-chloro-6-ethylphenyl)-4-methoxybicyclo[3.2.1]oct-3-en-2-one.

Step 5: Preparation of 3-[2-Chloro-6-ethyl-4-(4,4,5,5-tetramethyl[1,3,2]dioxaborolan-2-yl)phenyl]-4-methoxybicyclo[3.2.1]oct-3-en-2-one

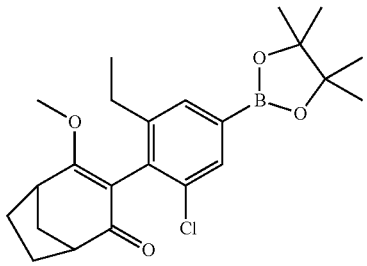 [SMILES: CCc1cc(B2OC(C)(C)C(C)(C)O2)cc(Cl)c1C1=C(OC)C2CCC(C2)C1=O]

Step 5a

To a mixture of bis(pinacolato)diboron (2.59 g, 10 mmol), (1,5-cyclooctadiene)(methoxy)iridium(I) dimer (0.104 g, 0.157 mmol) and 4,4'-di-t-butyl-2,2'-bipyridine (0.84 g, 0.312 mmol) under a nitrogen atmosphere, is added anhydrous methyl-tert-butyl ether (25 ml), and the solution is shaken for 15 minutes.

Step 5b

To 3-(2-chloro-6-ethylphenyl)-4-methoxybicyclo[3.2.1]oct-3-en-2-one (0.241 g, 0.83 mmol) under a nitrogen atmosphere is added 2.0 ml of the catalyst solution, prepared as described in Step 5a. After stirring at room temperature for 1 minute the reaction mixture is then heated at 80° C. for 60 minutes under microwave irradiation. After cooling to room temperature volatiles are removed in vacuo, and the crude product is purified by flash column chromatography (10-100% ethyl acetate in isohexanes as eluant) to afford 3-[2-chloro-6-ethyl-4-(4,4,5,5-tetramethyl[1,3,2]dioxaborolan-2-yl)phenyl]-4-methoxybicyclo[3.2.1]oct-3-en-2-one.

Step 6: Preparation of 3-(2-Chloro-6-ethyl-4-prop-1-ynylphenyl)-4-methoxybicyclo[3.2.1]oct-3-en-2-one

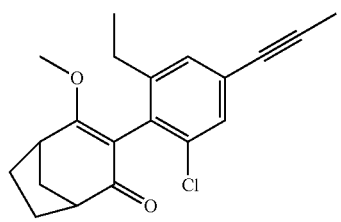 [SMILES: CC#Cc1cc(Cl)c(C2=C(OC)C3CCC(C3)C2=O)c(CC)c1]

To a solution of 1-propyn-1-yl iodide (0.89 g, 0.54 mmol) in toluene (5 ml), methanol (5 ml) and distilled water (2.5 ml) is added 3-[2-chloro-6-ethyl-4-(4,4,5,5-tetramethyl[1,3,2]dioxaborolan-2-yl)phenyl]-4-methoxybicyclo[3.2.1]oct-3-en-2-one (0.204 g, 0.49 mmol), palladium(II) chloride (0.09 g, 0.05 mmol) and potassium carbonate (135 mg, 0.98 mmol), and the reaction mixture is heated at 80° C. for 2 hours. The solution is then extracted with diethyl ether and the combined organic fractions are washed with distilled water, dried over anhydrous magnesium sulfate, filtered and the filtrate concentrated in vacuo. Purification by flash column chromatography (10-100% ethyl acetate in isohexanes as eluant) affords 3-(2-chloro-6-ethyl-4-prop-1-ynylphenyl)-4-methoxybicyclo[3.2.1]oct-3-en-2-one.

Step 7: Preparation of 3-(2-Chloro-6-ethyl-4-prop-1-ynylphenyl)bicyclo[3.2.1]octane-2,4-dione

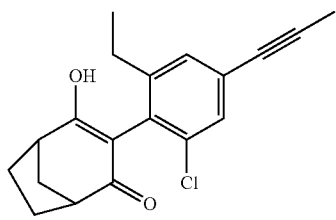 [SMILES: CC#Cc1cc(Cl)c(C2=C(O)C3CCC(C3)C2=O)c(CC)c1]

A solution of 3-(2-chloro-6-ethyl-4-prop-1-ynylphenyl)-4-methoxybicyclo[3.2.1]oct-3-en-2-one (0.48 g, 1.46 mmol) in acetone (1 ml) and 2N aqueous hydrochloric acid (1 ml) is heated at 120° C. under microwave irradiation for 10 minutes. The reaction mixture is then cooled to room temperature and partitioned between distilled water and ethyl acetate. The aqueous phase is extracted again with ethyl acetate (×3), and the combined organic fractions are washed with brine, dried over anhydrous magnesium sulfate, filtered and the filtrate concentrated in vacuo to afford 3-(2-chloro-6-ethyl-4-prop-1-ynyl-phenyl)-bicyclo[3.2.1]octane-2,4-dione.

EXAMPLE 4

Preparation of 3-(4-Chloroethynyl-2,6-dimethylphenyl)bicyclo[3.2.1]octane-2,4-dione

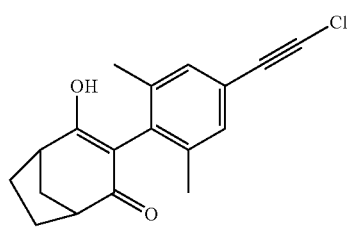 [SMILES: Cc1cc(C#CCl)cc(C)c1C1=C(O)C2CCC(C2)C1=O]

Step 1: Preparation of 3-[1-(4-Bromo-2,6-dimethylphenyl)methylidene]bicyclo[2.2.1]heptan-2-one

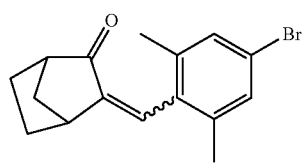 [SMILES: Cc1cc(Br)cc(C)c1C=C1C(=O)C2CCC1C2]

To a solution of norcamphor (1.18 g, 10.73 mmol) and 4-bromo-2,6-dimethyl-benzaldehyde (e.g. described in WO2008/021851) (3.43 g, 16.10 mmol) in ethanol (40 ml) is added solid potassium hydroxide (0.198 g, 3.52 mmol).

The reaction mixture is then heated at reflux for hours, cooled to 0° C. followed by the addition of distilled water (15 ml) and 2N aqueous hydrochloric acid (15 ml). The aqueous phase is then extracted with ethyl acetate (×3), and the combined organic fractions are washed with brine, dried over anhydrous magnesium sulfate, filtered and the filtrate concentrated in vacuo. Purification by flash column chromatography (5% ethyl acetate in isohexane as eluant) affords 3-[1-(4-bromo-2,6-dimethylphenyl)methylidene]bicyclo[2.2.1]heptan-2-one.

Step 2: Preparation of 4-[1-(4-Bromo-2,6-dimethylphenyl)methylidene]-3-oxabicyclo[3.2.1]octan-2-one

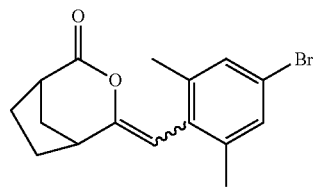 [SMILES: Cc1cc(Br)cc(C)c1C=C1OC(=O)C2CCC1C2]

To a solution of 3-[1-(4-bromo-2,6-dimethylphenyl)methylidene]bicyclo[2.2.1]heptan-2-one (6.50 g, 21.30 mmol) in tert-butanol (26 ml) is added hydrogen peroxide (3.46 ml, 36.23 mmol, 50% aqueous) and selenium dioxide (0.11 g, 1.0 mmol), and the solution is stirred at room temperature for 4 days. To the reaction mixture is then added distilled water and diethyl ether, the phases are separated, and the aqueous phase is extracted again with diethyl ether (×3). The combined organic fractions are washed with distilled water (×8), then concentrated in vacuo. The crude product is purified by flash column chromatography (5-50% ethyl acetate in isohexanes as eluant) to afford 4-[1-(4-bromo-2,6-dimethylphenyl)methylidene]-3-oxabicyclo[3.2.1]octan-2-one.

Step 3: Preparation of 3-(4-Bromo-2,6-dimethylphenyl)bicyclo[3.2.1]octane-2,4-dione

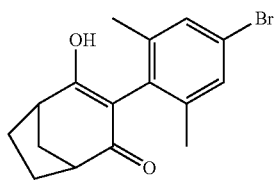 [SMILES: Cc1cc(Br)cc(C)c1C1=C(O)C2CCC(C2)C1=O]

To a solution of 4-[1-(4-bromo-2,6-dimethylphenyl)methylidene]-3-oxabicyclo[3.2.1]octan-2-one (3.185 g, 9.92 mmol) in N,N-dimethylformamide (65 ml) at 80° C. is added a second solution of sodium methoxide (4.29 ml, 19.83 mmol, 25 wt. % in methanol) dropwise. The reaction mixture is stirred at 80° C. for 1 hour 55 minutes, then cooled to to 0° C. 2N aqueous hydrochloric acid (30 ml) and water (30 ml) are added and the crude product is extracted with ethyl acetate (×3). The combined organic extracts are washed successively with distilled water (×3) then brine, and finally dried over magnesium sulfate, filtered and the filtrate concentrated in vacuo. Purification by flash column chromatography (30-100% ethyl acetate in isohexanes as eluant) affords 3-(4-bromo-2,6-dimethylphenyl)bicyclo[3.2.1]octane-2,4-dione.

Step 4: Preparation of 3-(4-Bromo-2,6-dimethylphenyl)-4-methoxybicyclo[3.2.1]oct-3-en-2-one

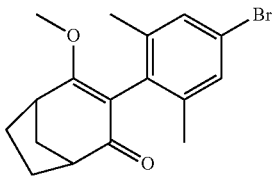 [SMILES: COC1=C(c2c(C)cc(Br)cc2C)C(=O)C2CCC1C2]

To a solution of 3-(4-bromo-2,6-dimethylphenyl)bicyclo[3.2.1]octane-2,4-dione (0.40 g, 1.25 mmol) in acetone (20 ml) is added potassium carbonate (0.343 g, 2.48 mmol) then iodomethane (0.51 ml, 8.25 mmol), and the suspension is stirred at room temperature for 18 hours. Volatile solvents are removed in vacuo, and the crude product is partitioned between distilled water and ethyl acetate. The phases are separated and the aqueous phase is extracted again with additional ethyl acetate (×3). Organic fractions are combined, washed with brine, dried over anhydrous magnesium sulfate, filtered and the filtrate concentrated in vacuo. Purification by flash column chromatography (5-90% ethyl acetate in isohexanes as eluant) affords 3-(4-bromo-2,6-dimethylphenyl)-4-methoxybicyclo[3.2.1]oct-3-en-2-one.

Step 5: Preparation of 3-(4-Ethynyl-2,6-dimethylphenyl)-4-methoxybicyclo[3.2.1]oct-3-en-2-one A mixture of 3-(4-bromo-2,6-dimethylphenyl)-4-methoxybicyclo[3.2.1]oct-3-en-2-one (0.21 g, 0.63 mmol), copper(I) iodide (0.012 g, 0.06 mmol), cesium fluoride (0.197 g, 1.30 mmol), [1,1'-bis(diphenylphosphino)ferrocene]palladium(II)chloride (0.027 g, 0.033 mmol), tributyl (1-propenyl) tin (0.54 ml, 1.87 mmol) and N,N-dimethylformamide (3 ml) is flushed with nitrogen, then heated at 110° C. under microwave irradiation for 45 minutes. Distilled water is added to the reaction mixture and the crude product is extracted with ethyl acetate (×3). Organic fractions are combined, washed with brine, dried over magnesium sulfate, filtered and the filtrate concentrated in vacuo. Purification by flash column chromatography (5-70% ethyl acetate in isohexane as eluant) affords 3-(4-ethynyl-2,6-dimethylphenyl)-4-methoxybicyclo[3.2.1]oct-3-en-2-one.

Step 6: Preparation of 3-(4-Chloroethynyl-2,6-dimethylphenyl)-4-methoxybicyclo[3.2.1]oct-3-en-2-one

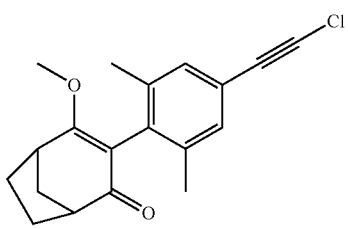 [SMILES: COC1=C(c2c(C)cc(C#CCl)cc2C)C(=O)C2CCC1C2]

A mixture of 3-(4-bromo-2,6-dimethylphenyl)-4-methoxybicyclo[3.2.1]oct-3-en-2-one (0.20 g, 0.71 mmol), N-chlorosuccinimide (0.114 g, 0.85 mmol) and silver acetate (0.012 g, 0.071 mmol) in acetone (5 ml) is heated at reflux overnight, then allowed to cool to room temperature. The reaction mixture is filtered then concentrated in vacuo. The crude product is purified by flash column chromatography (5-60% ethyl acetate in isohexane as eluant) to afford 3-(4-chloroethynyl-2,6-dimethylphenyl)-4-methoxybicyclo[3.2.1]oct-3-en-2-one.

Step 7: Preparation of 3-(4-Chloroethynyl-2,6-dimethylphenyl)bicyclo[3.2.1]octane-2,4-dione

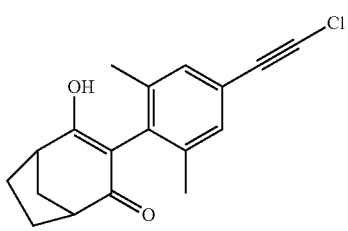 [SMILES: Cc1cc(C#CCl)cc(C)c1C1=C(O)C2CCC(C2)C1=O]

A solution of 3-(2-chloro-6-ethyl-4-prop-1-ynylphenyl)-4-methoxybicyclo[3.2.1]oct-3-en-2-one (0.170 g, 0.54 mmol) in acetone (3 ml) and 2N aqueous hydrochloric acid (1 ml) is heated at 120° C. under microwave irradiation for 10 minutes. The reaction mixture is then cooled to room temperature and partitioned between distilled water and ethyl acetate. The aqueous phase is extracted again with ethyl acetate (×3), and the combined organic fractions are washed with brine, dried over anhydrous magnesium sulfate, filtered and the filtrate concentrated in vacuo. The crude product is purified by flash column chromatography (5-70% ethyl acetate in isohexane as eluant) to afford 3-(4-chloroethynyl-2,6-dimethylphenyl)bicyclo[3.2.1]octane-2,4-dione.

EXAMPLE 5

Preparation of 2-[4-(2-chloroethynyl)-2,6-dimethyl phenyl]-5-(tetrahydropyran-4-ylmethyl)cyclohexane-1,3-dione

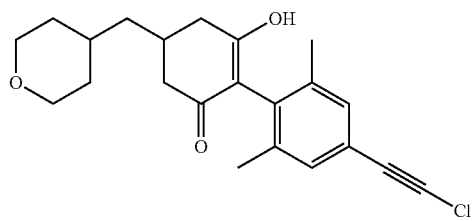 [SMILES: Cc1cc(C#CCl)cc(C)c1C1=C(O)CC(CC2CCOCC2)CC1=O]

Step 1: Preparation of 2-(4-bromo-2,6-dimethylphenyl)-5-(tetrahydropyran-4-ylmethyl)cyclohexane-1,3-dione

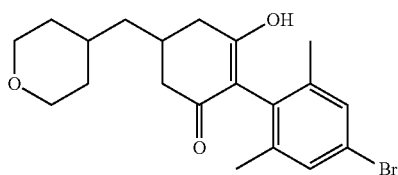 [SMILES: Cc1cc(Br)cc(C)c1C1=C(O)CC(CC2CCOCC2)CC1=O]

To a solution of 5-(tetrahydropyran-4-ylmethyl)cyclohexane-1,3-dione (0.420 g, 2.0 mmol) (e.g. reported in WO2010/046194) and 4-dimethylaminopyridine (1.22 g, 10.0 mmol) in chloroform (20 ml) is added 4-bromo-2,6-dimethylphenyllead triacetate (1.25 g, 2.2 mmol) (e.g. reported in WO2009/074314) and toluene (5 ml). The mixture is stirred under a nitrogen atmosphere then heated at 80° C. for 1.5 hours, followed cooling to room temperature. The reaction mixture is acidified with 2N aqueous hydrochloric acid, stirred vigorously for 10 minutes then filtered through a bed of diatomaceous earth and washed with dichloromethane (40 ml). The organic phase was washed with 2N aqueous hydrochloric acid then brine, dried over sodium sulphate, filtered and the filtrate concentrated in vacuo. The crude product is purified by flash column chromatography (20-100% ethyl acetate in isohexane as eluent) to afford 2-(4-bromo-2,6-dimethylphenyl)-5-(tetrahydropyran-4-ylmethyl)cyclohexane-1,3-dione.

Step 2: Preparation of 2-(4-bromo-2,6-dimethylphenyl)-3-methoxy-5-(tetrahydropyran-4-ylmethyl)cyclohex-2-en-1-one

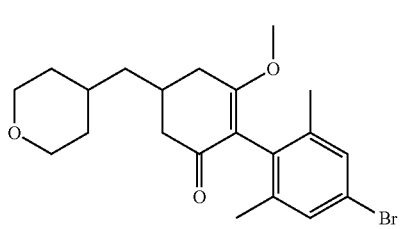 [SMILES: COC1=C(c2c(C)cc(Br)cc2C)C(=O)CC(CC2CCOCC2)C1]

To a solution of 2-(4-bromo-2,6-dimethylphenyl)-5-(tetrahydropyran-4-ylmethyl)cyclohexane-1,3-dione (0.470 g, 1.195 mmol) in acetone (20 ml) is added potassium carbonate (0.248 g, 1.80 mmol) then iodomethane (0.850 g, 5.99 mmol), and the suspension is stirred at room temperature for 16 hours. Volatile solvents are removed in vacuo, and the crude product is partitioned between distilled water and ethyl acetate. The phases are separated and the aqueous phase is extracted again with additional ethyl acetate (×3). Organic fractions are combined, washed with brine, dried over anhydrous magnesium sulfate, filtered and the filtrate concentrated in vacuo. Purification by flash column chromatography (20-70% ethyl acetate in isohexanes as eluent) affords 2-(4-bromo-2,6-dimethylphenyl)-3-methoxy-5-(tetrahydropyran-4-ylmethyl)cyclohex-2-en-1-one.

Step 3: Preparation of 2-(4-ethynyl-2,6-dimethylphenyl)-3-methoxy-5-(tetrahydropyran-4-ylmethyl)cyclohex-2-en-1-one

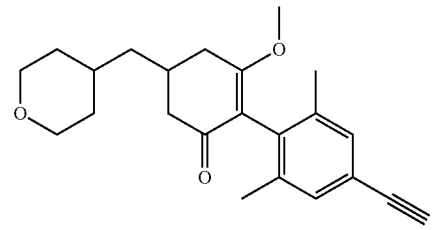 [SMILES: C#Cc1cc(C)c(C2=C(OC)CC(CC3CCOCC3)CC2=O)c(C)c1]

A mixture of 2-(4-bromo-2,6-dimethylphenyl)-3-methoxy-5-(tetrahydropyran-4-ylmethyl)cyclohex-2-en-1-one (0.203 g, 0.50 mmol), copper(I) iodide (0.019 g, 0.10 mmol), cesium fluoride (0.152 g, 1.00 mmol), [1,1'bis(diphenylphosphino)ferrocene]palladium(II)chloride (0.041 g, 0.05 mmol), tributyl(1-ethynyl) tin (0.550 g, 1.74 mmol) and N,N-dimethylacetamide (2 ml) is flushed with nitrogen, then heated at 110° C. under microwave irradiation for 2 hours. Distilled water is added to the reaction mixture and the crude product is extracted with ethyl acetate (×3). Organic fractions are combined, washed with brine, dried over magnesium sulfate, filtered and the filtrate concentrated in vacuo. Purification by reverse phase HPLC (15-70% acetonitrile in water as eluent) affords 2-(4-ethynyl-2,6-dimethyl phenyl)-3-methoxy-5-(tetrahydropyran-4-ylmethyl)cyclohex-2-en-1-one.

Step 4: Preparation of 2-[4-(2-chloroethynyl)-2,6-dimethylphenyl]-3-methoxy-5-(tetrahydropyran-4-ylmethyl)cyclohex-2-en-1-one

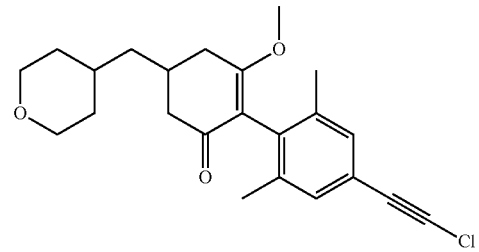 [SMILES: COC1=C(c2c(C)cc(C#CCl)cc2C)C(=O)CC(CC2CCOCC2)C1]

To a solution of 2-(4-ethynyl-2,6-dimethylphenyl)-3-methoxy-5-(tetrahydropyran-4-ylmethyl)cyclohex-2-en-1-one (0.220 g, 0.62 mmol) in acetone (5 ml) is added N-chlorosuccinimide (0.100 g, 0.75 mmol) and silver acetate (0.007 g, 0.06 mmol). The mixture is heated at reflux under a nitrogen atmosphere overnight, then allowed to cool to room temperature. The reaction mixture is filtered then concentrated in vacuo. The crude product is purified by flash column chromatography (10-100% ethyl acetate in isohexane as eluent) to afford 2-[4-(2-chloroethynyl)-2,6-dimethyl-phenyl]-3-methoxy-5-(tetrahydropyran-4-ylmethyl)cyclohex-2-en-1-one.

Step 5: Preparation of Preparation of 2-[4-(2-chloroethynyl)-2,6-dimethylphenyl]-5-(tetrahydropyran-4-ylmethyl)cyclohexane-1,3-dione

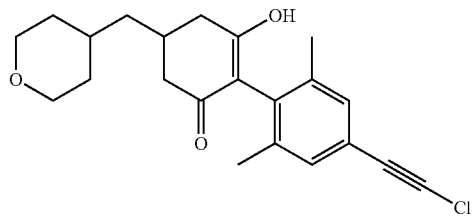 [SMILES: Cc1cc(C#CCl)cc(C)c1C1=C(O)CC(CC2CCOCC2)CC1=O]

A solution of 2-[4-(2-chloroethynyl)-2,6-dimethylphenyl]-3-methoxy-5-(tetrahydropyran-4-ylmethyl)cyclohex-2-en-1-one (0.030 g, 0.078 mmol) in acetone (1.5 ml) and 2N aqueous hydrochloric acid (0.5 ml) is heated at 60° C. under microwave irradiation for 30 minutes. The reaction mixture is then cooled to room temperature, concentrated in vacuo and the crude product is partitioned between distilled water and ethyl acetate. The aqueous phase is extracted again with ethyl acetate, and the combined organic fractions are washed with brine, dried over anhydrous magnesium sulfate, filtered and the filtrate concentrated in vacuo. The crude product is purified by flash column chromatography (10-100% ethyl acetate in isohexane as eluent) to afford 2-[4-(2-chloroethynyl)-2,6-dimethyl-phenyl]-5-(tetrahydropyran-4-ylmethyl)cyclohexane-1,3-dione.

EXAMPLE 6

Preparation of 2-(2,6-dimethyl-4-prop-1-ynylphenyl)-5-(tetrahydropyran-4-ylmethyl)cyclohexane-1,3-dione

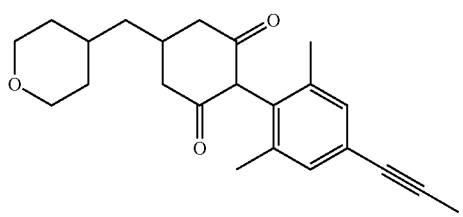 [SMILES: CC#Cc1cc(C)c(C2C(=O)CC(CC3CCOCC3)CC2=O)c(C)c1]

Step 1: 2-(2,6-dimethyl-4-prop-1-ynyl-phenyl)-3-methoxy-5-(tetrahydropyran-4-ylmethyl)cyclohex-2-en-1-one

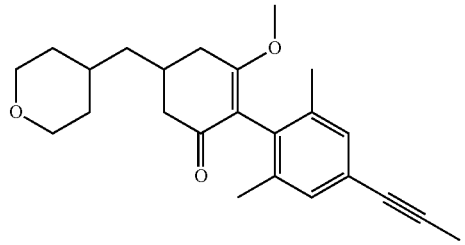 [SMILES: CC#Cc1cc(C)c(C2=C(OC)CC(CC3CCOCC3)CC2=O)c(C)c1]

A mixture of 2-(4-bromo-2,6-dimethylphenyl)-3-methoxy-5-(tetrahydropyran-4-ylmethyl)cyclohex-2-en-1-one (0.203 g, 0.50 mmol), copper(I) iodide (0.019 g, 0.10 mmol), cesium fluoride (0.152 g, 1.00 mmol), [1,1 bis(diphenylphosphino)ferrocene]palladium(I)chloride (0.041 g, 0.05 mmol), tributyl(1-propenyl) tin (0.574 g, 1.74 mmol) and N,N-dimethylacetamide (2 ml) is flushed with nitrogen, then heated at 110° C. under microwave irradiation for 60 minutes. Distilled water is added to the reaction mixture and the crude product is extracted with ethyl acetate (×3). Organic fractions are combined, washed with brine, dried over magnesium sulfate, filtered and the filtrate concentrated in vacuo. Purification by reverse phase HPLC (15-70% acetonitrile in water as eluent) affords 2-(2,6-dimethyl-4-prop-1-ynylphenyl)-3-methoxy-5-(tetrahydropyran-4-ylmethyl)cyclohex-2-en-1-one.

Step 2: Preparation of 2-(2,6-dimethyl-4-prop-1-ynylphenyl)-5-(tetrahydropyran-4-ylmethyl)cyclohexane-1,3-dione

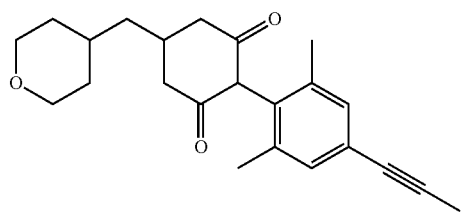 [SMILES: CC#Cc1cc(C)c(C2C(=O)CC(CC3CCOCC3)CC2=O)c(C)c1]

A solution of 2-(2,6-dimethyl-4-prop-1-ynylphenyl)-3-methoxy-5-(tetrahydropyran-4-ylmethyl)cyclohex-2-en-1-one (0.205 g, 0.58 mmol) in acetone (6 ml) and 2N aqueous hydrochloric acid (2 ml) is heated at 60° C. under microwave irradiation for 30 minutes. The reaction mixture is then cooled to room temperature, concentrated in vacuo and the crude product is partitioned between distilled water and ethyl acetate. The aqueous phase is extracted again with ethyl acetate, and the combined organic fractions are washed with brine, dried over anhydrous magnesium sulfate, filtered and the filtrate concentrated in vacuo. The crude product is purified by flash column chromatography (10-100% ethyl acetate in isohexane as eluent) to afford 2-(2,6-dimethyl-4-prop-1-ynylphenyl)-5-(tetrahydropyran-4-ylmethyl)cyclohexane-1,3-dione.

EXAMPLE 7

Preparation 3-(2-chloro-6-methoxy-4-prop-1-ynyl-phenyl)-bicyclo[3.2.1]octane-2,4-dione

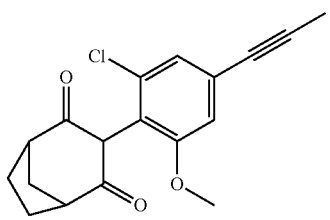 [SMILES: CC#Cc1cc(Cl)c(C2C(=O)C3CCC(C3)C2=O)c(OC)c1]

Step 1: Preparation of (3E)-3-[(2-chloro-6-methoxy-phenyl)methylene]norbornan-2-one

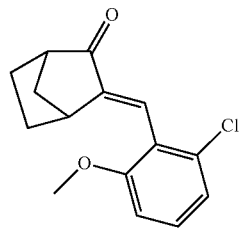 [SMILES: COc1cccc(Cl)c1/C=C1/C(=O)C2CCC1C2]

Norbornan-2-one (5.00 g, 45.39 mmol) and 2-chloro-6-methoxy-benzaldehyde (10.84 g, 63.55 mmol) was dissolved in ethanol (136 mL). Potassium hydroxide (0.76 g, 13.62 mmol) was added to the reaction in one portion and refluxed at 85° C. under nitrogen for 19 hours. The reaction mixture was concentrated to minimum volume. Ethyl acetate (100 mL) was added followed by 2N aqueous hydrochloric acid (100 mL) dropwise at 0° C. The mixture was diluted with ethyl acetate and the phases separated. The aqueous layer was extracted twice with ethyl acetate and the combined organics were washed with brine, dried over magnesium sulphate, filtered and reduced in vacuo. The crude product was purified by flash column chromatography over silica gel (5-30% ethyl acetate in hexanes as eluant) to afford (3E)-3-[(2-chloro-6-methoxy-phenyl)methylene]norbornan-2-one as an dark red oil.

Step 2: Preparation of (2Z)-2-[(2-chloro-6-methoxy-phenyl)methylene]-3-oxabicyclo[3.2.1]octan-4-one

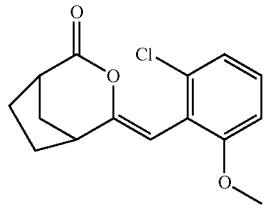 [SMILES: COc1cccc(Cl)c1/C=C1\OC(=O)C2CCC1C2]

(3E)-3-[(2-chloro-6-methoxy-phenyl)methylene]norbornan-2-one (11.93 g, 45.41 mmol) was stirred in 2-methyl-propan-2-ol (59 mL) at room temperature and hydrogen peroxide (5 mL, 77.19 mmol) was added dropwise to the mixture. Selenium dioxide (0.20 g, 1.82 mmol) was added to the reaction and stirred at room temperature for 24 hours. Another portion of hydrogen peroxide (5 mL, 77.19 mmol) was added dropwise to the reaction and stirred for an additional 24 hours. Pentane was added to the reaction mixture and the precipitate was filtered. The crude solid was washed with additional pentane and air dried to afford (2Z)-2-[(2-chloro-6-methoxy-phenyl)methylene]-3-oxabicyclo[3.2.1]octan-4-one as a colourless solid.

Step 3: Preparation of 3-(2-chloro-6-methoxy-phenyl)bicyclo[3.2.1]octane-2,4-dione

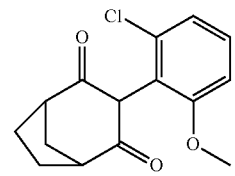 [SMILES: COc1cccc(Cl)c1C1C(=O)C2CCC(C2)C1=O]

(2Z)-2-[(2-chloro-6-methoxy-phenyl)methylene]-3-oxabicyclo[3.2.1]octan-4-one (8.74 g, 31.4 mmol) was dissolved in toluene (94 mL). Eaton's reagent (94 mL) was added in one portion at room temperature and stirred at 70° C. under nitrogen for 1 hour. The reaction mixture was quenched onto ice/6M NaOH (300 g:300 mL) and basified until the solution was pH 14. The mixture was stirred for 15 minutes and the phases were separated. The aqueous layer was extracted with additional ethyl acetate and acidified to pH 1-3 using concentrated aqueous hydrochloric acid. The acidic aqueous layer was extracted twice with dichloromethane, dried over magnesium sulphate, filtered and reduced in vacuo to afford 3-(2-chloro-6-methoxy-phenyl)bicyclo[3.2.1]octane-2,4-dione as a beige solid.

Step 4: Preparation of 3-(2-chloro-6-methoxy-phenyl)-2-methoxy-bicyclo[3.2.1]oct-2-en-4-one

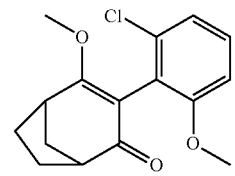 [SMILES: COC1=C(c2c(Cl)cccc2OC)C(=O)C2CCC1C2]

3-(2-chloro-6-methoxy-phenyl)bicyclo[3.2.1]octane-2,4-dione (5.75 g, 20.6 mmol) was dissolved in acetone (206 mL) to which potassium carbonate (4.34 g, 30.9 mmol) was added. Iodomethane (6.42 mL, 103 mmol) was added dropwise to the reaction and stirred at room temperature under nitrogen for 22 hours. The reaction mixture was concentrated in vacuo and dichloromethane/water (300 mL) was added. The mixture was extracted twice with dichloromethane, dried over magnesium sulphate, filtered and reduced in vacuo to afford 3-(2-chloro-6-methoxy-phenyl)-2-methoxy-bicyclo[3.2.1]oct-2-en-4-one as a beige solid after trituration with diethyl ether.

Step 5: Preparation of 3-[2-chloro-6-methoxy-4-(4,4,5,5-tetramethyl-1,3,2-dioxaborolan-2-yl)phenyl]-2-methoxy-bicyclo[3.2.1]oct-2-en-4-one

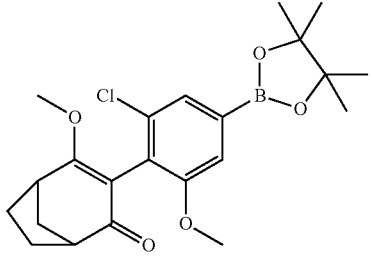 [SMILES: COC1=C(c2c(Cl)cc(B3OC(C)(C)C(C)(C)O3)cc2OC)C(=O)C2CCC1C2]

A mixture of 3-(2-chloro-6-methoxy-phenyl)-2-methoxy-bicyclo[3.2.1]oct-2-en-4-one (25.00 g, 85.39 mmol), (1,5-cyclooctadiene)(methoxy)iridium(I) dimer (2.55 g, 3.84 mmol), 4,4'-di-tert-butyl-2,2'-dipyridyl (2.11 g, 7.69 mmol) and bis(pinacolato)diboron (22.12 g, 85.39 mmol) was evacuated and purged three times with nitrogen. Anhydrous tert-butyl methyl ether (85.39 mL, 1 M) was added to the reaction mixture and refluxed at 80° C. for 4 hours under nitrogen. The reaction mixture was concentrated onto silica gel for purification by flash chromatography (10-100% ethyl acetate in hexanes as eluant) to afford 3-[2-chloro-6-methoxy-4-(4,4,5,5-tetramethyl-1,3,2-dioxaborolan-2-yl)phenyl]-2-methoxy-bicyclo[3.2.1]oct-2-en-4-one as a pale yellow oil.

Step 6: Preparation of 3-(4-bromo-2-chloro-6-methoxy-phenyl)bicyclo[3.2.1]octane-2,4-dione

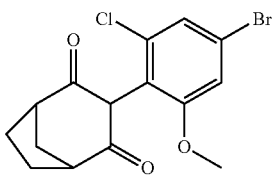 [SMILES: COc1cc(Br)cc(Cl)c1C1C(=O)C2CCC(C2)C1=O]

3-[2-chloro-6-methoxy-4-(4,4,5,5-tetramethyl-1,3,2-dioxaborolan-2-yl)phenyl]-2-methoxy-bicyclo[3.2.1]oct-2-en-4-one (5.00 g, 11.94 mmol) was dissolved in methanol (120 mL) and copper dibromide (5.33 g, 23.88 mmol) in water (120 mL) was added. The reaction was refluxed at 80° C. under nitrogen for 1 hour. The reaction mixture was concentrated under vacuum to remove the methanol and diluted with dichloromethane (100 mL). The phases were separated and extracted twice with dichloromethane. The organics were dried over magnesium sulphate, filtered through celite and reduced in vacuo. The crude residue was dissolved in acetone (120 mL) and 2M aqueous hydrochloric acid (120 mL) was added. The reaction mixture was heated at 60° C. for 2 hours. The phases were extracted three times with dichloromethane, dried over magnesium sulphate, filtered and reduced in vacuo. The crude product was purified by flash column chromatography over silica gel (10-100% ethyl acetate in hexanes as eluant) to afford 3-(4-bromo-2-chloro-6-methoxy-phenyl)bicyclo[3.2.1]octane-2,4-dione as an colourless solid.

Step 7: Preparation of 3-(2-chloro-6-methoxy-4-prop-1-ynyl-phenyl)bicyclo[3.2.1]octane-2,4-dione

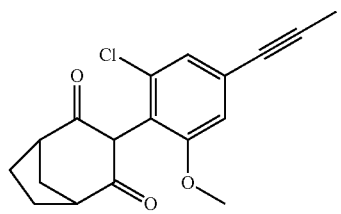 [SMILES: CC#Cc1cc(Cl)c(C2C(=O)C3CCC(C3)C2=O)c(OC)c1]

A mixture of 3-(4-bromo-2-chloro-6-methoxy-phenyl)bicyclo[3.2.1]octane-2,4-dione (0.12 g, 0.34 mmol), dichlorobis(triphenylphosphine)palladium(II) (0.01 g, 0.017 mmol), 1,4-bis-(diphenylphosphino)butane (0.014 g, 0.034 mmol) and but-2-ynoic acid (0.034 g, 0.40 mmol) was evacuated and purged three times with nitrogen. Dimethylsulfoxide (4 mL) was added to the reaction mixture followed by tetrabutylammonium fluoride (1 M in tetrahydrofuran, 1 mL, 1.00 mmol) and stirred at 110° C. under nitrogen for 1 hour. The reaction mixture was quenched with 2M aqueous hydrochloric acid and extracted three times with dichloromethane. The organics were dried over magnesium sulphate, filtered over celite and reduced in vacuo. The crude product was purified by flash column chromatography over silica gel (10-100% ethyl acetate in hexanes as eluant) to afford 3-(2-chloro-6-methoxy-4-prop-1-ynyl-phenyl)bicyclo[3.2.1]octane-2,4-dione as an colourless gum.

EXAMPLE 8

Preparation of 2-(2,6-dimethyl-4-prop-1-ynylphenyl)-5-(pyridin-2-yl)cyclohexane-1,3-dione, hydrochloride salt

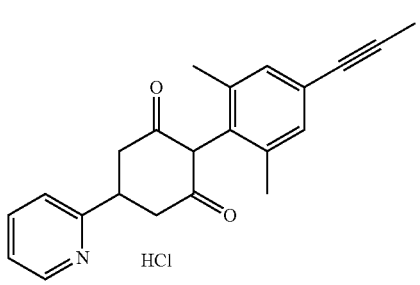 [SMILES: CC#Cc1cc(C)c(C2C(=O)CC(c3ccccn3)CC2=O)c(C)c1 ; Cl]

Step 1: Preparation of 2-(4-bromo-2,6-dimethylphenyl)-N-methoxy-N-methylacetamide

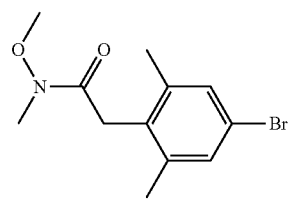 [SMILES: CON(C)C(=O)Cc1c(C)cc(Br)cc1C]

To a suspension of (4-bromo-2,6-dimethylphenyl)acetic acid (78.0 g, 0.32 mol) (e.g. described in DE 19603332) in anhydrous dichloromethane (1.3 L) was added N-hydroxybenzotriazole (65.0 g, 0.48 mol) then 1-ethyl-3-(3-dimethylaminopropyl)carbodiimide hydrochloride (92.3 g, 0.48 mol) at 0° C. under nitrogen. Diisopropylethylamine (165.8 g, 1.28 mol) was then added dropwise and the reaction mixture was stirred for approximately 15 minutes. N,O-dimethyl hydroxylamine hydrochloride (47.0 g, 0.48 mol) was next added, followed by stirring at room temperature for 4 h. After dillution with dichloromethane (1 L) the reaction mixture was washed with 2% aqueous hydrochloric acid solution, water then brine. The organic layer was dried over anhydrous sodium sulphate, solvents removed in vacuo, and the crude product was purified by flash column chromatography over silica gel (10-15% ethylacetate in hexanes as eluant). Further trituration with n-pentane afforded 2-(4-bromo-2,6-dimethylphenyl)-N-methoxy-N-methylacetamide as an off white solid.

Step 2: Preparation of 1-(4-bromo-2,6-dimethylphenyl)propan-2-one

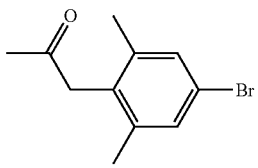

To a solution of 2-(4-bromo-2,6-dimethylphenyl)-N-methoxy-N-methylacetamide (71.0 g, 0.25 mol) in anhydrous tetrahydrofuran was added methyl magnesium bromide (355 ml, 0.49 mol, 1.4M solution in toluene) dropwise at 0° C. After stirring for a further 10 minutes the reaction was quenched by addition of saturated aqueous ammonium chloride at 0-50° C. The crude compound was extracted into ethyl acetate, washed with brine, dried over anhydrous sodium sulphate, and solvents were removed in vacuo. Purification by flash column chromatography over silica gel (3-5% ethylacetate in hexanes as eluant), followed by additional trituration with n-pentane afforded 1-(4-bromo-2,6-dimethylphenyl)propan-2-one as an off white solid.

Step 3: Preparation of 1-(4-bromo-2,6-dimethylphenyl)-4-(pyridin-2-yl)but-3-en-2-one

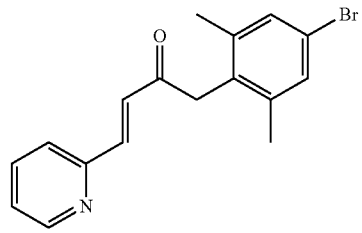 [SMILES: Cc1cc(Br)cc(C)c1CC(=O)/C=C/c1ccccn1]

To a solution of 1-(4-bromo-2,6-dimethylphenyl)propan-2-one (26.7 g, 110.7 mmol) in ethanol (250 ml) was added pyridine-2-carbaldehyde (11.9 g, 110.72 mmol) at room temperature. 3.5M aqueous sodium hydroxide (220 ml) was then added dropwise at room temperature, followed by additional stirring for 5 minutes. The reaction mass was poured into water, and the crude product was extracted with ethyl acetate (3×100 ml). Organic fractions were combined then washed with brine, dried over anhydrous sodium sulphate, and solvents were removed in vacuo. Purification by flash column chromatography over silica gel (20% ethylacetate in hexanes as eluant), followed by additional trituration with n-pentane afforded 1-(4-bromo-2,6-dimethylphenyl)-4-(pyridin-2-yl)but-3-en-2-one as a white solid.

Step 4: Preparation of 3-(4-bromo-2,6-dimethylphenyl)-2,4-dioxo-6-(pyridin-2-yl)cyclohexanecarboxylic acid methyl ester

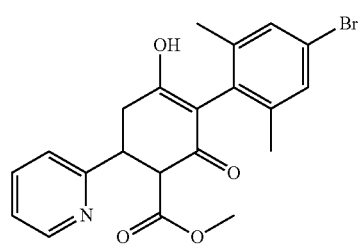 [SMILES: COC(=O)C1C(=O)C(c2c(C)cc(Br)cc2C)=C(O)CC1c1ccccn1]

To a solution of sodium methoxide (7.2 g, 33.2 mmol) in anhydrous methanol (150 ml) was added dimethyl malonate (17.6 g, 133.24 mmol), followed by stirring at room temperature for 10 minutes. 1-(4-Bromo-2,6-dimethylphenyl)-4-(pyridin-2-yl)but-3-en-2-one (20.0 g, 60.6 mmol) was then added and the reaction mixture was heated at reflux for 24 hours. Organic solvents were removed in vacuo, and the residue was dissolved in water then washed with diethyl ether. The aqueous phase was acidified to pH 4-5 by slow addition of 2% aqueous hydrochloric acid, and the resulting solid was dissolved in dichloromethane, washed with brine, dried over anhydrous sodium sulphate then concentrated in vacuo. The crude product was triturated with 1% diethylether in hexanes to afford 3-(4-bromo-2,6-dimethylphenyl)-2,4-dioxo-6-(pyridin-2-yl)cyclohexanecarboxylic acid methyl ester as a white solid.

Step 5: Preparation of 2-(4-bromo-2,6-dimethylphenyl)-5-(pyridin-2-yl)cyclohexane-1,3-dione

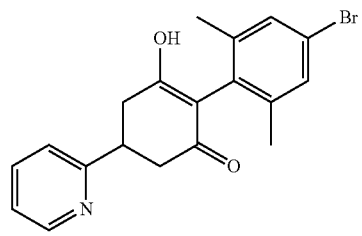 [SMILES: Cc1cc(Br)cc(C)c1C1=C(O)CC(c2ccccn2)CC1=O]

A suspension of 3-(4-bromo-2,6-dimethylphenyl)-2,4-dioxo-6-pyridin-2-ylcyclohexanecarboxylic acid methyl ester (23.0 g, 53.5 mmol) in 5M aqueous sulfuric acid (70 ml) was heated at reflux for 4 hours. The reaction mixture was then cooled to room temperature and poured into ice water, and the pH was adjusted to 4-5 by addition of 5% aqueous hydrochloric acid. The crude product was triturated with diethylether to afford 2-(4-bromo-2,6-dimethylphenyl)-5-(pyridin-2-yl)cyclohexane-1,3-dione as an off white solid.

Step 6: Preparation of 2-(4-bromo-2,6-dimethyl-phenyl)-3-methoxy-5-(2-pyridyl)cyclohex-2-en-1-one

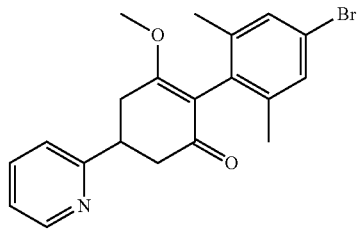 [SMILES: COC1=C(c2c(C)cc(Br)cc2C)C(=O)CC(c2ccccn2)C1]

To a cooled (ice-bath) suspension of 2-(4-bromo-2,6-dimethyl-phenyl)-5-(2-pyridyl)cyclohexane-1,3-dione (5.00 g, 13.4 mmol) in acetone (250 mL) was added potassium carbonate (2.78 g, 20.1 mmol) followed by iodomethane (9.53 g, 4.18 mL, 67.2 mmol). The mixture was stirred for 10 minutes and then cooling was removed and solution stirred at room temperature for 18 hours. Acetone was removed in vacuo and the residue was partitioned between water and ethyl acetate. The phases were separated and the aqueous phase was extracted into ethyl acetate (×2). Combined organic phases were washed with brine, dried over magnesium sulphate, filtered and concentrated to give an orange gum which, after column chromatography on silica gel, afforded 2-(4-bromo-2,6-dimethyl-phenyl)-3-methoxy-5-(2-pyridyl)cyclohex-2-en-1-one (4.97 g, 12.9 mmol, 96%) as a white solid.

Step 7: Preparation of 2-(2,6-dimethyl-4-prop-1-ynyl-phenyl)-3-methoxy-5-(2-pyridyl)-cyclohex-2-en-1-one

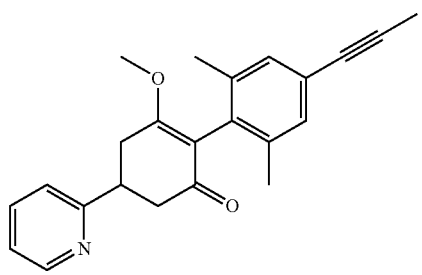 [SMILES: CC#Cc1cc(C)c(C2=C(OC)CC(c3ccccn3)CC2=O)c(C)c1]

2-(4-bromo-2,6-dimethyl-phenyl)-3-methoxy-5-(2-pyridyl)cyclohex-2-en-1-one (0.250 g, 0.647 mmol), cesium fluoride (0.197 g, 0.0478 mL, 1.29 mmol), cuprous iodide (0.0247 g, 0.129 mmol) and PdCl2(dppf) (0.0710 g, 0.0971 mmol) were combined in a 2-5 mL microwave vial and which was sealed and purged with nitrogen. Dimethylformamide (1.9 g, 2 mL, 26 mmol) was added followed by tributyl(prop-1-ynyl)stannane (0.852 g, 0.787 mL, 2.59 mmol). The reaction was heated in the microwave at 120° C. for 60 minutes. The reaction mixture was diluted with ethyl acetate and then poured into water. The biphasic mixture was filtered through diatomaceous earth and then the phases were separated. The aqueous phase was extracted into ethyl acetate (×2) then combined organic extracts were washed with brine, dried over magnesium sulphate, filtered and concentrated to a black residue which, after repeated column chromatography on silica gel, afforded 2-(2,6-dimethyl-4-prop-1-ynyl-phenyl)-3-methoxy-5-(2-pyridyl)cyclohex-2-en-1-one (0.216 g, 0.6253 mmol, 97%) as a white solid.

Step 8: Preparation of 2-(2,6-dimethyl-4-prop-1-ynylphenyl)-5-(pyridin-2-yl)cyclohexane-1,3-dione, hydrochloride salt

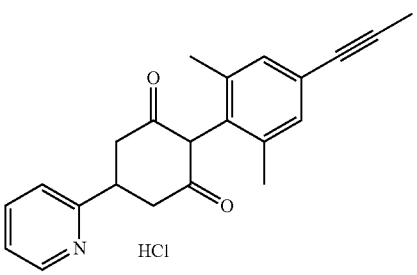 [SMILES: CC#Cc1cc(C)c(C2C(=O)CC(c3ccccn3)CC2=O)c(C)c1 ; Cl]

2-(2,6-dimethyl-4-prop-1-ynyl-phenyl)-3-methoxy-5-(2-pyridyl)cyclohex-2-en-1-one (0.198 g, 0.5732 mmol) was dissolved in acetone (2.5 mL) in a 0.5-2 mL microwave vial. 2M aqueous hydrochloric acid (0.2 mL, 0.4 mmol) was added and resultant solution was heated in the microwave at 70 to 90° C. until LCMS (liquid chromatography-mass spectrometry) analysis indicated reaction had proceeded to completion. The reaction mixture was concentrated in vacuo to afford a beige solid which was azeotroped with toluene to afford 2-(2,6-dimethyl-4-prop-1-ynyl-phenyl)-5-(pyridin-2-yl)cyclohexane-1,3-dione hydrochloride (0.1864 g, 0.5067 mmol, 88%) as a pale pink solid.

EXAMPLE 9

Preparation of 2-(2,6-dimethyl-4-prop-1-ynylphenyl)-3-(methoxycarbonyloxy)-5-(pyridin-2-yl)cyclohex-2-en-1-one

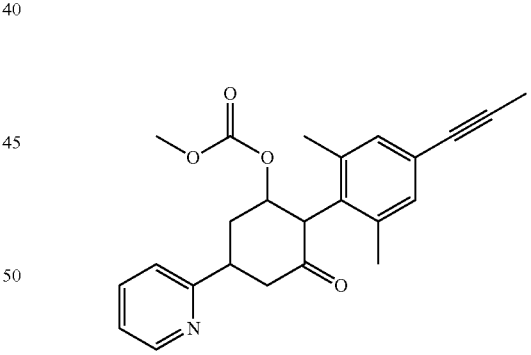

To a solution of 2-(2,6-dimethyl-4-prop-1-ynyl-phenyl)-5-(pyridin-2-yl)cyclohexane-1,3-dione hydrochloride (0.071 g, 0.193 mmol) in dichloromethane (2.0 mL) was added triethylamine (0.043 g, 0.059 mL, 0.425 mmol) followed by methyl carbonochloridate (0.022 g, 0.232 mmol). Reaction mixture was stirred at room temperature for 18 hours. The reaction mixture was diluted with dichloromethane (2 mL) and water (2 mL) and then passed through a phase separation cartridge, washing with dichloromethane. The organic filtrate was concentrated in vacuo to afford [2-(2,6-dimethyl-4-prop-1-ynyl-phenyl)-3-oxo-5-(pyridin-2-yl)cyclohexen-1-yl]methyl carbonate, which is also named 2-(2,6-dimethyl-4-prop-1-ynylphenyl)-3-(methoxycarbonyloxy)-5-(pyridin-2-yl)cyclohex-2-en-1-one, (0.072 g, 0.1849 mmol, 96% yield) as an orange solid.

EXAMPLE 10

Preparation of 9-(2-Chloro-6-methoxy-4-prop-1-ynyl-phenyl)-3-oxa-spiro[5.5]undecane-8,10-dione (Compound A-20)

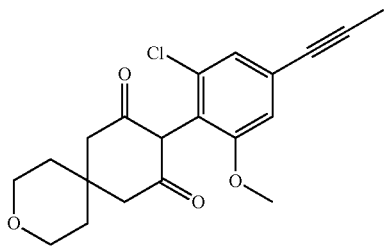 [SMILES: CC#Cc1cc(Cl)c(C2C(=O)CC3(CCOCC3)CC2=O)c(OC)c1]

Step 1: Preparation of Diacetoxy-(2-chloro-6-methoxy-phenyl)plumbyl acetate

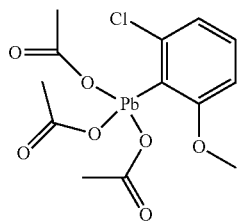

A solution of mercury (II) acetate (0.171 g) and lead (IV) acetate (5.70 g) in chloroform (20 mL) under nitrogen atmosphere was warmed to 40° C. To this was added (2-chloro-6-methoxy-phenyl)boronic acid (2.00 g, CAS 385370-80-9) in a single portion and heating at 40° C. continued for 4 hours. The reaction was left to cool and stand overnight.

The reaction was diluted with chloroform (50 mL) and cooled in an ice bath. Potassium carbonate (13.3 g) was added gradually with stirring and the mixture stirred for 5 minutes under nitrogen. This mixture was filtered through Celite and washed through with further chloroform (80 mL). The filtrate was concentrated in vacuo to leave a dark brown sticky mass. Trituration with iso-hexane (40 mL) gave a solid which was filtered off washed with a little cold iso-hexane and air-dried to give diacetoxy-(2-chloro-6-methoxy-phenyl)plumbyl acetate (4.66 g) as a beige solid.

$^1$H NMR (400 MHz, CDCl$_3$+a drop of d$_6$-DMSO) 7.35-7.43 (m, 1H), 7.16 (t, 1H), 6.98-7.03 (dd, 1H), 3.88-3.93 (d, 3H), 2.08 (s, 9H).

Step 2: Preparation of 9-(2-Chloro-6-methoxy-phenyl)-3-oxa-spiro[5.5]undecane-8,10-dione

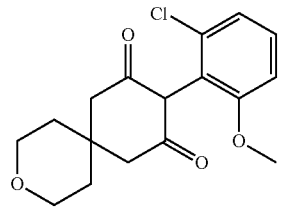 [SMILES: COc1cccc(Cl)c1C1C(=O)CC2(CCOCC2)CC1=O]

To a suspension of 3-oxaspiro[5.5]undecane-8,10-dione (0.40 g, CAS 1058731-65-9) and 4-(dimethylamino)pyridine (1.4 g) in chloroform (12 mL), under nitrogen atmosphere was added toluene (3 mL) followed by diacetoxy-(2-chloro-6-methoxy-phenyl)plumbyl acetate (1.4 g). This mixture was heated, under nitrogen, at 69° C. (internal temperature) for 3.5 hours.

The reaction was left to cool and stand overnight.

The reaction mixture was diluted with chloroform (20 mL), cooled in an ice bath and gradually acidified with aqueous 2M hydrochloric acid (8 mL). After stirring vigorously for 10 minutes a pale orange suspension resulted. The mixture was filtered through water-washed 'Celite' and washed through with chloroform. The organic layer was separated and extracted with aqueous sodium bicarbonate solution.

The aqueous layer was cooled in an ice-bath, acidified with aqueous 2M hydrochloric acid, extracted with dichloromethane (2×). The combined organic layers were dried over anhydrous magnesium sulfate. Concentration gave a thick oil, which was purified by chromatography on silica eluting with ethyl acetate in iso-hexane to give 9-(2-chloro-6-methoxy-phenyl)-3-oxaspiro[5.5]undecane-8,10-dione (0.429 g) as an off-white solid $^1$H NMR (400 MHz, CDCl$_3$) 7.28 (t, 1H), 7.08 (d, 1H), 6.84 (d, 1H), 5.85 (brs, 1H), 3.73 (s, 3H), 3.70 (t, 4H), 2.59 (brs, 4H), 1.75 (t, 2H), 1.70 (t, 2H)

The remaining steps to the desired compound 9-(2-chloro-6-methoxy-4-prop-1-ynyl-phenyl)-3-oxa-spiro[5.5]undecane-8,10-dione, Compound A-20, can be carried out substantially as described in Example 7.

EXAMPLE 11

Preparation of 2-(2,6-Dimethyl-4-prop-1-ynyl-phenyl)-5-(2-methylsulfanyl-ethyl)cyclohexane-1,3-dione, Compound A-21

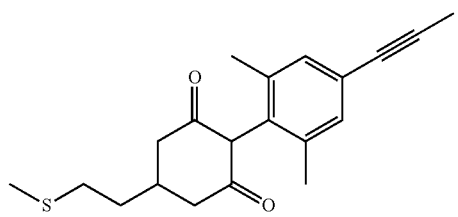

Step 1: Preparation of (E)-6-Methylsulfanylhex-3-en-2-one

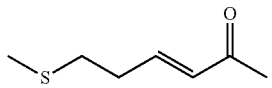

To a solution of 3-methylsulfanylpropanal (CAS 3268-49-3, 5.6 g) in dichloromethane (120 mL) was added 1-(triphenylphosphoranylidene)-2-propanone (CAS 1439-36-7, 17 g) in a single portion. The reaction mixture was heated and stirred at reflux for 5 hours. The cooled reaction mixture was concentrated to leave a pale yellow solid which was triturated with a 1:1 mixture of ether:iso-hexane (100 mL). The resulting solid was collected by filtration and washed with further 1:1 ether:iso-hexane (50 mL). The filtrate was concentrated to a yellow oil and purified by chromatography on silica eluting with ethyl acetate in iso-hexane to give (E)-6-methylsulfanylhex-3-en-2-one (5.890 g) as a colourless liquid.

$^1$H NMR (400 MHz, CDCl$_3$) 6.81 (dt, 1H), 6.08-6.15 (m, 1H), 2.61-2.67 (m, 2H), 2.49-2.58 (m, 2H), 2.24-2.27 (m, 3H), 2.10-2.15 (m, 3H)

Step 2: Preparation of Ethyl 2-(2-methylsulfanylethyl)-4,6-dioxo-cyclohexanecarboxylate

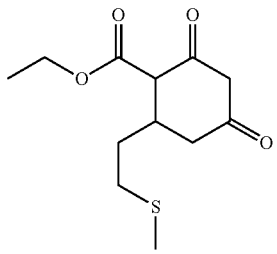 [SMILES: CCOC(=O)C1C(=O)CC(=O)CC1CCSC]

To ice cooled ethanol (50 mL) was added sodium metal (1.249 g) in small portions under nitrogen and the resulting solution was stirred for 15 minutes. Diethyl propanedioate (7.901 g) in ethanol (25 mL) was added drop wise to this cooled solution over 20 minutes. The reaction was allowed to warm to ambient temperature and stirred for a further 2 hours. The mixture was cooled in an ice bath and a solution of (E)-6-methylsulfanylhex-3-en-2-one (5.890 g) in ethanol (25 mL) was added drop wise. The reaction was allowed to warm to ambient temperature, stirred for 4 hours and then left to stand overnight. The reaction was concentrated to a yellow slurry which was poured into a cooled solution of 2M hydrochloric acid and stirred for 5 minutes. This was extracted with dichloromethane (×2) and the combined organic layers dried over anhydrous magnesium sulfate and concentrated to give ethyl 2-(2-methylsulfanylethyl)-4,6-dioxo-cyclohexanecarboxylate (11.446 g) as a yellow oil.

$^1$H NMR (400 MHz, CDCl$_3$) 5.48-5.56 (m, 1H), 4.13-4.33 (m, 2H), 3.38-3.48 (m, 1H), 3.11-3.21 (m, 1H), 2.44-2.75 (m, 3H), 2.17-2.26 (m, 1H), 2.09 (s, 3H), 1.63-1.86 (m, 2H), 1.30 (t, 3H)

Step 3: Preparation of 5-(2-Methylsulfanylethyl)cyclohexane-1,3-dione

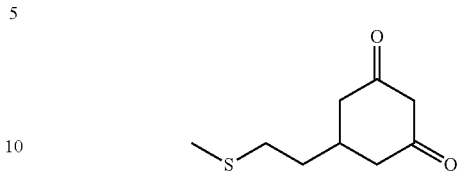

A solution of ethyl 2-(2-methylsulfanylethyl)-4,6-dioxo-cyclohexanecarboxylate (11.446 g) in propan-2-ol (32 mL) was stirred with 2M sodium hydroxide solution (115.2 mL) for 4 hours. The reaction was concentrated to remove the propan-2-ol and the remaining aqueous solution was taken to pH 1 by the addition of conc. hydrochloric acid. This solution was heated to 70° C. for 1.5 hours, then left to cool overnight. The resulting solid was collected by filtration and washed with water then iso-hexane and air dried to leave a pale yellow powder. The powder was washed further with water (×4) and air dried to give 5-(2-methylsulfanylethyl)cyclohexane-1,3-dione (6.583 g) as a yellow solid $^1$H NMR (400 MHz, CDCl$_3$) 5.48 (s, 1H), 3.41 (d, 1H), 2.77 (dd, 3H), 2.45-2.61 (m, 2H), 2.25-2.43 (m, 2H), 2.08-2.18 (m, 3H), 1.63-1.74 (m, 2H)

Step 4: Preparation of 2-(4-Bromo-2,6-dimethyl-phenyl)-5-(2-methylsulfanylethyl)cyclohexane-1,3-dione

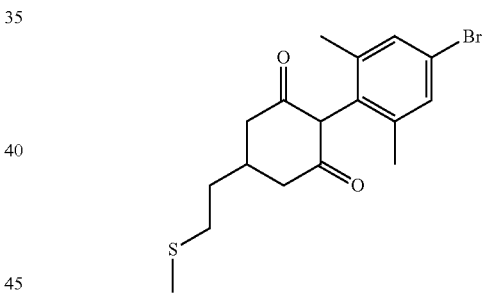

A mixture of 5-(2-methylsulfanylethyl)cyclohexane-1,3-dione (0.425 g) and 4-(dimethylamino)pyridine (1.41 g) in chloroform (12 mL) was stirred under nitrogen for 10 minutes. Toluene (3 mL) was added followed by diacetoxy-(4-bromo-2,6-dimethyl-phenyl)plumbyl acetate (1.56 g, CAS 1160561-25-0). The resulting yellow suspension was heated under nitrogen at 75° C. for 3 hours. The reaction mixture was cooled in an ice bath and diluted with dichloromethane (25 mL) and acidified with aqueous 2M hydrochloric acid (30 mL). After stirring vigorously for 10 minutes the resulting white suspension was filtered through 'Celite' then washed through with dichloromethane. The organic layer was separated, dried over anhydrous magnesium sulfate and concentrated to leave an orange gum. The gum was purified by chromatography on silica eluting with ethyl acetate in iso-hexane to give 2-(4-bromo-2,6-dimethyl-phenyl)-5-(2-methylsulfanylethyl)cyclohexane-1,3-dione (0.496 g) as a white solid.

$^1$H NMR (500 MHz, CDCl$_3$) 7.28 (s, 2H), 5.46 (brs, 1H), 2.63-2.75 (m, 2H), 2.63-2.75 (m, 2H), 2.56-2.61 (m, 2H), 2.36-2.47 (m, 2H), 2.17-2.29 (m, 1H), 2.10-2.14 (m, 3H), 2.07-2.09 (m, 3H), 1.75-1.83 (m, 2H)

Step 5: Preparation of 2-(2,6-Dimethyl-4-prop-1-ynyl-phenyl)-5-(2-methylsulfanyl-ethyl)cyclohexane-1,3-dione, Compound A-21

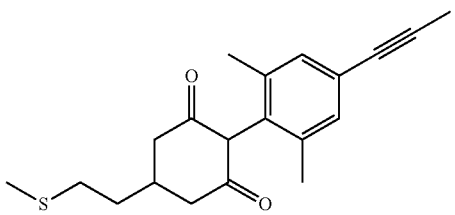 [SMILES: CC#Cc1cc(C)c(C2C(=O)CC(CCSC)CC2=O)c(C)c1]

To a mixture of 2-(4-bromo-2,6-dimethyl-phenyl)-5-(2-methylsulfanylethyl)cyclohexane-1,3-dione (0.200 g), bis(triphenylphosphine)palladium(II) dichloride (CAS 13965-03-2, 0.0192 g), 1,4-bis(diphenylphosphino)butane (CAS 7688-25-7, 0.0231 g) and but-2-ynoic acid (0.0546 g) under nitrogen was added dimethyl sulfoxide (6.5 mL) and tetrabutylammonium fluoride (1M in tetrahydrofuran, 1.62 mL) and the mixture stirred at 110° C. for 2 hours. The reaction was cooled and partitioned between 2M hydrochloric acid and ethyl acetate. The aqueous layer was extracted with further ethyl acetate. The combined organic layers were dried over anhydrous magnesium sulfate, concentrated to an orange gum and purified by chromatography on silica eluting with ethyl acetate in iso-hexane to give 2-(2,6-dimethyl-4-prop-1-ynyl-phenyl)-5-(2-methylsulfanylethyl)cyclohexane-1,3-dione (0.0548 g) as a pale yellow gum.

EXAMPLE 12

Preparation of 2-(2-Chloro-6-methoxy-4-prop-1-ynyl-phenyl)cyclohexane-1,3-dione, Compound A-22

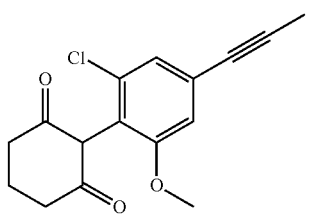 [SMILES: CC#Cc1cc(Cl)c(C2C(=O)CCCC2=O)c(OC)c1]

Step 1: Preparation of 2-(4-Bromo-2-chloro-6-methoxy-phenyl)-3-methoxy-cyclohex-2-en-1-one

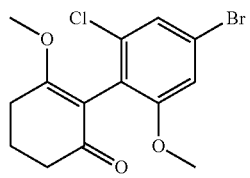 [SMILES: COC1=C(c2c(Cl)cc(Br)cc2OC)C(=O)CCC1]

To a solution of 2-(4-bromo-2-chloro-6-methoxy-phenyl)cyclohexane-1,3-dione (0.86 g, which can be prepared e.g. generally following procedures described in Examples 10 and 11) in acetone (20 mL) was added potassium carbonate (0.85 g) followed by iodomethane (0.81 mL) and water (2 μL). The reaction mixture was stirred at ambient temperature overnight. The mixture was partitioned between dichloromethane and water. The organic layer was reduced under vacuum to give 2-(4-bromo-2-chloro-6-methoxy-phenyl)-3-methoxy-cyclohex-2-en-1-one (0.7 g) as a yellow gum.
$^1$H NMR (500 MHz, CDCl$_3$) 7.17-7.22 (m, 1H), 6.93 (s, 1H), 3.73 (s, 3H), 3.70 (s, 3H), 2.70 (t, 2H), 2.45-2.54 (m, 2H), 2.09-2.18 (m, 2H).

Step 2: Preparation of 2-(2-Chloro-6-methoxy-4-prop-1-ynyl-phenyl)-3-methoxy-cyclohex-2-en-1-one

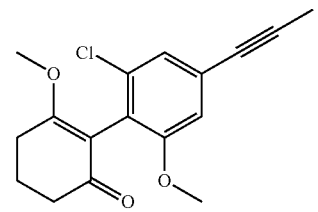 [SMILES: CC#Cc1cc(Cl)c(C2=C(OC)CCCC2=O)c(OC)c1]

To a mixture of 2-(4-bromo-2,6-dimethyl-phenyl)-5-(2-methylsulfanylethyl)cyclohexane-1,3-dione (0.35 g), bis(triphenylphosphine)palladium(II) dichloride (CAS 13965-03-2, 0.036 g), 1,4-bis(diphenylphosphino)butane (CAS 7688-25-7, 0.043 g) and but-2-ynoic acid (0.102 g) under nitrogen was added dimethyl sulfoxide (8 mL) and tetrabutylammonium fluoride (1M in tetrahydrofuran, 3.04 mL) and the mixture stirred at 110° C. for 2 hours. The reaction was cooled and partitioned between 2M hydrochloric acid and extracted with ethyl acetate. The aqueous layer was extracted with further ethyl acetate. The combined organic layers were dried over anhydrous magnesium sulfate, concentrated to an orange gum and purified by chromatography on silica eluting with ethyl acetate in iso-hexane to give 2-(2-chloro-6-methoxy-4-prop-1-ynyl-phenyl)-3-methoxy-cyclohex-2-en-1-one (0.18 g) as a yellow gum.
$^1$H NMR (500 MHz, CDCl$_3$) 7.06 (d, 1H), 6.81 (d, 1H), 3.71 (s, 3H), 3.67 (s, 3H), 2.69 (td, 2H), 2.46-2.51 (m, 2H), 2.08-2.17 (m, 2H), 2.02-2.05 (m, 3H).

Step 3: Preparation of 2-(2-Chloro-6-methoxy-4-prop-1-ynyl-phenyl)cyclohexane-1,3-dione

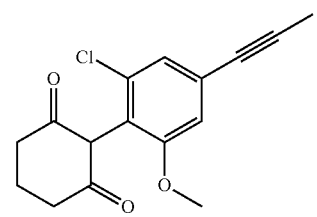 [SMILES: CC#Cc1cc(Cl)c(C2C(=O)CCCC2=O)c(OC)c1]

To a solution of 2-(2-chloro-6-methoxy-4-prop-1-ynyl-phenyl)-3-methoxy-cyclohex-2-en-1-one (0.18 g) in acetone (2 mL) was added 2M hydrochloric acid (2 mL) and the mixture heated to 60° C. for 1 hour. The reaction mixture was reduced under vacuum at 500 mbar. The remaining aqueous solution was partitioned with dichloromethane. The organic layer was concentrated to give 2-(2-chloro-6-methoxy-4-prop-1-ynyl-phenyl)cyclohexane-1,3-dione (0.18 g) as a cream solid.

EXAMPLE 13

Preparation of 2-(2-Chloro-6-methoxy-4-prop-1-ynyl-phenyl)-5-(2-methylsulfanylethyl)cyclohexane-1,3-dione, Compound A-23

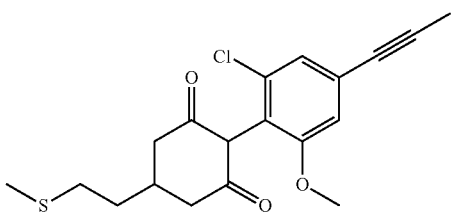 [SMILES: CC#Cc1cc(Cl)c(C2C(=O)CC(CCSC)CC2=O)c(OC)c1]

Step 1: Preparation of 5-Bromo-1-chloro-2-iodo-3-methoxy-benzene

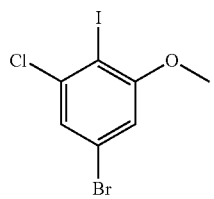

Dry methanol (160 mL) was cooled to 10° C. and potassium hydroxide (14.9 g) was added portion wise over 25 minutes. Once dissolved, this solution was added over 15 minutes to a refluxing solution of 5-bromo-1-chloro-3-fluoro-2-iodo-benzene (CAS 83027-73-0, 40.0 g) in dry methanol (320 mL). After 46 hours refluxing the reaction mixture was concentrated and partitioned between water (500 mL) and ethyl acetate (500 mL). The aqueous phase was extracted with further ethyl acetate (2×200 mL). The combined organic layers were washed with brine (400 mL), dried over magnesium sulfate, concentrated and purified by chromatography on silica eluting with ethyl acetate in iso-hexane to give 5-bromo-1-chloro-2-iodo-3-methoxy-benzene (37.767 g) as a pale pink solid $^1$H NMR (500 MHz, CDCl$_3$) 7.28 (d, 1H), 6.82 (d, 1H), 3.90 (s, 3H).

Step 2: Preparation of (4-Bromo-2-chloro-6-methoxy-phenyl)boronic acid

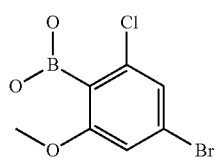

A solution of 5-bromo-1-chloro-2-iodo-3-methoxy-benzene (15.0 g) in dry tetrahydrofuran (173 mL) was cooled to −78° C. under nitrogen. A solution of isopropyl magnesium chloride (2M in tetrahydrofuran, 43.2 mL) was added dropwise over 30 minutes, maintaining an internal temperature below −65° C. The reaction mixture was stirred at −78° C. for 25 minutes and then allowed to warm to ambient temperature with stirring. After approximately 2 hours the reaction solution was cooled to −70° C. and trimethyl borate (14.4 g) was added dropwise over 15 minutes. On completion of addition, the solution was stirred at −78° C. for 20 minutes and then the cooling was removed and mixture stirred for 18 hours. The reaction mixture was diluted with water (50 mL) and acidified with 2M hydrochloric acid (150 mL) and stirred for 2 hours. Ethyl acetate was added and the layers were separated. The aqueous was extracted with further ethyl acetate (×2) then the combined organic phases were washed with brine, dried over magnesium sulfate and concentrated to afford an orange-brown residue. This residue was dissolved in ethyl acetate (200 mL) and washed sequentially with 4:1 water:saturated aqueous sodium thiosulfate solution (2×100 mL), water (100 mL) and brine (100 mL), dried over magnesium sulfate and concentrated to a pale yellow solid. This sample was triturated with iso-hexane (100 mL) and the solid filtered off, washed with further iso-hexane and air-dried to give (4-bromo-2-chloro-6-methoxy-phenyl)boronic acid (10.160 g) as a white solid.

$^1$H NMR (500 MHz, CDCl$_3$+3 drops CD$_3$OD) 7.11 (m, 1H), 6.87 (m, 1H), 3.77 (s, 3H)

Step 3: Preparation of (4-Bromo-2-chloro-6-methoxy-phenyl)-diisopropoxy-borane

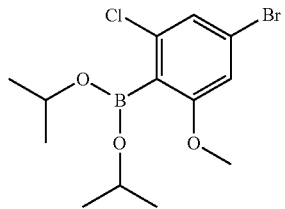 [SMILES: COc1cc(Br)cc(Cl)c1B(OC(C)C)OC(C)C]

A solution of (4-bromo-2-chloro-6-methoxy-phenyl)boronic acid (2.00 g) in propan-2-ol (13 mL) and toluene (13 mL) was refluxed using a Dean-Stark apparatus for 24 hours. The reaction mixture was concentrated to give (4-bromo-2-chloro-6-methoxy-phenyl)-diisopropoxy-borane (2.612 g) as a pale orange oil.

$^1$H NMR (500 MHz, CDCl$_3$) 7.11 (s, 1H), 6.87 (s, 1H), 4.25 (sept, 2H), 3.78 (s, 3H), 1.19 (d, 6H).

Step 4: Preparation of Diacetoxy-(4-bromo-2-chloro-6-methoxy-phenyl)plumbyl acetate

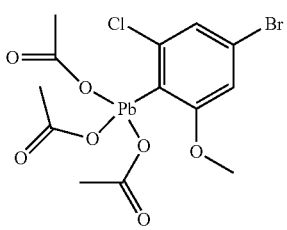

A mixture of mercury (11) trifluoroacetate (0.310 g) and lead (IV) acetate (1.898 g) in chloroform (20 mL) under nitrogen was warmed to 40° C. with stirring. Heating was removed and a solution of (4-bromo-2-chloro-6-methoxy-phenyl)-diisopropoxy-borane (1.248 g) in chloroform (3 mL) was added over 5 minutes. This mixture was heated 55° C. for 3 hours and left to cool overnight. The reaction mixture was cooled in an ice bath to 5° C. and chloroform (20 mL) added. To this suspension was added potassium carbonate (2.221 g) and the mixture stirred for 10 minutes. The suspension was filtered through chloroform washed 'Celite' and washed through with fresh chloroform (50 mL). The pale yellow filtrate was concentrated to leave a pale brown solid. This solid was triturated with iso-hexane and a little chloroform, filtered, washed with iso-hexane and air-dried to give diacetoxy-(4-bromo-2-chloro-6-methoxy-phenyl)plumbyl acetate (1.466 g) as a pale pink-beige solid.

$^1$H NMR (500 MHz, CDCl$_3$) 7.32 (s, 1H), 7.10 (s, 1H), 3.92 (s, 3H), 2.10 (s, 9H).

Step 5: Preparation of 2-(4-Bromo-2-chloro-6-methoxy-phenyl)-5-(2-methylsulfanylethyl)cyclohexane-1,3-dione

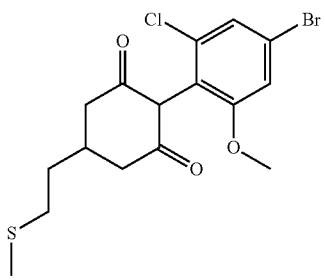 [SMILES: COc1cc(Br)cc(Cl)c1C1C(=O)CC(CCSC)CC1=O]

A mixture of 5-(2-methylsulfanylethyl)cyclohexane-1,3-dione (0.375 g) and 4-(dimethylamino)pyridine (1.24 g) in chloroform (15 mL) was stirred under nitrogen for 10 minutes. Toluene (4 mL) was added followed by diacetoxy-(4-bromo-2-chloro-6-methoxy-phenyl)plumbyl acetate (1.46 g). The resulting yellow suspension was heated under nitrogen at 75° C. for 5 hours. The reaction mixture was cooled in an ice bath and acidified with aqueous 2M hydrochloric acid. After stirring vigorously for 10 minutes the resulting white suspension was filtered through 'Celite' then washed through with dichloromethane. The organic layer was separated, dried over anhydrous magnesium sulfate and concentrated to leave an orange solid. The solid was purified by chromatography on silica eluting with ethyl acetate in iso-hexane to give 2-(4-bromo-2-chloro-6-methoxy-phenyl)-5-(2-methylsulfanylethyl)cyclohexane-1,3-dione (0.456 g) as a white foam.

$^1$H NMR (500 MHz, CD$_3$OD) 7.18-7.26 (m, 1H), 7.09 (t, 1H), 3.76 (d, 3H), 2.58-2.68 (m, 4H), 2.32-2.45 (m, 3H), 2.12-2.18 (m, 3H), 1.76-1.86 (m, 2H).

The remaining step to the desired compound, 2-(2-chloro-6-methoxy-4-prop-1-ynyl-phenyl)-5-(2-methylsulfanylethyl)cyclohexane-1,3-dione, Compound A-23 can e.g. be carried out substantially as described in Example 11.

EXAMPLE 14

Preparation of 2-(2,6-Dimethyl-4-prop-1-ynyl-phenyl)-5-(2-methylsulfanylpropyl)cyclohexane-1,3-dione, Compound A-24

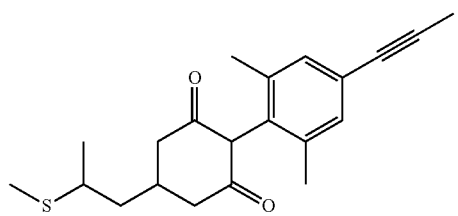 [SMILES: CC#Cc1cc(C)c(C2C(=O)CC(CC(C)SC)CC2=O)c(C)c1]

Step 1: Preparation of (E)-6-Methylsulfanylhept-3-en-2-one

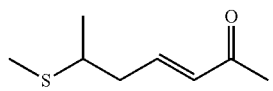

To a solution of 3-methylsulfanylbutanal (CAS 16630-52-7, 6.4 g) in dichloromethane (120 mL) was added 1-(triphenylphosphoranylidene)-2-propanone (CAS 1439-36-7, 17 g) in a single portion. The reaction mixture was heated and stirred at reflux for 7 hours and left to cool overnight. The cooled reaction mixture was concentrated to leave a pale yellow solid which was triturated with a 1:1 mixture of ether:iso-hexane (100 mL). The resulting solid was collected by filtration and washed with further 1:1 ether:iso-hexane (50 mL). The filtrate was concentrated to a yellow oil and purified by chromatography on silica eluting with ethyl acetate in iso-hexane to give (E)-6-methylsulfanylhept-3-en-2-one (5.409 g) as a yellow liquid.

$^1$H NMR (400 MHz, CDCl$_3$) 6.82 (dt, 1H), 6.12 (d, 1H), 2.84 (sxt, 1H), 2.37-2.56 (m, 2H), 2.27 (s, 3H), 2.08-2.14 (m, 3H), 1.27-1.34 (m, 3H)

Step 2: Preparation of Ethyl 2-(2-methylsulfanyl-propyl)-4,6-dioxo-cyclohexanecarboxylate

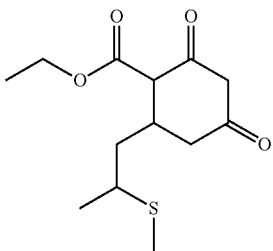 [SMILES: CCOC(=O)C1C(=O)CC(=O)CC1CC(C)SC]

To ice cooled ethanol (50 mL) was added sodium metal (1.045 g) in small portions under nitrogen, and the resulting solution was stirred for 15 minutes. Diethyl propanedioate (6.613 g) in ethanol (25 mL) was added drop wise to this cooled solution over 20 minutes. The reaction was allowed to warm to ambient temperature and stirred for a further 1 hour. The mixture was cooled in an ice bath and a solution of (E)-6-methylsulfanylhept-3-en-2-one (5.409 g) in ethanol (25 mL) was added drop wise. The reaction was allowed to warm to ambient temperature, stirred for 4 hours and then left to stand overnight. The reaction was concentrated to a yellow slurry which was poured into a cooled solution of 2M hydrochloric acid and stirred for 5 minutes. This was extracted with dichloromethane (×2) and the combined organic layers were dried over anhydrous magnesium sulfate, concentrated and purified by chromatography on silica eluting with ethyl acetate in iso-hexane to give ethyl 2-(2-methylsulfanylpropyl)-4,6-dioxo-cyclohexanecarboxylate (3.227 g) as a yellow oil.

$^1$H NMR (400 MHz, CDCl$_3$) 5.38-5.43 (m, 1H), 4.13-4.31 (m, 2H), 3.86-3.96 (m, 2H), 3.05-3.18 (m, 1H), 2.53-2.88 (m, 2H), 2.12-2.37 (m, 1H), 1.99-2.09 (m, 3H), 1.44-1.75 (m, 2H), 1.22-1.41 (m, 6H).

Step 3: Preparation of 5-(2-Methylsulfanylpropyl)cyclohexane-1,3-dione

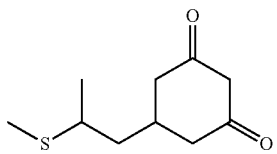

A mixture of 3-ethoxy-5-(2-methylsulfanylpropyl)cyclohex-2-en-1-one (5.846 g) was heated and stirred in 5M hydrochloric acid (30 mL) for 6 hours and left to stand overnight. The reaction mixture was extracted with ethyl acetate (×2). The combined organic layers were dried over anhydrous magnesium sulfate, concentrated and purified by chromatography on silica eluting with ethyl acetate in iso-hexane to give 5-(2-methylsulfanylpropyl)cyclohexane-1,3-dione (1.734 g) as a white solid $^1$H NMR (400 MHz, CDCl$_3$) 7.55 (brs, 1H), 3.41 (d, 1H), 2.65-2.82 (m, 2H), 2.33-2.55 (m, 3H), 2.01-2.16 (m, 4H), 1.42-1.67 (m, 2H), 1.24-1.33 (m, 3H)

The remaining steps to 2-(2,6-dimethyl-4-prop-1-ynyl-phenyl)-5-(2-methylsulfanylpropyl)cyclohexane-1,3-dione, Compound A-24, can e.g. be carried out using substantially the methods described in Example 11.

EXAMPLE 15

Preparation of 3-[2-Chloro-4-(2-chloroethynyl)-6-methoxy-phenyl]bicyclo[3.2.1]octane-2,4-dione, Compound A-25

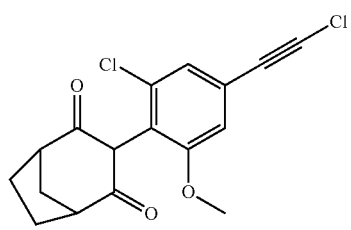 [SMILES: COc1cc(C#CCl)cc(Cl)c1C1C(=O)C2CCC(C2)C1=O]

Step 1: Preparation of 3-(2-Chloro-4-ethynyl-6-methoxy-phenyl)-2-methoxy-bicyclo[3.2.1]oct-2-en-4-one

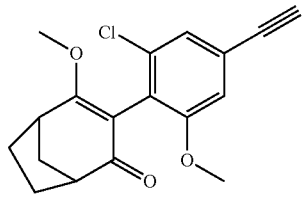 [SMILES: C#Cc1cc(Cl)c(C2=C(OC)C3CCC(C3)C2=O)c(OC)c1]

To a solution of 3-(2-chloro-4-ethynyl-6-methoxy-phenyl)bicyclo[3.2.1]octane-2,4-dione (0.200 g, Compound B-3) in acetone (6.6 mL) was added potassium carbonate (0.139 g). Iodomethane (0.206 mL) was added and the reaction mixture stirred at room temperature for 16 hours. The organic layer was concentrated and purified by chromatography on silica eluting with ethyl acetate in iso-hexane to give 3-(2-chloro-4-ethynyl-6-methoxy-phenyl)-2-methoxy-bicyclo[3.2.1]oct-2-en-4-one (0.200 g).

$^1$H NMR (500 MHz, CDCl$_3$) 7.16 (m, 1H), 6.88 (m, 1H), 3.73 (d, 3H), 3.64 (d, 3H), 3.20 (m, 1H), 3.07 (s, 1H), 3.02 (d, 1H), 2.25 (d, 1H), 2.07-2.17 (m, 2H), 1.78-2.02 (m, 2H), 1.63-1.71 (m, 1H).

Step 2: Preparation of 3-[2-Chloro-4-(2-chloroethynyl)-6-methoxy-phenyl]bicyclo[3.2.1]octane-2,4-dione, Compound A-25

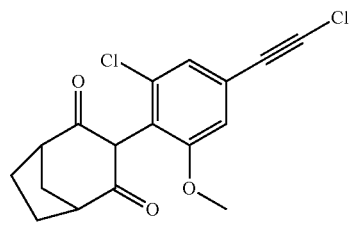

To a solution of 3-(2-chloro-4-ethynyl-6-methoxy-phenyl)-2-methoxy-bicyclo[3.2.1]oct-2-en-4-one (0.095 g) in carbon tetrachloride (0.9 mL) was added potassium carbonate (0.046 g) and tetrabutylammonium fluoride trihydrate (0.019 g). The mixture was stirred at room temperature for 3 hours. Further tetrabutylammonium fluoride trihydrate (0.020 g) was added and stirring continued for 1 hour. After this time further tetrabutylammonium fluoride trihydrate (0.020 g), potassium carbonate (0.046 g) and carbon tetrachloride (1 mL) were added and the mixture stirred for 1 hour and then left to stand overnight. The reaction mixture was concentrated and the residue was dissolved in acetone (3 mL). To this was added 2M hydrochloric acid (3 mL) and the mixture heated at 60° C. for 3 hours. The reaction mixture was extracted with ethyl acetate (×2) and the combined organic layers were washed with brine, dried over anhydrous magnesium sulfate and concentrated. The residue was purified by chromatography on silica eluting with ethyl acetate in iso-hexane to give 3-[2-chloro-4-(2-chloroethynyl)-6-methoxy-phenyl]bicyclo[3.2.1]octane-2,4-dione, Compound A-25 (0.0937 g).

EXAMPLE 16

Preparation of [3-[2-Chloro-4-prop-1-ynyl-6-(2,2,2-trifluoroethoxyl)phenyl]-4-oxo-2-bicyclo[3.2.1]oct-2-enyl]ethylsulfanylformate, Compound P-6

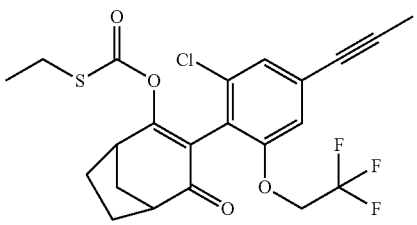 [SMILES: CC#Cc1cc(Cl)c(C2=C(OC(=O)SCC)C3CCC(C3)C2=O)c(OCC(F)(F)F)c1]

To a suspension of 3-[2-chloro-4-prop-1-ynyl-6-(2,2,2-trifluoroethoxy)phenyl]bicyclo[3.2.1]octane-2,4-dione (Compound A-19, 0.04 g) in dichloromethane (2 mL) was added pyridine (0.0168 mL) and 4-(dimethylamino)pyridine (0.001 g) and the mixture stirred for 5 min. S-ethyl chlorothioformate (0.0169 mL) was added and the reaction mixture was stirred for 2 hours. The reaction mixture was evaporated to a gum and purified on silica eluting with 10% ether in iso-hexane to give [3-[2-chloro-4-prop-1-ynyl-6-(2,2,2-trifluoroethoxy)phenyl]-4-oxo-2-bicyclo[3.2.1]oct-2-enyl]ethylsulfanylformate (0.041 g) as a white solid.

EXAMPLE 17

Preparation of 9-(2-Chloro-4-ethynyl-6-methoxyphenyl)-3-oxaspiro[5.5]undecane-8,10-dione, Compound B-1

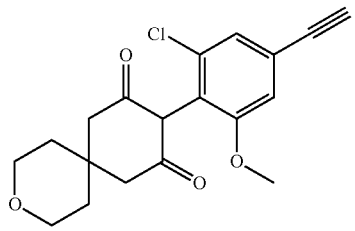 [SMILES: C#Cc1cc(Cl)c(C2C(=O)CC3(CCOCC3)CC2=O)c(OC)c1]

Step 1: Preparation of 9-[2-Chloro-6-methoxy-4-(2-trimethylsilylethynyl)phenyl]-3-oxaspiro[5.5]undecane-8,10-dione

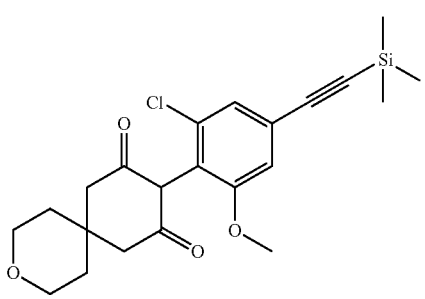 [SMILES: COc1cc(C#C[Si](C)(C)C)cc(Cl)c1C1C(=O)CC2(CCOCC2)CC1=O]

To a suspension of 9-(4-bromo-2-chloro-6-methoxy-phenyl)-3-oxaspiro[5.5]undecane-8,10-dione (0.050 g, e.g. see Example 10) in toluene (2.1 mL) was added [1,1'-bis(diphenylphosphino)ferrocene]dichloro-palladium(II) dichloromethane complex (0.0051 g) and trimethyl(2-tributylstannylethynyl)silane (0.072 g) and the mixture heated at reflux for 3.5 hours. The reaction was cooled, diluted with ethyl acetate and filtered through water-washed 'Celite'. This was washed through with further ethyl acetate and water. The layers were partitioned and the aqueous extracted with further ethyl acetate. The combined organic layers were washed with water, brine and dried over anhydrous magnesium sulfate, concentrated to an orange gum and purified by chromatography on silica eluting with ethyl acetate in iso-hexane to give 9-[2-chloro-6-methoxy-4-(2-trimethylsilylethynyl)phenyl]-3-oxaspiro[5.5]undecane-8,10-dione (0.041 g) as a brown sticky gum.

$^1$H NMR (500 MHz, CDCl$_3$) 7.20 (s, 1H), 6.90 (s, 1H), 5.90 (s, 1H), 3.74 (s, 3H), 3.70 (t, 4H), 2.59 (m, 4H), 1.75 (t, 2H), 1.68 (t, 2H), 0.25 (s, 9H).

Step 2: Preparation of 9-(2-Chloro-4-ethynyl-6-methoxy-phenyl)-3-oxaspiro[5.5]undecane-8,10-dione, Compound B-1

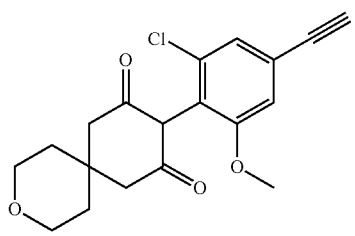 [SMILES: C#Cc1cc(Cl)c(C2C(=O)CC3(CCOCC3)CC2=O)c(OC)c1]

To a solution of 9-[2-chloro-6-methoxy-4-(2-trimethylsilylethynyl)phenyl]-3-oxaspiro[5.5]undecane-8,10-dione (0.11 g) in methanol (5.25 mL) was added potassium carbonate (0.053 g) and the suspension was stirred for 2 hours and left to stand overnight. Water (25 mL) was added and the mixture washed with ethyl acetate. The aqueous layer was acidified with a few drops of conc. hydrochloric acid and stirred for 15 minutes. The aqueous mixture was extracted with ethyl acetate. The organic layer was separated, washed with water, dried over anhydrous magnesium sulfate and concentrated to an orange gum. Trituration with cold ether gave a solid which was filtered off and air-dried to give 9-(2-chloro-4-ethynyl-6-methoxy-phenyl)-3-oxaspiro[5.5]undecane-8,10-dione (0.072 g) as a beige solid.

EXAMPLE 18

Preparation of 2-(2-Chloro-4-ethynyl-6-methoxy-phenyl)-3-hydroxy-cyclohex-2-en-1-one, Compound B-2

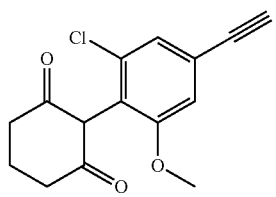 [SMILES: C#Cc1cc(Cl)c(C2C(=O)CCCC2=O)c(OC)c1]

Step 1: Preparation of 2-[2-Chloro-6-methoxy-4-(2-trimethylsilylethynyl)phenyl]-3-methoxy-cyclohex-2-en-1-one

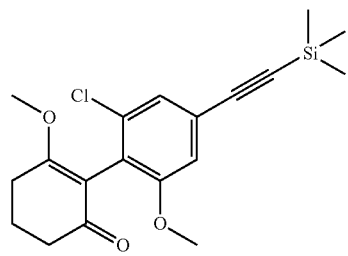 [SMILES: COC1=C(c2c(Cl)cc(C#C[Si](C)(C)C)cc2OC)C(=O)CCC1]

To a suspension of 2-(4-bromo-2-chloro-6-methoxy-phenyl)-3-methoxy-cyclohex-2-en-1-one (0.35 g, e.g. see Example 12, Step 1) in toluene (17.22 mL) was added [1,1'-bis(diphenylphosphino)ferrocene]dichloro-palladium (II) dichloromethane complex (0.042 g) and trimethyl(2-tributylstannylethynyl)silane (0.5883 g) under nitrogen. The mixture was heated at reflux for 3 hours. The reaction mixture was partitioned between dichloromethane and water. The organic layer was concentrated and purified by chromatography on silica eluting with ethyl acetate in isohexane to give 2-[2-chloro-6-methoxy-4-(2-trimethylsilylethynyl)phenyl]-3-methoxy-cyclohex-2-en-1-one (0.200 g) as a yellow gum.

$^1$H NMR (500 MHz, CDCl$_3$) 7.13-7.17 (m, 1H), 6.86 (s, 1H), 3.73 (s, 3H), 3.66 (s, 3H), 2.69 (t, 2H), 2.45-2.52 (m, 2H), 2.11-2.17 (m, 2H)

Step 2: Preparation of 2-(2-Chloro-4-ethynyl-6-methoxy-phenyl)-3-hydroxy-cyclohex-2-en-1-one

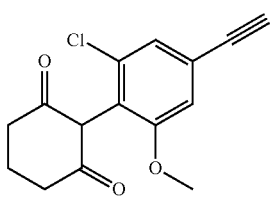 [SMILES: C#Cc1cc(Cl)c(C2C(=O)CCCC2=O)c(OC)c1]

To a solution of 2-[2-chloro-6-methoxy-4-(2-trimethylsilylethynyl)phenyl]-3-methoxy-cyclohex-2-en-1-one (0.200 g) in methanol (11.02 mL) was added potassium carbonate (0.116 g). After stirring for 2 hours the reaction mixture was partitioned between dichloromethane and water. The aqueous layer was acidified with conc. hydrochloric acid and extracted with dichloromethane. The organic layer was concentrated to give 2-(2-chloro-4-ethynyl-6-methoxy-phenyl)-3-hydroxy-cyclohex-2-en-1-one, Compound B-2 (0.064 g) as an orange foamy solid.

EXAMPLE 19

Preparation of 3-(2-Chloro-4-ethynyl-6-methoxy-phenyl)bicyclo[3.2.1]octane-2,4-dione, Compound B-3

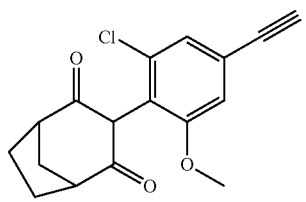 [SMILES: C#Cc1cc(Cl)c(C2C(=O)C3CCC(C3)C2=O)c(OC)c1]

Step 1: Preparation of 3-[2-Chloro-6-methoxy-4-(2-trimethylsilylethynyl)phenyl]bicyclo[3.2.1]octane-2,4-dione

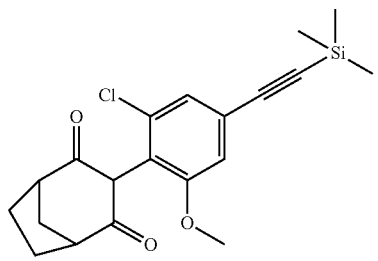 [SMILES: COc1cc(C#C[Si](C)(C)C)cc(Cl)c1C1C(=O)C2CCC(C2)C1=O]

A mixture of 3-(4-bromo-2-chloro-6-methoxy-phenyl)bicyclo[3.2.1]octane-2,4-dione (Example 7 Step 6, 0.500 g,), trimethyl(2-tributylstannylethynyl)silane (0.812 g) and [1,1'-bis(diphenylphosphino)ferrocene]dichloro-palladium (II) dichloromethane complex (0.0569 g) was dissolved in toluene (17 mL) and the mixture vigorously refluxed for 3 hours under air. The reaction mixture was filtered through 'Celite', washing through with ethyl acetate. Water was added to the filtrate and the mixture partitioned. The aqueous layer was extracted with further ethyl acetate (×3). The combined organic layers were washed with brine, dried over anhydrous magnesium sulfate, concentrated and purified by chromatography on silica eluting with ethyl acetate in isohexane to give 3-[2-chloro-6-methoxy-4-(2-trimethylsilylethynyl)phenyl]bicyclo[3.2.1]octane-2,4-dione (0.305 g).

$^1$H NMR (CDCl$_3$) 7.19 (m, 1H), 6.89 (m, 1H), 5.48-5.67 (m, 1H), 3.75 (d, 3H), 2.96-3.07 (m, 2H), 2.26 (d, 1H), 2.07-2.18 (m, 2H), 1.74-2.03 (m, 2H), 1.65 (dm, 1H), 0.25 (s, 9H).

Step 2: Preparation of 3-(2-Chloro-4-ethynyl-6-methoxy-phenyl)bicyclo[3.2.1]octane-2,4-dione

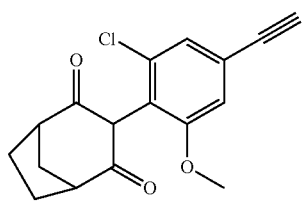 [SMILES: C#Cc1cc(Cl)c(C2C(=O)C3CCC(C3)C2=O)c(OC)c1]

To a solution of 3-[2-chloro-6-methoxy-4-(2-trimethylsilylethynyl)phenyl]bicyclo[3.2.1]octane-2,4-dione (0.270 g) in methanol (7.2 mL) was added potassium carbonate (0.303 g) and the mixture stirred for 2 hours. The reaction mixture was concentrated and partitioned between water and dichloromethane. The aqueous layer was washed with further dichloromethane and then acidified using 2M hydrochloric acid and extracted with dichloromethane (×2). The combined organic layers were dried over anhydrous magnesium sulfate and concentrated to give 3-(2-chloro-4-ethynyl-6-methoxy-phenyl)bicyclo[3.2.1]octane-2,4-dione, Compound B-3 (0.2165 g) as a pale yellow solid.

Additional compounds in Table T1 below illustrate the present invention, and are particular embodiments of the compounds of formula (I) according to the present invention. For the most part, these compounds can generally be prepared by methods similar to those shown in the Examples and/or shown in the process section hereinabove using appropriate starting materials.

TABLE T1

| Compound Number | Structure | $^1$H NMR data (in CDCl$_3$ solvent unless stated) or other physical data |
|---|---|---|
| A-1 | 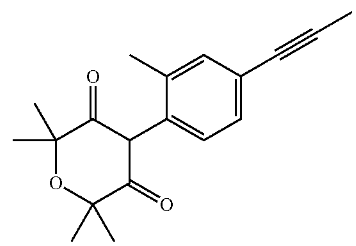 [SMILES: CC#Cc1ccc(C2C(=O)C(C)(C)OC(C)(C)C2=O)c(C)c1] | δ (delta) 7.34 (d, 1H), 7.29 (dd, 1H), 7.01 (d, 1H), 5.37-5.81 (br. s), 2.1 (s, 3H), 2.06 (s, 3H), 1.4-1.68 (m, 12H). |
| A-2 | 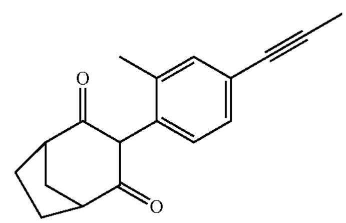 [SMILES: CC#Cc1ccc(C2C(=O)C3CCC(C3)C2=O)c(C)c1] | δ (delta) (d4-MeOD) 7.17 (m, 1H), 7.10 (m, 1H), 6.86 (d, 0.5H, isomer A), 6.81 (d, 0.5H, isomer B), 2.97 (q, 2H), 1.71-2.26 (m, 11H), 1.67 (m, 1H, isomer A or B). |
| A-3 | 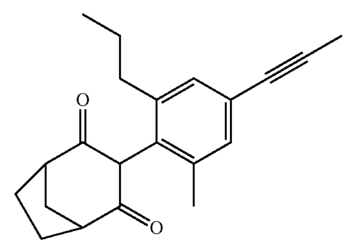 [SMILES: CC#Cc1cc(C)c(C2C(=O)C3CCC(C3)C2=O)c(CCC)c1] | δ (delta) 7.16-7.13 (m, 2H), 5.31-5.27 (m, 1H), 3.11-3.03 (m, 2H), 2.37-2.15 (m, 6H), 2.08 (s, 2H), 2.04 (s, 3H), 1.96 (s, 1H), 1.86-1.67 (m, 2H), 1.48-1.32 (m, 2H), 0.92-0.85 (m, 3H). |
| A-4 | 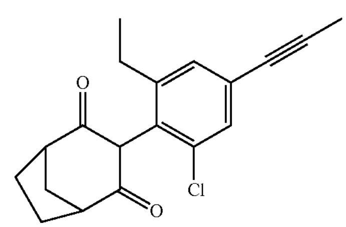 [SMILES: CC#Cc1cc(Cl)c(C2C(=O)C3CCC(C3)C2=O)c(CC)c1] | δ (delta) 7.35-7.31 (m, 1H), 7.23-7.20 (m, 1H), 5.40-5.33 (m, 1H), 3.12-3.01 (m, 2H), 2.51-2.26 (m, 3H), 2.24-2.12 (m, 3H), 2.01-1.86 (m,2H), 1.74-1.67 (m, 1H), 1.28-1.24 (m, 2H), 1.13-1.04 (m, 3H). |
| A-5 | 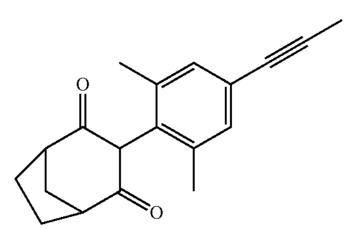 [SMILES: CC#Cc1cc(C)c(C2C(=O)C3CCC(C3)C2=O)c(C)c1] | δ (delta) (d4-MeOD) 7.02-6.99 (m, 2H), 2.99-2.95 (m, 2H), 2.23-2.17 (m, 3H), 2.03 (s, 3H), 1.98 (s, 3H), 1.92 (s, 3H), 1.83-1.79 (m, 2H), 1.73-1.66 (m, 1H). |

TABLE T1-continued

| Compound Number | Structure | ¹H NMR data (in CDCl₃ solvent unless stated) or other physical data |
|---|---|---|
| A-6 | 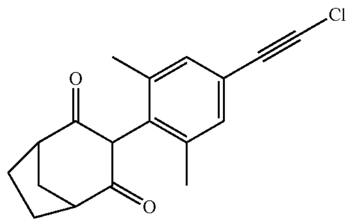 [SMILES: Cc1cc(C#CCl)cc(C)c1C1C(=O)C2CCC(C2)C1=O] | δ (delta) (d4-MeOD) 7.10 (d, 2H), 3.01-2.95 (m, 2H), 2.25-2.18 (m, 3H), 2.06 (s, 3H), 1.94 (s, 3H), 1.86-1.79 (m, 2H), 1.73-1.66 (m, 1H). |
| A-7 | 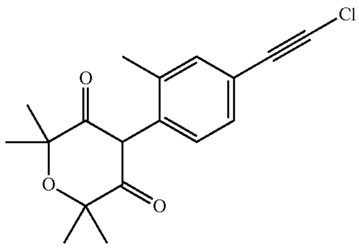 [SMILES: Cc1cc(C#CCl)ccc1C1C(=O)C(C)(C)OC(C)(C)C1=O] | δ (delta) 7.41 (d, 1H), 7.34 (dd, 1H), 7.05 (d, 1H), 2.1 (s, 3H), 1.37-1.83 (brs, 12H). |
| A-8 | 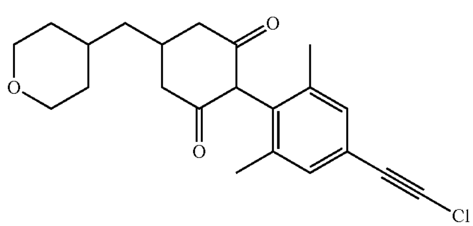 [SMILES: Cc1cc(C#CCl)cc(C)c1C1C(=O)CC(CC2CCOCC2)CC1=O] | δ (delta) 7.20 (s, 2H), 3.96 (dd, 2H), 3.39 (dd, 2H), 2.62 (dd, 2H), 2.37 (dd, 2H), 2.20 (m, 1H), 2.07 (s, 3H), 2.04 (s, 3H), 1.62 (m, 3H), 1.42 (m, 2H), 1.32 (m, 2H). |
| A-9 | 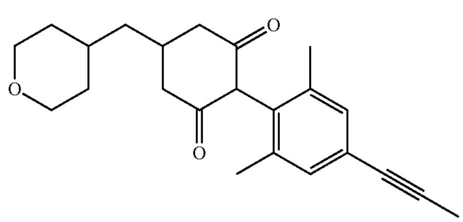 [SMILES: CC#Cc1cc(C)c(C2C(=O)CC(CC3CCOCC3)CC2=O)c(C)c1] | δ (delta) 7.13 (s, 2H), 6.15-6.25 (br. s), 3.94 (dd, 2H), 3.39 (dd, 2H), 2.60 (dd, 2H), 2.34 (dd, 2H), 2.22 (m, 1H), 2.05 (s, 3H), 2.03 (s, 3H), 2.02 (s, 3H), 1.62 (m, 3H), 1.40 (m, 2H), 1.31 (m, 2H). |
| A-10 | 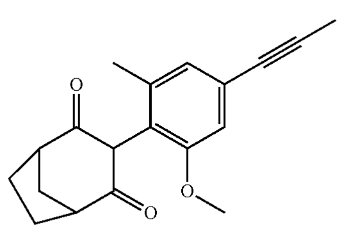 [SMILES: CC#Cc1cc(C)c(C2C(=O)C3CCC(C3)C2=O)c(OC)c1] | δ (delta) 6.94-6.92 (m, 1 H), 6.79-6.78 (m, 1 H), 3.71-3.69 (m, 3 H), 3.02-3.01 (m, 2 H), 2.31-2.28 (m, 1 H), 2.20-2.13 (m, 2 H), 2.08-1.97 (m, 6 H), 1.93-1.81 (m, 2 H), 1.65 (dtd, J = 11.3, 4.4, 1.4 Hz, 1 H). |
| A-11 | 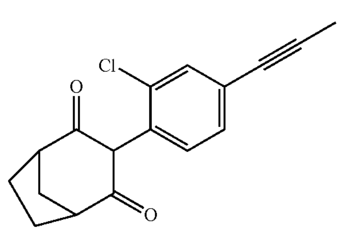 [SMILES: CC#Cc1ccc(C2C(=O)C3CCC(C3)C2=O)c(Cl)c1] | δ (delta) 7.48-7.46 (m, 1 H), 7.31-7.26 (m, 2 H), 7.08-7.01 (m, 1 H), 5.95 (br, 1 H), 3.05-3.02 (m, 2 H), 2.28-2.13 (m, 4 H), 2.05 (s, 3 H), 1.94 (br, 1 H), 1.69-1.62 (m, 1 H). |

TABLE T1-continued

| Compound Number | Structure | ¹H NMR data (in CDCl₃ solvent unless stated) or other physical data |
|---|---|---|
| A-12 | 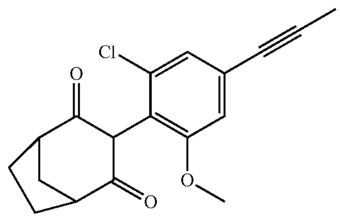 | δ (delta) 7.12-7.09 (m, 1 H), 6.84-6.83 (m, 1 H), 5.66-5.53 (m, 1 H), 3.74-3.72 (m, 3 H), 3.04-3.01 (m, 2 H), 2.28-2.25 (m, 1 H), 2.13-2.09 (m, 2 H), 2.05 (s, 3 H), 2.04-1.94 (m, 1 H), 1.89-1.76 (m, 1 H), 1.67-1.63 (m, 1 H). |
| A-13 | 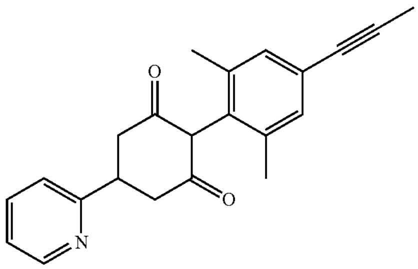 | δ (delta) (d4 MeOD): 8.80 (d, 1H), 8.59 (td, 1H), 8.14 (d, 1H), 7.97 (t, 1H), 7.07 (d, 2H), 4.05-3.98 (m, 1H), 3.11 (dd, 2H), 2.95 (dd, 2H), 2.09 (s, 3H), 2.00 (app. d, 6H). |
| A-14 | 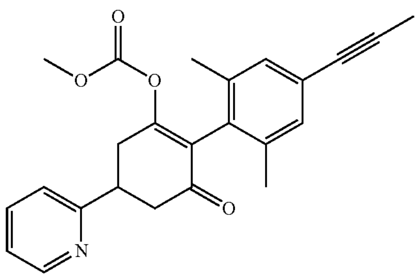 [SMILES: CC#Cc1cc(C)c(C2=C(OC(=O)OC)CC(c3ccccn3)CC2=O)c(C)c1] | δ (delta) 8.60 (d, 1H), 7.69 (td, 1H), 7.28-7.27 (m, 1H), 7.21 (dd, 1H), 7.08 (d, 2H), 3.78-3.74 (m, 1H), 3.66 (s, 3H), 3.38 (dd, 1H), 3.10-3.01 (m, 2H), 2.93-2.89 (m, 1H), 2.10 (s, 3H), 2.03 (s, 3H), 1.98 (s, 3H). |
| A-15 | 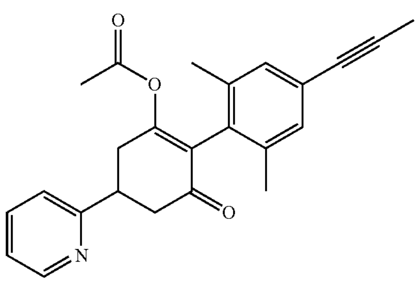 [SMILES: CC#Cc1cc(C)c(C2=C(OC(C)=O)CC(c3ccccn3)CC2=O)c(C)c1] | δ (delta) 8.60 (d, 1H), 7.69 (td, 1H), 7.28-7.27 (m, 1H), 7.21 (dd, 1H), 7.08 (d, 2H), 3.78-3.73 (m, 1H), 3.33 (dd, 1H), 3.06 (dd, 1H), 2.99-2.88 (m, 2H), 2.09 (s, 3H), 2.04 (s, 3H), 1.98 (s, 3H), 1.86 (s, 3H). |
| X-4 (Reference compound; Comparator compound; to be compared with A-13) | 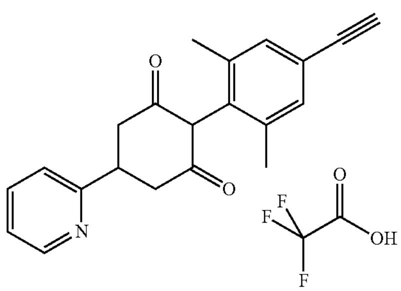 | δ (delta) (d4 MeOD): 8.70 (dd, 1H), 8.28 (td, 1H), 7.87 (d, 1H), 7.70 (ddd, 1H), 7.16 (d, 2H), 3.94-3.87 (m, 1H), 3.38 (s, 1H), 3.13-3.06 (m, 2H), 2.93-2.88 (m, 2H), 2.12 (s, 3H), 2.01 (s, 3H). |
| A-16 | 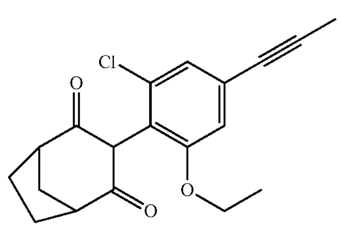 [SMILES: CC#Cc1cc(Cl)c(C2C(=O)C3CCC(C3)C2=O)c(OCC)c1] | δ (delta) (d4 MeOD): 6.99 (dd, 1 H), 6.81-6.87 (m, 1 H), 3.94 (dq, 2 H), 2.98 (br. s., 2 H), 2.13-2.27 (m, 3 H), 2.03 (s, 3 H), 1.79-1.91 (m, 2 H), 1.62-1.73 (m, 1 H), 1.30 (q, 3 H). |

TABLE T1-continued

| Compound Number | Structure | ¹H NMR data (in CDCl₃ solvent unless stated) or other physical data |
|---|---|---|
| A-17 | 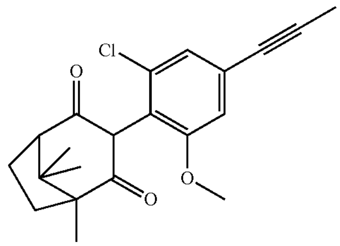 [SMILES: CC#Cc1cc(Cl)c(C2C(=O)C3CCC(C)(C2=O)C3(C)C)c(OC)c1] | δ (delta) (d4 MeOD): 7.02-7.01 (m, 1H), 6.89-6.87 (m, 1H), 3.72-3.70 (m, 3H), 2.53-2.51 (m, 1H), 2.37-2.30 (m, 1H), 2.04 (s, 3H), 2.00-1.92 (m, 1H), 1.89-1.76 (m, 2H), 1.20-1.09 (m, 6H), 1.02 (s, 3H). |
| A-18 | 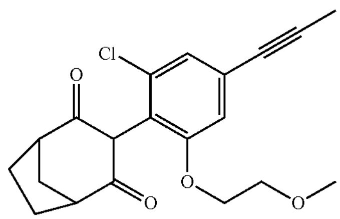 [SMILES: CC#Cc1cc(Cl)c(C2C(=O)C3CCC(C3)C2=O)c(OCCOC)c1] | δ (delta) 7.12-7.10 (m, 1H), 6.86-6.82 (m, 1H), 6.01-5.80 (m, 1H), 4.11-3.97 (m, 2H), 3.65-3.60 (m, 2H), 3.37-3.34 (m, 3H), 3.03-2.99 (m, 2H), 2.27-1.78 (m, 5H), 2.04 (s, 3H), 1.37-1.30 (m, 1H). |
| A-19 | 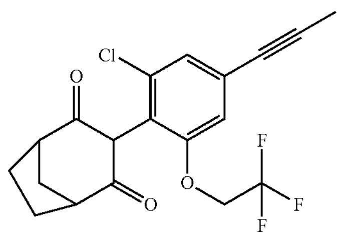 [SMILES: CC#Cc1cc(Cl)c(C2C(=O)C3CCC(C3)C2=O)c(OCC(F)(F)F)c1] | δ (delta) (CD₃OD) 7.10 (s, 1H), 6.96-6.90 (m, 1H), 4.44-4.36 (m, 2H), 2.96 (br, 2H), 2.22-2.14 (m, 3H), 2.02 (s, 3H), 1.87-1.81 (m, 2H), 1.71-1.67 (m, 1H) |
| A-20 | 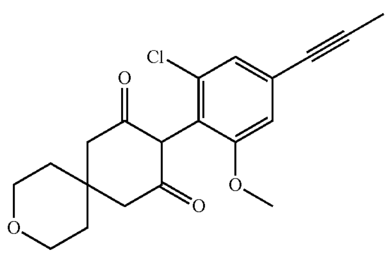 [SMILES: CC#Cc1cc(Cl)c(C2C(=O)CC3(CCOCC3)CC2=O)c(OC)c1] | δ (delta) 7.12 (s, 1H), 6.84 (s, 1H), 6.00 (br s, 1H), 3.72 (s, 3H), 3.70 (m, 4H), 2.57 (br s, 4H), 2.05 (s, 3H), 1.73 (brt, 2H), 1.67 (brt, 2H) |
| A-21 | 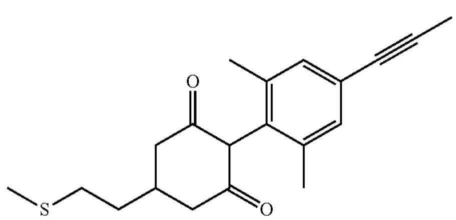 [SMILES: CC#Cc1cc(C)c(C2C(=O)CC(CCSC)CC2=O)c(C)c1] | δ (delta) (500 MHz) 7.16 (s, 2H), 5.38 (br s, 1H), 2.64-2.76 (m, 2H), 2.56-2.63 (m, 2H), 2.37-2.49 (m, 2H), 2.26 (dd, 1H), 2.13 (s, 3H), 2.01-2.07 (m, 9H), 1.76-1.83 (m, 2H) |
| A-22 | 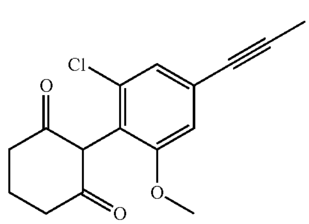 [SMILES: CC#Cc1cc(Cl)c(C2C(=O)CCCC2=O)c(OC)c1] | δ (delta) (500 MHz) 7.12 (d, 1H), 6.80-6.89 (m, 1H), 5.74 (br s, 1H), 3.66-3.78 (m, 3H), 2.69 (br s, 4H), 2.00-2.15 (m, 5H) |

TABLE T1-continued

| Compound Number | Structure | ¹H NMR data (in CDCl₃ solvent unless stated) or other physical data |
|---|---|---|
| A-23 | 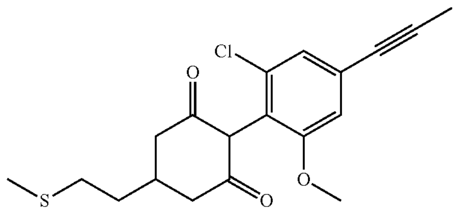 [SMILES: CC#Cc1cc(Cl)c(C2C(=O)CC(CCSC)CC2=O)c(OC)c1] | δ (delta) (500 MHz, CD₃OD) 7.03 (s, 1H), 6.90 (d, 1H), 3.73 (d, 3H), 2.59-2.68 (m, 4H), 2.33-2.46 (m, 3H), 2.13 (d, 3H), 2.04-2.06 (m, 3H), 1.81 (quin, 2H) |
| A-24 | 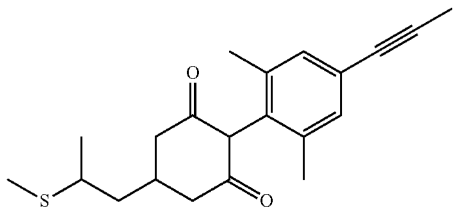 [SMILES: CC#Cc1cc(C)c(C2C(=O)CC(CC(C)SC)CC2=O)c(C)c1] | δ (delta) (500 MHz) 7.26 (s, 1H), 7.15 (s, 1H), 2.45-2.81 (m, 4H), 2.17-2.39 (m, 2H), 1.99-2.11 (m, 12H), 1.66-1.75 (m, 1H), 1.56-1.64 (m, 1H), 1.33 (d, 3H) |
| A-25 | 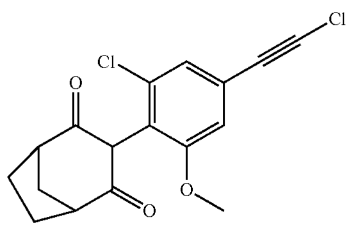 [SMILES: COc1cc(C#CCl)cc(Cl)c1C1C(=O)C2CCC(C2)C1=O] | δ (delta) (500 MHz, CD₃OD) 7.09 (m, 1H), 6.95 (m, 1H), 3.72 (d, 3H), 2.95 (br s, 2H), 2.14-2.25 (m, 3H), 1.78-1.90 (m, 2H), 1.68 (m, 1H) |
| A-26 | 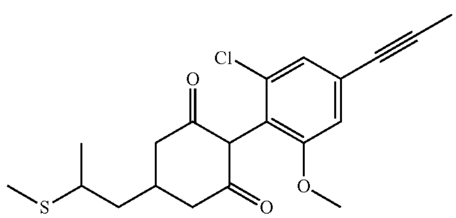 [SMILES: CC#Cc1cc(Cl)c(C2C(=O)CC(CC(C)SC)CC2=O)c(OC)c1] | |
| A-27 | 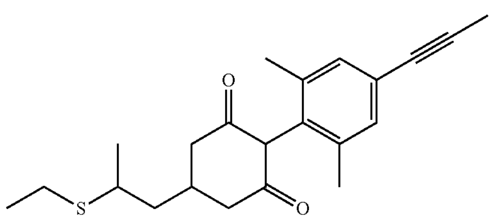 [SMILES: CC#Cc1cc(C)c(C2C(=O)CC(CC(C)SCC)CC2=O)c(C)c1] | |
| A-28 | 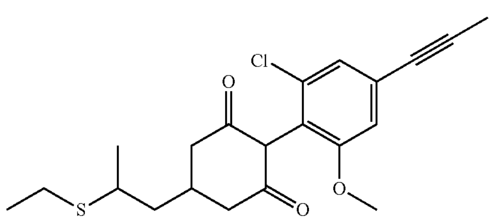 [SMILES: CC#Cc1cc(Cl)c(C2C(=O)CC(CC(C)SCC)CC2=O)c(OC)c1] | |
| A-29 | 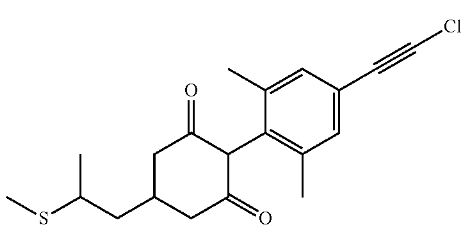 [SMILES: CSC(C)CC1CC(=O)C(c2c(C)cc(C#CCl)cc2C)C(=O)C1] | |

TABLE T1-continued

| Compound Number | Structure | ¹H NMR data (in CDCl₃ solvent unless stated) or other physical data |
|---|---|---|
| A-30 | 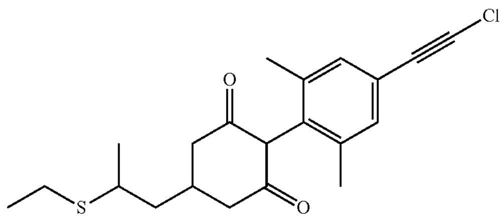 [SMILES: CCSC(C)CC1CC(=O)C(c2c(C)cc(C#CCl)cc2C)C(=O)C1] | |
| A-31 | 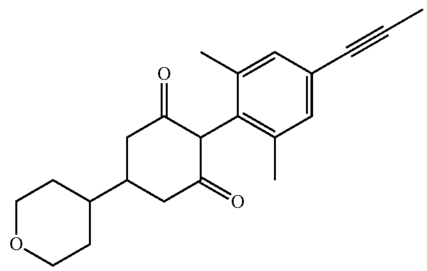 [SMILES: CC#Cc1cc(C)c(C2C(=O)CC(C3CCOCC3)CC2=O)c(C)c1] | |
| A-32 | 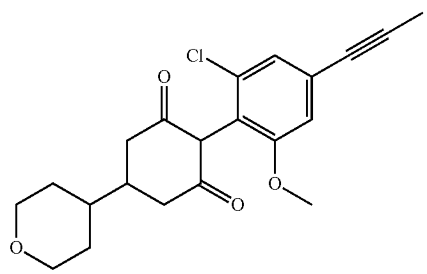 [SMILES: CC#Cc1cc(Cl)c(C2C(=O)CC(C3CCOCC3)CC2=O)c(OC)c1] | |
| A-33 | 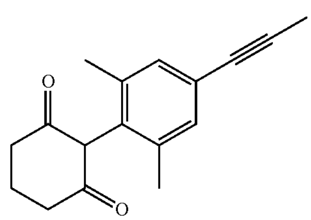 [SMILES: CC#Cc1cc(C)c(C2C(=O)CCCC2=O)c(C)c1] | |
| A-34 | 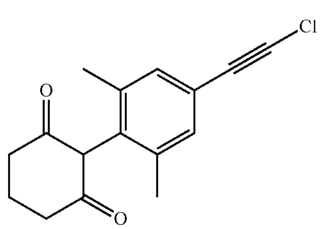 [SMILES: Cc1cc(C#CCl)cc(C)c1C1C(=O)CCCC1=O] | |
| A-35 | 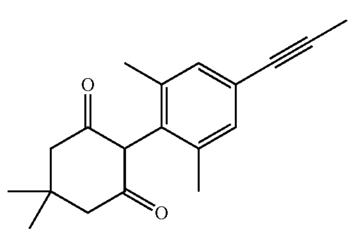 [SMILES: CC#Cc1cc(C)c(C2C(=O)CC(C)(C)CC2=O)c(C)c1] | |

TABLE T1-continued

| Compound Number | Structure | $^1$H NMR data (in CDCl$_3$ solvent unless stated) or other physical data |
|---|---|---|
| A-36 | 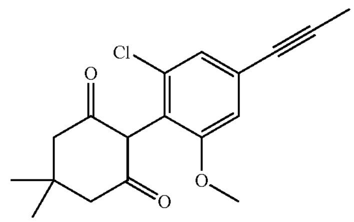 [SMILES: CC#Cc1cc(Cl)c(C2C(=O)CC(C)(C)CC2=O)c(OC)c1] | δ (delta) (400 MHz, CDCl$_3$ +1 drop of CD$_3$OD) 7.12 (d, 1H), 6.83 (d, 1H), 3.72 (s, 3H), 2.42 (brs, 4H), 2.05 (s, 3H), 1.19 (s, 3H), 1.16 (s, 3H) |
| A-37 | 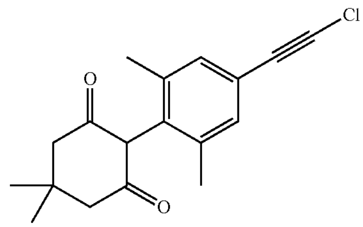 [SMILES: Cc1cc(C#CCl)cc(C)c1C1C(=O)CC(C)(C)CC1=O] | |
| A-38 | 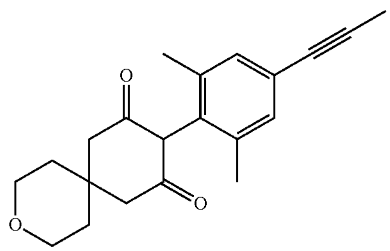 [SMILES: CC#Cc1cc(C)c(C2C(=O)CC3(CCOCC3)CC2=O)c(C)c1] | |
| A-39 | 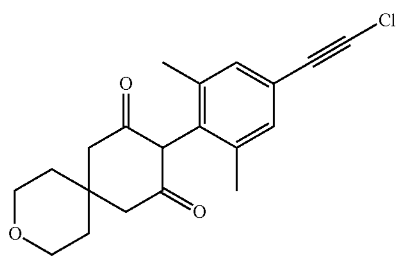 [SMILES: Cc1cc(C#CCl)cc(C)c1C1C(=O)CC2(CCOCC2)CC1=O] | |
| A-40 | 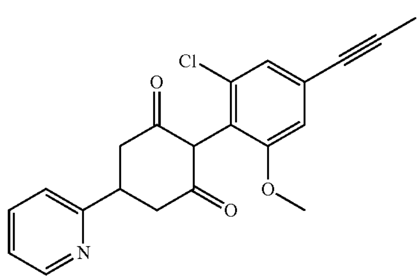 [SMILES: CC#Cc1cc(Cl)c(C2C(=O)CC(c3ccccn3)CC2=O)c(OC)c1] | |
| A-41 | 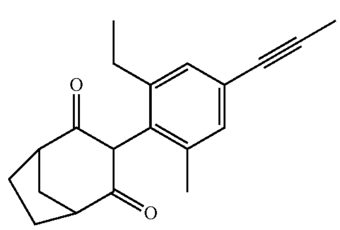 [SMILES: CC#Cc1cc(C)c(C2C(=O)C3CCC(C3)C2=O)c(CC)c1] | |

TABLE T1-continued

| Compound Number | Structure | ¹H NMR data (in CDCl₃ solvent unless stated) or other physical data |
|---|---|---|
| P-1 (=A-14) | 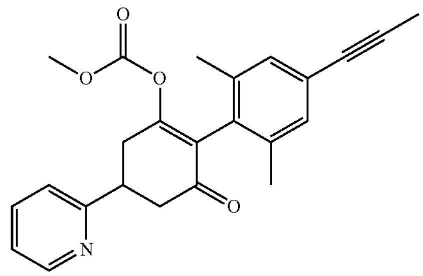 [SMILES: CC#Cc1cc(C)c(C2=C(OC(=O)OC)CC(c3ccccn3)CC2=O)c(C)c1] | δ (delta) 8.60 (d, 1H), 7.69 (td, 1H), 7.28-7.27 (m, 1H), 7.21 (dd, 1H), 7.08 (d,2H), 3.78-3.74 (m, 1H), 3.66 (s, 3H), 3.38 (dd, 1H), 3.10-3.01 (m, 2H), 2.93-2.89 (m, 1H), 2.10 (s, 3H), 2.03 (s, 3H), 1.98 (s, 3H). |
| P-2 (=A-15) | 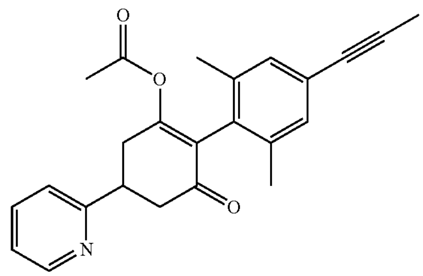 [SMILES: CC#Cc1cc(C)c(C2=C(OC(C)=O)CC(c3ccccn3)CC2=O)c(C)c1] | δ (delta) 8.60 (d, 1H), 7.69 (td, 1H), 7.28-7.27 (m, 1H), 7.21 (dd, 1H), 7.08 (d, 2H), 3.78-3.73 (m, 1H), 3.33 (dd, 1H), 3.06 (dd, 1H), 2.99-2.88 (m, 2H), 2.09 (s, 3H), 2.04 (s, 3H), 1.98 (s, 3H), 1.86 (s, 3H). |
| P-3 | 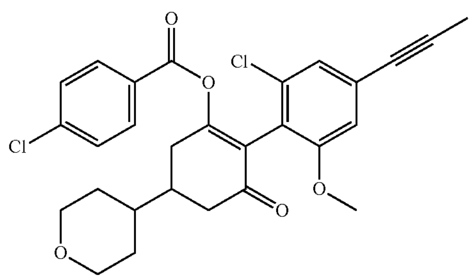 [SMILES: CC#Cc1cc(Cl)c(C2=C(OC(=O)c3ccc(Cl)cc3)CC(C3CCOCC3)CC2=O)c(OC)c1] | δ (delta) (500 MHz) 7.71 (d, 2H), 7.35 (d, 2H), 7.03 (s, 1H), 6.72 (3, 1H), 3.77 (dd, 4H), 3.64 (s, 3H), 3.07 (d, 2H), 2.89 (d, 2H), 2.67 (dd, 2H), 2.02 (s, 3H), 1.86-1.71 (m, 4H). |
| P-4 | 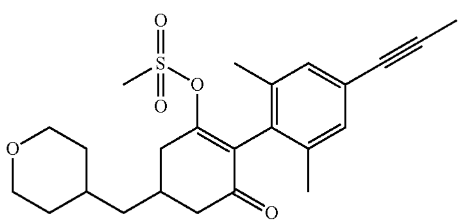 [SMILES: CC#Cc1cc(C)c(C2=C(OS(C)(=O)=O)CC(CC3CCOCC3)CC2=O)c(C)c1] | δ (delta) (500 MHz) 7.11 (s, 2H) 3.97 (dd, 2H) 3.40 (tdd, 2H) 2.93 (dd, 1H) 2.64-2.74 (m, 2H) 2.45 (s, 3H) 2.29-2.37 (m, 1H) 2.06-2.10 (m, 3H) 2.05 (s, 3H) 2.03 (s, 3H) 1.57-1.71 (m, 4H) 1.39-1.51 (m, 2H) 1.25-1.36 (m, 2H) |
| P-5 | 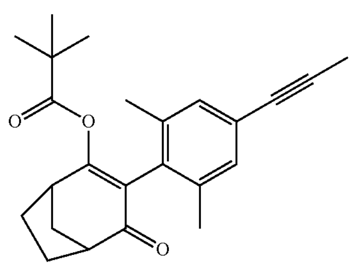 [SMILES: CC#Cc1cc(C)c(C2=C(OC(=O)C(C)(C)C)C3CCC(C3)C2=O)c(C)c1] | δ (delta) (500 MHz) 7.04 (s, 2H) 3.13-3.17 (m, 1H) 3.02 (t, 1H) 2.39 (d, 1H) 2.05-2.29 (m, 3H) 2.04 (s, 3H) 2.02 (s, 3H) 1.95-1.99 (m, 3H) 1.70-1.83 (m, 2H) 0.92 (s, 9H) |
| P-6 | 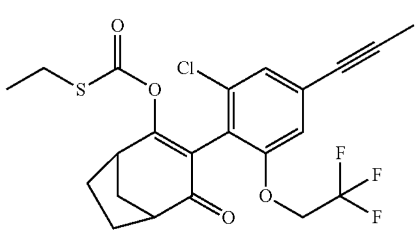 [SMILES: CC#Cc1cc(Cl)c(C2=C(OC(=O)SCC)C3CCC(C3)C2=O)c(OCC(F)(F)F)c1] | δ (delta) (500 MHz) 7.15 (s, 1H) 6.70-6.81 (m, 1H) 4.19-4.28 (m, 2H) 3.23 (dt, 1H) 3.12 (brs, 1H) 2.74-2.83 (m, 2H) 2.29-2.42 (m, 1H) 2.05-2.29 (m, 3H) 2.04 (s, 3H) 1.70-1.91 (m, 2H) 1.23 (t, 3H) |

TABLE T1-continued

| Compound Number | Structure | $^1$H NMR data (in CDCl$_3$ solvent unless stated) or other physical data |
|---|---|---|
| P-7 | 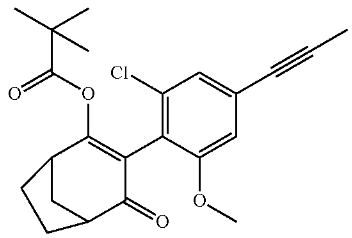 [SMILES: CC#Cc1cc(Cl)c(C2=C(OC(=O)C(C)(C)C)C3CCC(C3)C2=O)c(OC)c1] | δ (delta) (500 MHz) 7.03 (s, 1H) 6.75-6.78 (m, 1H) 3.69 (d, 3H) 3.07-3.13 (m, 2H) 2.41 (d, 1H) 2.14-2.25 (m, 2H) 2.03-2.04 (m, 3H) 2.02-2.11 (m, 1H) 1.78-1.91 (m, 1H) 1.71 (dtd, 1H) 1.01 (d, 9H) |

It should be noted that certain compounds of the invention may exist as a mixture of isomers, including sometimes atropisomers, e.g. as noted above, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

The following compounds B-1, B-2, B-3 or B-4 are not compounds of formula (I) according to the present invention. However, a further, independent, aspect of the invention provides a compound which is one of compounds B-1, B-2, B-3 or B-4 or a salt (e.g. agrochemcially acceptable salt) thereof:

| Compound Number | Structure | $^1$H NMR data (400 MHz, in CDCl$_3$ solvent, unless otherwise stated) or other physical data |
|---|---|---|
| B-1 | 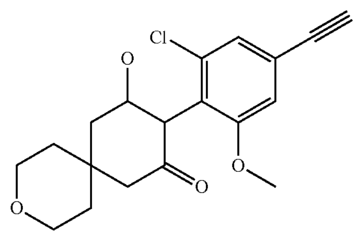 [SMILES: C#Cc1cc(Cl)c(C2C(=O)CC3(CCOCC3)CC2O)c(OC)c1] | δ (delta) (500 MHz) 7.15 (s, 1H), 6.87 (s, 1H), 5.69 (brs, 1H), 3.68 (s, 3H), 3.64 (t, 4H), 3.07 (s, 1H), 2.55 (brs, 2H), 2.48 (dd, 2H), 1.68 (t, 2H), 1.63 (t, 2H) |
| B-2 | 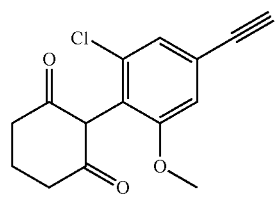 [SMILES: C#Cc1cc(Cl)c(C2C(=O)CCCC2=O)c(OC)c1] | δ (delta) (500 MHz) 7.22 (d, 1H), 6.91-6.97 (m, 1H), 6.03 (brs, 1H), 3.74 (s, 3H), 3.09-3.16 (s, 1H), 2.39-2.66 (m, 4H), 2.06-2.16 (m, 2H) |
| B-3 | 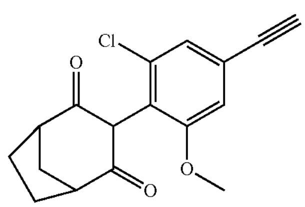 [SMILES: C#Cc1cc(Cl)c(C2C(=O)C3CCC(C3)C2=O)c(OC)c1] | δ (delta) (500 MHz, CD$_3$OD) 7.10 (m, 1H), 6.96 (m, 1H), 3.72 (d, 3H), 3.55 (d, 1H), 2.96 (brs, 2H), 2.12-2.26 (m, 3H), 1.79-1.91 (m, 2H), 1.68 (m, 1H) |
| B-4 | 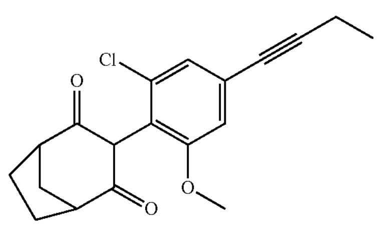 [SMILES: CCC#Cc1cc(Cl)c(C2C(=O)C3CCC(C3)C2=O)c(OC)c1] | |

Compounds of Tables 1 to 27

The compounds of the following Tables 1 to 25 and Tables 26 and 27 also illustrate the present invention, and are also particular embodiments of the compounds of formula (I) according to the present invention. For the most part, these compounds can generally be prepared by methods similar or analogous to those shown in the Examples and/or in the process section hereinabove using appropriate starting materials.

Table 1 covers 34 compounds of the following type

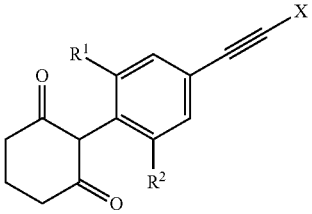

wherein $R^1$, $R^2$ and X are as defined in Table 1.

TABLE 1

| Compound Number | $R^1$ | $R^2$ | X |
|---|---|---|---|
| 1.01 | methyl | hydrogen | methyl |
| 1.02 | methyl | methyl | methyl |
| 1.03 | methyl | chlorine | methyl |
| 1.04 | methyl | methoxy | methyl |
| 1.05 | methyl | ethynyl | methyl |
| 1.06 | methyl | ethyl | methyl |
| 1.07 | methyl | vinyl | methyl |
| 1.07A | methyl | 2-methoxyethoxy | methyl |
| 1.07B | methyl | ethoxy | methyl |
| 1.08 | chlorine | hydrogen | methyl |
| 1.09 | chlorine | chlorine | methyl |
| 1.10 | chlorine | methoxy | methyl |
| 1.11 | chlorine | ethynyl | methyl |
| 1.12 | chlorine | ethyl | methyl |
| 1.13 | chlorine | vinyl | methyl |
| 1.13A | chlorine | 2-methoxyethoxy | methyl |
| 1.13B | chlorine | ethoxy | methyl |
| 1.14 | methyl | hydrogen | chlorine |
| 1.15 | methyl | methyl | chlorine |
| 1.16 | methyl | chlorine | chlorine |
| 1.17 | methyl | methoxy | chlorine |
| 1.18 | methyl | ethynyl | chlorine |
| 1.19 | methyl | ethyl | chlorine |
| 1.20 | methyl | vinyl | chlorine |
| 1.20A | methyl | 2-methoxyethoxy | chlorine |
| 1.20B | methyl | ethoxy | chlorine |
| 1.21 | chlorine | hydrogen | chlorine |
| 1.22 | chlorine | chlorine | chlorine |
| 1.23 | chlorine | methoxy | chlorine |
| 1.24 | chlorine | ethynyl | chlorine |
| 1.25 | chlorine | ethyl | chlorine |
| 1.26 | chlorine | vinyl | chlorine |
| 1.27 | chlorine | 2-methoxyethoxy | chlorine |
| 1.28 | chlorine | ethoxy | Chlorine |

Table 2 covers 34 compounds of the following type

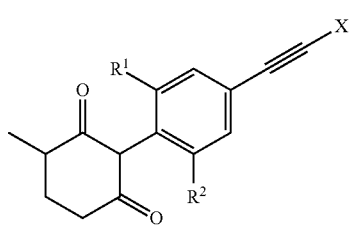

wherein $R_1$, $R_2$ and X are as defined in Table 1. The 34 compounds are compounds 2.01 to 2.07, 2.07A, 2.07B, 2.08 to 2.13, 2.13A, 2.13B, 2.14 to 2.20, 2.20A, 2.20B, and 2.21 to 2.28.

Table 3 covers 34 compounds of the following type

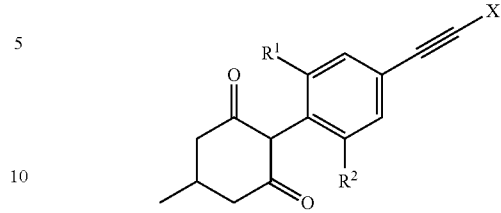

wherein $R^1$, $R^2$ and X are as defined in Table 1. The 34 compounds are compounds 3.01 to 3.07, 3.07A, 3.07B, 3.08 to 3.13, 3.13A, 3.13B, 3.14 to 3.20, 3.20A, 3.20B, and 3.21 to 3.28.

Table 4 covers 34 compounds of the following type

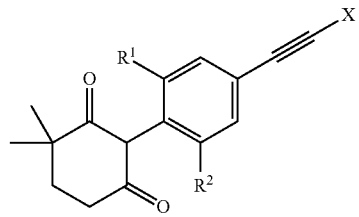

wherein $R^1$, $R^2$ and X are as defined in Table 1. The 34 compounds are compounds 4.01 to 4.07, 4.07A, 4.07B, 4.08 to 4.13, 4.13A, 4.13B, 4.14 to 4.20, 4.20A, 4.20B, and 4.21 to 4.28.

Table 5 covers 34 compounds of the following type

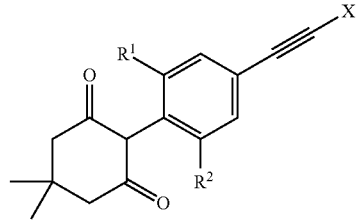

wherein $R^1$, $R^2$ and X are as defined in Table 1. The 34 compounds are compounds 5.01 to 5.07, 5.07A, 5.07B, 5.08 to 5.13, 5.13A, 5.13B, 5.14 to 5.20, 5.20A, 5.20B, and 5.21 to 5.28.

Table 6 covers 34 compounds of the following type

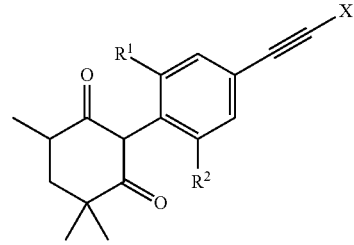

wherein $R^1$, $R^2$ and X are as defined in Table 1. The 34 compounds are compounds 6.01 to 6.07, 6.07A, 6.07B, 6.08 to 6.13, 6.13A, 6.13B, 6.14 to 6.20, 6.20A, 6.20B, and 6.21 to 6.28.

Table 7 covers 34 compounds of the following type

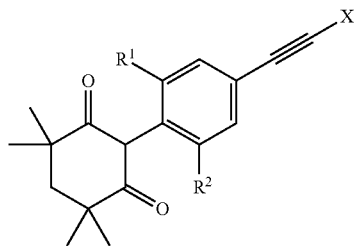

wherein R¹, R² and X are as defined in Table 1. The 34 compounds are compounds 7.01 to 7.07, 7.07A, 7.07B, 7.08 to 7.13, 7.13A, 7.13B, 7.14 to 7.20, 7.20A, 7.20B, and 7.21 to 7.28.

Table 8 covers 34 compounds of the following type

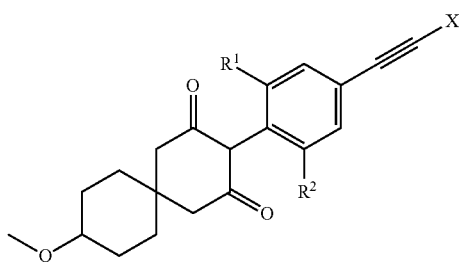

wherein R¹, R² and X are as defined in Table 1. The 34 compounds are compounds 8.01 to 8.07, 8.07A, 8.07B, 8.08 to 8.13, 8.13A, 8.13B, 8.14 to 8.20, 8.20A, 8.20B, and 8.21 to 8.28.

Table 9 covers 34 compounds of the following type

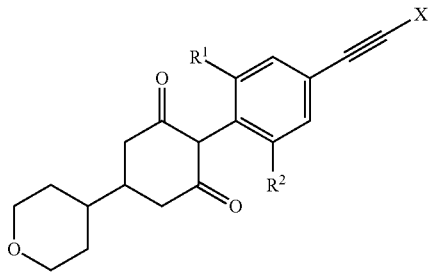

wherein R¹, R² and X are as defined in Table 1. The 34 compounds are compounds 9.01 to 9.07, 9.07A, 9.07B, 9.08 to 9.13, 9.13A, 9.13B, 9.14 to 9.20, 9.20A, 9.20B, and 9.21 to 9.28.

Table 10 covers 34 compounds of the following type

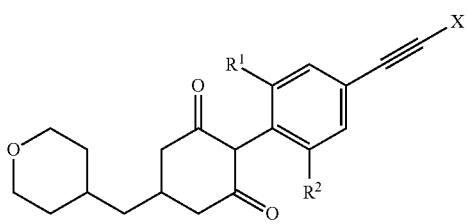

wherein R¹, R² and X are as defined in Table 1. The 34 compounds are named as compounds 10.01 to 10.07, 10.07A, 10.07B, 10.08 to 10.13, 10.13A, 10.13B, 10.14 to 10.20, 10.20A, 10.20B, and 10.21 to 10.28.

Table 11 covers 34 compounds of the following type

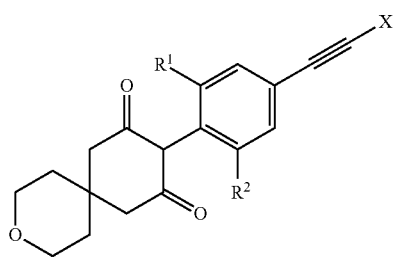

wherein R¹, R² and X are as defined in Table 1. The 34 compounds are named as compounds 11.01 to 11.07, 11.07A, 11.07B, 11.08 to 11.13, 11.13A, 11.13B, 11.14 to 11.20, 11.20A, 11.20B, and 11.21 to 11.28.

Table 12 covers 34 compounds of the following type

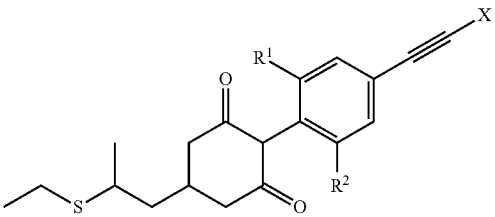

wherein R¹, R² and X are as defined in Table 1. The 34 compounds are named as compounds 12.01 to 12.07, 12.07A, 12.07B, 12.08 to 12.13, 12.13A, 12.13B, 12.14 to 12.20, 12.20A, 12.20B, and 12.21 to 12.28.

Table 13 covers 34 compounds of the following type

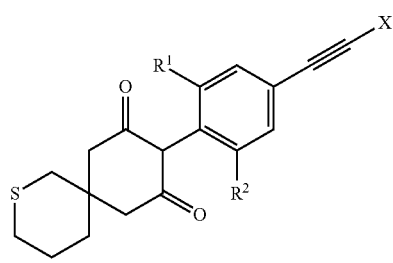

wherein R¹, R² and X are as defined in Table 1. The 34 compounds are named as compounds 13.01 to 13.07, 13.07A, 13.07B, 13.08 to 13.13, 13.13A, 13.13B, 13.14 to 13.20, 13.20A, 13.20B, and 13.21 to 13.28.

Table 14 covers 34 compounds of the following type

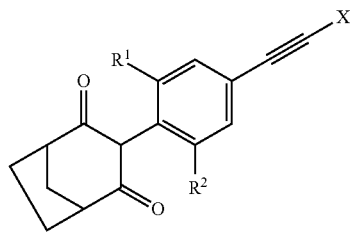

wherein $R^1$, $R^2$ and X are as defined in Table 1. The 34 compounds are named as compounds 14.01 to 14.07, 14.07A, 14.07B, 14.08 to 14.13, 14.13A, 14.13B, 14.14 to 14.20, 14.20A, 14.20B, and 14.21 to 14.28.

Table 15 covers 34 compounds of the following type

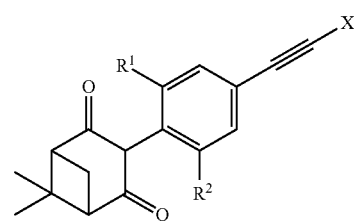

wherein $R^1$, $R^2$ and X are as defined in Table 1. The 34 compounds are named as compounds 15.01 to 15.07, 15.07A, 15.07B, 15.08 to 15.13, 15.13A, 15.13B, 15.14 to 15.20, 15.20A, 15.20B, and 15.21 to 15.28.

Table 16 covers 34 compounds of the following type

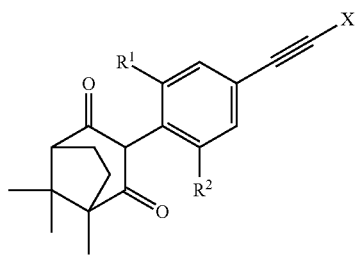

wherein $R^1$, $R^2$ and X are as defined in Table 1. The 34 compounds are named as compounds 16.01 to 16.07, 16.07A, 16.07B, 16.08 to 16.13, 16.13A, 16.13B, 16.14 to 16.20, 16.20A, 16.20B, and 16.21 to 16.28.

Table 17 covers 34 compounds of the following type

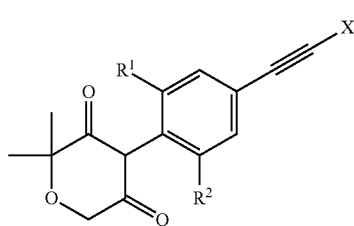

wherein $R^1$, $R^2$ and X are as defined in Table 1. The 34 compounds are named as compounds 17.01 to 17.07, 17.07A, 17.07B, 17.08 to 17.13, 17.13A, 17.13B, 17.14 to 17.20, 17.20A, 17.20B, and 17.21 to 17.28.

Table 18 covers 34 compounds of the following type

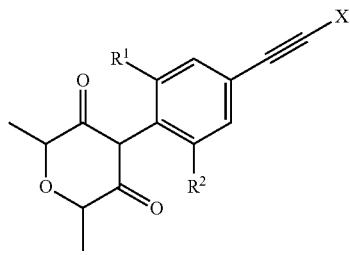

wherein $R^1$, $R^2$ and X are as defined in Table 1. The 34 compounds are named as compounds 18.01 to 18.07, 18.07A, 18.07B, 18.08 to 18.13, 18.13A, 18.13B, 18.14 to 18.20, 18.20A, 18.20B, and 18.21 to 18.28.

Table 19 covers 34 compounds of the following type

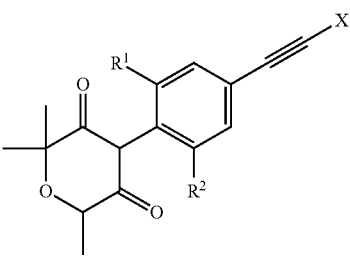

wherein $R^1$, $R^2$ and X are as defined in Table 1. The 34 compounds are named as compounds 19.01 to 19.07, 19.07A, 19.07B, 19.08 to 19.13, 19.13A, 19.13B, 19.14 to 19.20, 19.20A, 19.20B, and 19.21 to 19.28.

Table 20 covers 34 compounds of the following type

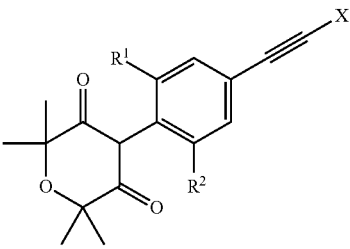

wherein $R^1$, $R^2$ and X are as defined in Table 1. The 34 compounds are named as compounds 20.01 to 20.07, 20.07A, 20.07B, 20.08 to 20.13, 20.13A, 20.13B, 20.14 to 20.20, 20.20A, 20.20B, and 20.21 to 20.28.

Table 21 covers 34 compounds of the following type

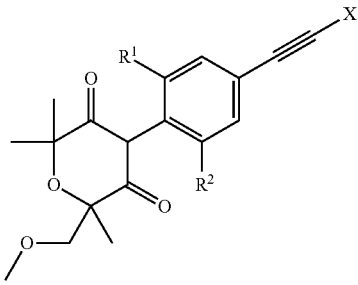

wherein $R^1$, $R^2$ and X are as defined in Table 1. The 34 compounds are named as compounds 21.01 to 21.07, 21.07A, 21.07B, 21.08 to 21.13, 21.13A, 21.13B, 21.14 to 21.20, 21.20A, 21.20B, and 21.21 to 21.28.

Table 22 covers 34 compounds of the following type

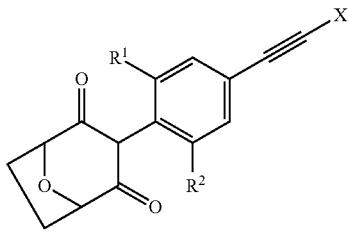

wherein $R^1$, $R^2$ and X are as defined in Table 1. The 34 compounds are named as compounds 22.01 to 22.07, 22.07A, 22.07B, 22.08 to 22.13, 22.13A, 22.13B, 22.14 to 22.20, 22.20A, 22.20B, and 22.21 to 22.28.

Table 23 covers 34 compounds of the following type

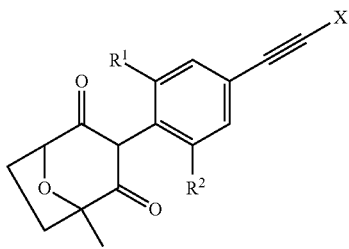

wherein $R^1$, $R^2$ and X are as defined in Table 1. The 34 compounds are named as compounds 23.01 to 23.07, 23.07A, 23.07B, 23.08 to 23.13, 23.13A, 23.13B, 23.14 to 23.20, 23.20A, 23.20B, and 23.21 to 23.28.

Table 24 covers 34 compounds of the following type

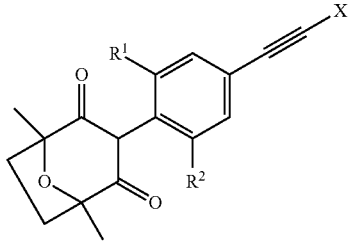

wherein $R^1$, $R^2$ and X are as defined in Table 1. The 34 compounds are named as compounds 24.01 to 24.07, 24.07A, 24.07B, 24.08 to 24.13, 24.13A, 24.13B, 24.14 to 24.20, 24.20A, 24.20B, and 24.21 to 24.28.

Table 25 covers 34 compounds of the following type

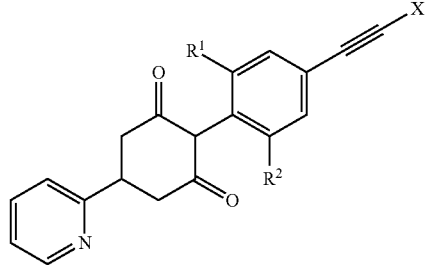

wherein $R^1$, $R^2$ and X are as defined in Table 1. The 34 compounds are named as compounds 25.01 to 25.07, 25.07A, 25.07B, 25.08 to 25.13, 25.13A, 25.13B, 25.14 to 25.20, 25.20A, 25.20B, and 25.21 to 25.28.

Table 26 covers 34 compounds of the following type

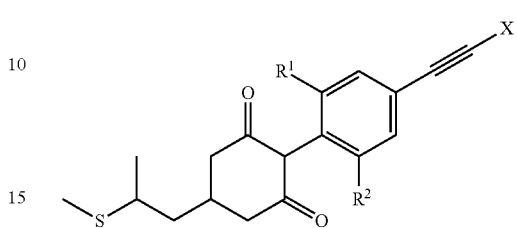

wherein $R^1$, $R^2$ and X are as defined in Table 1. The 34 compounds are named as compounds 26.01 to 26.07, 26.07A, 26.07B, 26.08 to 26.13, 26.13A, 26.13B, 26.14 to 26.20, 26.20A, 26.20B, and 26.21 to 26.28.

Table 27 covers 34 compounds of the following type

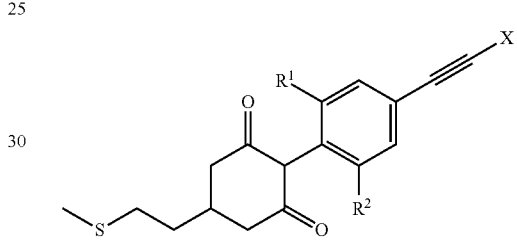

wherein $R^1$, $R^2$ and X are as defined in Table 1. The 34 compounds are named as compounds 27.01 to 27.07, 27.07A, 27.07B, 27.08 to 27.13, 27.13A, 27.13B, 27.14 to 27.20, 27.20A, 27.20B, and 27.21 to 27.28.

BIOLOGICAL EXAMPLES

Biological Example 1A

Test 1A

Glasshouse Assay for Herbicidal Activity

Seeds of a variety of test species were sown in standard soil in pots. After cultivation for one day (pre-emergence) or after 8 days cultivation (post-emergence) under controlled conditions in a glasshouse (at 24/16° C., day/night; 14 hours light; 65% humidity), the plants were sprayed with an aqueous spray solution derived from the formulation of the technical active ingredient in acetone/I water (50:50) solution containing 0.5% Tween 20 (polyoxyethelyene sorbitan monolaurate, CAS RN 9005-64-5). The test plants were then grown in a glasshouse under controlled conditions in a glasshouse (at 24/16° C., day/night; 14 hours light; 65% humidity) and watered twice daily. After 13 days for pre and post-emergence, the test was evaluated visually for percentage phytotoxicity to the plant (where 100=total damage to plant; 0=no damage to plant).

Biological Example 1A

Pre-Emergence Herbicidal Activity

Test Plants:

*Alopecurus myosuroides* (ALOMY), *Setaria faberi* (SETFA), *Echinochloa crus-galli* (ECHCG), *Solanum nigrum* (SOLNI), *Amaranthus retroflexus* (AMARE), *Ipomoea hederacea* (IPOHE), and *Abutilon theophasti Medik.* (ABUTH, common English name "velvetleaf"). Of these, *Alopecurus myosuroides* (ALOMY), *Setaria faberi* (SETFA), and *Echinochloa crus-galli* (ECHCG) are grassy monocotyledonous weeds.

| Compound Number | Application Rate g/ha | SOLNI | AMARE | SETFA | ALOMY | ECHCG | IPOHE | ABUTH |
|---|---|---|---|---|---|---|---|---|
| A-1 | 250 | 0 | 0 | 90 | 90 | 80 | 0 | - |
| A-2 | 250 | 0 | 0 | 70 | 90 | 100 | 10 | - |
| A-3 | 250 | 0 | 0 | 100 | 100 | 100 | 40 | - |
| A-4 | 250 | 0 | 0 | 70 | 100 | 100 | 0 | - |
| A-5 | 250 | - | 0 | 90 | 100 | 100 | - | 0 |
| A-6 | 250 | 20 | 30 | 100 | 100 | 100 | 10 | - |
| A-7 | 250 | 40 | 60 | 30 | 80 | 80 | 20 | - |
| A-8 | 250 | 70 | 90 | 90 | 90 | 100 | 30 | - |
| A-9 | 250 | 70 | 100 | 100 | 100 | 100 | 20 | - |
| A-10 | 250 | - | 0 | 100 | 100 | 100 | - | 0 |
| A-11 | 250 | - | 70 | 80 | 100 | 100 | - | 50 |
| A-12 | 250 | - | 0 | 100 | 100 | 100 | - | 0 |
| A-12 | 62.5 | - | 0 | 100 | 90 | 90 | - | 0 |
| Reference (Comparator) Compound X-4 | 250 | - | 0 | 100 | 70 | 90 | - | 0 |
| Reference (Comparator) Compound X-4 | 30 | - | 0 | 40 | 0 | 30 | - | 0 |
| A-13 (compound of the invention, to be compared with X-4 above) | 250 | - | 80 | 100 | 100 | 100 | - | 70 |
| A-13 (compound of the invention, to be compared with X-4 above) | 30 | - | 100 | 70 | 70 | 100 | - | 30 |
| A-14 (=P-1) | 250 | - | 70 | 100 | 100 | 100 | - | 70 |
| A-15 (=P-2) | 250 | - | 40 | 100 | 100 | 100 | - | 50 |
| A-16 | 250 | - | 80 | 100 | 100 | 100 | - | 70 |
| A-17 | 250 | - | 60 | 90 | 90 | 100 | - | 70 |
| A-19 | 250 | - | 0 | 60 | 40 | 60 | - | 0 |
| A-20 | 250 | - | 90 | 100 | 100 | 100 | - | 80 |
| A-21 | 250 | - | 90 | 100 | 100 | 100 | - | 10 |
| A-22 | 250 | - | 70 | 100 | 90 | 100 | - | 60 |
| A-23 | 250 | - | 70 | 90 | 90 | 100 | - | 30 |
| A-24 | 250 | - | 80 | 100 | 90 | 100 | - | 20 |
| P-3 | 250 | - | 100 | 100 | 100 | 100 | - | 80 |
| P-4 | 250 | - | 20 | 80 | 80 | 100 | - | 10 |
| P-5 | 250 | - | 0 | 100 | 100 | 100 | - | 0 |
| P-6 | 250 | - | 20 | 10 | 10 | - | - | 0 |
| P-7 | 250 | - | 0 | 100 | 100 | 100 | - | 0 |
| B-1 | 250 | - | 20 | 80 | 90 | 100 | - | 0 |
| B-2 | 250 | - | 10 | 90 | 60 | 90 | - | 10 |
| B-3 | 250 | - | 90 | 100 | 80 | 90 | - | 100 |
| B-4 | 250 | - | 40 | 70 | 100 | 100 | - | 10 |

Note:

a hyphen (-) in the table above indicates that no measurement was made.

Biological Example 1A

Post-Emergence Herbicidal Activity

Test Plants:
 *Alopecurus myosuroides* (ALOMY), *Setaria faberi* (SETFA), *Echinochloa crus-galli* (ECHCG), *Solanum nigrum* (SOLNI), *Amaranthus retroflexus* (AMARE), *Ipomoea hederacea* (IPOHE), and *Abutilon theophasti Medik.* (ABUTH, common English name "velvetleaf"). Of these, *Alopecurus myosuroides* (ALOMY), *Setaria faberi* (SETFA), and *Echinochloa crus-galli* (ECHCG) are grassy monocotyledonous weeds.

| Compound Number | Application Rate g/ha | SOLNI | AMARE | SETFA | ALOMY | ECHCG | IPOHE | ABUTH |
|---|---|---|---|---|---|---|---|---|
| A-1 | 250 | 30 | 10 | 70 | 90 | 100 | 90 | - |
| A-2 | 250 | 20 | 0 | 100 | 90 | 100 | 30 | - |
| A-3 | 250 | 20 | 10 | 90 | 90 | 100 | 0 | - |
| A-4 | 250 | 0 | 0 | 80 | 90 | 100 | 0 | - |
| A-5 | 250 | - | 0 | 100 | 100 | 100 | - | 60 |
| A-5 | 30 | - | 10 | 70 | 80 | 100 | - | 0 |
| A-6 | 250 | 20 | 0 | 90 | 70 | 100 | 20 | - |
| A-6 | 62.5 | 20 | 10 | 90 | 70 | 100 | 30 | - |
| A-7 | 250 | 50 | 0 | 80 | 80 | 80 | 20 | - |
| A-8 | 250 | 80 | 40 | 90 | 80 | 100 | 70 | - |
| A-9 | 250 | 80 | 30 | 90 | 100 | 100 | 50 | - |
| A-10 | 250 | - | 50 | 100 | 100 | 100 | - | 80 |
| A-11 | 250 | - | 30 | 100 | 100 | 100 | - | 80 |
| A-12 | 250 | - | 0 to 10 | 100 | 90 to 100 | 100 | - | 50 to 60 |
| A-12 | 62.5 | - | 0 | 100 | 80 | 100 | - | 0 |
| Reference (Comparator) Compound X-4 | 250 | - | 0 | 100 | 80 | 100 | - | 80 |
| Reference (Comparator) Compound X-4 | 30 | - | 0 | 50 | 60 | 40 | - | 0 |
| A-13 (compound of the invention, to be compared with X-4 above) | 250 | - | 60 | 100 | 100 | 100 | - | 80 |
| A-13 (compound of the invention, to be compared with X-4 above) | 30 | - | 30 | 90 | 70 | 80 | - | 40 |
| A-14 (=P-1) | 250 | - | 20 | 100 | 100 | 100 | - | 80 |
| A-15 (=P-2) | 250 | - | 60 | 100 | 100 | 100 | - | 80 |
| A-15 | 30 | - | 0 | 100 | 90 | 100 | - | 20 |
| A-16 | 250 | - | 70 | 100 | 100 | 100 | - | 60 |
| A-16 | 30 | - | 30 | 100 | 90 | 100 | - | 60 |
| A-17 | 250 | - | 0 | 90 | 90 | 100 | - | 10 |
| A-19 | 250 | - | 0 | 90 | 70 | 100 | - | 0 |
| A-20 | 250 | - | 80 | 100 | 100 | 100 | - | 80 |
| A-20 | 30 | - | 80 | 100 | 100 | 100 | - | 80 |
| A-20 | 8 | - | 10 | 90 | 90 | 100 | - | 50 |
| A-21 | 250 | - | 20 | 100 | 90 | 100 | - | 60 |
| A-21 | 30 | - | 80 | 70 | 50 | 80 | - | 10 |
| A-22 | 250 | - | 0 | 100 | 90 | 100 | - | 70 |
| A-22 | 30 | - | 20 | 80 | 60 | 90 | - | 10 |
| A-23 | 250 | - | 20 | 100 | 90 | 100 | - | 70 |
| A-23 | 30 | - | 10 | 100 | 60 | 100 | - | 30 |
| A-24 | 250 | - | 60 | 100 | 100 | 100 | - | 60 |
| A-24 | 30 | - | 0 | 100 | 90 | 100 | - | 0 |
| P-3 | 250 | - | 80 | 100 | 90 | 100 | - | 80 |
| P-3 | 30 | - | 80 | 100 | 100 | 100 | - | 70 |
| P-3 | 8 | - | 20 | 100 | 90 | 100 | - | 20 |
| P-4 | 250 | - | 0 | 80 | 80 | 80 | - | 0 |
| P-5 | 250 | - | 10 | 90 | 90 | 100 | - | 70 |
| P-5 | 30 | - | 0 | 70 | 60 | 80 | - | 0 |
| P-6 | 250 | - | 20 | 50 | 50 | 80 | - | 0 |
| P-7 | 250 | - | 0 | 100 | 100 | 100 | - | 70 |
| P-7 | 30 | - | 0 | 90 | 90 | 100 | - | 10 |
| B-1 | 250 | - | 0 | 100 | 100 | 100 | - | 60 |
| B-2 | 250 | - | 0 | 90 | 70 | 100 | - | 0 |
| B-3 | 250 | - | 0 | 90 | 80 | 100 | - | 0 |
| B-4 | 250 | - | 30 | 90 | 100 | 100 | - | 70 |

Note:
a hyphen (-) in the table above indicates that no measurement was made.

Biological Example 1B

Test 1B

Glasshouse Assay for Herbicidal Activity

Seeds of a variety of monocotyledonous and dicotyledonous test plants are sown in standard soil in pots. The plants are cultivated for one day (for pre-emergence) or for about 12 days (range=10-13 days) (for post-emergence) under controlled conditions in a glasshouse (warm climate species at 24/18° C., cool climate species at 20/16° C., both at day/night; 16 hours light; 65% humidity).

An "instant formulation", known as the "IF50", containing 50 g/liter (i.e. 5% w/v) of the "technical" (i.e. unformulated) active ingredient is prepared by dissolving the active ingredient in a mixture of organic solvents and emulsifier, details of which are provided in the Table below. This IF50 is then mixed with a small, variable amount of acetone to aid dissolution, before addition of a 0.2% v/v aqueous solution of the adjuvant X-77 (which is a mixture of alkyl aryl polyoxyethylene glycols and free fatty acids in isopropanol, CAS Registry number 11097-66-8), as the aqueous diluent, to form an aqueous spray solution which contains a predetermined concentration of the active ingredient (which varies depending on the application rate of the active ingredient to the plants) and 0.2% v/v of the adjuvant X-77. This aqueous spray solution is then sprayed onto the plants, after one day's cultivation (for pre-emergence) or after about 12 days' cultivation (for post-emergence).

TABLE

Composition of the mixture of organic solvents and emulsifier used as a base for the instant formulation (IF50).

| Component | Supplier | Chemical description | CAS Registry number | Amount/ % w/w |
|---|---|---|---|---|
| Emulsogen EL360 ™ | Clariant | castor oil ethoxylate (as emulsifier) | 61791-12-6 | 11.12 |
| N-methylpyrrolidone | widely available | 1-methyl-2-pyrrolidone | 872-50-4 | 44.44 |
| Dowanol DPM ™ glycol ether | Dow | dipropylene glycol monomethyl ether | 34590-94-8 | 44.44 |

The test plants are then grown on, in a glasshouse (greenhouse) under controlled conditions (at either 24/18° C. or 20/16° C. (day/night) as mentioned above; 16 hours light; 65% humidity) and are watered twice daily. Either 15 days after application of the herbicide (15 DAA) (for post-emergence), or 20 days after application of the herbicide (20 DAA) (for pre-emergence), the test plants are evaluated visually, and an assessed percentage phytotoxicity score is given for each herbicidal application on each plant species (where 100%=total damage to plant; 0%=no damage to plant).

Some of the test plants are as follows:
Cool climate crop plants: *Triticum aestivum* (TRZAW, winter wheat), *Brassica napus* (BRSNN, rape, also called oilseed rape or rapeseed), *Beta vulgaris* (BEAVA, sugar beet).
Warm climate crop plants: *Glycine max* (GLXMA, soybean).
Cool climate ("cool season") grassy monocotyledonous weeds: *Alopecurus myosuroides* (ALOMY), *Avena fatua* (AVEFA), *Lolium perenne* (LOLPE).
Warm climate ("warm season") grassy monocotyledonous weeds: *Setaria faberi* (SETFA), SORVU (*Sorghum bicolor* (L.) Moench ssp. Bicolor, or *Sorghum vulgare* Pers.), *Digitaria sanguinalis* (DIGSA), *Echinochloa crus-galli* (ECHCG), and *Brachiaria plantaginea* (BRAPL).

Biological Example 1B

Pre-Emergence Herbicidal Activity

| Compound Number | Appl. Rate (g/ha) | TRZAW | GLXMA | BRSNN | BEAVA | ALOMY | AVEFA | LOLPE | SETFA | SORVU | DIGSA | ECHCG | BRAPL |
|---|---|---|---|---|---|---|---|---|---|---|---|---|---|
| A-1 | 500 g/ha | 40 | 10 | 60 | 10 | 70 | 10 | 100 | 50 | 60 | 60 | 100 | 90 |
| A-2 | 500 g/ha | 60 | 0 | 40 | 0 | 100 | 80 | 100 | 90 | 80 | 100 | 100 | 100 |
| A-5 | 500 g/ha | 20 | 0 | 90 | 0 | 80 | 40 | 100 | 90 | 90 | 100 | 100 | 100 |
| A-6 | 125 g/ha | 10 | 0 | 70 | 0 | 60 | 40 | 80 | 80 | 80 | 100 | 60 | 80 |
| A-9 | 125 g/ha | 20 | 10 | 80 | 20 | 80 | 80 | 100 | 100 | 90 | 100 | 90 | - |
| A-10 | 125 g/ha | 20 | 0 | 0 | 0 | 80 | 60 | 100 | 80 | 80 | 90 | 90 | 80 |
| A-12 | 250 g/ha | 30 | 40 | 20 | 10 | 60 | 50 | 100 | 100 | 90 | 100 | 100 | 100 |
| A-13 | 250 g/ha | 20 | 20 | 70 | 10 | 80 | 30 | 100 | 80 | 80 | 100 | 90 | 90 |
| A-14 (=P-1) | 250 g/ha | 40 | 20 | 60 | 30 | 80 | 70 | 100 | 90 | 80 | 100 | 80 | 90 |
| A-15 (=P-2) | 125 g/ha | 0 | 10 | 80 | 0 | 80 | 50 | 90 | 80 | 80 | 100 | 80 | 90 |

-continued

| Compound Number | Appl. Rate (g/ha) | TRZAW | GLXMA | BRSNN | BEAVA | ALOMY | AVEFA | LOLPE | SETFA | SORVU | DIGSA | ECHCG | BRAPL |
|---|---|---|---|---|---|---|---|---|---|---|---|---|---|
| A-16 | 250 g/ha | 0 | 20 | 0 | 0 | 50 | 40 | 70 | 90 | 80 | 100 | 80 | - |
| A-17 | 250 g/ha | 0 | 10 | 0 | 0 | 0 | 60 | 50 | 50 | 50 | 100 | 100 | - |

Note:
A hyphen (-) in the table above indicates that no measurement was made.

Biological Example 1B

Post-Emergence Herbicidal Activity

| Compound Number | Appl. Rate (g/ha) | TRZAW | GLXMA | BRSNN | BEAVA | ALOMY | AVEFA | LOLPE | SETFA | SORVU | DIGSA | ECHCG | BRAPL |
|---|---|---|---|---|---|---|---|---|---|---|---|---|---|
| A-1 | 60 g/ha | 80 | 70 | 70 | 30 | 80 | 60 | 80 | 70 | 0 | 80 | 90 | 90 |
| A-2 | 60 g/ha | 80 | 40 | 70 | 10 | 90 | 80 | 80 | 100 | 80 | 100 | 100 | 100 |
| A-5 | 500 g/ha | 80 | 40 | 80 | 30 | 90 | 80 | 80 | 100 | 100 | 100 | 100 | 100 |
| A-5 | 125 g/ha | 70 | 30 | 80 | 30 | 80 | 80 | 80 | 100 | 100 | 100 | 100 | 100 |
| A-5 | 60 g/ha | 30 | 20 | 70 | 40 | 80 | 30 | 70 | 90 | 80 | 100 | 100 | 100 |
| A-5 | 30 g/ha | 30 | 10 | 70 | 40 | 70 | 30 | 30 | 80 | 70 | 90 | 100 | 90 |
| A-6 | 60 g/ha | 40 | 0 | 60 | 50 | 50 | 60 | 70 | 100 | 90 | 100 | 90 | 100 |
| A-6 | 30 g/ha | - | 0 | 40 | 40 | 50 | 50 | 40 | 100 | 90 | 100 | 90 | 90 |
| A-8 | 30 g/ha | 50 | 50 | 70 | 30 | 80 | 70 | 40 | 90 | 90 | 100 | 100 | 90 |
| A-9 | 30 g/ha | 60 | 60 | 50 | 0 | 80 | 70 | 60 | 90 | 80 | 100 | 100 | - |
| A-10 | 125 g/ha | 80 | 20 | 60 | 20 | 100 | 40 | 80 | 100 | 100 | 100 | 100 | 100 |
| A-10 | 30 g/ha | 60 | 10 | 40 | 20 | 60 | 20 | 30 | 80 | 100 | 90 | 90 | 90 |
| A-12 | 125 g/ha | 60 | 10 | 80 | 20 | 70 | 30 | 70 | 80 | 100 | 100 | 100 | 100 |
| A-12 | 30 g/ha | 40 | 0 | 60 | 0 | 10 | 0 | 0 | 70 | 80 | 100 | 90 | 70 |
| A-13 | 125 g/ha | 30 | 60 | 70 | 20 | 30 | 20 | 70 | 80 | 80 | 80 | 80 | 100 |
| A-14 (=P-1) | 125 g/ha | 80 | 70 | 70 | 40 | 80 | 60 | 80 | 90 | 100 | 100 | 100 | 100 |
| A-14 (=P-1) | 30 g/ha | 60 | 40 | 60 | 30 | 70 | 20 | 70 | 80 | 80 | 80 | 80 | 70 |
| A-15 (=P-2) | 125 g/ha | 80 | 60 | 70 | 30 | 80 | 80 | 90 | 100 | 100 | 100 | 100 | 100 |
| A-15 (=P-2) | 30 g/ha | 70 | 20 | 60 | 30 | 70 | 60 | 80 | 80 | 80 | 90 | 80 | 100 |
| A-16 | 125 g/ha | 60 | 30 | 50 | 0 | 80 | 60 | 70 | 100 | 100 | 100 | 100 | - |
| A-16 | 30 g/ha | 10 | 0 | 10 | 0 | 20 | 0 | 20 | 80 | 80 | 80 | 80 | - |
| A-17 | 250 g/ha | 10 | 10 | 10 | 10 | 50 | 0 | 20 | 80 | 80 | 70 | 90 | - |
| A-18 | 250 g/ha | 10 | 20 | 30 | 30 | 0 | 20 | 0 | 80 | 100 | 90 | 90 | 70 |
| Comparator compound X-9 | 125 g/ha | 0 | 0 | 20 | - | 40 | 0 | 40 | 80 | - | 80 | 60 | 80 |
| Comparator compound X-9 | 60 g/ha | 0 | 0 | 0 | - | 20 | 0 | 0 | 80 | - | 70 | 40 | 80 |

-continued

| Compound Number | Appl. Rate (g/ha) | TRZAW | GLXMA | BRSNN | BEAVA | ALOMY | AVEFA | LOLPE | SETFA | SORVU | DIGSA | ECHCG | BRAPL |
|---|---|---|---|---|---|---|---|---|---|---|---|---|---|
| Comparator compound X-10 | 60 g/ha | 20 | 0 | 0 | - | 80 | 50 | 70 | 100 | - | 100 | 70 | 90 |

Note:
A hyphen (-) in the table above indicates that no measurement was made.

Note: Compound A-5 has the following structure:

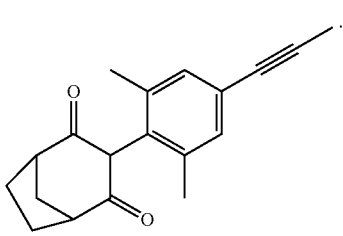 [SMILES: CC#Cc1cc(C)c(C2C(=O)C3CCC(C3)C2=O)c(C)c1]

Comparator compound X-9 is

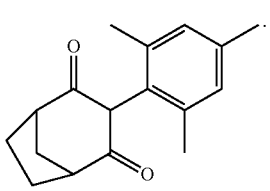 [SMILES: Cc1cc(C)c(C2C(=O)C3CCC(C3)C2=O)c(C)c1]

Comparator compound X-10 is

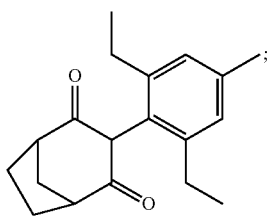 [SMILES: CCc1cc(C)cc(CC)c1C1C(=O)C2CCC(C2)C1=O]

this is compound 21.115 disclosed on page 105 of WO 01/17972 A2. Comparator compound X-10 appears at first sight to have a lower post-emergence activity on ECHCG (at 60 g/ha) than Compound A-5 of the present invention.

Note: The herbicidal activity data (e.g. post-emergence) shown above in Biological Example 1B for Comparator compounds X-9 and X-10 is thought likely to have been measured some years ago, probably using a variant of the above-described test method. Also, for the post-emergence activity of X-9 and X-10 it is not currently known exactly how many days after application of the herbicide the phytotoxicity on the plants was measured.

Biological Example 2

Comparative Herbicidal Data

Comparative herbicidal data is given below for certain exemplified compounds with 4-(prop-1-ynyl)-2,6-dimethylphenyl or 4-(chloroethynyl)-2,6-dimethylphenyl headgroups, compared to the corresponding compounds with either 4-ethynyl-2,6-dimethylphenyl or 2,4,6-trimethylphenyl headgroups, as follows. Comparative herbicidal data is also given below for certain exemplified compounds with 4-(prop-1-ynyl)-2-chloro-6-methoxyphenyl headgroups, compared to the corresponding compounds with 4-ethynyl-2-chloro-6-methoxyphenyl or 4-(but-1-ynyl)-2-chloro-6-methoxyphenyl or 4-methyl-2-chloro-6-methoxyphenyl or 2-chloro-6-methoxyphenyl headgroups, as follows.

Except where specified otherwise, the glasshouse screen for herbicidal activity is substantially the same as that presented in Biological Example 1A (Test 1A) hereinabove. The weed abbreviations are as defined in Biological Example 1A.

Biological Example 2

Post-Emergence Herbicidal Activity (Comparative Data)

TABLE B2(A)

Post-emergence herbicidal activities (percentage phytotoxicity) at 62.5 g/ha application rate are as folows:

| Compound no. | Structure | LOLPE | ALOMY | ECHCG | AVEFA | SETFA |
|---|---|---|---|---|---|---|
| A-1 | 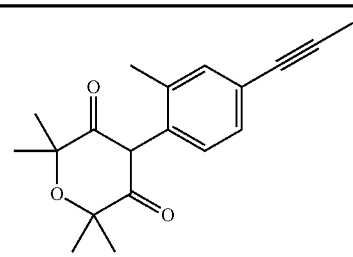 | not tested | 80 | 90 | not tested | 40 |

TABLE B2(A)-continued

Post-emergence herbicidal activities (percentage phytotoxicity) at 62.5 g/ha application rate are as folows:

| Compound no. | Structure | LOLPE | ALOMY | ECHCG | AVEFA | SETFA |
|---|---|---|---|---|---|---|
| A-7 | 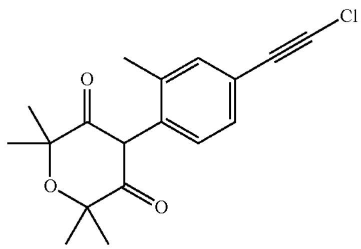 [SMILES: Cc1cc(C#CCl)ccc1C1C(=O)C(C)(C)OC(C)(C)C1=O] | not tested | 50 | 60 | not tested | 60 |
| Comparative example X-1 | 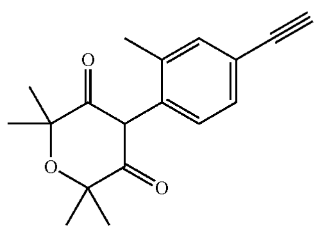 [SMILES: C#Cc1ccc(C2C(=O)C(C)(C)OC(C)(C)C2=O)c(C)c1] | not tested | 10 | 0 | not tested | 30 |
| A-6 | 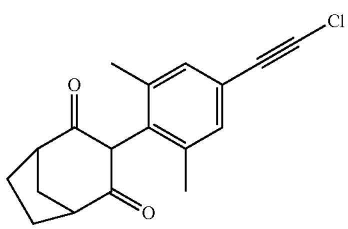 [SMILES: Cc1cc(C#CCl)cc(C)c1C1C(=O)C2CCC(C2)C1=O] | not tested | 70 | 100 | not tested | 90 |
| Comparative example X-2 | 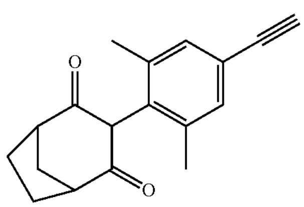 [SMILES: C#Cc1cc(C)c(C2C(=O)C3CCC(C3)C2=O)c(C)c1] | not tested | 10 | 70 | not tested | 60 |
| A-8 | 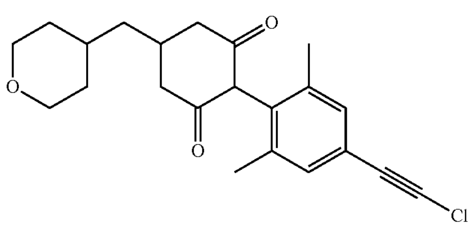 [SMILES: Cc1cc(C#CCl)cc(C)c1C1C(=O)CC(CC2CCOCC2)CC1=O] | not tested | 80 | 100 | not tested | 90 |
| A-9 | 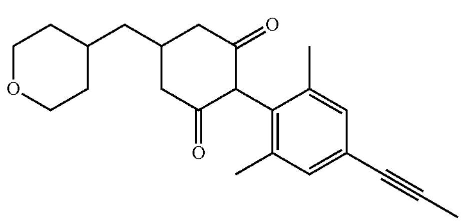 [SMILES: CC#Cc1cc(C)c(C2C(=O)CC(CC3CCOCC3)CC2=O)c(C)c1] | not tested | 90 | 100 | not tested | 90 |

TABLE B2(A)-continued

Post-emergence herbicidal activities (percentage phytotoxicity) at 62.5 g/ha application rate are as folows:

| Compound no. | Structure | LOLPE | ALOMY | ECHCG | AVEFA | SETFA |
|---|---|---|---|---|---|---|
| Comparative example X-3 | 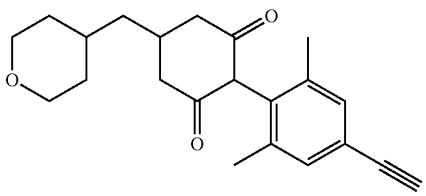 [SMILES: C#Cc1cc(C)c(C2C(=O)CC(CC3CCOCC3)CC2=O)c(C)c1] | not tested | 60 | 50 | not tested | 70 |

Note: Comparative example compound X-3

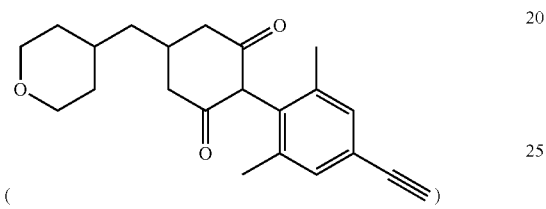

is disclosed as compound 13.041 within Table 13 on page 78 of WO 2010/046194 A1 (Syngenta Limited), after cross-referencing to the phenyl substituents disclosed in compound 1.041 in Table 1 on pages 67-69 of of WO 2010/046194 A1.

TABLE B2(B)

Post-emergence herbicidal activities (percentage phytotoxicity) at 15.625 g/ha application rate are as folows:

| Compound no. | Structure | LOLPE | ALOMY | ECHCG | AVEFA | SETFA |
|---|---|---|---|---|---|---|
| A-1 | 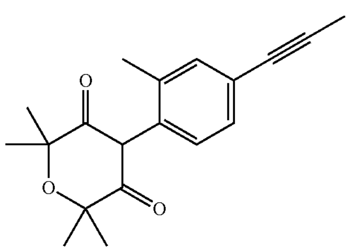 [SMILES: CC#Cc1ccc(C2C(=O)C(C)(C)OC(C)(C)C2=O)c(C)c1] | not tested | 10 | 20 | not tested | 20 |
| A-7 | 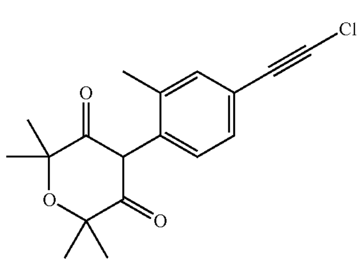 [SMILES: Cc1cc(C#CCl)ccc1C1C(=O)C(C)(C)OC(C)(C)C1=O] | not tested | 30 | 0 | not tested | 40 |

TABLE B2(B)-continued

Post-emergence herbicidal activities (percentage phytotoxicity) at 15.625 g/ha application rate are as folows:

| Compound no. | Structure | LOLPE | ALOMY | ECHCG | AVEFA | SETFA |
|---|---|---|---|---|---|---|
| Comparative example X-1 | 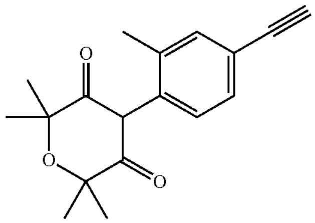 [SMILES: C#Cc1ccc(C2C(=O)C(C)(C)OC(C)(C)C2=O)c(C)c1] | not tested | 20 | 0 | not tested | 0 |
| A-6 | 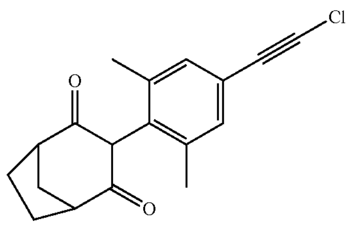 [SMILES: Cc1cc(C#CCl)cc(C)c1C1C(=O)C2CCC(C2)C1=O] | not tested | 70 | 90 | not tested | 90 |
| Comparative example X-2 | 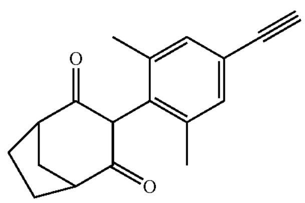 [SMILES: C#Cc1cc(C)c(C2C(=O)C3CCC(C3)C2=O)c(C)c1] | not tested | 0 | 0 | not tested | 50 |
| A-8 | 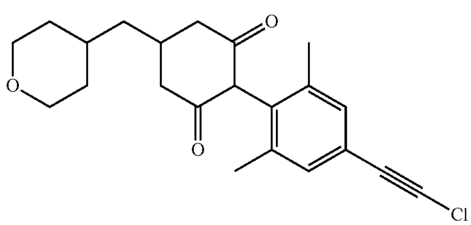 [SMILES: Cc1cc(C#CCl)cc(C)c1C1C(=O)CC(CC2CCOCC2)CC1=O] | not tested | 70 | 90 | not tested | 80 |
| A-9 | 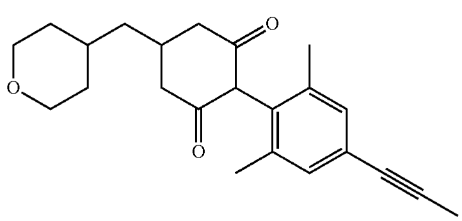 [SMILES: CC#Cc1cc(C)c(C2C(=O)CC(CC3CCOCC3)CC2=O)c(C)c1] | not tested | 80 | 100 | not tested | 80 |
| Comparative example X-3 | 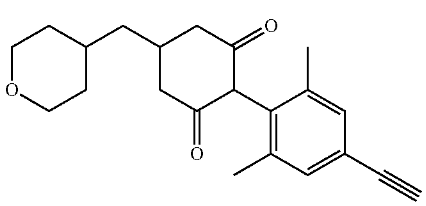 [SMILES: C#Cc1cc(C)c(C2C(=O)CC(CC3CCOCC3)CC2=O)c(C)c1] | not tested | 30 | 20 | not tested | 60 |

Note: Comparative example compound X-3

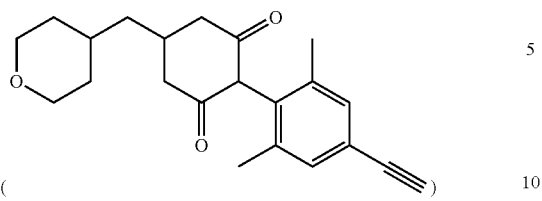

is disclosed as compound 13.041 within Table 13 on page 78 of WO 2010/046194 A1 (Syngenta Limited), after cross-referencing to the phenyl substituents disclosed in compound 1.041 in Table 1 on pages 67-69 of of WO 2010/046194 A1.

TABLE B2(C)

Post-emergence herbicidal activities (percentage phytotoxicity) at 30 g/ha application rate are as folows:

| Compound no. | Structure | AMARE | SETFA | ALOMY | ECHCG | ABUTH |
|---|---|---|---|---|---|---|
| A-5 | 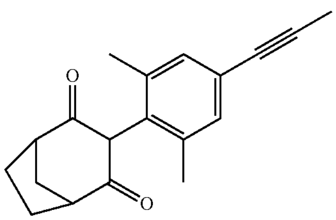 [SMILES: CC#Cc1cc(C)c(C2C(=O)C3CCC(C3)C2=O)c(C)c1] | 10 | 70 | 80 | 100 | 0 |
| A-12 | 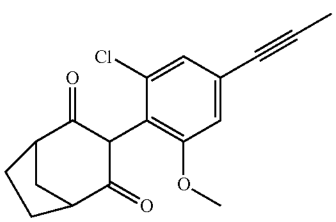 [SMILES: CC#Cc1cc(Cl)c(C2C(=O)C3CCC(C3)C2=O)c(OC)c1] | 0 | 90 | 90 | 100 | 40 |
| B-3 | 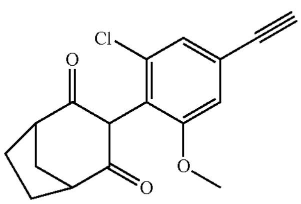 [SMILES: C#Cc1cc(Cl)c(C2C(=O)C3CCC(C3)C2=O)c(OC)c1] | 0 | 690 | 30 | 70 | 0 |
| B-4 | 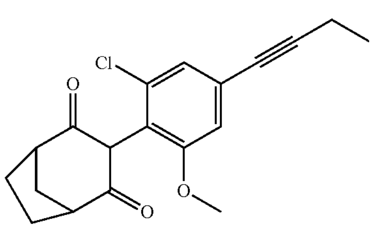 [SMILES: CCC#Cc1cc(Cl)c(C2C(=O)C3CCC(C3)C2=O)c(OC)c1] | 20 | 70 | 60 | 80 | 0 |
| Reference (Comparator) Compound X-5 | 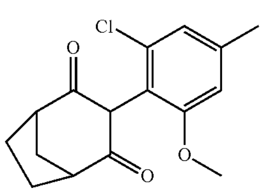 [SMILES: COc1cc(C)cc(Cl)c1C1C(=O)C2CCC(C2)C1=O] | 30 | 60 | 30 | 80 | 10 |

TABLE B2(C)-continued

Post-emergence herbicidal activities (percentage phytotoxicity) at 30 g/ha application rate are as folows:

| Compound no. | Structure | AMARE | SETFA | ALOMY | ECHCG | ABUTH |
|---|---|---|---|---|---|---|
| A-13 | (structure, HCl salt) | 30 | 90 | 70 | 80 | 40 |
| Reference (Comparator) Compound X-4 | (structure, TFA salt) | 0 | 50 | 60 | 40 | 0 |
| A-20 | (structure) | 80 | 100 | 100 | 100 | 80 |
| B-1 | (structure) | 0 | 70 | 70 | 80 | 10 |
| Reference (Comparator) Compound X-6 | (structure) | 20 | 10 | 20 | 10 | 0 |
| A-22 | (structure) | 20 | 80 | 60 | 90 | 10 |

TABLE B2(C)-continued

Post-emergence herbicidal activities (percentage phytotoxicity) at 30 g/ha application rate are as folows:

| Compound no. | Structure | AMARE | SETFA | ALOMY | ECHCG | ABUTH |
|---|---|---|---|---|---|---|
| B-2 | 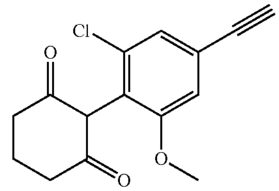 [SMILES: C#Cc1cc(Cl)c(C2C(=O)CCCC2=O)c(OC)c1] | 0 | 70 | 0 | 80 | 0 |
| A-21 | 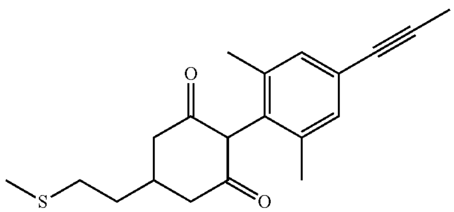 [SMILES: CC#Cc1cc(C)c(C2C(=O)CC(CCSC)CC2=O)c(C)c1] | 80 | 70 | 50 | 80 | 10 |
| Reference (Comparator) Compound X-7 | 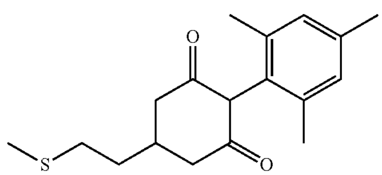 | 0 | 20 | 30 | 10 | 0 |
| A-24 | 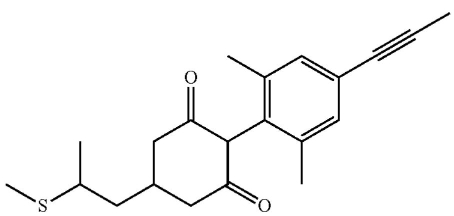 [SMILES: CC#Cc1cc(C)c(C2C(=O)CC(CC(C)SC)CC2=O)c(C)c1] | 0 | 100 | 90 | 100 | 0 |
| Reference (Comparator) Compound X-8 | 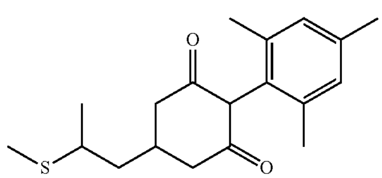 | 0 | 80 | 70 | 70 | 0 |

Test plants:
*Alopecurus myosuroides* (ALOMY), *Setaria faberi* (SETFA), *Echinochloa crus-galli* (ECHCG), *Amarantus retroflexus* (AMARE), and *Abutilon theophasti* Medik. (ABUTH, common English name "velvetleaf"). Of these, *Alopecurus myosuroides* (ALOMY), *Setaria faberi* (SETFA), and *Echinochloa crus-galli* (ECHCG) are grassy monocotyledonous weeds.

Note: Reference (Comparator) Compounds X-7

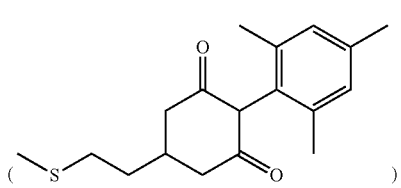

and X-8

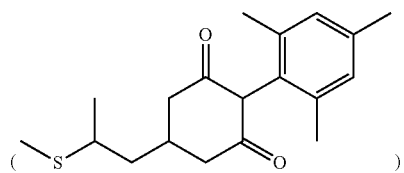

are disclosed as compounds T12 and T18 respectively on page 47 of WO 2008/110308 A1 (Syngenta Participations AG).

TABLE B2(D)
| Post-emergence herbicidal activities (percentage phytotoxicity) at 8 g/ha application rate are as folows: | | | | | | |
|---|---|---|---|---|---|---|
| Compound no. | Structure | AMARE | SETFA | ALOMY | ECHCG | ABUTH |
| A-5 | 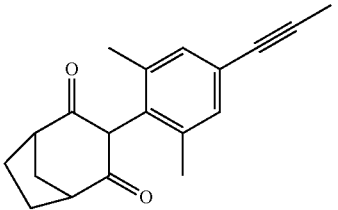 [SMILES: CC#Cc1cc(C)c(C2C(=O)C3CCC(C3)C2=O)c(C)c1] | 0 | 30 | 50 | 80 | 0 |
| A-12 | 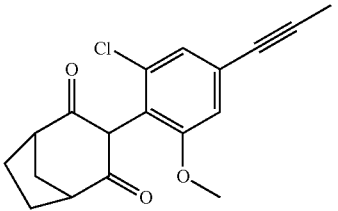 | 0 | 50 | 40 | 90 | 10 |
| B-3 | 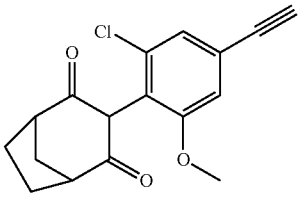 [SMILES: C#Cc1cc(Cl)c(C2C(=O)C3CCC(C3)C2=O)c(OC)c1] | 0 | 20 | 0 | 20 | 0 |
| Reference (Comparator) Compound X-5 | 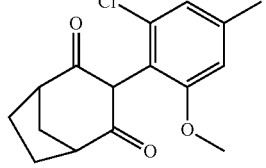 | 30 | 20 | 0 | 0 | 0 |
| A-13 | 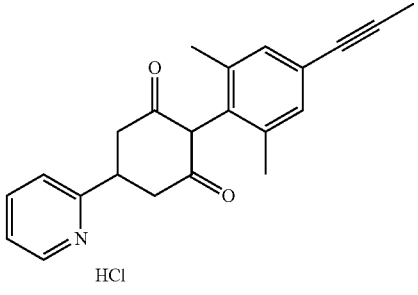 [SMILES: CC#Cc1cc(C)c(C2C(=O)CC(c3ccccn3)CC2=O)c(C)c1 ; Cl] | 0 | 80 | 60 | 80 | 0 |
| Reference (Comparator) Compound X-4 | 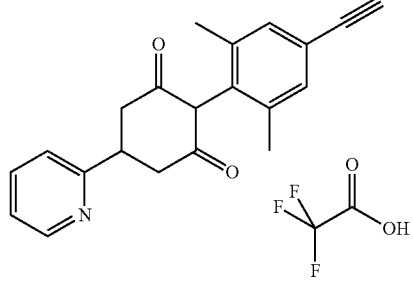 | 0 | 40 | 40 | 20 | 0 |

TABLE B2(D)-continued

Post-emergence herbicidal activities (percentage phytotoxicity) at 8 g/ha application rate are as folows:

| Compound no. | Structure | AMARE | SETFA | ALOMY | ECHCG | ABUTH |
|---|---|---|---|---|---|---|
| A-20 | 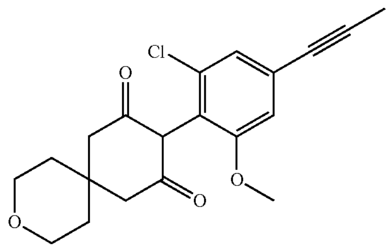 [SMILES: CC#Cc1cc(Cl)c(C2C(=O)CC3(CCOCC3)CC2=O)c(OC)c1] | 10 | 90 | 90 | 100 | 50 |
| B-1 | 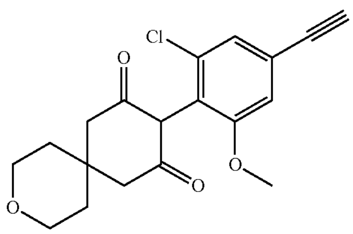 [SMILES: C#Cc1cc(Cl)c(C2C(=O)CC3(CCOCC3)CC2=O)c(OC)c1] | 0 | 30 | 10 | 20 | 0 |
| A-22 | 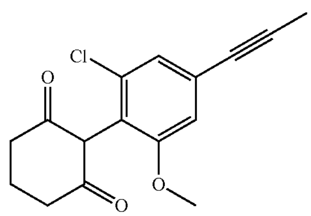 [SMILES: CC#Cc1cc(Cl)c(C2C(=O)CCCC2=O)c(OC)c1] | 0 | 70 | 10 | 80 | 0 |
| B-2 | 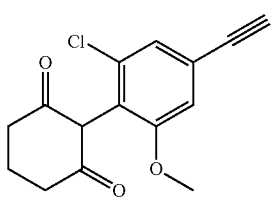 [SMILES: C#Cc1cc(Cl)c(C2C(=O)CCCC2=O)c(OC)c1] | 0 | 10 | 0 | 0 | 0 |
| A-21 | 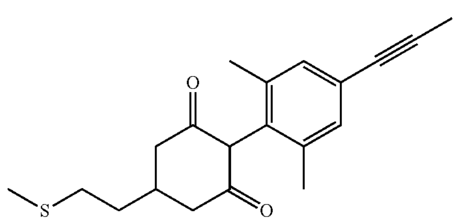 [SMILES: CC#Cc1cc(C)c(C2C(=O)CC(CCSC)CC2=O)c(C)c1] | 30 | 50 | 50 | 80 | 70 |
| Reference (Comparator) Compound X-7 | 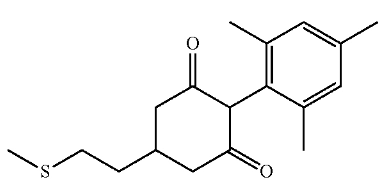 | 0 | 0 | 0 | 0 | 0 |

Note: Reference (Comparator) Compound X-7

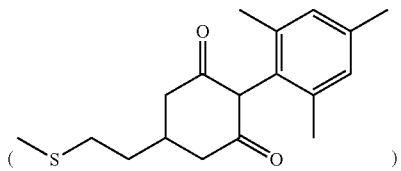

is disclosed as compound T12 on page 47 of WO 2008/110308 A1 (Syngenta Participations AG).

Biological Example 3

Assay for Biological Example 3

Glasshouse Assay for Herbicidal Activity, Using Various Adjuvant Systems

Materials and Methods
Herbicide Application:
Post-emergence foliar spray application, 200 L/ha, usually one or two replicates for the weeds (depending on application rate), and two replicates for soybean.
Climate:
Standard warm conditions (tropical), in glasshouse. Specifically, the glasshouse bay conditions are 24° C./18° C. day/night; 16/8 hours light/dark; 65% humidity.
Plants:
The herbicidal application takes place at the following growth stages for plants which include inter alia one or more of the following plants (usually the herbicidal application takes place on at least the following six plants: DIGSA, ELEIN, SETFA, GLXMA Nikko, and GLXMA TMG133, and either BRADC or BRAPP):
Brachiaria decumbens (BRADC)— growth stage (GS) 12 or 13 (or GS 12)—or, if BRADC is not used, then Brachiaria platyphylla (BRAPP)—growth stage 12 or 13
Digitaria sanguinalis (DIGSA)—growth stage 12 or 13
Eleusine indica (ELEIN)—growth stage 12 or 13
Setaria faberi (SETFA)—growth stage 12 or 13
Echinochloa crus-galli (ECHCG)—growth stage 12 or 13
Sorghum halepense (annual) (SORHA)—growth stage 12 or 13
Panicum dichotomiflorum (PANDI)—growth stage 12 or 13
Glycine max (GLXMA, soybean) cultivar "Nikko"—growth stage: $1^{st}$ trifoliate
Glycine max (GLXMA, soybean) cultivar "TMG133"— which is Roundup Ready™glyphosate-tolerant soybean cultivar TMG133 (typically available from Monsanto in Brazil)—growth stage: $1^{st}$ trifoliate.
Herbicidal Compositions Tested:
Each test Compound is applied with one of the following adjuvant systems (all percentages are final concentrations in the aqueous spray mixture):
Adjuvant system 1: 0.5% v/v Adigor™ *, 1.0% v/v AMS (ammonium sulphate) and 12.5% v/v IPA (isopropyl alcohol).
Adjuvant system 2: 0.5% v/v Adigor™ * and 12.5% v/v IPA (isopropyl alcohol).
Adjuvant system 3: 0.5% v/v Hexamoll™ DINCH **, 1.0% v/v AMS (ammonium sulphate) and 12.5% v/v IPA (isopropyl alcohol).
* Adigor™ (currently available in many countries from Syngenta) is an emulsifiable concentrate which consists of:
(i) ethoxylated alcohols, which typically includes ethoxylated higher alcohols (e.g. ethoxylates of alcohols wherein the alcohols are within the range of $C_{12}$-$C_{22}$); and
(ii) a mixture of heavy aromatic hydrocarbons, which typically includes (e.g. includes 50% or more by weight of the heavy aromatic hydrocarbons of) a mixture of naphthalenes each of which is substituted by one or more alkyls wherein the alkyl(s) in total have 1-4 carbon atoms per naphthalene molecule (e.g. Solvesso 200 ND™); and
(iii) about 47% w/w and/or about 45% w/v (with respect to the emulsifiable concentrate) of methylated rapeseed oil (rapeseed oil methyl ester) (e.g. Agnique ME 18 RD-F™), as an adjuvant.
** Hexamoll™ DINCH™ is 1,2-cyclohexane dicarboxylic acid di-isononyl ester

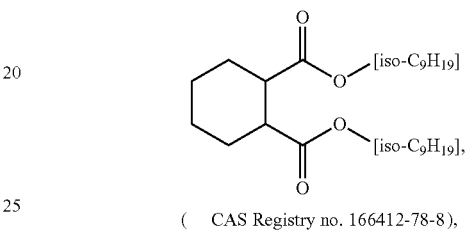

( CAS Registry no. 166412-78-8), and is usually available from BASF. "Isononyl" in this context is thought to mean a mixture of two or more branched isomers of $C_9H_{19}$.
Method:
Seeds of the weed plants, typically including inter alia [either Brachiaria decumbens (BRADC) or Brachiaria platyphylla (BRAPP)], Digitaria sanguinalis (DIGSA), Eleusine indica (ELEIN), Setaria faberi (SETFA) are sown in seed trays (troughs) containing clay loam soil (pH 7.0, 2.2% organic matter, "Trough Mix A"); and soybean seed is sown in pots containing the same soil with 3 soybean seedlings per pot. The plants are sprayed with the test herbicide when they reach the growth stages mentioned above.
The test herbicidal solutions are prepared by mixing the appropriate aliquots of the test substance(s) and the adjuvant system indicated above *** in deionised water to give the desired treatment concentration.
The herbicidal application is made as a foliar spray, using a tracksprayer. Following the herbicidal application, the plants are watered twice per day for the duration of the test.
A visual assessment of the % herbicidal damage is made 7 and 14 Days After herbicide Application (DAA) (or, in a minority of cases, 7 and 15 DAA), and the results are recorded as % visual herbicidal damage where 0%=no damage to plants and 100%=plant totally killed.
*** Adjuvant system=either Adigor™ or Hexamoll DINCH™ at 0.5% v/v, and 12.5% v/v IPA (isopropyl alcohol), and in most cases also 1.0% v/v AMS (ammonium sulphate); all percentages are final concentrations in the aqueous spray mixture.

Biological Example 3

Post-Emergence Activity—Results at 14 or 15 Days after Herbicide Application

Compounds A-5, A-6, A-10, A-12, A-16, A-20, A-21, A-22, A-23 and A-25, which are compounds of formula (I) according to the present invention, and compound B-1, were tested in a test method substantially as described above.

Compounds A-5 and A-10 were tested using the 0.5% v/v Adigor™+12.5% v/v IPA adjuvant system. Compounds A-6, A-12, A-20, A-21, A-22, A-23, A-25 and B-1 were tested using the 0.5% v/v Adigor™+1.0% v/v AMS+12.5% v/v IPA adjuvant system. Compound A-16 was tested using the 0.5% v/v Hexamol Dinch™+1.0% v/v AMS+12.5% v/v IPA adjuvant system.

The percentages of herbicidal damage/plant control, at 14 Days After herbicide Application (DAA) (or, in a minority of cases, at 15 DAA), for the Compounds tested and for some of the plants tested, were in the following percentage ranges.

Control of *Brachiaria decumbens* (BRADC) or *Brachiaria platyphylla* (BRAPP), Both Warm-Climate (Warm-Season) Grassy Weeds At 14 or 15 DAA, certain test compounds (Compound A-12, A-16, A-22 or A-23) showed percentage control of (percentage phytotoxicities on) *Brachiaria decumbens* (BRADC) in the range of from 80% to 95%, when applied post-emergence at an application rate of 8 g/ha.

At 14 DAA, certain test compounds (Compound A-5 or A-10) showed percentage control of *Brachiaria decumbens* (BRADC) in the range of from 65% to 75%, when applied post-emergence at an application rate of 8 g/ha.

At 15 DAA, certain test compounds (Compound A-21 or B-1) showed percentage control of *Brachiaria decumbens* (BRADC) in the range of from 50% to 55%, when applied post-emergence at an application rate of 8 g/ha.

At 14 DAA, Compound A-25 showed percentage control of *Brachiaria decumbens* (BRADC) of 15%, when applied post-emergence at an application rate of 8 g/ha.

At 14 DAA, certain test compounds (Compound A-6 or A-20) showed percentage control of *Brachiaria platyphylla* (BRAPP) in the range of from 95% to 100%, when applied post-emergence at an application rate of 8 g/ha.

Control of *Digitaria sanguinalis* (DIGSA), a Warm-Climate (Warm-Season) Grassy Weed At 14 or 15 DAA, certain test compounds (Compound A-5, A-6, A-10, A-12, A-16, A-21, A-22 or A-23) showed percentage control of (percentage phytotoxicities on) *Digitaria sanguinalis* (DIGSA) in the range of from 85% to 95%, when applied post-emergence at an application rate of 8 g/ha.

At 14 DAA, Compound A-20 showed a percentage control of *Digitaria sanguinalis* (DIGSA) of 100%, when applied post-emergence at an application rate of 8 g/ha.

At 15 DAA, Compound B-1 showed a percentage control of *Digitaria sanguinalis* (DIGSA) of 85%, when applied post-emergence at an application rate of 8 g/ha.

At 14 DAA, Compound A-25 showed a percentage control of *Digitaria sanguinalis* (DIGSA) of 60%, when applied post-emergence at an application rate of 8 g/ha.

Control of *Eleusine indica* (ELEIN), a Warm-Climate (Warm-Season) Grassy Weed

At 14 or 15 DAA, certain test compounds (Compound A-6, A-10, A-12, A-16, A-21, A-22, or A-23) showed percentage control of (percentage phytotoxicities on) *Eleusine indica* (ELEIN) in the range of from 80% to 99%, when applied post-emergence at an application rate of 8 g/ha.

At 14 DAA, Compound A-5 showed a percentage control of *Eleusine indica* (ELEIN) of 45%, when applied post-emergence at an application rate of 8 g/ha.

At 14 DAA, Compound A-20 showed a percentage control of *Eleusine indica* (ELEIN) of 95%, when applied post-emergence at an application rate of 8 g/ha.

At 15 DAA, Compound B-1 showed a percentage control of *Eleusine indica* (ELEIN) of 20%, when applied post-emergence at an application rate of 8 g/ha.

Control of *Setaria faberi* (SETFA), a Warm-Climate (Warm-Season) Grassy Weed

At 14 or 15 DAA, certain test compounds (Compound A-5, A-6, A-10, A-12, A-16, A-21, A-22 or A-23) showed percentage control of (percentage phytotoxicities on) *Setaria faberi* (SETFA) in the range of from 85% to 95%, when applied post-emergence at an application rate of 8 g/ha.

At 14 DAA, Compound A-20 showed a percentage control of *Setaria faberi* (SETFA) of 98%, when applied post-emergence at an application rate of 8 g/ha.

At 15 DAA, Compound B-1 showed a percentage control of *Setaria faberi* (SETFA) of 50%, when applied post-emergence at an application rate of 8 g/ha.

At 14 DAA, Compound A-25 showed a percentage control of *Setaria faberi* (SETFA) of 40%, when applied post-emergence at an application rate of 8 g/ha.

Control of *Echinochloa crus-galli* (ECHCG), a Warm-Climate (Warm-Season) Grassy Weed At 14 DAA, certain test compounds (Compound A-5, A-10, A-12 or A-22) showed a percentage control of *Echinochloa crus-galli* (ECHCG) in the range of from 95% to 98%, when applied post-emergence at an application rate of 8 g/ha.

At 14 DAA, Compound A-25 showed a percentage control of *Echinochloa crus-galli* (ECHCG) of 45%, when applied post-emergence at an application rate of 8 g/ha.

Control of *Sorghum halepense* (Annual) (SORHA), a Warm-Climate (Warm-Season) Grassy Weed At 14 DAA, certain test compounds (Compound A-5, A-10, A-12, A-22 or A-25) showed a percentage control of *Sorghum halepense* (annual) (SORHA) in the range of from 70% to 99%, when applied post-emergence at an application rate of 8 g/ha.

Control of *Panicum dichotomiflorum* (PANDI), a Warm-Climate (Warm-Season) Grassy Weed At 14 DAA, certain test compounds (Compound A-5, A-10, A-12, A-22 or A-25) showed a percentage control of *Panicum dichotomiflorum* (PANDI) in the range of from 85% to 99%, when applied post-emergence at an application rate of 8 g/ha.

Phytotoxicity on *Glycine max* (GLXMA, Soybean) Cultivar "Nikko"

At 14 or 15 DAA, certain test compounds (Compound A-6, A-12, A-16, A-22 or A-25) showed percentage phytotoxicities on *Glycine max* (GLXMA, soybean) cultivar "Nikko" in the range of from 0% to 30%, when applied post-emergence at an application rate of 120 g/ha.

At 14 or 15 DAA, certain test compounds (Compound A-5, A-10, A-23 or B-1) showed percentage phytotoxicities on *Glycine max* (GLXMA, soybean) cultivar "Nikko" in the range of from 50% to 70%, when applied post-emergence at an application rate of 120 g/ha.

At 14 or 15 DAA, certain test compounds (Compound A-20 or A-21) showed percentage phytotoxicities on *Glycine max* (GLXMA, soybean) cultivar "Nikko" of 85%, when applied post-emergence at an application rate of 120 g/ha.

Phytotoxicity on *Glycine max* (GLXMA, Soybean) Cultivar "TMG 133"

*Glycine max* (GLXMA, soybean) cultivar "TMG133" is Roundup Ready™ glyphosate-tolerant soybean cultivar TMG133, and is typically available from Monsanto in Brazil.

At 14 or 15 DAA, certain test compounds (Compound A-6, A-12, A-16, A-22 or A-25) showed percentage phytotoxicities on *Glycine max* (GLXMA, soybean) cultivar "TMG133" in the range of from 5% to 40%, when applied post-emergence at an application rate of 120 g/ha.

At 14 or 15 DAA, certain test compounds (Compound A-5, A-10, A-23 or B-1) showed percentage phytotoxicities on *Glycine max* (GLXMA, soybean) cultivar "TMG133" in the range of from 50% to 65%, when applied post-emergence at an application rate of 120 g/ha.

At 14 or 15 DAA, certain test compounds (Compound A-20 or A-21) showed percentage phytotoxicities on *Glycine max* (GLXMA, soybean) cultivar "TMG133" of 85%, when applied post-emergence at an application rate of 120 g/ha.

The invention claimed is:
1. A compound of formula (I):

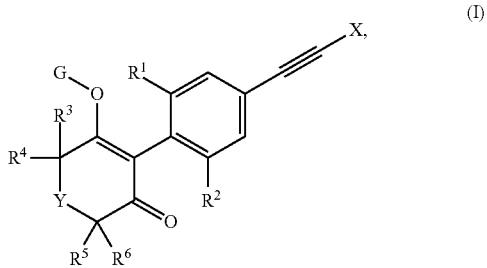

wherein:
X is methyl or chlorine;
$R^1$ is methyl or chlorine;
$R^2$ is hydrogen, methyl, ethyl, n-propyl, cyclopropyl, vinyl, ethynyl, fluorine, chlorine, bromine, $C_1$-$C_3$alkoxy, $C_1$-$C_2$fluoroalkoxy, $C_1$-$C_2$alkoxy-$C_1$-$C_3$alkoxy-, or $C_1$fluoroalkoxy-$C_1$-$C_3$alkoxy-; and
$R^3$, $R^4$, $R^5$ and $R^6$, independently of each other, are hydrogen, $C_1$-$C_5$alkyl, $C_2$-$C_4$alkenyl, $C_2$-$C_4$alkynyl, $C_1$-$C_2$fluoroalkyl, $C_1$-$C_3$alkoxy$C_1$-$C_3$alkyl, $C_1$-$C_3$alkylthio$C_1$-$C_3$alkyl, $C_1$-$C_3$alkylsulfinyl$C_1$-$C_3$alkyl, $C_1$-$C_3$alkylsulfonyl$C_1$-$C_3$alkyl; $C_3$-$C_4$cycloalkyl; or an unsubstituted 4, 5 or 6 membered monocyclic heterocyclyl having one ring heteroatom independently selected from oxygen, sulfur and nitrogen, and attached at a ring carbon atom within the heterocyclyl;
provided that no more than one of $R^3$, $R^4$, $R^5$ and $R^6$ is alkenyl, alkynyl, alkoxyalkyl, alkylthioalkyl, alkylsulfinylalkyl, alkylsulfonylalkyl, cycloalkyl or heterocyclyl;
or $R^3$ and $R^4$ taken together are —$(CH_2)_{n1}$— or —$(CH_2)_{n2}$—$X^1$—$(CH_2)_{n3}$— and $R^5$ and $R^6$ are as defined herein, or $R^5$ and $R^6$ taken together are —$(CH_2)_{n1}$— or —$(CH_2)_{n2}$—$X^1$—$(CH_2)_{n3}$— and $R^3$ and $R^4$ are as defined herein;
wherein $X^1$ is O, S, S(O), S(O)$_2$, NH, N($C_1$-$C_2$alkyl), N($C_1$-$C_2$alkoxy), C(H)($C_1$-$C_2$alkyl), C($C_1$-$C_2$alkyl)$_2$ or C(H)($C_1$-$C_2$alkoxy);
n1 is 2, 3, 4 or 5; and
n2 and n3 are independently 1, 2 or 3 provided that n2+n3 is 2, 3 or 4;
or $R^4$ and $R^5$ taken together are —$(CH_2)_{n4}$— or —$(CH_2)_{n5}$—$C(R^{7a})(R^{7b})$—$(CH_2)_{n6}$— or —$C(R^{7c})$=$C(R^{7d})$—;

wherein $R^{7a}$ is $C_1$-$C_2$alkyl or $C_1$-$C_2$alkoxy; and IC' is hydrogen or $C_1$-$C_2$alkyl provided that IC' is hydrogen when $R^{7a}$ is $C_1$-$C_2$alkoxy;
n4 is 1, 2 or 3; and
n5 and n6 are independently 0, 1 or 2 provided that n5+n6 is 0, 1 or 2;
and $R^{7c}$ and $R^{7d}$ independently are hydrogen or $C_1$-$C_2$alkyl; and
Y is O, S, S(O), S(O)$_2$, N($C_1$-$C_2$alkyl), N($C_1$-$C_2$alkoxy), C(O), $CR^8R^9$ or —$CR^{10}R^{11}CR^{12}R^{13}$—; and
$R^8$ and $R^9$ are, independently of each other:
hydrogen, $C_1$-$C_6$alkyl, $C_2$-$C_4$alkenyl, $C_2$-$C_4$alkynyl, $C_1$-$C_2$fluoroalkyl, $C_1$-$C_3$alkoxy$C_1$-$C_3$alkyl, $C_1$-$C_3$alkylthio$C_1$-$C_3$alkyl, $C_1$-$C_3$alkylsulfinyl$C_1$-$C_3$alkyl, or $C_1$-$C_3$alkylsulfonyl$C_1$-$C_3$alkyl; $C_3$-$C_6$cycloalkyl or $C_3$-$C_6$cycloalkyl substituted by one or two substituents which independently are $C_1$-$C_3$alkyl or $C_1$-$C_2$fluoroalkyl; and in which one ring $CH_2$ moiety of a $C_4$-$C_6$cycloalkyl is optionally replaced by an oxygen or sulfur atom or by a S(O), S(O)$_2$, NH, N($C_1$-$C_3$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety;
$C_3$-$C_6$cycloalkyl substituted by one substituent being $C_1$-$C_3$ alkoxy and optionally further substituted by one substituent being $C_1$-$C_2$alkyl;
$C_5$-$C_6$cycloalkenyl or $C_5$-$C_6$cycloalkenyl substituted by one or two $C_1$-$C_3$ alkyl substituents;
$C_3$-$C_6$cycloalkyl$C_1$-$C_2$alkyl- or $C_3$-$C_6$cycloalkyl$C_1$-$C_2$alkyl- substituted by one or two ring substituents which independently are $C_1$-$C_3$alkyl or $C_1$-$C_2$fluoroalkyl; and in which one ring $CH_2$ moiety of a $C_4$-$C_6$cycloalkyl$C_1$-$C_2$alkyl- is optionally replaced by an oxygen or sulfur atom or by a S(O), S(O)$_2$, NH, N($C_1$-$C_2$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety;
$C_3$-$C_6$cycloalkyl$C_1$-$C_2$alkyl- substituted by one ring substituent being $C_1$-$C_3$ alkoxy and optionally further substituted by one ring substituent being $C_1$-$C_2$alkyl; or
Het or Het-$CH_2$—, wherein Het is a heteroaryl, attached at a ring-carbon, which is optionally substituted by 1, 2 or 3 ring-carbon substituents independently being $C_1$-$C_3$alkyl, $C_1$-$C_2$fluoroalkyl, $C_1$-$C_3$alkyl-C(O)—, $C_1$-$C_2$fluoroalkyl-C(O)—, hydroxy (including any oxo tautomer), $C_2$-$C_3$alkenyl, $C_2$-$C_3$alkynyl, $C_1$-$C_3$alkoxy, $C_1$-$C_2$fluoroalkoxy, halogen, cyano or nitro, provided that any non-fluorine halogen, alkoxy or fluoroalkoxy is not substituted at any ring-carbon bonded directly to a ring-nitrogen of the heteroaryl; and/or, in the case of a 5-membered heteroaryl ring containing a ring-nitrogen atom not partaking in a C=N ring double bond, the heteroaryl is optionally substituted on the ring-nitrogen atom not partaking in a C=N ring double bond by one $C_1$-$C_3$alkyl, $C_1$-$C_2$fluoroalkyl, $C_1$-$C_3$alkyl-C(O)—, $C_1$-$C_2$fluoroalkyl-C(O)— or $C_1$-$C_2$alkyl-S(O)$_2$— substituent;
provided that no more than one of $R^8$ and $R^9$ is an optionally substituted cycloalkyl; an optionally substituted cycloalkyl in which one ring $CH_2$ moiety has been replaced by an oxygen or sulfur atom or by a S(O), S(O)$_2$, NH, N($C_1$-$C_3$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety; an optionally substituted cycloalkenyl; an optionally substituted cycloalkyl-alkyl-; an optionally substituted cycloalkyl-alkyl- in which one ring $CH_2$ moiety has been replaced by an oxygen or sulfur atom or by a S(O), S(O)$_2$, NH, N(C$_1$-C$_3$alkyl), N(C$_1$-C$_2$fluoroalkyl), N[C(O)C$_1$-C$_3$alkyl], N[C(O)C$_1$-C$_2$fluoroalkyl] or N(C$_1$-C$_2$alkoxy) moiety; or Het or Het-CH$_2$—;

or R$^8$ is hydrogen or C$_1$-C$_2$alkyl, and R$^9$ is C$_1$-C$_2$alkoxy; or R$^8$ and R$^9$ taken together are —(CH$_2$)$_{n7}$— or —(CH$_2$)$_{n8}$—X$^2$—(CH$_2$)$_{n9}$—;

wherein X$^2$ is O, S, S(O), S(O)$_2$, NH, N(C$_1$-C$_3$alkyl), N(C$_1$-C$_2$fluoroalkyl), N[C(O)C$_1$-C$_3$alkyl], N[C(O)C$_1$-C$_2$fluoroalkyl], N(C$_1$-C$_2$alkoxy), C(H)(C$_1$-C$_3$alkyl), C(C$_1$-C$_2$alkyl)$_2$ or C(H)(C$_1$-C$_3$alkoxy);

n7 is 2, 3, 4, 5 or 6; and n8 and n9 are independently 0, 1, 2 or 3 provided that n8+n9 is 2, 3, 4 or 5; and R$^{10}$, R$^{11}$, R$^{12}$ and R$^{13}$ are independently of each other hydrogen or C$_1$-C$_4$alkyl provided that no more than one of R$^{10}$, R$^{11}$, R$^{12}$ and R$^{13}$ is C$_3$-C$_4$alkyl; and and wherein:

G is hydrogen; or

G is —C(X$^a$)—R$^a$, —C(X$^b$)—X$^c$—R$^b$, —C(X$^d$)—N(R$^c$)—SO$_2$—R$^e$, —P(X$^e$)(R$^f$)—R$^g$, —CH$_2$—X$^f$—R$^h$; or phenyl-CH$_2$— or phenyl-CH(C$_1$-C$_2$alkyl)- (in each of which the phenyl is optionally substituted by 1, 2 or 3 of, independently, C$_1$-C$_2$alkyl, C$_1$fluoroalkyl, C$_1$-C$_2$alkoxy, C$_1$fluoroalkoxy, fluorine, chlorine, bromine, cyano or nitro), or heteroaryl-CH$_2$— or heteroaryl-CH(C$_1$-C$_2$alkyl)- (in each of which the heteroaryl is optionally substituted by 1, 2 or 3 of, independently, C$_1$-C$_2$alkyl, C$_1$fluoroalkyl, C$_1$-C$_2$alkoxy, C$_1$fluoroalkoxy, fluorine, chlorine, bromine, cyano or nitro), or phenyl-C(O)—CH$_2$— (wherein the phenyl is optionally substituted by 1, 2 or 3 of, independently, C$_1$-C$_2$alkyl, C$_1$fluoroalkyl, C$_1$-C$_2$alkoxy, C$_1$fluoroalkoxy, fluorine, chlorine, bromine, cyano or nitro); or C$_1$-C$_6$alkoxy-C(O)—CH$_2$—, C$_1$-C$_6$alkoxy-C(O)—CH=CH—, C$_2$-C$_7$alken-1-yl-CH$_2$—, C$_2$-C$_7$alken-1-yl-CH(C$_1$-C$_2$alkyl)-, C$_2$-C$_4$fluoroalken-1-yl-CH$_2$—, C$_2$-C$_7$alkyn-1-yl-CH$_2$—, or C$_2$-C$_7$alkyn-1-yl-CH(C$_1$-C$_2$alkyl)-;

wherein X$^a$, X$^b$, X$^c$, X$^d$, X$^e$ and X$^f$ are independently of each other oxygen or sulfur; and wherein R$^a$ is H, C$_1$-C$_{21}$alkyl, C$_2$-C$_{21}$alkenyl, C$_2$-C$_{18}$alkynyl, C$_1$-C$_{10}$fluoroalkyl, C$_1$-C$_{10}$cyanoalkyl, C$_1$-C$_{10}$aminoalkyl, C$_1$-C$_5$alkylamino(C$_1$-C$_5$)alkyl, C$_2$-C$_8$dialkylamino(C$_1$-C$_5$)alkyl, C$_3$-C$_7$cycloalkyl(C$_1$-C$_5$)alkyl, C$_1$-C$_5$alkoxy(C$_1$-C$_5$)alkyl, C$_3$-C$_5$alkenyloxy(C$_1$-C$_5$)alkyl, C$_3$-C$_5$alkynyloxy(C$_1$-C$_5$)alkyl, C$_1$-C$_5$alkylthio(C$_1$-C$_5$)alkyl, C$_1$-C$_5$alkylsulfinyl(C$_1$-C$_5$)alkyl, C$_1$-C$_5$alkylsulfonyl(C$_1$-C$_5$)alkyl, C$_2$-C$_8$alkylideneaminoxy(C$_1$-C$_5$)alkyl, C$_1$-C$_5$alkylcarbonyl(C$_1$-C$_5$)alkyl, C$_1$-C$_5$alkoxycarbonyl(C$_1$-C$_5$)alkyl, aminocarbonyl(C$_1$-C$_5$)alkyl, C$_1$-C$_5$alkylaminocarbonyl(C$_1$-C$_5$)alkyl, C$_2$-C$_8$dialkylaminocarbonyl(C$_1$-C$_5$)alkyl, C$_1$-C$_5$alkylcarbonylamino(C$_1$-C$_5$)alkyl, N—(C$_1$-C$_5$)alkylcarbonyl-N—(C$_1$-C$_5$)alkylamino(C$_1$-C$_5$)alkyl, C$_3$-C$_6$trialkylsilyl(C$_1$-C$_5$)alkyl, phenyl(C$_1$-C$_5$)alkyl (wherein the phenyl is optionally substituted by 1, 2 or 3 of, independently, C$_1$-C$_3$alkyl, C$_1$-C$_1$fluoroalkyl, C$_1$-C$_3$alkoxy, C$_1$-C$_1$fluoroalkoxy, C$_1$-C$_3$alkylthio, C$_1$-C$_3$alkylsulfinyl, C$_1$-C$_3$alkylsulfonyl, halogen, cyano, or nitro), heteroaryl(C$_1$-C$_5$)alkyl (wherein the heteroaryl is optionally substituted by 1, 2 or 3 of, independently, C$_1$-C$_3$alkyl, C$_1$-C$_3$fluoroalkyl, C$_1$-C$_3$alkoxy, C$_1$-C$_3$fluoroalkoxy, C$_1$-C$_3$alkylthio, C$_1$-C$_3$alkylsulfinyl, C$_1$-C$_3$alkyl sulfonyl, halogen, cyano, or nitro), C$_2$-C$_5$fluoroalkenyl, C$_3$-C$_8$cycloalkyl; phenyl or phenyl substituted by 1, 2 or 3 of, independently, C$_1$-C$_3$alkyl, C$_1$-C$_3$fluoroalkyl, C$_1$-C$_3$alkoxy, C$_1$-C$_3$fluoroalkoxy, halogen, cyano or nitro; or heteroaryl or heteroaryl substituted by 1, 2 or 3 of, independently, C$_1$-C$_3$ alkyl, C$_1$-C$_3$fluoroalkyl, C$_1$-C$_3$alkoxy, C$_1$-C$_3$fluoroalkoxy, halogen, cyano or nitro;

R$^b$ is C$_1$-C$_{18}$alkyl, C$_3$-C$_{18}$alkenyl, C$_3$-C$_{18}$alkynyl, C$_2$-C$_{10}$fluoroalkyl, C$_1$-C$_{10}$cyanoalkyl, C$_1$-C$_{10}$nitroalkyl, C$_2$-C$_{10}$aminoalkyl, C$_1$-C$_5$alkylamino(C$_1$-C$_5$)alkyl, C$_2$-C$_8$dialkylamino(C$_1$-C$_5$)alkyl, C$_3$-C$_7$cycloalkyl(C$_1$-C$_5$)alkyl, C$_1$-C$_5$alkoxy(C$_1$-C$_5$)alkyl, C$_3$-C$_5$alkenyloxy(C$_1$-C$_5$)alkyl, C$_3$-C$_5$alkynyloxy(C$_1$-C$_5$)alkyl, C$_1$-C$_5$alkylthio(C$_1$-C$_5$)alkyl, C$_1$-C$_5$alkylsulfinyl(C$_1$-C$_5$)alkyl, C$_1$-C$_5$alkylsulfonyl(C$_1$-C$_5$)alkyl, C$_2$-C$_8$alkylideneaminoxy(C$_1$-C$_5$)alkyl, C$_1$-C$_5$alkylcarbonyl(C$_1$-C$_5$)alkyl, C$_1$-C$_5$alkoxycarbonyl(C$_1$-C$_5$)alkyl, aminocarbonyl(C$_1$-C$_5$)alkyl, C$_1$-C$_5$alkylaminocarbonyl(C$_1$-C$_5$)alkyl, C$_2$-C$_8$dialkylaminocarbonyl(C$_1$-C$_5$)alkyl, C$_1$-C$_5$alkylcarbonylamino(C$_1$-C$_5$)alkyl, N—(C$_1$-C$_5$)alkylcarbonyl-N—(C$_1$-C$_5$)alkylamino(C$_1$-C$_5$)alkyl, C$_3$-C$_6$trialkylsilyl(C$_1$-C$_5$)alkyl, phenyl(C$_1$-C$_5$)alkyl (wherein the phenyl is optionally substituted by 1, 2 or 3 of, independently, C$_1$-C$_3$alkyl, C$_1$-C$_3$fluoroalkyl, C$_1$-C$_3$alkoxy, C$_1$-C$_3$fluoroalkoxy, C$_1$-C$_3$alkylthio, C$_1$-C$_3$alkylsulfinyl, C$_1$-C$_3$alkyl sulfonyl, halogen, cyano, or nitro), heteroarylC$_1$-C$_5$alkyl (wherein the heteroaryl is optionally substituted by 1, 2 or 3 of, independently, C$_1$-C$_3$alkyl, C$_1$-C$_3$fluoroalkyl, C$_1$-C$_3$alkoxy, C$_1$-C$_3$fluoroalkoxy, C$_1$-C$_3$alkyl-thio, C$_1$-C$_3$alkylsulfinyl, C$_1$-C$_3$alkyl sulfonyl, halogen, cyano, or nitro), C$_3$-C$_5$fluoroalkenyl, C$_3$-C$_8$cycloalkyl; phenyl or phenyl substituted by 1, 2 or 3 of, independently, C$_1$-C$_3$alkyl, C$_1$-C$_3$fluoroalkyl, C$_1$-C$_3$alkoxy, C$_1$-C$_3$fluoroalkoxy, halogen, cyano or nitro; or heteroaryl or heteroaryl substituted by 1, 2 or 3 of, independently, C$_1$-C$_3$ alkyl, C$_1$-C$_3$fluoroalkyl, C$_1$-C$_3$alkoxy, C$_1$-C$_3$fluoroalkoxy, halogen, cyano or nitro; and R$^c$ and R$^d$ are each independently of each other hydrogen, C$_1$-C$_{10}$alkyl, C$_3$-C$_{10}$alkenyl, C$_3$-C$_{10}$alkynyl, C$_2$-C$_{10}$fluoroalkyl, C$_1$-C$_{10}$cyanoalkyl, C$_1$-C$_{10}$nitroalkyl, C$_1$-C$_5$alkylamino(C$_1$-C$_5$)alkyl, C$_2$-C$_8$dialkylamino(C$_1$-C$_5$)alkyl, C$_3$-C$_7$cycloalkyl(C$_1$-C$_5$)alkyl, C$_1$-C$_5$alkoxy(C$_1$-C$_5$)alkyl, C$_3$-C$_5$alkenyloxy(C$_1$-C$_5$)alkyl, C$_3$-C$_5$alkynyloxy(C$_1$-C$_5$)alkyl, C$_1$-C$_5$alkylthio(C$_1$-C$_5$)alkyl, C$_1$-C$_5$alkylsulfinyl(C$_1$-C$_5$)alkyl, C$_1$-C$_5$alkylsulfonyl(C$_1$-C$_5$)alkyl, C$_2$-C$_8$alkylideneaminoxy(C$_1$-C$_5$)alkyl, C$_1$-C$_5$alkylcarbonyl(C$_1$-C$_5$)alkyl, C$_1$-C$_5$alkoxycarbonyl(C$_1$-C$_5$)alkyl, aminocarbonyl(C$_1$-C$_5$)alkyl, C$_1$-C$_5$alkylaminocarbonyl(C$_1$-C$_5$)alkyl, C$_2$-C$_8$dialkylaminocarbonyl(C$_1$-C$_5$)alkyl, C$_1$-C$_5$alkylcarbonylamino(C$_1$-C$_5$)alkyl, N—(C$_1$-C$_5$)alkylcarbonyl-N—(C$_2$-C$_5$)alkylaminoalkyl, C$_3$-C$_6$trialkylsilyl(C$_1$-C$_5$)alkyl, phenyl(C$_1$-C$_5$)alkyl (wherein the phenyl is optionally substituted by 1, 2 or 3 of, independently, C$_1$-C$_3$alkyl, C$_1$-C$_3$fluoroalkyl, C$_1$-C$_3$alkoxy, C$_1$-C$_3$fluoroalkoxy, C$_1$-C$_3$alkylthio, C$_1$-C$_3$alkylsulfinyl, C$_1$-C$_3$alkylsulfonyl, halogen, cyano, or nitro), heteroaryl(C$_1$-C$_5$)alkyl (wherein the heteroaryl is optionally substituted by 1, 2 or 3 of, independently, C$_1$-C$_3$alkyl, C$_1$-C$_3$fluoroalkyl, C$_1$-C$_3$alkoxy, C$_1$-C$_3$fluoroalkoxy, C$_1$-C$_3$alkylthio, C$_1$-C$_3$alkylsulfinyl, C$_1$-C$_3$alkylsulfonyl, halogen, cyano, or nitro), C$_2$-C$_5$fluoroalkenyl, C$_3$-C$_8$cycloalkyl;

phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or by nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino or $C_3$-$C_7$cycloalkoxy;

or $R^c$ and $R^d$, together with the nitrogen to which they are bonded, to form an unsubstituted 4, 5, 6 or 7 membered ring, optionally containing one heteroatom selected from O or S; and $R^e$ is $C_1$-$C_{10}$alkyl, $C_2$-$C_{10}$alkenyl, $C_2$-$C_{10}$alkynyl, $C_1$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkyl sulfonyl, halogen, cyano, or nitro), $C_2$-$C_5$fluoroalkenyl, $C_3$-$C_8$ cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino, $C_3$-$C_7$cycloalkoxy, $C_1$-$C_{10}$alkoxy, $C_1$-$C_{10}$fluoroalkoxy, $C_1$-$C_5$alkylamino or di($C_1$-$C_4$alkyl)amino;

$R^f$ and $R^g$ are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino, $C_3$-$C_7$cycloalkoxy, $C_1$-$C_{10}$fluoroalkoxy, $C_1$-$C_5$alkylamino or di($C_1$-$C_4$alkyl)amino; or benzyloxy or phenoxy, wherein the benzyl and phenyl groups are in turn optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; and $R^h$ is $C_1$-$C_{10}$alkyl, $C_3$-$C_{10}$alkenyl, $C_3$-$C_{10}$alkynyl, $C_1$-$C_{10}$fluoroalkyl, $C_1$-$C_{10}$cyanoalkyl, $C_2$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-

C₅)alkyl, C₁-C₅alkylsulfonyl(C₁-C₅)alkyl, C₂-C₈alkylideneaminoxy(C₁-C₅)alkyl, C₁-C₅alkylcarbonyl(C₁-C₅)alkyl, C₁-C₅alkoxycarbonyl(C₁-C₅)alkyl, aminocarbonyl(C₁-C₅)alkyl, C₁-C₅alkylaminocarbonyl(C₁-C₅)alkyl, C₂-C₈dialkylaminocarbonyl(C₁-C₅)alkyl, C₁-C₅alkylcarbonylamino(C₁-C₅)alkyl, N—(C₁-C₅)alkylcarbonyl-N—(C₁-C₅)alkylamino(C₁-C₅)alkyl, C₃-C₆trialkylsilyl(C₁-C₅)alkyl, phenyl(C₁-C₅)alkyl (wherein the phenyl is optionally substituted by 1, 2 or 3 of, independently, C₁-C₃alkyl, C₁-C₃fluoroalkyl, C₁-C₃alkoxy, C₁-C₃fluoroalkoxy, C₁-C₃alkylthio, C₁-C₃alkylsulfinyl, C₁-C₃ alkyl sulfonyl, halogen, cyano or nitro), heteroaryl(C₁-C₅)alkyl (wherein the heteroaryl is optionally substituted by 1, 2 or 3 of, independently, C₁-C₃alkyl, C₁-C₃fluoroalkyl, C₁-C₃alkoxy, C₁-C₃fluoroalkoxy, C₁-C₃alkylthio, C₁-C₃alkylsulfinyl, C₁-C₃ alkylsulfonyl, halogen, cyano or nitro), phenoxy(C₁-C₅)alkyl (wherein the phenyl is optionally substituted by 1, 2 or 3 of, independently, C₁-C₃alkyl, C₁-C₃fluoroalkyl, C₁-C₃alkoxy, C₁-C₃fluoroalkoxy, C₁-C₃alkylthio, C₁-C₃alkylsulfinyl, C₁-C₃ alkylsulfonyl, halogen, cyano or nitro), heteroaryloxy(C₁-C₅)alkyl (wherein the heteroaryl is optionally substituted by 1, 2 or 3 of, independently, C₁-C₃alkyl, C₁-C₃fluoroalkyl, C₁-C₃alkoxy, C₁-C₃fluoroalkoxy, C₁-C₃alkylthio, C₁-C₃alkylsulfinyl, C₁-C₃ alkyl sulfonyl, halogen, cyano or nitro), C₃-C₅fluoroalkenyl, C₃-C₈cycloalkyl; phenyl or phenyl substituted by 1, 2 or 3 of, independently, C₁-C₃alkyl, C₁-C₃fluoroalkyl, C₁-C₃alkoxy, C₁-C₃fluoroalkoxy, halogen, cyano or nitro; or heteroaryl or heteroaryl substituted by 1, 2 or 3 of, independently, C₁-C₃alkyl, C₁-C₃fluoroalkyl, C₁-C₃alkoxy, C₁-C₃fluoroalkoxy, halogen, cyano or nitro; C₁-C₆alkyl-C(O)—; or phenyl-C(O)— wherein the phenyl is optionally substituted by 1 or 2 of, independently, C₁-C₂alkyl, C₁fluoroalkyl, C₁-C₂alkoxy, C₁fluoroalkoxy, fluorine, chlorine, bromine, cyano or nitro; and wherein "heteroaryl" means an aromatic ring system containing at least one ring heteroatom and consisting either of a single ring or of two fused rings and wherein the compound of formula (I) is optionally present as an agrochemically acceptable salt thereof.

2. The compound as claimed in claim 1, wherein G is hydrogen or G is —C(Xᵃ)—Rᵃ or —C(Xᵇ)—Xᶜ—Rᵇ.

3. The compound as claimed in claim 1, wherein X is methyl.

4. The compound as claimed in claim 1, wherein X is chlorine.

5. The compound as claimed in claim 1, wherein R¹ is methyl.

6. The compound as claimed in claim 1, wherein R¹ is chlorine.

7. The compound as claimed in claim 1, wherein X is methyl, and R¹ is methyl.

8. The compound as claimed in claim 1, wherein X is methyl, and R¹ is chlorine.

9. The compound as claimed in claim 1, wherein R² is methyl or methoxy.

10. The compound as claimed in claim 1, wherein:
R¹ is chlorine, and R² is methoxy.

11. The compound as claimed in claim 1, wherein R³, R⁴, R⁵ and R⁶, independently of each other, are hydrogen or C₁-C₂alkyl; or R⁴ and R⁵ taken together are —(CH₂)ₙ₄— wherein n4 is 2 or 3.

12. The compound as claimed in claim 1, wherein Y is CR⁸R⁹.

13. The compound as claimed in claim 1, wherein Y is CH₂.

14. The compound as claimed in claim 1, wherein the compound of formula (I) is a compound of one of the following types, described and illustrated below, optionally present as an agrochemically acceptable salt thereof:

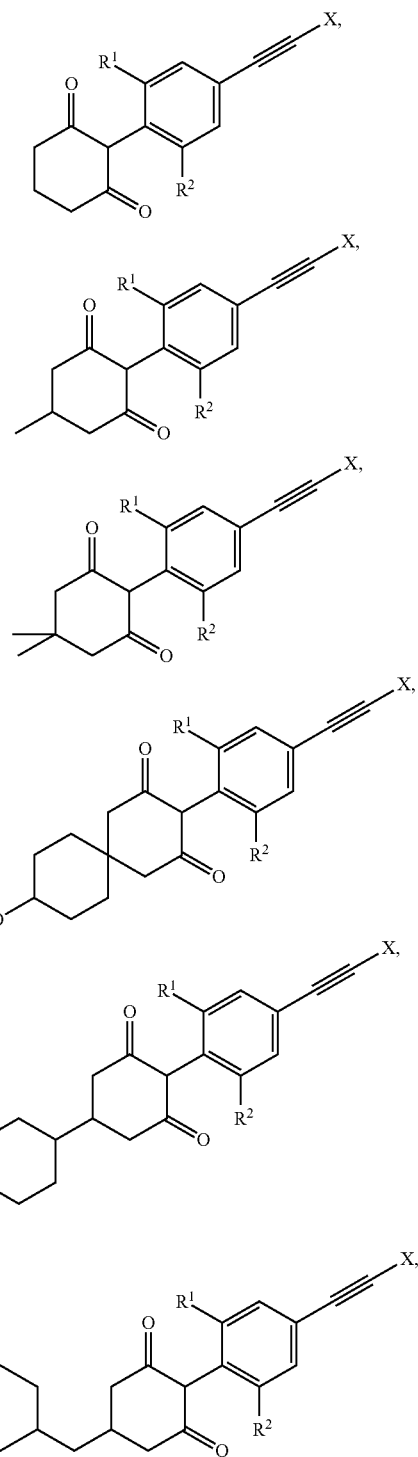

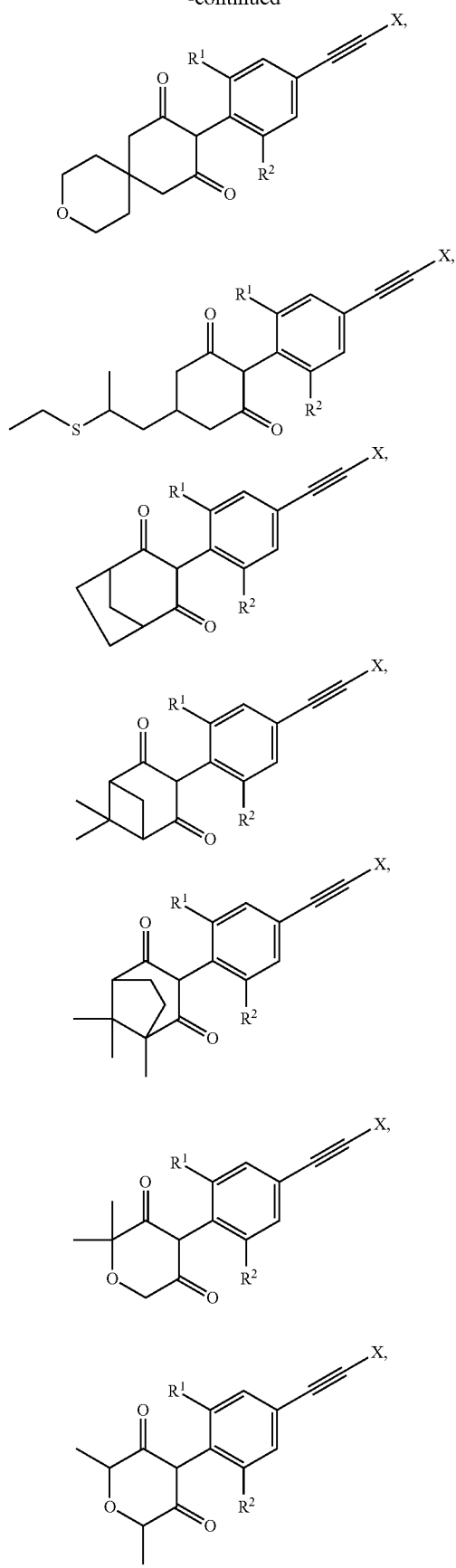
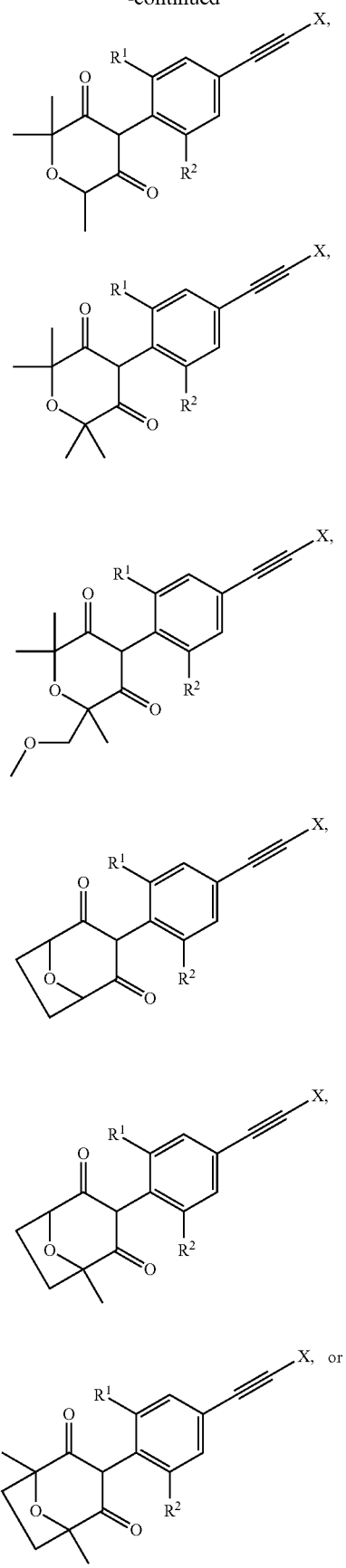

-continued

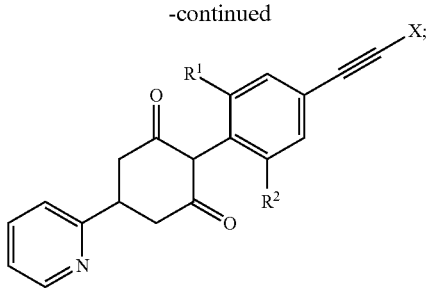

wherein:
$R^1$ is methyl, X is methyl, and $R^2$ is hydrogen, methyl, chlorine, methoxy, ethynyl, ethyl, vinyl, 2-methoxyethoxy or ethoxy; or
$R^1$ is chlorine, X is methyl, and $R^2$ is hydrogen, chlorine, methoxy, ethynyl, ethyl, vinyl, 2-methoxyethoxy or ethoxy; or
$R^1$ is methyl, X is chlorine, and $R^2$ is hydrogen, methyl, chlorine, methoxy, ethynyl, ethyl, vinyl, 2-methoxyethoxy or ethoxy; or
$R^1$ is chlorine, X is chlorine, and $R^2$ is hydrogen, chlorine, methoxy, ethynyl, ethyl, vinyl, 2-methoxyethoxy or ethoxy.

15. The compound as claimed in claim 1 wherein the compound of formula (I) is a compound of one of the following types, described and illustrated below, optionally present as an agrochemically acceptable salt thereof:

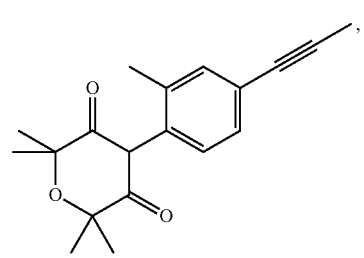

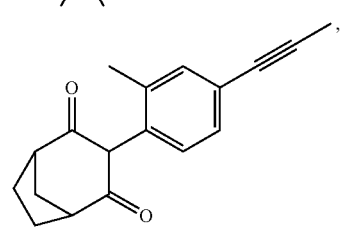

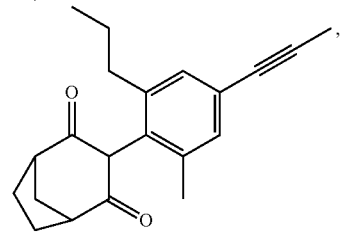

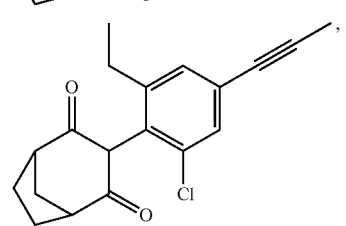

-continued

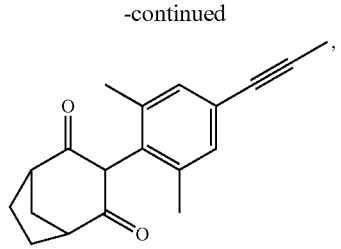

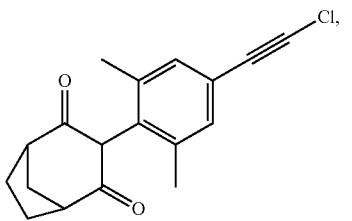

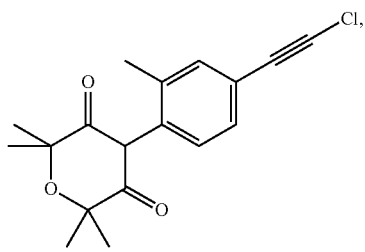

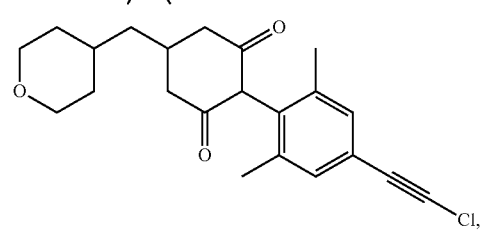

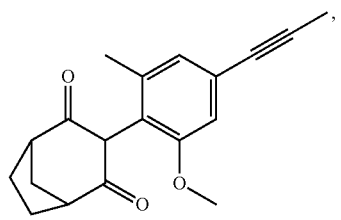

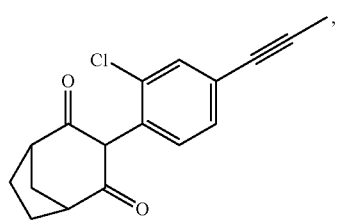

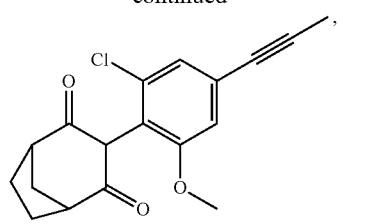
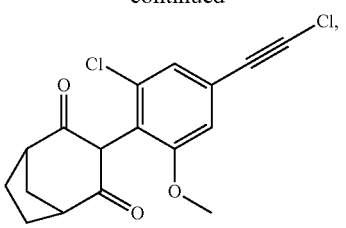
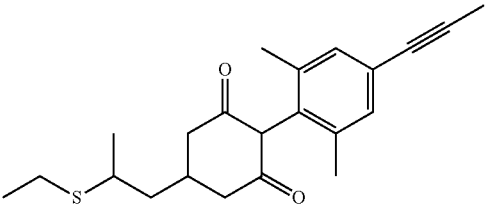
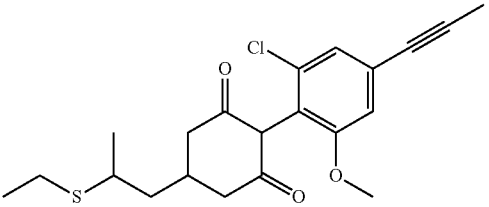
, or
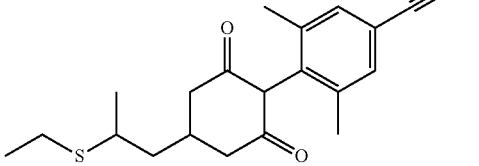
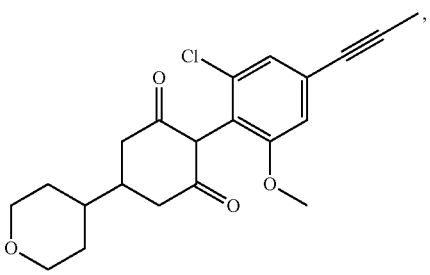
16. The compound as claimed in claim 1 wherein the compound of formula (I) is a compound of one of the following types, described and illustrated below, optionally present as an agrochemically acceptable salt thereof:
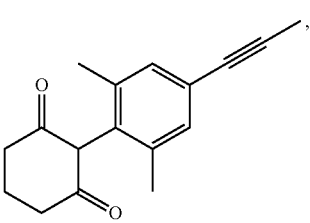

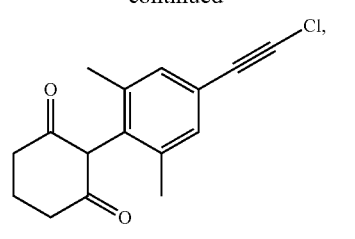
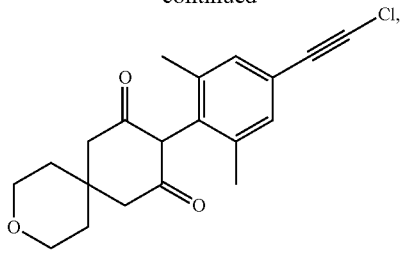

17. A herbicidal composition which comprises a compound of formula (I), as defined in claim 1, and an agrochemically acceptable carrier, diluent and/or solvent.

18. A herbicidal composition according to claim 17, which comprises one or more further herbicides and/or a safener.

19. A method of controlling weeds in crops of useful plants, comprising applying a compound of formula (I), as defined in claim 1, or a herbicidal composition comprising such a compound, to the plants or to the locus thereof.

20. The compound as claimed in claim 1, wherein G is hydrogen.

21. The compound as claimed in claim 20, where the agrochemically acceptable salt is a metal, sulfonium or ammonium salt.

* * * * *